United States Patent
Seko et al.

(10) Patent No.: US 6,677,333 B1
(45) Date of Patent: Jan. 13, 2004

(54) 2H-PHTHALAZIN-1-ONE DERIVATIVES AND DRUG CONTAINING ITS DERIVATIVES AS ACTIVE INGREDIENT

(75) Inventors: Takuya Seko, Osaka (JP); Jun Takeuchi, Osaka (JP); Shinya Takahashi, Osaka (JP); Masao Naka, Osaka (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/889,925

(22) PCT Filed: Jan. 24, 2000

(86) PCT No.: PCT/JP00/00319

§ 371 (c)(1),
(2), (4) Date: Jul. 25, 2001

(87) PCT Pub. No.: WO00/44726

PCT Pub. Date: Aug. 3, 2000

(30) Foreign Application Priority Data

Jan. 26, 1999 (JP) .......................... 11-016788
Aug. 19, 1999 (JP) .......................... 11-233099

(51) Int. Cl.$^7$ .................. A61K 31/502; C07D 237/32; C07D 401/12; C07D 403/12; C07D 405/12
(52) U.S. Cl. .................. 514/218; 514/228.2; 514/234.8; 514/248; 540/575; 544/62; 544/119; 544/237
(58) Field of Search ................... 544/237, 62, 119; 540/575; 514/218, 228.2, 234.8, 248

(56) References Cited

U.S. PATENT DOCUMENTS 5,668,279 A    9/1997    Chakravarty et al. ....... 544/119

FOREIGN PATENT DOCUMENTS

| JP | 54-32489 A | 3/1979 |
| JP | 57-167974 | 10/1982 |
| WO | WO99/11624 A1 | 3/1999 |
| WO | 99/11649 | 3/1999 |
| WO | WO00/50419 A1 | 8/2000 |

OTHER PUBLICATIONS

Kitagawa et al, Chemical Abstracts, vol. 91, No. 107991 (1979), Abstract for JP 54032489 (Mar. 9, 1979.*
Yamaguchi, M. et al., "Novel Antiasthmatic Agents with Dual Activities of Thromboxane A$_2$ Synthetase Inhibition and Bronchodilation. 1.2[2–(1–Imidazoly)alkyl]–1(2H)–phthalazinones", J. Med. Chem. (1993), p. 4054–4060.
Shinkwin, A. et al., "Synthesis of Thiophenecarboxamides, Thieno[3,4–c]pyridin–4(5H)–ones and Thieno 3,4–d pyrimidin–4(3H)–ones and Preliminary Evaluation as Inhibitors of Poly(ADP–ribose)polymerase (PARP)", Bioorganic & Medicinal Chemistry 7 (1999), p. 297–308.

* cited by examiner

Primary Examiner—Richard L. Raymond
(74) Attorney, Agent, or Firm—Sughrue Mion, PLLC

(57) ABSTRACT

Poly(ADP-ribose)polymerase inhibitors containing as the active ingredient 2H-phthalazin-1-one derivatives represented by general formula (I) (wherein each symbol is as defined in the description) or salts thereof. The compounds of the general formula (I) inhibit poly(ADP-ribose) polymerase and are useful as preventives and/or remedies for various ischemic diseases (brain, heart, digestive tract, skeletal muscle, retina, etc.), inflammatory diseases (inflammatory intestinal diseases, multiple encephalosclerosis, arthritis, etc.), nerve degeneration diseases (extrapyramidal disorder, Alzheimer's disease, muscular dystrophy, etc.), diabetes, shock, head trauma, renal insufficiency, hyperalgesia, etc. These compounds are also useful as sensitizers for agents against retroviruses (HIV, etc.) and chemotherapy for cancer.

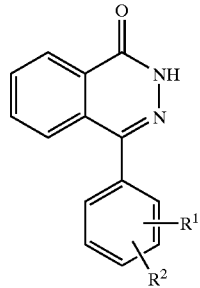

(I)

9 Claims, No Drawings

2H-PHTHALAZIN-1-ONE DERIVATIVES AND DRUG CONTAINING ITS DERIVATIVES AS ACTIVE INGREDIENT

TECHNICAL FIELD

This invention relates to 2H-phthalazin-1-one derivatives and poly (ADP-ribose) polymerase inhibitors containing 2H-phthalazin-1-one derivatives as active ingredient.

More particularly, this invention relates to poly (ADP-ribose) polymerase inhibitors containing 2H-phthalazin-1-one derivatives of the formula (I)

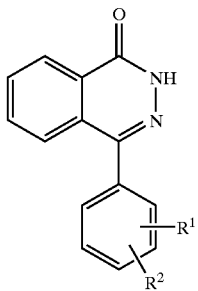

(I)

(wherein all symbols are as hereinafter defined) and non-toxic salts thereof as active ingredient, novel 2H-phthalazin-1-one derivatives of the formula (Ia) as hereinafter defined and non-toxic salts thereof, and processes for the preparation thereof.

BACKGROUND

Poly(ADP-ribose)polymerase (abbreviated as PARP hereinafter) is a nuclear enzyme activated by DNA strand breaks, which play an important role the reaction that transfer of the ADP-ribose moiety from nicotinamide adenine dinucleotide (abbreviated as AND$^+$ hereinafter) to various proteins such as histones, DNA-polymerases and DNA-topoisomerases, etc. DNA strand breaks is caused by Peroxynitrite (ONOO$^-$) and oxygen radicals that leads to overactivation of PARP. (PARP on Zn finger domain binds to DNA with nicks and then PARP is activated up to 100 times.) Overactivation of PARP elicits depletion of AND$^+$ which essential of electron transport and then ATP depletion leads to disturbance of energy production system, consequently cause to cell death. (The suicide theory of PARP activation: Free Radic. Biol. Med., 21, 855 (1996); TIPS., 19, 287 (1998)). Therefore, it is considered that PARP inhibitor may be useful as inhibition of cell death. Since caspase-3, one of interleukin-1β-converting enzyme family, specifically cleaves PARP as the substrate, it is suggested PARP is associated with apoptosis. (Cell., 81, 801 (1995).

It is reported that 3-aminobenzamide and nicotinamide generally known as inhibitors of PARP are useful for inhibition of cell death and improvement of diseases on various models of ischemic diseases (cerebral, myocardial, intestinal, skeletal muscular or retinal ischemia etc.), inflammatory diseases (inflammatory bowel disease, multiple sclerosis or arthritis etc.), diabetes, shock, extrapyramidal disease (TIPS., 19, 287 (1998); Eur. J. Pharmacol., 350, 1 (1998)) and hyperalgesia (Pain, 72, 355 (1997)) in vitro, in vivo and in the knockout mouse. And it is known they are increased the effects of antiretroviral (HIV etc.) (Biochem. Biophys. Res. Commum., 180, 504 (1991)) or anticancer drugs. (Radiat. Res., 126, 367 (1991); Br. J. Cancer., 72, 849 (1995)).

PARP inhibitor may be useful for prevention and/or treatment of various diseases, for example, ischemic diseases (cerebral, myocardial, intestinal, skeletal muscular or retinal ischemia etc.), inflammatory diseases (inflammatory bowel disease, multiple sclerosis or arthritis etc.), neurodegenerative disorders (extrapyramidal disease, Alzheimer's disease or muscular dystrophy etc.), diabetes, shock, head trauma, renal insufficiency or hyperalgesia etc. And it may be increased the effects of antiretroviral (HIV etc.) or anticancer drugs.

For example, it is disclosed in JP kokai hei 2-124874 that the compound of formula (A)

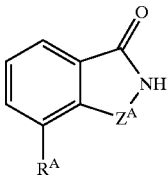

(A)

(wherein $R^A$ is $OR^{1A}$, lower alkyl, $NR^{1A}R^2A$, a halogen, trifluoromethyl, $C(O)X^{2A}$, CN, $COX^{2A}$ (wherein $X^{2A}$ is lower alkyl, aryl, or aralkyl), $R^{1A}$ is a hydrogen, lower alkyl, benzyl, etc., $R^{2A}$ is a hydrogen, lower alkyl, phenyl or benzyl, $Z^A$ is (i) —$CHR^{2A}CHR^{3A}$— (wherein $R^{3A}$ is a hydrogen, alkyl, phenyl or benzyl), (ii) —$CR^{5A}$=$CR^{3A}$, or (iii) —$CR^{3A}$=N— (when $Z^A$ is (iii), then N of $Z^A$ binds to N of ring), $R^{3A}$ is a hydrogen, lower alkyl, phenyl or benzyl, $R^{5A}$ is a hydrogen, lower alkyl, phenyl, benzyl, chlorine, bromine or $NR^{7A}R^{8A}$ (wherein $R^{7A}$ and $R^{8A}$ each, independently, is a hydrogen or lower alkyl)) have an inhibitory activity on PARP (with the proviso that, definitions not related are omitted).

It is disclosed in SU 1378303 that the compound of formula (B)

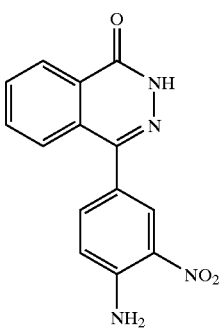

(B)

and it is not disclosed about the biological activity.

It is disclosed in JP kokai sho 57-167974 that the compound of formula (C)

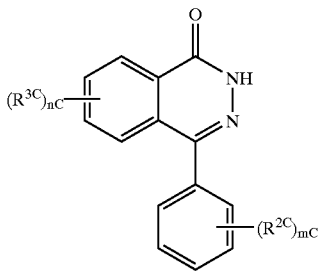

(wherein $R^{2c}$ and $R^{3c}$ each, independently, is C1–5 alkyl, C1–5 alkoxy, a halogen, C2–6 alkoxycarbonyl, carboxy, cyano, C2–4 alkylcarbonyl, hydroxy or trifluoromethyl, mC and nC is 0–3) is an intermediate of platelet aggregate inhibitor.

It is disclosed in JP kokai sho 54-032489 that the compound of formula (D)

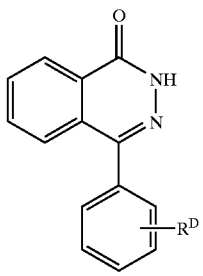

(wherein $R^D$ is hydroxy, methoxy or protected hydroxy) is an intermediate of antihypertensive.

It is disclosed in EP 534443 that the compound of formula (E)

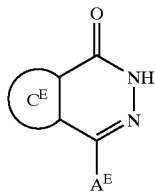

(wherein $A^E$ is C3–6 alkyl, C5–7 cycloalkyl, phenyl, thienyl, furyl, thiazolyl, phenoxy, C7–9 phenylalkyl, phenylthio, azacycloalkyl, pyridyl or imidazolyl, all of which may be substituted by C1–4 alkyl, C1–4 alkoxy and/or halogen; ring $C^E$ is benzene, furan or thiophene, all of which may be subsituted by C1–4 alkyl)
is an intermediate of platelet aggregate inhibitor.

It is disclosed in WO 9911624 that the compound of formula (F)

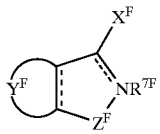

(wherein $X^F$ is double-bonded oxygen or OH; $R^{7F}$ when present, is hydrogen or lower alkyl; $Y^F$ represents the atoms necessary to form a fused mono-, bi- or tricyclic, carbocyclic or heterocyclic ring, wherein each individual ring has 5–6 ring member atoms; $Z^F$ is (i) —$CHR^{2F}CHR^{3F}$— ($R^{2F}$ and $R^{3F}$ are independently hydrogen, alkyl, aryl, aralkyl); (ii) —$R^{6F}FC=CR^{3F}$— ($R^{3F}$ and $R^{6F}$ are independently hydrogen, lower alkyl, aryl, aralkyl, halo, nitro, —$COOR^{7F}$, —$NR^{7F}R^{8F}$ where $R^{8F}$ is independently hydrogen or C1–9 alkyl, or $R^{6F}$ and $R^{3F}$, taken together, form a fused aromatic ring, wherein each individual ring has 5–6 ring members); (iii) —$R^{2F}C=N$—; (iv) —$CR^{2F}(OH)$—$NR^{7F}$—, (v) —(C(O)$NR^{7F}$— or (vi) —$NR^{9F}$—C(O)—$CHR^{10F}$— ($R^{9F}$ and $R^{10F}$ are independently hydrogen or lower alkyl, etc.), wherein said alkyl,aryl and aralkyl, are substituted at one or more positions with hydrogen, hydroxy, halo, haloalkyl, alkoxy, alkenyloxy, alkaryloxy, aryloxy, arylalkoxy, cyano, amino, imino, sulfhydryl, thioalkyl, carboxy, carbocycle, heterocycle, lower alkyl, lower alkenyl, cycloalkyl, aryl, arylalkyl, haloaryl, amino, nitro, nitroso, dimethylamino) have an inhibitory activity on PARP. the following compound is known.

compound (1): 4-(2-acetyloxyphenyl)-2H-phthalazin-1-one (CAS Registry No. 71271-37-9).

DISCLOSURE OF THE INVENTION

Energetic investigations have been carried out to find a compound having poly(ADP-ribose)polymerase inhibitory activity. As a result, the present inventor have found that these aims may be accomplished by a 2H-phthalazin-1-one derivatives of the formula (I).

The 2H-phthalazin-1-one derivatives of the formula (I) have not been known as poly(ADP-ribose)polymerase inhibitor at all. The 2H-phthalazin-1-one derivatives of the formula (Ia) are novel compounds, which have been unknown so far.

The present invention relates to (1) Poly(ADP-ribose)polymerase inhibitors containing a 2H-phthalazin-1-one derivatives of the formula (I)

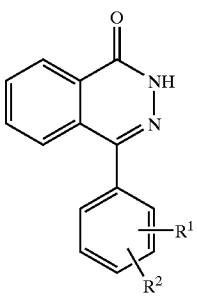

wherein $R^1$ is
(i) C1–4 alkyl substituted by hydroxy or amino, or
(ii) —$A^1$—$A^2$—$A^3$,
in which $A^1$ is
(i) —$NR^3C(O)$—,
(ii) —$NR^4C(S)$—,
(iii) —$NR^5SO_2$—,
(iv) —$CH_2$—$NR^6$—,
(v) —$CH_2$—O—,
(vi) —OC(O)—,
(vii) —$CH_2$—$NR^7C(O)$—,
(viii) —$NR^8C(O)NR^9$—,
(ix) —$NR^{10}C(O)O$—, (x) —NR¹¹C(S)NR¹²—,
(xi) —NR¹³—, or

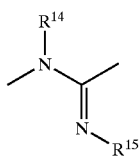
(xii)

with the proviso that the linkage of the right side of each group represented by $A^1$ binds to $A^2$, wherein $R^3, R^4, R^5, R^6, R^7, R^8, R^9, R^{10}, R^{11}, R^{12}, R^{13}, R^{14}$ and $R^{15}$ each, independently, is a hydrogen atom, C1–4 alkyl, phenyl or C1–4 alkyl substituted by phenyl, $A^2$ is
(i) C1–8 alkylene,
(ii) C2–8 alkenylene,
(iii) $Cyc^1$,
(iv) —(C1–4 alkylene)—O—(C1–4 alkylene)—,
(v) —(C1–4 alkylene)—S—(C1–4 alkylene)—,
(vi) —(C1–4 alkylene)—NR¹⁶—(C1–4 alkylene)—,
(vii) —($Cyc^1$)—(C1–8 alkylene)—,
(viii) —(C1–8 alkylene)—($Cyc^1$)—, or
(ix) —(C1–4 alkylene)—($Cyc^1$)—(C1–4 alkylene), $R^{16}$ is a hydrogen atom, C1–8 alkyl, C1–8 alkoxycarbonyl, phenyl or C1–8 alkyl substituted by phenyl, $Cyc^1$ is
(i) a 3–10 membered mono-cyclic or bi-cyclic carbocyclic ring, or
(ii) a 3–10 membered mono-cyclic or bi-cyclic hetero ring containing 1–4 nitrogen atoms, 1–2 oxygen atoms and/or one sulfur atom, $A^3$ is
(i) a hydrogen atom,
(ii) —NR¹⁷R¹⁸,
(iii) $Cyc^2$,
(iv) —OR¹⁹,
(v) —COOR²⁰,
(vi) —CONR²¹R²²,
(vii) C≡N,
(viii) a halogen atom,

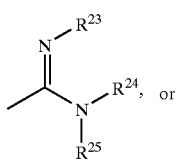
(ix)

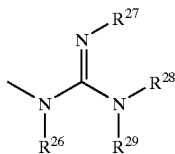
(x)

$R^{17}, R^{21}$ and $R^{22}$ each, independently, is
(i) a hydrogen atom,
(ii) C1–8 alkyl,
(iii) C2–8 alkenyl,
(iv) C2–8 alkynyl,
(v) $Cyc^3$,
(vi) C1–8 alkoxy, (vii) C2–8 alkenyloxy,
(viii) C2–8 alkynyloxy, or
(ix) C1–8 alkyl substituted by $Cyc^3$, C1–8 alkoxy, 1–8 alkylthio, CN, hydroxy or 1–3 of halogen atom, $R^{18}$ is
(i) a hydrogen atom,
(ii) C1–8 alkyl,
(iii) C2–8 alkenyl,
(iv) C2–8 alkynyl,
(v) C1–8 alkoxycarbonyl,
(vi) C2–8 acyl,
(vii) C3–8 cycloalkyl,
(viii) C1–8 alkoxycarbonyl substituted by $Cyc^3$ or 1–3 of halogen atom, or
(ix) C1–8 alkyl substituted by C1–8 alkoxy, $R^{19}$ and $R^{20}$ each, independently, is a hydrogen atom or C1–8 alkyl, $R^{23}, R^{24}, R^{25}, R^{26}, R^{27}, R^{28}$ and $R^{29}$ each, independently, is a hydrogen atom, C1–4 alkyl, C1–8 alkoxycarbonyl, phenyl, or C1–4 alkyl substituted by phenyl, $Cyc^2$ is a 3–10 membered mono-cyclic or bi-cyclic hetero ring containing 1–4 nitrogen atoms, 1–2 oxygen atoms and/or one sulfur atom, $Cyc^3$ is
(i) a 3–10 membered mono-cyclic or bi-cyclic carbocyclic ring, or
(ii) a 3–10 membered mono-cyclic or bi-cyclic hetero ring containing 1–4 nitrogen atoms, 1–2 oxygen atoms and/or one sulfur atom, the above-mentioned $Cyc^1$, $Cyc^2$ and $Cyc^3$ each, independently, may be optionally substituted by 1–3 of substituents selected from the following (i)–(vii):
(i) C1–8 alkyl,
(ii) C2–8 alkenyl,
(iii) C2–8 alkynyl,
(iv) C1–8 alkoxy,
(v) C1–8 alkoxycarbonyl,
(vi) oxo, or
(vii) C1–8 alkyl substituted by C1–8 alkoxy;

$R^2$ is a hydrogen atom, a halogen atom, nitro, hydroxy, —NR³⁰R³¹, C1–8 alkyl, C1~8 alkoxy, or C1–8 alkyl or C1–8 alkoxy substituted by 1–3 of halogen atoms, $R^{30}$ and $R^{31}$ each, independently, is a hydrogen atom, C1–4 alkyl, C1–8 alkoxycarbonyl, phenyl, C1–4 alkyl substituted by phenyl, with the proviso that, $R^1$ is not dimethylamino,
or a non-toxic salts as active ingredient.

(2) A 2H-phthalazin-1-one derivatives of the formula (Ia)

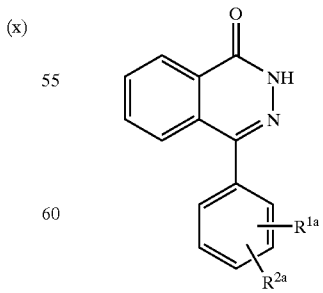
(Ia)

wherein $R^{1a}$ is
(i) C1–4 alkyl substituted by hydroxy or amino, or
(ii) —$A^{1a}$—$A^{2a}$—$A^{3a}$, in which $A^{1a}$ is
- (i) —$NR^{3a}C(O)$—,
- (ii) —$NR^{4a}C(S)$—,
- (iii) —$NR^{5a}SO_2$—,
- (iv) $CH_2$—$NR^{6a}$—,
- (v) —$CH_2$—O—,
- (vi) —$OC(O)$—,
- (vii) —$CH_2$—$NR^{7a}C(O)$—,
- (viii) —$NR^{8a}C(O)NR^{9a}$—,
- (ix) —$NR^{10a}C(O)O$—,
- (x) —$NR^{11a}C(S)NR^{12a}$—,
- (xi) —$NR^{13a}$—, or

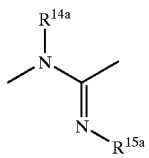 (xii)

with the proviso that the linkage of the right side of each group represented by $A^{1a}$ binds to $A^{2a}$, wherein $R^{3a}$, $R^{4a}$, $R^{5a}$, $R^{6a}$, $R^{7a}$, $R^{8a}$, $R^{9a}$, $R^{10a}$, $R^{11a}$, $R^{12a}$, $R^{13a}$, $R^{14a}$ and $R^{15a}$ each independently, is a hydrogen atom, C1–4 alkyl, phenyl or C1–4 alkyl substituted by phenyl, $A^{2a}$ is
- (i) C1–8 alkylene,
- (ii) C2–8 alkenylene,
- (iii) $Cyc^{1a}$,
- (iv) —(C1–4 alkylene)—O—(C1–4 alkylene)—,
- (v) —(C1–4 alkylene)—S—(C1–4 alkylene)—,
- (vi) —(C1–4 alkylene)-$NR^{16a}$—(C1–4 alkylene)—,
- (vii) —($Cyc^{1a}$)—(C1–8 alkylene)—,
- (viii) —(C1–8 alkylene)—($Cyc^{1a}$)—, or
- (ix) —(C1–4 alkylene)—($Cyc^{1a}$)—(C1–4 alkylene), $R^{16a}$ is a hydrogen atom, C1–8 alkyl, C1–8 alkoxycarbonyl, phenyl or C1–8 alkyl substituted by phenyl, $Cyc^{1a}$ is
- (i) a 3–10 membered mono-cyclic or bi-cyclic carbocyclic ring, or
- (ii) a 3–10 membered mono-cyclic or bi-cyclic hetero ring containing 1–4 nitrogen atoms, 1–2 oxygen atoms and/or one sulfur atom, $A^{3a}$ is
- (i) a hydrogen atom,
- (ii) $NR^{17a}R^{18a}$,
- (iii) $Cyc^{2a}$,
- (iv) —$OR^{19a}$,
- (v) —$COOR^{20a}$,
- (vi) —$CONR^{21a}R^{22a}$,
- (vii) C≡N,
- (viii) a halogen atom,

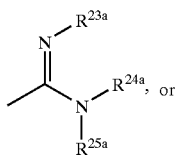 (ix)

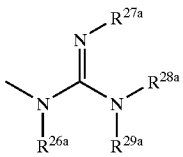 (x)

$R^{17a}$, $R^{21a}$ and $R^{22a}$ each, independently, is
- (i) a hydrogen atom,
- (ii) C1–8 alkyl,
- (iii) C2–8 alkenyl,
- (iv) C2–8 alkynyl,
- (v) $Cyc^{3a}$,
- (vi) C1–8 alkoxy,
- (vii) C2–8 alkenyloxy,
- (viii) C2–8 alkynyloxy, or
- (ix) C1–8 alkyl substituted by $Cyc^{3a}$, C1–8 alkoxy, C1–8 alkylthio, CN, hydroxy or 1–3 of halogen atom, $R^{18a}$ is
- (i) a hydrogen atom,
- (ii) C1–8 alkyl,
- (iii) C2–8 alkenyl,
- (iv) C2–8 alkynyl,
- (v) C1–8 alkoxycarbonyl,
- (vi) C2–8 acyl,
- (vii) C3–8 cycloalkyl,
- (viii) C1–8 alkoxycarbonyl substituted by $Cyc^{3a}$ or 1–3 of halogen atom, or
- (ix) C1–8 alkyl substituted by C1–8 alkoxy, $R^{19a}$ and $R^{20a}$ each, independently, is a hydrogen atom or C1–8 alkyl, $R^{23a}$, $R^{24a}$, $R^{25a}$, $R^{26a}$, $R^{27a}$, $R^{28a}$ and $R^{29a}$ each, independently, is a hydrogen atom, C1–4 alkyl, C1–8 alkoxycarbonyl, phenyl, or C1–4 alkyl substituted by phenyl, $Cyc^{2a}$ is a 3–10 membered mono-cyclic or bi-cyclic hetero ring containing 1–4 nitrogen atoms, 1–2 oxygen atoms and/or one sulfur atom, $Cyc^{3a}$ is
- (i) a 3–10 membered mono-cyclic or bi-cyclic carbocyclic ring, or
- (ii) a 3–10 membered mono-cyclic or bi-cyclic hetero ring containing 1–4 nitrogen atoms, 1–2 oxygen atoms and/or one sulfur atom, the above-mentioned $Cyc^{1a}$, $Cyc^{2a}$ and $Cyc^{3a}$ each, independently, may be optionally substituted by 1–3 of substituents selected from the following (i)–(vii):
- (i) C1–8 alkyl,
- (ii) C2–8 alkenyl,
- (iii) C2–8 alkynyl,
- (iv) C1–8 alkoxy,
- (v) C1–8 alkoxycarbonyl,
- (vi) oxo, or
- (vii) C1–8 alkyl substituted by C1–8 alkoxy;

$R^{2a}$ is a hydrogen atom, a halogen atom, nitro, hydroxy, —$NR^{30a}R^{31a}$, C1–8 alkyl C1–8 alkoxy, or C1–8 alkyl or C1–8 alkoxy substituted by 1–3 of halogen atoms, $R^{30a}$ and $R^{31a}$ each, independently, is a hydrogen atom, C1–4 alkyl, C1–8 alkoxycarbonyl, phenyl, C1–4 alkyl substituted by phenyl, with the proviso that, $R^{1a}$ is not dimethylamino, 4-(2-acetyloxyphenyl)-2H-phthalazin-1-one is excluded], or a non-toxic salt thereof.

(3) A compound of the formula (Ia) described in the above-mentioned (2),
in which $R^1$ has the same meaning as hereinbefore (2),
$R^{16a}$ is a hydrogen atom, C1–4 alkyl, C1–8 alkoxycarbonyl, phenyl, or C1–4 alkyl substituted by phenyl,
$Cyc^{1a}$ is
(i) a 3–10 membered mono-cyclic or bi-cyclic carbocyclic ring, or
(ii) a 3–10 membered mono-cyclic or bi-cyclic hetero ring containing 1–4 nitrogen atoms, one oxygen atoms and/or one sulfur atom, and $Cyc^{1a}$ may be substituted by C1–8 alkoxycarbonyl,
$A^{3a}$ is
(i) a hydrogen atom,
(ii) —$NR^{17a}R^{18a}$,
(iii) $Cyc^{2a}$,
(iv) —$OR^{19a}$,
(v) —$COOR^{20a}$,
(vi) —$CONR^{21a}R^{22a}$,

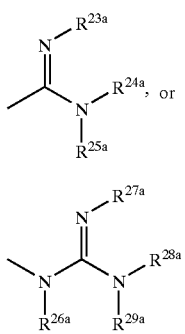

$R^{17a}$, $R^{21a}$ and $R^{22a}$ each, independently, is a hydrogen atom, C1–4 alkyl, phenyl, or C1–4 alkyl substituted by phenyl,
$R^{18a}$ is a hydrogen atom, C1–4 alkyl, C1–8 alkoxycarbonyl, C2–5 acyl, or C1–4 alkoxycarbonyl substituted by phenyl,
$R^{19a}$ and $R^{20a}$ each, independently, is a hydrogen atom or C1–4 alkyl,
$Cyc^{2a}$ is a 3–10 membered mono-cyclic or bi-cyclic hetero ring containing 1–4 nitrogen atoms, one oxygen atoms and/or one sulfur atom, substituted by C1–8 alkoxycarbonyl,
$R^{2a}$ is a hydrogen atom, a halogen atom, nitro, or $NR^{30a}R^{31a}$.
(4) A compound of the formula (Ia) described in the above-mentioned (2)
wherein
$R^{1a}$ is —$A^{1a}$—$A^{2a}$—$A^{3a}$,
$A^{1a}$ and $A^{2a}$ is the same meaning as hereinbefore (2),
$A^{3a}$ is (ii) —$NR^{17a}R^{18a}$, (iii) $Cyc^{2a}$, (vii) —C≡N, or (viii) a halogen atom, with the
proviso that, when $A^{3a}$ is $NR^{17a}R^{18a}$, then $R^{17a}$ represents the groups except a hydrogen atom, C1–4 alkyl, phenyl, or C1–4 alkyl substituted by phenyl in the above-mentioned (2), $Cyc^{2a}$ is a 3–10 membered mono-cyclic or bi-cyclic hetero ring containing 1–4 nitrogen atoms, 1–2 oxygen atoms and/or one sulfur atom, substituted by 1–3 of substituent selected from C1–8 alkyl, C2–8 alkenyl, C2–8 alkynyl, C1–8 alkoxy, oxo, or C1–8 alkyl substituted by C1–8 alkoxy (with the proviso that when the substituent is selected from C1–8 alkyl, C1–8 alkoxy, or C1–8 alkyl substituted by C1–8 alkoxy, then the number of the substituent is 2 or 3).
(5) A compound of the formula (Ia) described in above-mentioned (2)
wherein,
$R^{2a}$ is hydroxy, C1–8 alkyl, C1–8 alkoxy, or
C1–8 alkyl or C1–8 alkoxy substituted by 1–3 of halogen, and
(6) The process for the preparation of the novel 2H-phthalazin-1-one derivatives of the formula (Ia), or a non-toxic salts thereof.

DETAILED DESCRIPTION OF THE INVENTION

Unless othewise specified, all isomers are included in the present invention.

For example, alkyl, alkenyl, alkynyl, alkoxy, alkylthio, alkylene, alkenylene and alkynylene include straight and branched isomers.

Isomers in the double bonds, rings, fused rings (E, Z, cis, trans isomers), isomers generated by the existence of asymmetric carbon atom(s) (R, S isome, α,β isomers, enantiomers, diastereomers), optically active isomers having optically rotatory power (D, L, d, l isomers), polar isomers separated by chromatography (more polar, less polar isomers), equilibrium compounds, arbitrary, ratios of these compounds, racemic mixtures are all included in the present invention.

Optically active isomers of formula (I) and (Ia) may be obtained by general methods of optically separation (for example, separation by gas chromatography or high performance liquid chromatography, separation by crystallization as diastereomeric salts or clathrates, separation by prior crystallization etc.) or may be prepared by general methods of asymmetric synthesis.

In the present invention, C1–4 alkyl means methyl, ethyl, propyl, butyl and isomers thereof.

C1–8 alkyl means methyl, ethyl, propyl, butyl, pentyl, hexyl, heptyl, octyl and isomers thereof.

C2–8 alkenyl means ethenyl, propenyl, butenyl, pentenyl, hexenyl, eptenyl, octenyl and isomers thereof.

C2–8 alkynyl means ethynyl, propynyl, butynyl, pentynyl, hexynyl, heptynyl, octynyl and isomers thereof.

C1–4 alkylene means methylene, ethylene, trimethylene, tetramethylene and isomers thereof.

C1–8 alkylene means methylene, ethylene, trimethylene, tetramethylene, pentamethylene, hexamethylene, heptamethylene, octamethylene and isomers thereof.

C2–8 alkenylene means ethenylene, propenylene, butenylene, pentenylene, hexenylene, heptenylene, octenylene and isomers thereof.

C1–8 alkoxy means methoxy, ethoxy, propoxy, butoxy, pentyloxy, hexyloxy, heptyloxy, octyloxy and isomers thereof.

C2–8 alkenyloxy means ethenyloxy, propenyloxy, butenyloxy, pentenyloxy, hexenyloxy, heptenyloxy, octenyloxy and isomers thereof.

C2–8 alkynyloxy means ethynyloxy, propynyloxy, butynyloxy, pentynyloxy, hexynyloxy, heptynyloxy, octynyloxy and isomers thereof.

C1–8 alkoxycarbonyl means methoxycarbonyl, ethoxycarbonyl, propoxycarbonyl, butoxycarbonyl, pentyloxycarbonyl, hexyloxycarbonyl, heptyloxycarbonyl, octyloxycarbonyl and isomers thereof.

C2–5 acyl means acetyl, propionyl, butyryl, valeryl and isomers thereof.

C2–8 acyl means acetyl, propionyl, butyryl, valery, hexanoyl, heptanoyl, octanoyl and isomers thereof.

C3–8 cycloalkyl means cyclopropyl, cyclobutyl, cyclopentyl, cyclohexyl, cycloheptyl and cyclooctyl.

C1–8 alkylthio means methylthio, ethylthio, propylthio, butylthio, pentylthio, hexylthio, heptylthio, octylthio and isomers thereof.

C3–10 membered mono- or bicarbocyclic ring means, for example, (1) C3–10 cycloalkyl, cycloalkenyl, cycloalkanediene and cycloalkanetriene, such as cyclopropane, cyclobutane, cyclopentane, cyclohexane, cycloheptane, cyclooctane, cyclononane, cyclodecane, cyclopentene, cyclohexene, cyclooctene, cyclononene, cyclodecene, cyclopentadiene, cyclohexadiene, cycloheptadiene, cyclooctadiene, cyclononadiene, cyclodecadiene, cycloheptatriene, cyclooctatriene, cyclononatriene, cyclodecatriene, (2) C6–10 aromatic carbocyclic ring such as benzene, pentalene, indan, indene, naphthalene, azulene, (3) perhydropentalene, perhydroindene, dihydronaphthalene, tetrahydronaphthalene, perhydronaphthalene, perhydroazulene, etc.

a 3–10 membered mono-cyclic or bi-cyclic hetero ring containing 1–4 nitrogen atoms, 1–2 oxygen atoms and/or one sulfur atom includes a 3–10 membered mono-cyclic or bi-cyclic hetero aryl, partially saturated or fully saturated hetero aryl containing 1-4 nitrogen atoms, 1–2 oxygen atoms and/or one sulfur atom.

Above-mentioned 3–10 membered mono-cyclic or bi-cyclic hetero aryl ring containing 1–4 nitrogen atoms, 1–2 oxygen atoms and/or one sulfur atom means, for example, pyrrole, imidazole, triazole, tetrazole, pyrazole, pyridine, pyrazine, pyrimidine, pyridazine, azepine, diazepine, furan, pyran, oxepin, oxazepine, thiophene, thiin (thiopyran), thiepin, oxazole, isoxazole, thiazole, isothiazole, oxadiazole, oxazine, oxadiazine,oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzimidazole, carbazole, acridine, etc.

Above-mentioned 3–10 membered mono-cyclic or bi-cyclic partially saturated or fully saturated hetero aryl containing 1–4 nitrogen atoms, 1–2 oxygen atoms and/or one sulfur atom means, for example, pyrroline, pyrrolidine, imidazoline, imidazolidine, triazoline, triazolidine, tetraazoline, tetraazolidine, dihydropyridine, dihydropyrazine, dihydropyrimidine, dihydropyridazine, piperidine, tetrahydropyridine, piperazine, tetrahydropyrimidine, tetrahydropyridazine, dihydrofuran, tetrahydrofuran, dihydropyran, tetrahydropyran, dihydrothiophene, tetrahydrothiophene, dihydrothiine (dihydrothiopyran), tetrahydrothiine (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothi ophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, benzoxazepine, benzoxadiazepine, benzothiazepine, benzoth iadiazepine, benzazepine, benzodiazepine, indoloxazepine, indolotetrahydrooxazepine, indolooxadiazepine, indolotetrahydrooxadiazepine, indolothiazepine, indolotetrahydrothiazepine, indolothiadiazepine, indolotetrahydrothiadiazepine, indoloazepine, indolotetrahydroazepine, indolodiazepine, indolotetrahydrodiazepine, benzofurazan, benzothiadiazole, benzotriazole, camphor, imidazothiazole, dihydrocarbazole, tetrahydrocarbazole, perhydrocarbazole, dihydroacridine, tetrahydroacridine, perhydroacridine, 1,3-dioxoindane, 1,4-benzodioxane, quinuclidine, aziridine, dioxane, oxirane, thioxirane, azetidine, oxetane, thioxetane, etc.

Above-mentioned 3–7 membered mono-cyclic hetero ring containing 1–2 nitrogen atoms and/or one oxygen atom means, for example, aziridine, azetidine, pyrrole, pyrroline, pyrrolidine, piperidine, pyridine, dihydropyridine, tetrahydropyridine, azepine, dihydroazepine, tetrahydroazepine, perhydroazepine, oxirane, oxetane, fu ran, dihydrofu ran, tetrahydrofuran, pyran, dihydropyran, tetrahydropyran, oxepi n, dihydrooxepin, tetrahydrooxepin, perhydrooxepin, imidazole, imidazoline, imidazolidine, pyrazole, pyrazoline, piperazine, dehydropiperadine, pyrimidine, dihydropyrimidine, tetrahydropyrimidine, pyrazine, dihydropyrazine, tetrahydropyrazine, pyridazine, dihydropyridazine, tetrahydropyridazine, diazepine, dihydrodiazepine, tetrahydrodiazepine, perhydrodiazepine, morpholine, oxazole, isoxazole, oxazine, dihydrooxazole, tetrahydrooxazole, dihydroisoxazole, tetrahydroisoxazole, oxazepine, dihydrooxazepine, tetrahydrooxazepine, perhydrooxazepine, oxadiazole, dihydrooxadiazole, perhydrooxadiazole, isoxadiazole, dihydroisoxadiazole, perhydroisoxadiazole, oxadiazine dihydrooxadiazine, perhydrooxadiazine, oxadiazepine, dihydrooxadiazepine, tetrahydrooxadiazepine, perhydrooxadiazepine, etc.

A halogen atom is chlorine, bromine, fluorine or iodine.

In the compound of formula (I), $R^1$ is preferably —$A^1$—$A^2$—$A^3$.

$A^1$ is preferably —$NR^3C(O)$—, —$NR^4C(S)$—, —$NR^5SO_2$—, —$NR^8C(O)NR^9$— or —$NR^{10}C(O)O$—, more preferably —$NR^3C(O)$ or —$NR^5SO_2$—, even more preferably —$NR^3C(O)$—, and most preferably —NHC(O)—.

$A^2$ is preferably C1–8 alkylene, C2–8 alkenylene, —(C1–4 alkylene)—O—(C1–4 alkylene)—, —(C1–4 alkylene)—S—(C1–4 alkylene)—, —(C1–4 alkylene)—NR$^{16}$—(C1–4 alkylene)— or —(C1–8 alkylene)—(Cyc$^1$)—, more preferably C1–8 alkylene, C1–4 alkylene)—O—(C1–4 alkylene)—, —(C1–4 alkylene)—S—(C1–4 alkylene)— or —(C1–8 alkylene)—(Cyc$^1$)—, and most preferably C3–4 alkylene.

A$^3$ is preferably OR$^{19}$, NR$^{17}$R$^{18}$ or Cyc$^2$, and more preferably Cyc$^2$.

Cyc$^1$ and Cyc$^2$ are preferably 3–7 membered mono-cyclic hetero ring containing 1–2 nitrogen atoms and/or one oxygen atom, for example, pyridine, pyrrole, pyrazine, pyrimidine, pyridazine, azepine, pyrroline, pyrrolidine, imidazoline, imidazolidine, dihydropyridine, dihydropyrazine, dihydropyrimidine, dihydropyridazine, piperidine, tetrahydropyridine, piperazine, tetrahydropyrimidine, tetrahydropyridazine, dihydrofuran, tetrahydrofuran, dihydropyran, tetrahydropyran, dihydrooxazole, tetrahydrooxazole, dihydroisoxazole, tetrahydroisoxazole, dihydroazepine, tetrahydroazepine, perhydroazepine, hexahydropyrimidine, morpholine, etc.

Cyc$^1$ is preferably 3–7 membered mono-cyclic hetero ring containing 1–2 nitrogen atoms, for example, pyridine, pyrrole, pyrazine, pyrimidine, pyridazine, azepine, pyrroline, pyrrolidine, imidazoline, imidazolidine, dihydropyridine, dihydropyrazine, dihydropyrimidine, dihydropyridazine, piperidine, tetrahydropyridine, piperazine, tetrahydropyrimidine, tetrahydropyridazine, dihydroazepine, tetrahydroazepine, perhydroazepine, hexahydropyrimidine, etc.

Cyc$^2$ is preferably 3–7 membered mono-cyclic hetero ring containing one nitrogen atom and one oxygen atom, for example, dihydrooxazole, tetrahydrooxazole, dihydroisoxazole, tetrahydroisoxazole, morpholine, etc., and most preferably morpholine.

Cyc$^3$ is preferably C3–10 membered mono-carbocyclic ring or 3–7 membered mono-cyclic hetero ring containing 1–2 nitorogen atoms and/or one oxygen atom, for example, C3–10 cycloalkyl, cycloalkenyl, cycloalkanediene and cycloalkanetriene such as cyclopropane, cyclobutane, cyclopentane, cyclohexane, cycloheptane, cyclooctane, cyclononane, cyclodecane, cyclopentene, cyclohexene, cyclooctene, cyclononene, cyclodecene, cyclopentadiene, cyclohexadiene, cycloheptadiene, cyclooctadiene, cyclononadiene, cyclodecadiene, cycloheptatriene, cyclooctatriene, cyclononatriene, cyclodecatriene, benzene, pyridine, pyrrole, pyrazine, pyrimidine, pyridazine, azepine, pyrroline, pyrrolidine, imidazoline, imidazolidine, dihydropyridine, dihydropyrazine, dihydropyrimidine, dihydropyridazine, piperidine, tetrahydropyridine, piperazine, tetrahydropyrimidine, tetrahydropyridazine, dihydrofuran, tetrahydrofuran, dihydropyran, tetrahydropyran, dihydrooxazole, tetrahydrooxazole, dihydroisoxazole, tetrahydroisoxazole, dihydroazepine, tetrahydroazepine, perhydroazepine, hexahydropyrimidine, morpholine, etc.

In the compound of formula (I), R$^2$ is preferably a hydrogen atom, a halogen atom, nitro, NR$^{30}$R$^{31}$ or trifluoromethyl, more preferably a hydrogen atom, a halogen atom or trifluoromethyl, and most preferably a hydrogen atom.

In the compound of formula (I), R$^{1a}$ is preferably —A$^{1a}$—A$^{2a}$—A$^{3a}$.

A$^{1a}$ is preferably —NR$^{3a}$C(O)—, —NR$^{4a}$C(S), —NR$^{5a}$SO$_2$, NR$^{8a}$C(O)NR$^{9a}$— or —NR$^{10a}$C(O)O—, more preferably —NR$^{3a}$C(O)— or —NR$^{5a}$SO2—, even more preferably —NR$^{3a}$C(O)—, and most preferably —NHC(O)—.

A$^{2a}$ is preferably C1–8 alkylene, C2–8 alkenylene, —(C1–4 alkylene)—O—(C1–4 alkylene)—, —(C1–4 alkylene)—S—(C1–4 alkylene)—, —(C1–4 alkylene)—NR$^{16a}$—(C1–4 alkylene)— or or —(C1–8 alkylene)—(Cyc$^{1a}$)—, more preferably C1–8 alkylene, —(C1–4 alkylene)—O—(C1–4 alkylene)—, —(C1–4 alkylene)—S—(C1–4 alkylene)— or —(C1–8 alkylene)—(Cyc$^{1a}$)—, and most preferably C3–4 alkylene.

A$^{3a}$ is preferably OR$^{19a}$, NR$^{17a}$R$^{18a}$ or Cyc$^{2a}$, and more preferably Cyc$^2$.

Cyc$^{1a}$ and Cyc$^{2a}$ is preferably 3–7 membered mono-cyclic hetero ring containing 1–2 nitrogen atoms and/or one oxygen atom, for example, pyridine, pyrrole, pyrazine, pyrimidine, pyridazine, azepine, pyrroline, pyrrolidine, imidazoline, imidazolidine, dihydropyridine, dihydropyrazine, dihydropyrimidine, dihydropyridazine, piperidine, tetrahydropyridine, piperazine, tetrahydropyrimidine, tetrahydropyridazine, dihydrofuran, tetrahydrofuran, dihydropyran, tetrahydropyran, dihydrooxazole, tetrahydrooxazole, dihydroisoxazole, tetrahydroisoxazole, dihydroazepine, tetrahydroazepine, perhydroazepine, hexahydropyrimidine, morpholine, etc.

Cyc$^{1a}$ is preferably 3–7 membered mono-cyclic hetero ring containing 1–2 nitrogen atoms, for example, pyridine, pyrrole, pyrazine, pyrimidine, pyridazine, zepine, pyrroline, pyrrolidine, imidazoline, imidazolidine, dihydropyridine, dihydropyrazine, dihydropyrimidine, dihydropyridazine, piperidine, tetrahydropyridine, piperazine, tetrahydropyrimidine, tetrahydropyridazine, dihydroazepine, tetrahydroazepine, perhydroazepine, hexahydropyrimidine, etc.

Cyc$^{2a}$ is preferably 3–7 membered mono-cyclic hetero ring containing one nitrogen atom and one oxygen atom, for example, dihydrooxazole, tetrahydrooxazole, dihydroisoxazole, tetrahydroisoxazole, morp holine, etc., and most preferably morpholine.

Cyc$^{3a}$ is preferably C3–10 mono-carbocyclic ring or mono-cyclic hetero ring containing 1–2 nitrogen atoms and/or one oxygen atom, for example, C3–10 cycloalkyl, cycloalkenyl, cycloalkanediene and cycloalkanetriene such as cyclopropane, cyclobutane, cyclopentane, cyclohexane, cycloheptane, cyclooctane, cyclononane, cyclodecane, cyclopentene, cyclohexene, cyclooctene, cyclononene, cyclodecene, cyclopentadiene, cyclohexadiene, cycloheptadiene, cyclooctadiene, cyclononadiene, cyclodecadiene, cycloheptatriene, cyclooctatriene, cyclononatriene, cyclodecatriene, benzene, pyridine, pyrrole, pyrazine, pyrimidine, pyridazine, azepine, pyrroline, pyrrolidine, imidazoline, imidazolidine, dihydropyridine, dihydropyrazine, dihydropyrimidine, dihydropyridazine, piperidine, tetrahydropyridine, piperazine, tetrahydropyrimidine, tetrahydropyridazine, dihydrofuran, tetrahydrofuran, dihydropyran, tetrahydropyran, dihydrooxazole, tetrahydrooxazole, dihydroisoxazole, tetrahydroisoxazole, dihydroazepine, tetrahydroazepine, perhydroazepine, hexahydropyrimidine, morpholine, etc.

In the compound of formula (I), $R^{2a}$ is preferably a hydrogen atom, a halogen atom, nitro, $NR^{30a}R^{31a}$ or trifluoromethyl, more preferably a hydrogen atom, a halogen atom or trifluoromethyl, and most preferably a hydrogen atom.

Salt

Non-toxic salts of the present invention include all pharmaceutically acceptable salts, for example, general salts, acid addition salts, hydrate salts.

The compounds of formulae (I) and (Ia) of the present invention may be converted into the corresponding salts by conventional method. Non-toxic and water-soluble salts are preferred. Suitable salts, for example, include:

salts of alkali metals (e.g. potassium, sodium, etc.), salts of alkaline earth metals (e.g. calcium, magnesium, etc.), ammonium salts, salts of pharmaceutically acceptable organic amines (e.g. tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine, etc.).

The compounds of formulae (I) and (Ia) of the present invention may be converted into the corresponding acid addition salts by conventional method. Non-toxic and water-soluble salts are preferred. Suitable salts, for example, include:

salts of inorganic acid e.g. hydrochloride, hydrobromide, sulfate, phosphate, nitrate; or salts of organic acids e.g. acetate, trifluoroacetate, lactate, tartarate, oxalate, fumarate, maleate, citrate, benzoate, methanesulphonate, ethanesulphonate, benzenesulphonate, toluenesulphonate, isethionate, glucuronate, gluconate.

The compounds of formulae (I) and (Ia) of the present invention and salts thereof may be converted into the corresponding hydrates by conventional means.

In the compounds of the present invention of formula (I), the compound of the formula (I-A)

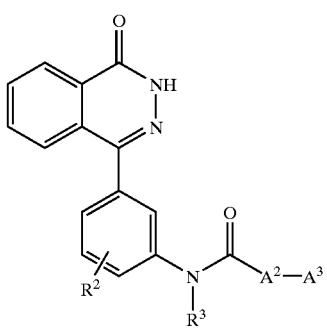

(I-A)

wherein all symbols are the same meaning as hereinbefore defined, the formula (I-B)

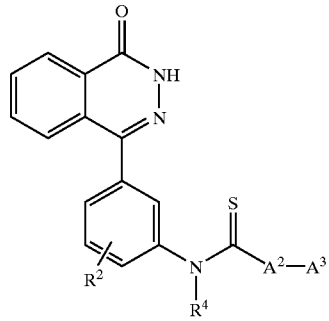

(I-B)

wherein all symbols are the same meaning as hereinbefore defined, the formula (I-C)

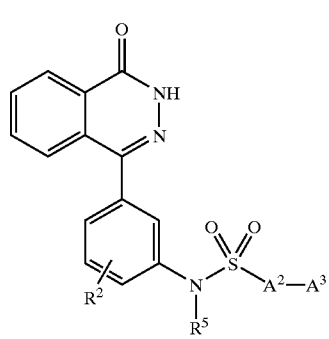

(I-C)

wherein all symbols are the same meaning as hereinbefore defined, the formula (I-D)

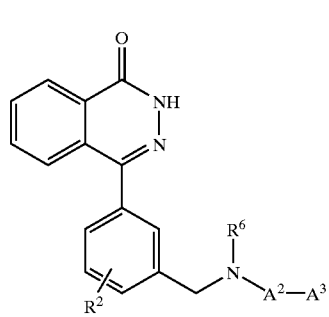

(I-D)

wherein all symbols are the same meaning as hereinbefore defined, the formula (I-E)

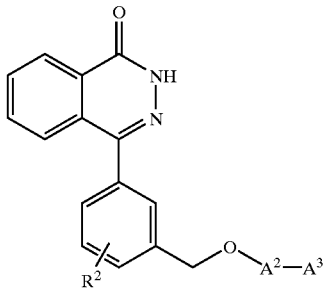
(I-E)

wherein all symbols are the same meaning as hereinbefore defined, the formula (I-F)

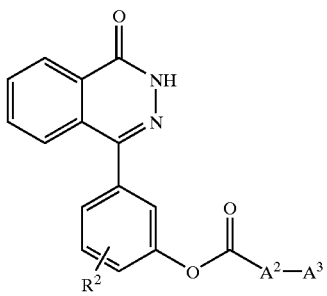
(I-F)

wherein all symbols are the same meaning as hereinbefore defined, the formula (I-G)

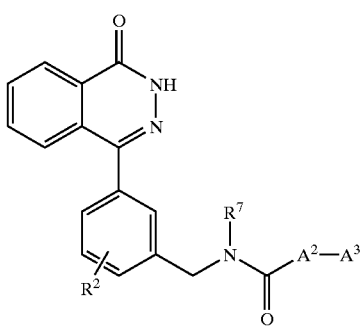
(I-G)

wherein all symbols are the same meaning as hereinbefore defined, the formula (I-H)

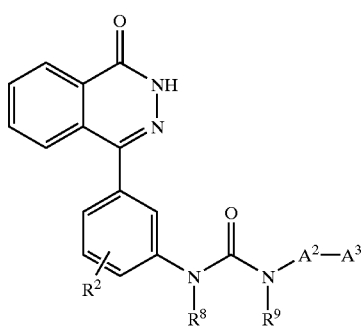
(I-H)

wherein all symbols are the same meaning as hereinbefore defined, the formula (I-J)

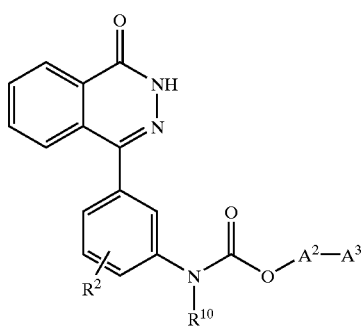
(I-J)

wherein all symbols are the same meaning as hereinbefore defined, the formula (I-K)

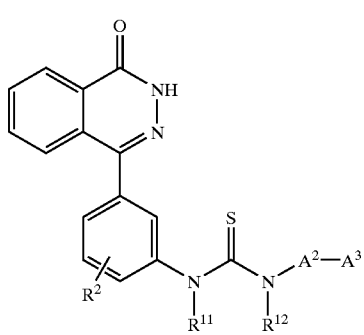
(I-K)

wherein all symbols are the same meaning as hereinbefore defined, the formula (I-M)

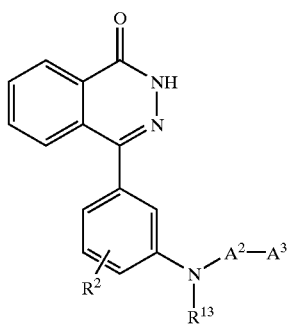

(I-M)

wherein all symbols are the same meaning as hereinbefore defined, or the formula (I-N)

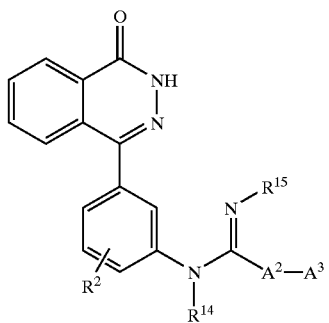

(I-N)

wherein all symbols are the same meaning as hereinbefore defined are preferably.

The preferred specific compounds are the compounds in following tables 1–27, the compounds described in the examples and non-toxic salts thereof.

In the following tables, Me is methyl group and the other symbols are the same meaning as hereinbefore defined.

TABLE 1

(I-A-1)

| No. | —A²—A³ |
|-----|--------|
| 1 | Me |
| 2 | ~CH₃ (ethyl chain) |
| 3 | ~CH₃ (propyl chain) |

TABLE 1-continued (I-A-1)

| No. | —A²—A³ |
|-----|--------|
| 4 | ~NH₂ |
| 5 | ~NH₂ |
| 6 | ~NH₂ |
| 7 | ~NHMe |
| 8 | ~NMe₂ |
| 9 | ~NH-CH₂CH₂-NH₂ |
| 10 | ~S-CH₂CH₂-NH₂ |
| 11 | ~O-CH₂CH₂-NH₂ |
| 12 | ~OH |
| 13 | ~CO₂H |
| 14 | ~CO₂Me |
| 15 | ~N-pyrrolidinyl |
| 16 | ~N-piperidinyl |
| 17 | ~N-morpholinyl |
| 18 | ~4-pyridyl |
| 19 | ~3-pyridyl |

TABLE 1-continued (I-A-1)

| No. | —A²—A³ |
|---|---|
| 20 | 3-aminophenyl-ethyl |
| 21 | 3-(aminomethyl)phenyl-methyl |
| 22 | 4-methylcyclohexylamine |
| 23 | pentanimidamide |
| 24 | N-propylguanidine |

TABLE 2

(I-B-1)

| No. | —A²—A³ |
|---|---|
| 1 | Me |
| 2 | –CH₂CH₂CH₂CH₃ (butyl with CH₃) |
| 3 | pentyl |
| 4 | butyl-NH₂ |
| 5 | pentyl-NH₂ |
| 6 | hexyl-NH₂ |
| 7 | pentyl-NHMe |
| 8 | pentyl-NMe₂ |
| 9 | EtNH-CH₂CH₂-NH₂ |
| 10 | EtS-CH₂CH₂-NH₂ |
| 11 | EtO-CH₂CH₂-NH₂ |
| 12 | pentyl-OH |
| 13 | butyl-CO₂H |
| 14 | butyl-CO₂Me |
| 15 | pentyl-pyrrolidinyl |
| 16 | pentyl-piperidinyl |
| 17 | pentyl-morpholinyl |
| 18 | 4-pyridyl-ethyl |
| 19 | 3-pyridyl-propyl |

TABLE 2-continued (I-B-1)

| No. | —A²—A³ |
|---|---|
| 20 | 3-aminophenyl-ethyl |
| 21 | 3-methylbenzylamine |
| 22 | 4-methylcyclohexylamine |
| 23 | pentanamidine |
| 24 | N-propylguanidine |

TABLE 3

(I-C-1)

| No. | —A²—A³ |
|---|---|
| 1 | Me |
| 2 | butyl-CH₃ |
| 3 | pentyl-CH₃ |
| 4 | butyl-NH₂ |
| 5 | pentyl-NH₂ |
| 6 | hexyl-NH₂ |
| 7 | pentyl-NHMe |
| 8 | pentyl-NMe₂ |
| 9 | N-ethyl-ethylenediamine |
| 10 | ethylthio-ethyl-NH₂ |
| 11 | ethoxy-ethyl-NH₂ |
| 12 | pentyl-OH |
| 13 | pentyl-CO₂H |
| 14 | pentyl-CO₂Me |
| 15 | pentyl-pyrrolidinyl |
| 16 | pentyl-piperidinyl |
| 17 | pentyl-morpholinyl |
| 18 | ethyl-4-pyridyl |
| 19 | propyl-3-pyridyl |

TABLE 3-continued (I-C-1)

| No. | —A²—A³ |
|---|---|
| 20 | 3-ethylaniline with NH₂ |
| 21 | 3-methylbenzylamine |
| 22 | 4-methylcyclohexylamine |
| 23 | pentanamidine |
| 24 | propylguanidine |

TABLE 4

(I-D-1)

| No. | —A²—A³ |
|---|---|
| 1 | Me |
| 2 | butyl-CH₃ |
| 3 | pentyl-CH₃ |
| 4 | butyl-NH₂ |

TABLE 4-continued (I-D-1)

| No. | —A²—A³ |
|---|---|
| 5 | pentyl-NH₂ |
| 6 | hexyl-NH₂ |
| 7 | pentyl-NHMe |
| 8 | pentyl-NMe₂ |
| 9 | Et-NH-CH₂CH₂-NH₂ |
| 10 | Et-S-CH₂CH₂-NH₂ |
| 11 | Et-O-CH₂CH₂-NH₂ |
| 12 | pentyl-OH |
| 13 | pentyl-CO₂H |
| 14 | pentyl-CO₂Me |
| 15 | pentyl-pyrrolidinyl |
| 16 | pentyl-piperidinyl |
| 17 | pentyl-morpholinyl |
| 18 | ethyl-4-pyridyl |
| 19 | propyl-3-pyridyl |

TABLE 4-continued
(I-D-1)
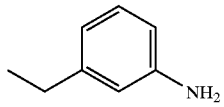
| No. | —A²—A³ |
|---|---|
| 20 | 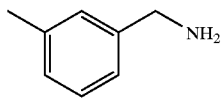 |
| 21 | 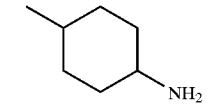 |
| 22 | 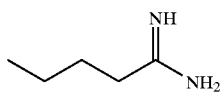 |
| 23 | 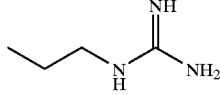 |
| 24 | 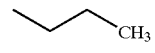 |
TABLE 5
(I-E-1)
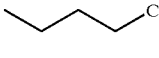
| No. | —A²—A³ |
|---|---|
| 1 | Me |
| 2 | 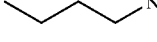 |
| 3 | 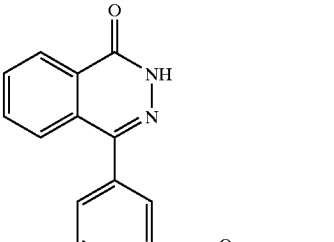 |
| 4 | 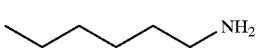 |
TABLE 5-continued
(I-E-1)
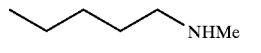
| No. | —A²—A³ |
|---|---|
| 5 | 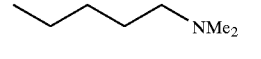 |
| 6 | 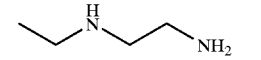 |
| 7 | 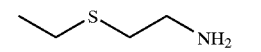 |
| 8 | 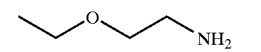 |
| 9 | 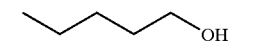 |
| 10 | 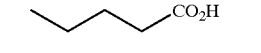 |
| 11 | 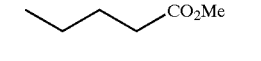 |
| 12 | 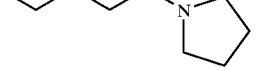 |
| 13 | 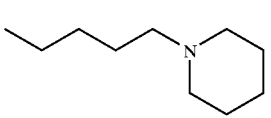 |
| 14 |  |
| 15 | 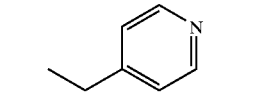 |
| 16 | 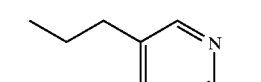 |
| 17 |  |
| 18 |  |
| 19 |  |

TABLE 5-continued
(I-E-1)
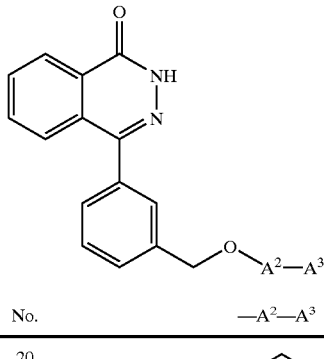
| No. | —A²—A³ |
|---|---|
| 20 | 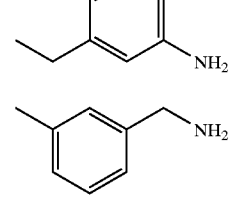 |
| 21 | 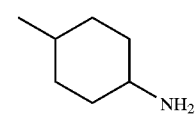 |
| 22 | 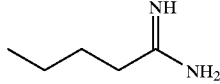 |
| 23 | 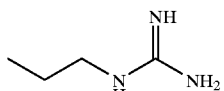 |
| 24 | 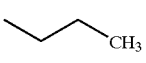 |
TABLE 6
(I-F-1)
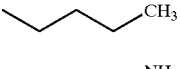
| No. | —A²—A³ |
|---|---|
| 1 | Me |
| 2 | 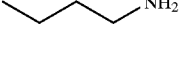 |
| 3 | 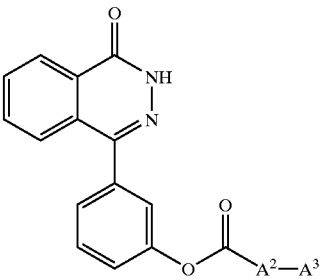 |
| 4 | 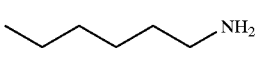 |
TABLE 6-continued
(I-F-1)
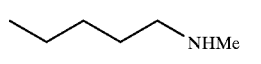
| No. | —A²—A³ |
|---|---|
| 5 | 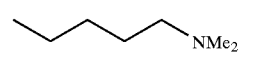 |
| 6 | 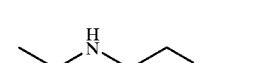 |
| 7 | 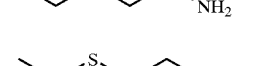 |
| 8 | 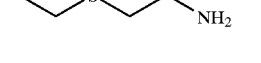 |
| 9 | 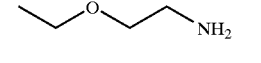 |
| 10 | 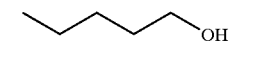 |
| 11 | 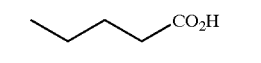 |
| 12 | 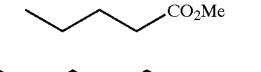 |
| 13 | 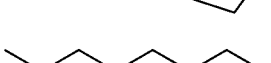 |
| 14 | 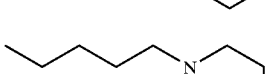 |
| 15 | 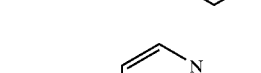 |
| 16 | 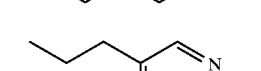 |
| 17 |  |
| 18 |  |
| 19 |  |

TABLE 6-continued

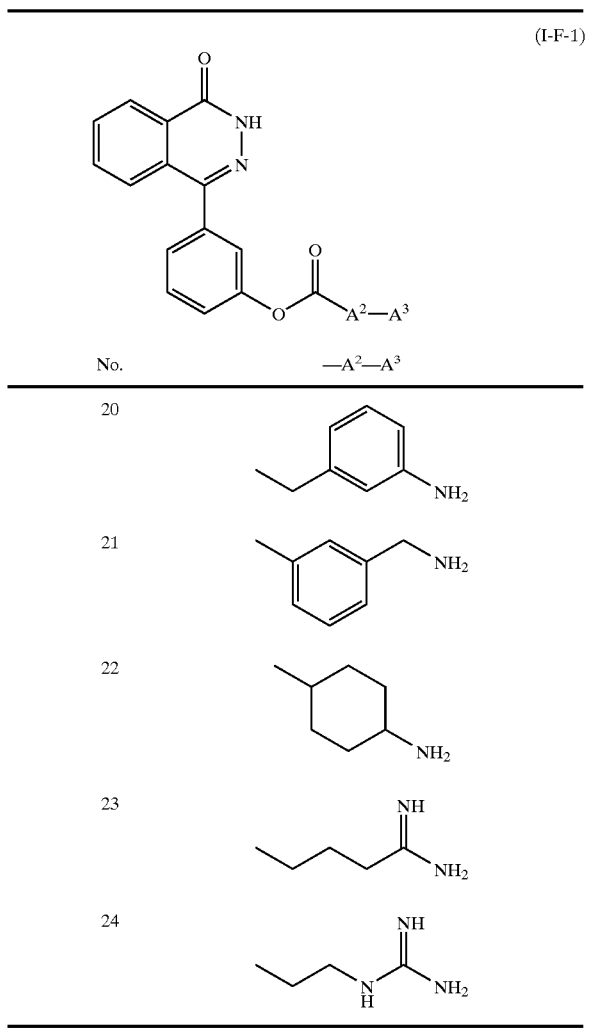

| No. | —A²—A³ |
|---|---|
| 20 | (3-aminophenyl-ethyl) |
| 21 | (3-aminomethyl-phenyl-methyl) |
| 22 | (4-aminocyclohexyl-methyl) |
| 23 | pentanamidine |
| 24 | propyl-guanidine |

TABLE 7

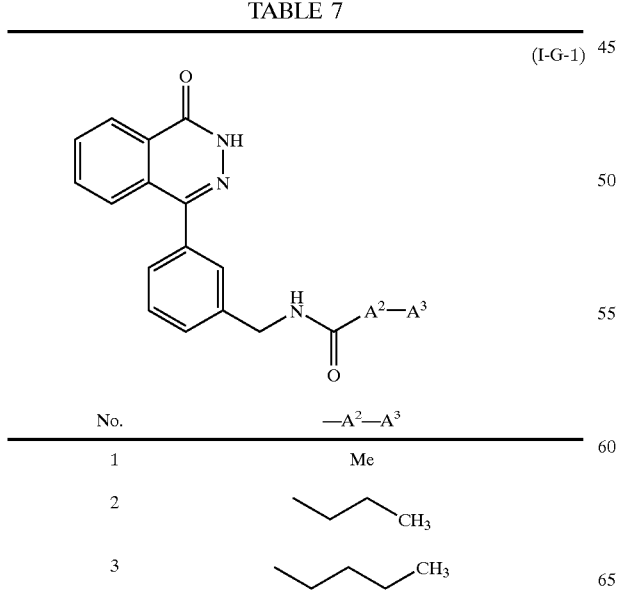

| No. | —A²—A³ |
|---|---|
| 1 | Me |
| 2 | CH₂CH₃ (butyl) |
| 3 | pentyl |

TABLE 7-continued

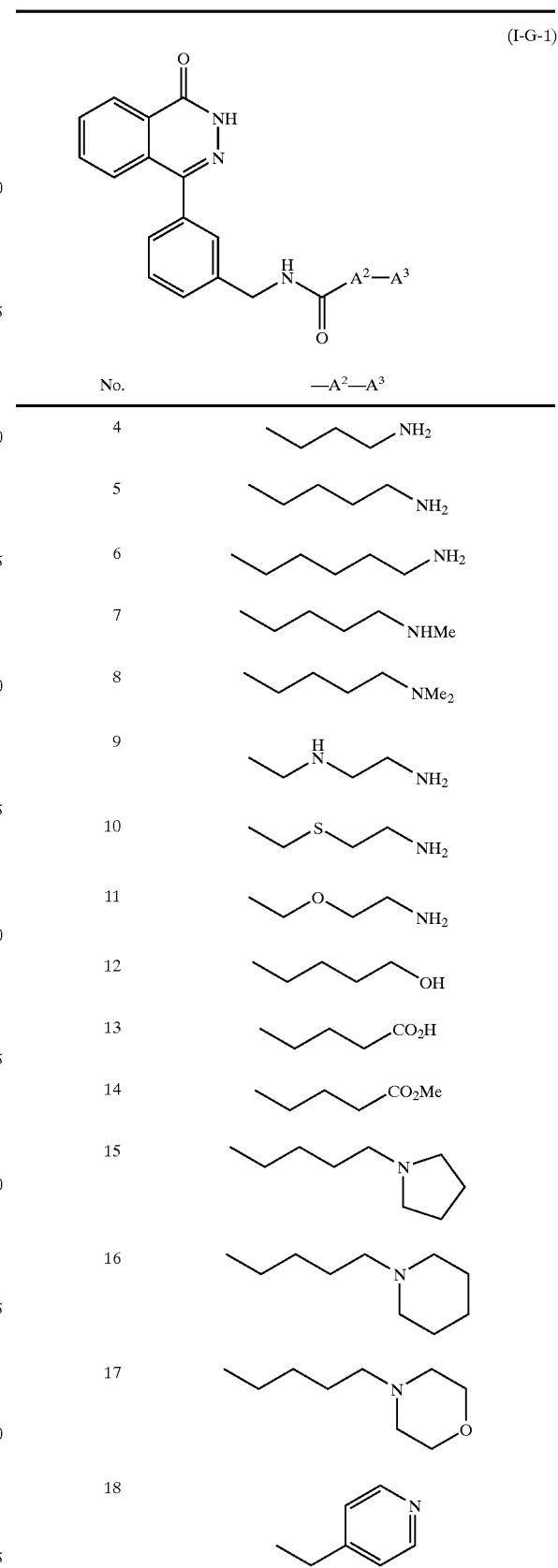

| No. | —A²—A³ |
|---|---|
| 4 | butyl-NH₂ |
| 5 | pentyl-NH₂ |
| 6 | hexyl-NH₂ |
| 7 | pentyl-NHMe |
| 8 | pentyl-NMe₂ |
| 9 | ethyl-NH-ethyl-NH₂ |
| 10 | ethyl-S-ethyl-NH₂ |
| 11 | ethyl-O-ethyl-NH₂ |
| 12 | pentyl-OH |
| 13 | pentyl-CO₂H |
| 14 | pentyl-CO₂Me |
| 15 | pentyl-pyrrolidine |
| 16 | pentyl-piperidine |
| 17 | pentyl-morpholine |
| 18 | (4-pyridyl)-ethyl |

TABLE 7-continued
(I-G-1)
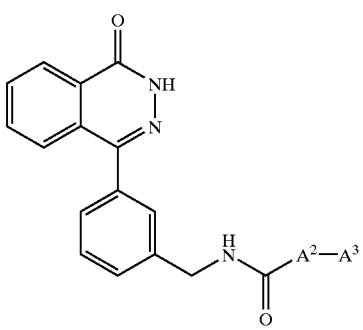
| No. | —A²—A³ |
|---|---|
| 19 | 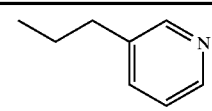 |
| 20 | 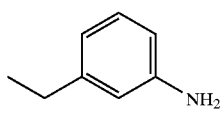 |
| 21 | 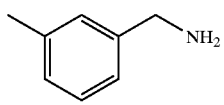 |
| 22 | 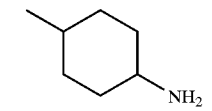 |
| 23 | 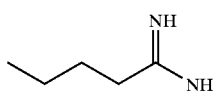 |
| 24 | 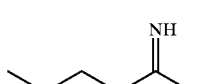 |
TABLE 8
(I-H-1)
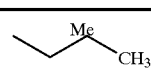
| No. | —A²—A³ |
|---|---|
| 1 |  |
| 2 | |
TABLE 8-continued
(I-H-1)
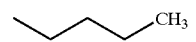
| No. | —A²—A³ |
|---|---|
| 3 | 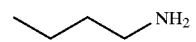 |
| 4 | 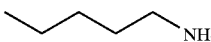 |
| 5 | 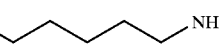 |
| 6 | 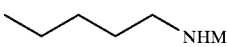 |
| 7 | 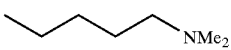 |
| 8 |  |
| 9 |  |
| 10 | 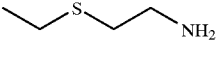 |
| 11 | 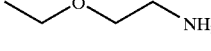 |
| 12 | 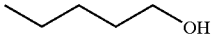 |
| 13 | 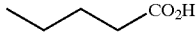 |
| 14 | 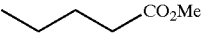 |
| 15 | 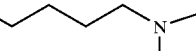 |
| 16 |  |
| 17 |  |
| 18 | |

TABLE 8-continued
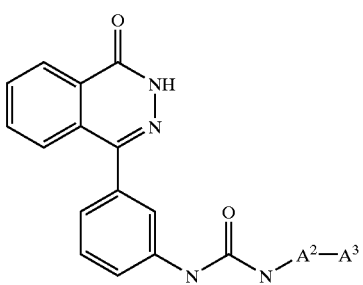
(I-H-1)
| No. | —A²—A³ |
|---|---|
| 19 | 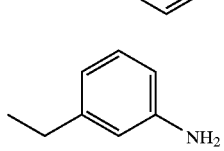 |
| 20 | 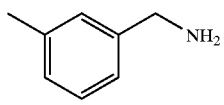 |
| 21 | 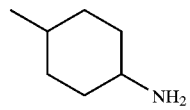 |
| 22 | 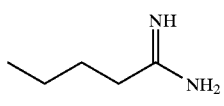 |
| 23 | 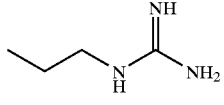 |
| 24 | 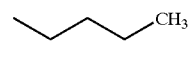 |
TABLE 9
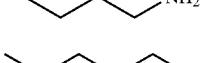
(I-J-1)
| No. | —A²—A³ |
|---|---|
| 1 | Me |
| 2 | 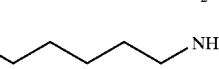 |
TABLE 9-continued
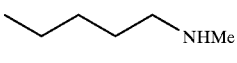
(I-J-1)
| No. | —A²—A³ |
|---|---|
| 3 | 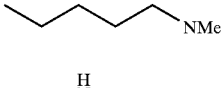 |
| 4 | 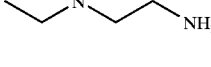 |
| 5 | 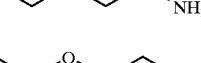 |
| 6 | 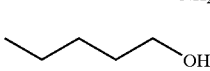 |
| 7 | 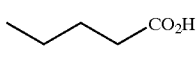 |
| 8 | 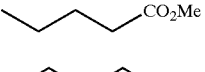 |
| 9 |  |
| 10 | 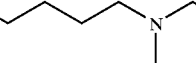 |
| 11 | 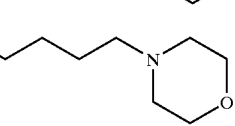 |
| 12 |  |
| 13 | 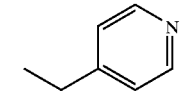 |
| 14 |  |
| 15 | 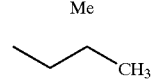 |
| 16 | |
| 17 | |
| 18 | |

TABLE 9-continued (I-J-1)

| No. | —A²—A³ |
|---|---|
| 19 | (propyl-3-pyridyl) |
| 20 | (3-ethylphenyl)-NH₂ |
| 21 | (3-methylbenzyl)-NH₂ |
| 22 | (4-methylcyclohexyl)-NH₂ |
| 23 | pentanimidamide |
| 24 | propyl-guanidine |

TABLE 10

(I-K-1)

| No. | —A²—A³ |
|---|---|
| 1 | Me |
| 2 | propyl-CH₃ |
| 3 | butyl-CH₃ |
| 4 | butyl-NH₂ |
| 5 | pentyl-NH₂ |
| 6 | hexyl-NH₂ |
| 7 | pentyl-NHMe |
| 8 | pentyl-NMe₂ |
| 9 | ethyl-NH-ethyl-NH₂ |
| 10 | ethyl-S-ethyl-NH₂ |
| 11 | ethyl-O-ethyl-NH₂ |
| 12 | pentyl-OH |
| 13 | pentyl-CO₂H |
| 14 | pentyl-CO₂Me |
| 15 | pentyl-pyrrolidinyl |
| 16 | pentyl-piperidinyl |
| 17 | pentyl-morpholinyl |
| 18 | ethyl-4-pyridyl |

TABLE 10-continued
(I-K-1)
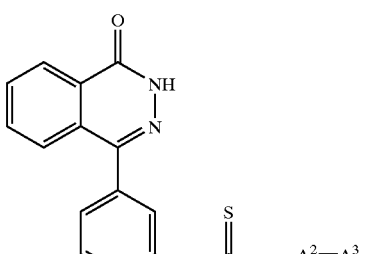
| No. | —A²—A³ |
|---|---|
| 19 | 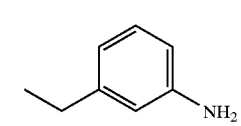 |
| 20 | 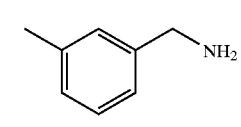 |
| 21 | 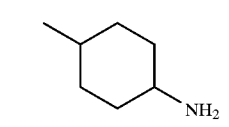 |
| 22 | 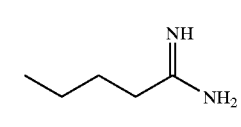 |
| 23 | 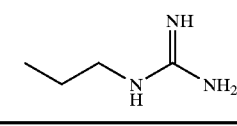 |
| 24 | 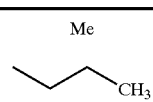 |
TABLE 11
(I-L-1)
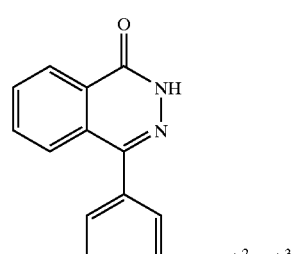
| No. | —A²—A³ |
|---|---|
| 1 | Me |
| 2 | 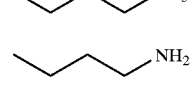 |
TABLE 11-continued
(I-L-1)
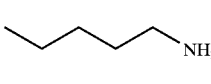
| No. | —A²—A³ |
|---|---|
| 3 | 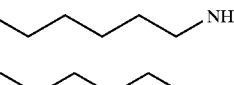 |
| 4 | 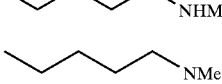 |
| 5 | 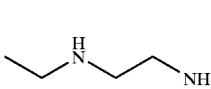 |
| 6 | 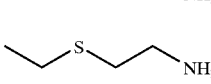 |
| 7 | 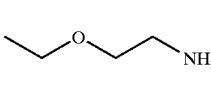 |
| 8 | 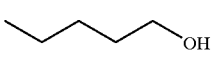 |
| 9 | 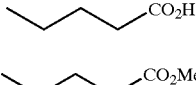 |
| 10 | 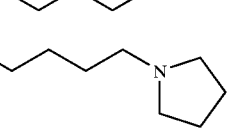 |
| 11 |  |
| 12 | 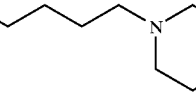 |
| 13 | 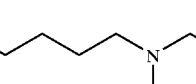 |
| 14 |  |
| 15 | 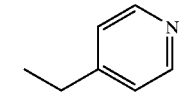 |
| 16 |  |
| 17 |  |
| 18 |  |

TABLE 11-continued
(I-L-1)
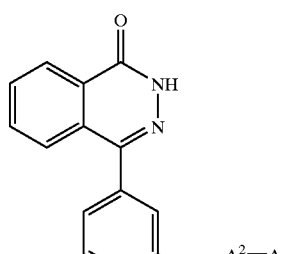
| No. | —A²—A³ |
|---|---|
| 19 | 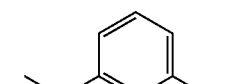 |
| 20 | 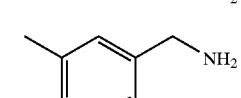 |
| 21 | 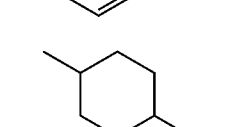 |
| 22 | 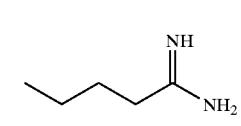 |
| 23 | 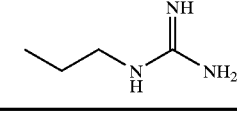 |
| 24 | 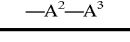 |
TABLE 12
(I-M-1)
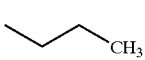
| No. | —A²—A³ |
|---|---|
| 1 | Me |
| 2 | 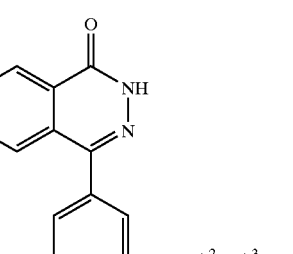 |
TABLE 12-continued
(I-M-1)
| No. | —A²—A³ |
|---|---|
| 3 |  |
| 4 |  |
| 5 | 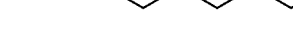 |
| 6 |  |
| 7 |  |
| 8 |  |
| 9 |  |
| 10 |  |
| 11 |  |
| 12 | 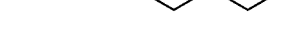 |
| 13 | 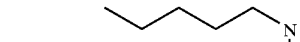 |
| 14 |  |
| 15 | 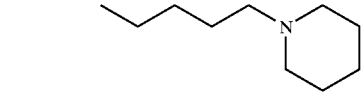 |
| 16 |  |
| 17 |  |
| 18 |  |

TABLE 12-continued
(I-M-1)
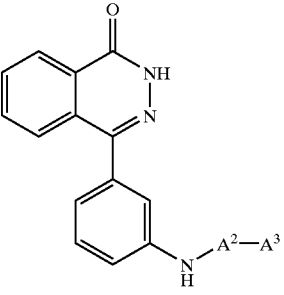
| No. | —A²—A³ |
|---|---|
| 19 | 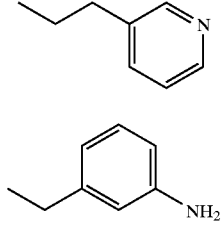 |
| 20 | 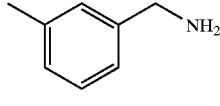 |
| 21 | 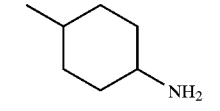 |
| 22 | 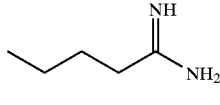 |
| 23 | 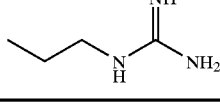 |
| 24 | 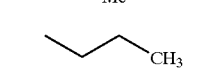 |
TABLE 13
(I-N-1)
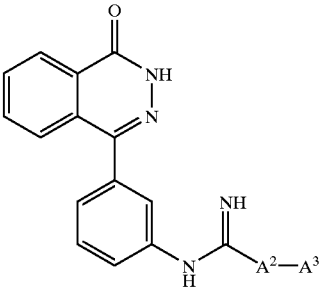
| No. | —A²—A³ |
|---|---|
| 1 | Me |
| 2 | 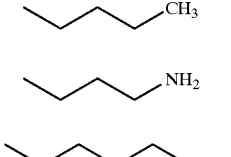 |
TABLE 13-continued
(I-N-1)
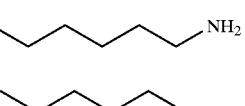
| No. | —A²—A³ |
|---|---|
| 3 | 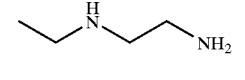 |
| 4 | 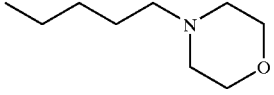 |
| 5 | |
| 6 | |
| 7 | |
| 8 | |
| 9 | |
| 10 | |
| 11 | |
| 12 | |
| 13 | |
| 14 | |
| 15 | |
| 16 | |
| 17 | |

TABLE 13-continued (I-N-1)

| No. | —A²—A³ |
|---|---|
| 18 | 4-ethylpyridine |
| 19 | 3-propylpyridine |
| 20 | 3-ethylaniline |
| 21 | 3-methylbenzylamine |
| 22 | 4-methylcyclohexylamine |
| 23 | pentanamidine |
| 24 | propylguanidine |

TABLE 14

(I-C-1)

| No. | —A²—A³ |
|---|---|
| 25 | pentyl-(3-methoxypyrrolidin-1-yl) |
| 26 | pentyl-(3-methoxypiperidin-1-yl) |
| 27 | pentyl-(4-methoxypiperidin-1-yl) |
| 28 | pentyl-(1,2,3,6-tetrahydropyridin-1-yl) |
| 29 | pentyl-N-(2-methylallyl) |
| 30 | pentyl-N-(3-methylbut-2-enyl) |
| 31 | pentyl-N-methyl-propargyl |
| 32 | 4,4-dimethylpentyl-(3-methoxypyrrolidin-1-yl) |
| 33 | 4,4-dimethylpentyl-(3-methoxypiperidin-1-yl) |
| 34 | 4,4-dimethylpentyl-(4-methoxypiperidin-1-yl) |
| 35 | 4,4-dimethylpentyl-(1,2,3,6-tetrahydropyridin-1-yl) |

TABLE 14-continued (I-C-1)

| No. | —A²—A³ |
|---|---|
| 36 | CH₂=C(Me)−CH₂−NH−CH₂−CH₂−CH₂−C(Me)(Me)− |
| 37 | Me₂C=CH−CH₂−NH−CH₂−CH₂−CH₂−C(Me)(Me)− |
| 38 | HC≡C−CH₂−N(Me)−CH₂−CH₂−CH₂−C(Me)(Me)− |
| 39 | morpholino−CH₂−CH₂−CH₂−C(Me)(Me)− |
| 40 | (3-OMe-pyrrolidin-1-yl)−CH₂−CH₂−O−CH₂−CH₂− |
| 41 | (3-OMe-piperidin-1-yl)−CH₂−CH₂−O−CH₂−CH₂− |
| 42 | (4-OMe-piperidin-1-yl)−CH₂−CH₂−O−CH₂−CH₂− |
| 43 | (1,2,3,6-tetrahydropyridin-1-yl)−CH₂−CH₂−O−CH₂−CH₂− |
| 44 | CH₂=C(Me)−CH₂−NH−CH₂−CH₂−O−CH₂−CH₂− |
| 45 | Me₂C=CH−CH₂−NH−CH₂−CH₂−O−CH₂−CH₂− |
| 46 | HC≡C−CH₂−N(Me)−CH₂−CH₂−O−CH₂−CH₂− |
| 47 | morpholino−CH₂−CH₂−O−CH₂−CH₂− |
| 48 | (3-OMe-pyrrolidin-1-yl)−CH₂−CH₂−S−Et |
| 49 | (3-OMe-piperidin-1-yl)−CH₂−CH₂−S−Et |
| 50 | (4-OMe-piperidin-1-yl)−CH₂−CH₂−S−Et |
| 51 | (1,2,3,6-tetrahydropyridin-1-yl)−CH₂−CH₂−S−Et |
| 52 | CH₂=C(Me)−CH₂−NH−CH₂−CH₂−S−Et |
| 53 | Me₂C=CH−CH₂−NH−CH₂−CH₂−S−Et |
| 54 | HC≡C−CH₂−N(Me)−CH₂−CH₂−S−Et |
| 55 | morpholino−CH₂−CH₂−S−Et |

TABLE 15
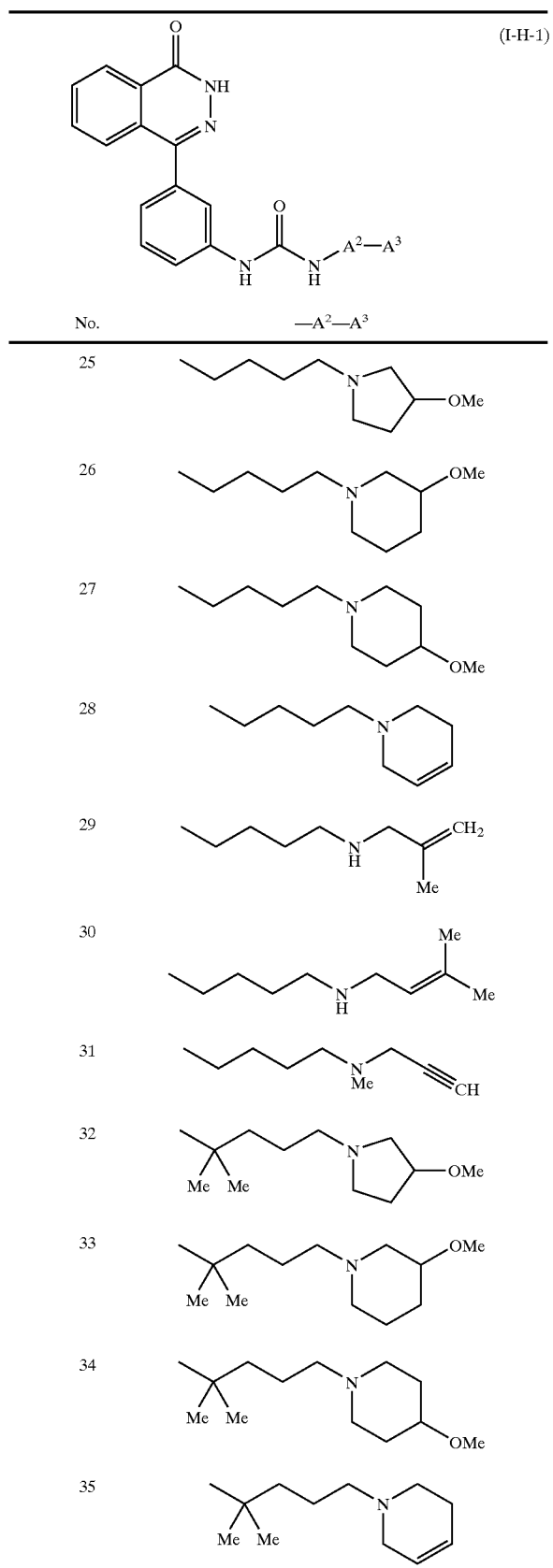
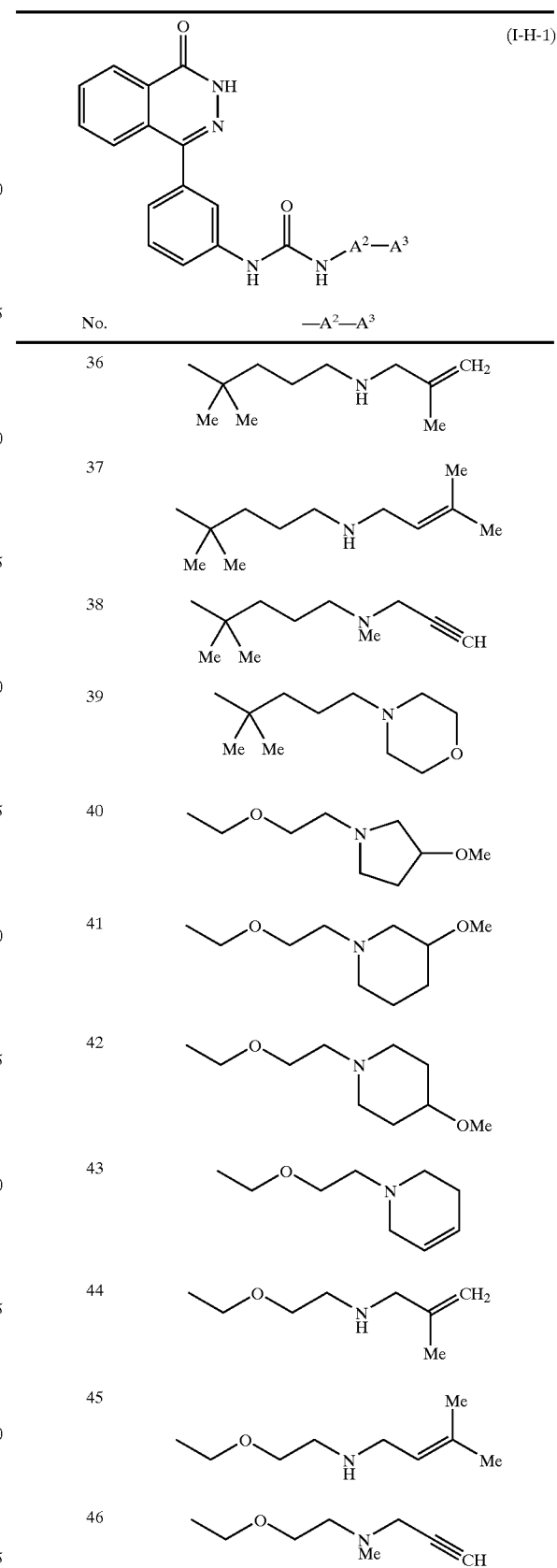

TABLE 15-continued (I-H-1)

| No. | —A²—A³ |
|---|---|
| 47 | ethoxyethyl-morpholine |
| 48 | ethylthioethyl-(3-methoxy)pyrrolidine |
| 49 | ethylthioethyl-(3-methoxy)piperidine |
| 50 | ethylthioethyl-(4-methoxy)piperidine |

TABLE 15-continued (I-H-1)

| No. | —A²—A³ |
|---|---|
| 51 | ethylthioethyl-tetrahydropyridine |
| 52 | ethylthioethyl-NH-CH₂-C(Me)=CH₂ |
| 53 | ethylthioethyl-NH-CH₂-CH=C(Me)Me |
| 54 | ethylthioethyl-N(Me)-CH₂-C≡CH |
| 55 | ethylthioethyl-morpholine |

TABLE 16

(I-J-1)

| No. | —A²—A³ | No. | —A²—A³ |
|---|---|---|---|
| 25 | pentyl-(3-methoxy)pyrrolidine | 40 | ethoxyethyl-(3-methoxy)pyrrolidine |

TABLE 16-continued
(I-J-1)
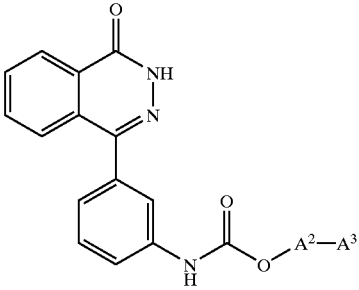
| No. | —A²—A³ | No. | —A²—A³ |
|---|---|---|---|
| 26 | 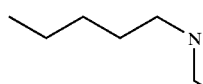 | 41 | 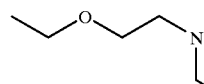 |
| 27 | 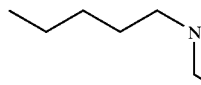 | 42 | 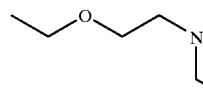 |
| 28 | 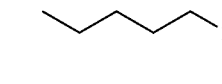 | 43 | 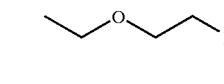 |
| 29 | 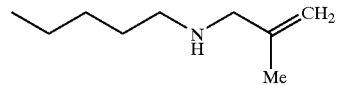 | 44 | 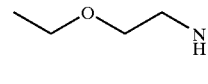 |
| 30 | 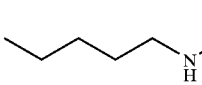 | 45 | 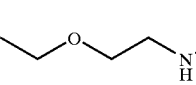 |
| 31 |  | 46 | 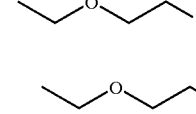 |
| 32 | 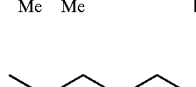 | 47 | 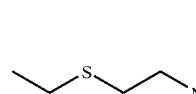 |
| 33 | 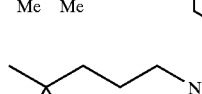 | 48 | 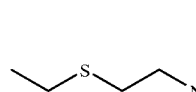 |
| 34 | 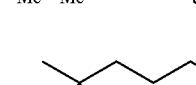 | 49 | 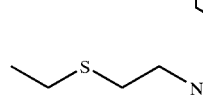 |
| 35 | 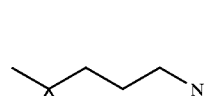 | 50 | 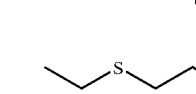 |
| 36 |  | 51 |  |

TABLE 16-continued
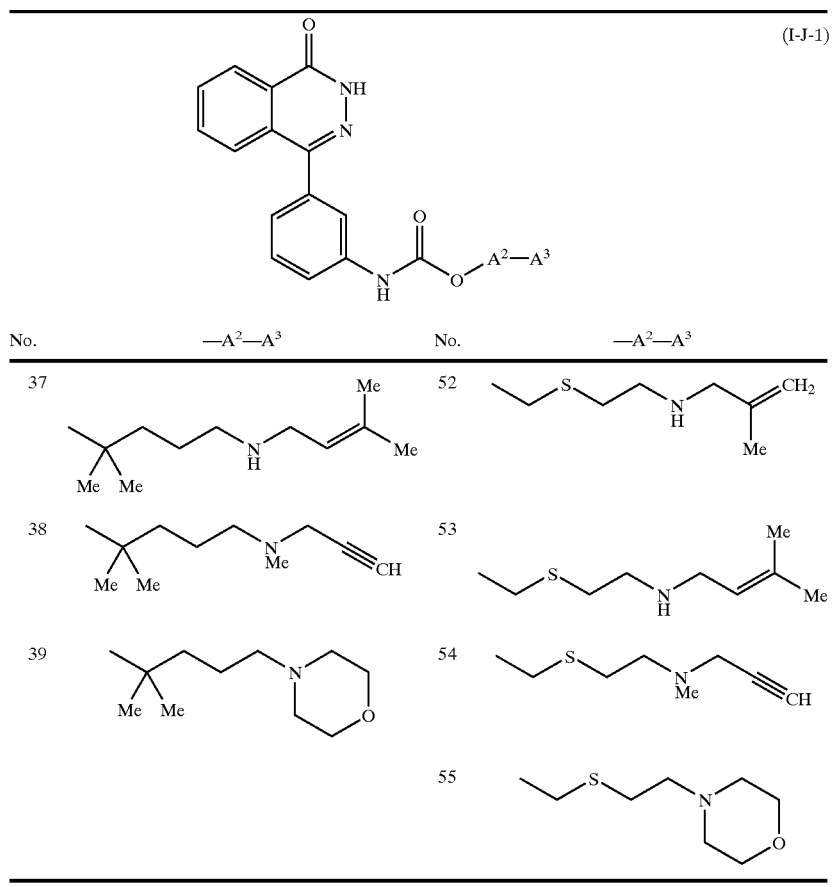
TABLE 17
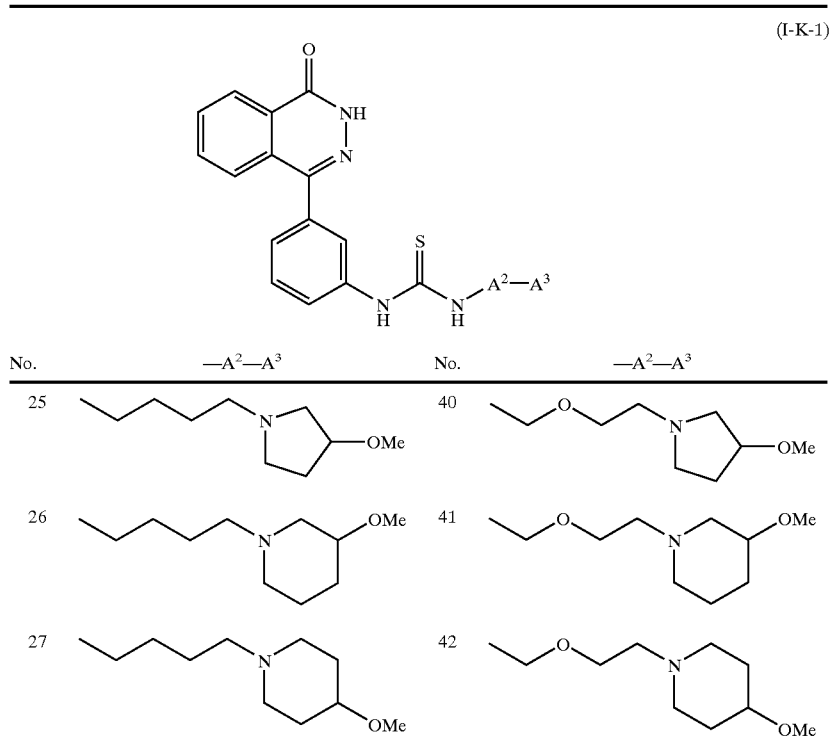

TABLE 17-continued
(I-K-1)
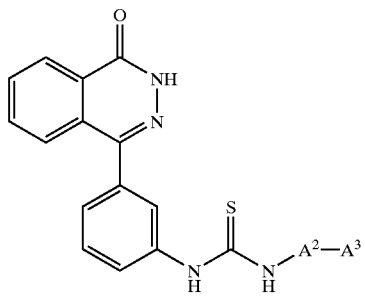
| No. | —A²—A³ | No. | —A²—A³ |
|---|---|---|---|
| 28 | | 43 | |
| 29 | | 44 | |
| 30 | | 45 | |
| 31 | | 46 | |
| 32 | | 47 | |
| 33 | | 48 | |
| 34 | | 49 | |
| 35 | | 50 | |
| 36 | | 51 | |
| 37 | | 52 | |

TABLE 17-continued (I-K-1)

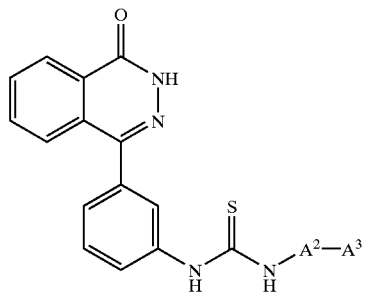

| No. | —A²—A³ | No. | —A²—A³ |
|---|---|---|---|
| 38 | Me₃C-CH₂CH₂CH₂-N(Me)-CH₂-C≡CH | 53 | EtS-CH₂CH₂-NH-CH₂-CH=CMe₂ |
| 39 | Me₃C-CH₂CH₂CH₂-morpholino | 54 | EtS-CH₂CH₂-N(Me)-CH₂-C≡CH |
|  |  | 55 | EtS-CH₂CH₂-morpholino |

TABLE 18

(I-A-2)

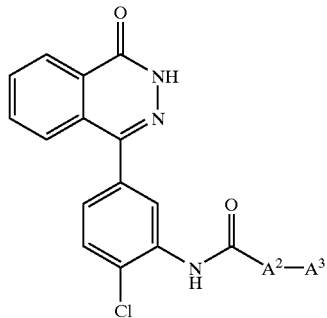

| No. | —A²—A³ | No. | —A²—A³ |
|---|---|---|---|
| 1 | pentyl-(3-methoxypyrrolidin-1-yl) | 16 | (2-ethoxyethyl)-(3-methoxypyrrolidin-1-yl) |
| 2 | pentyl-(3-methoxypiperidin-1-yl) | 17 | (2-ethoxyethyl)-(3-methoxypiperidin-1-yl) |
| 3 | pentyl-(4-methoxypiperidin-1-yl) | 18 | (2-ethoxyethyl)-(4-methoxypiperidin-1-yl) |

TABLE 18-continued
(I-A-2)
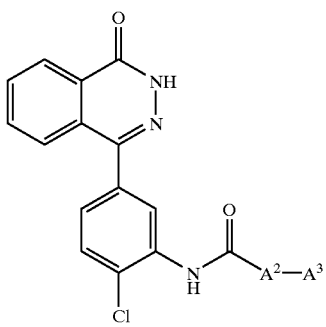
| No. | —A²—A³ | No. | —A²—A³ |
|---|---|---|---|
| 4 | 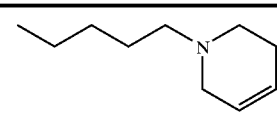 | 19 | 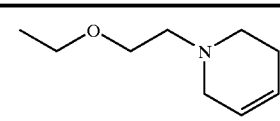 |
| 5 | 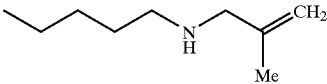 | 20 | 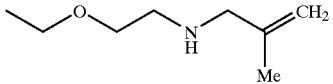 |
| 6 | 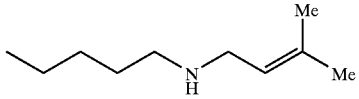 | 21 | 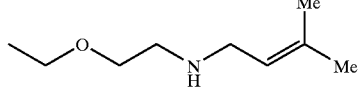 |
| 7 | 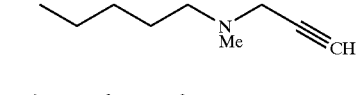 | 22 | 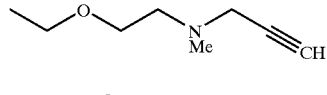 |
| 8 | 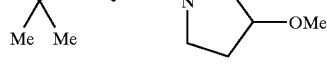 | 23 |  |
| 9 | 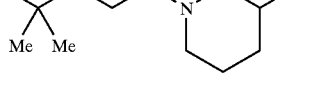 | 24 |  |
| 10 | 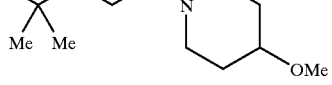 | 25 | 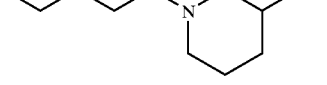 |
| 11 | 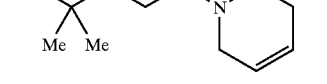 | 26 | 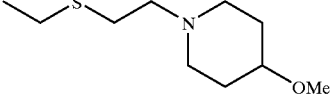 |
| 12 | 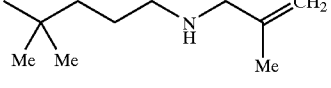 | 27 | 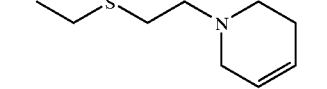 |
| 13 | 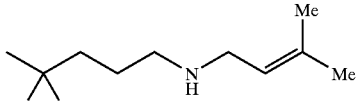 | 28 | 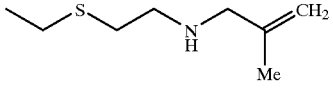 |

TABLE 18-continued
(I-A-2)
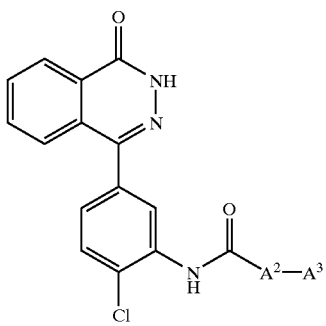
| No. | —A²—A³ | No. | —A²—A³ |
|---|---|---|---|
| 14 | 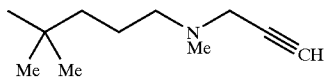 | 29 | 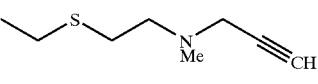 |
| 15 | 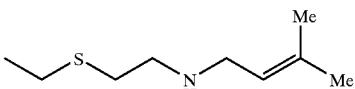 | 30 | 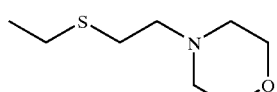 |
|  |  | 31 | 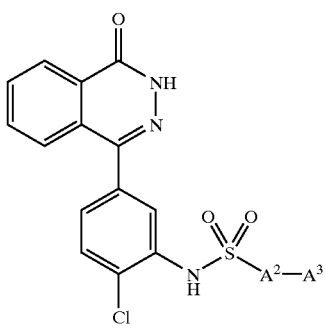 |
TABLE 19
(I-C-2)
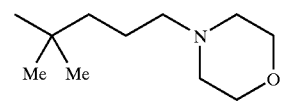
| No. | —A²—A³ | No. | —A²—A³ |
|---|---|---|---|
| 1 | 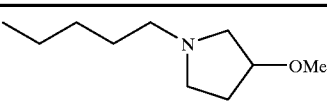 | 16 | 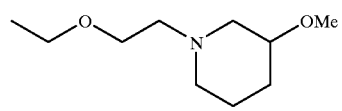 |
| 2 | 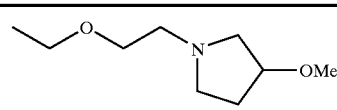 | 17 | 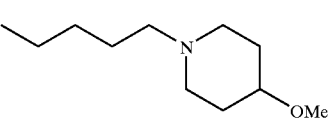 |
| 3 | 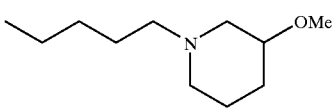 | 18 | 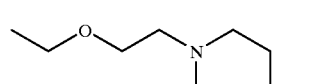 |

TABLE 19-continued
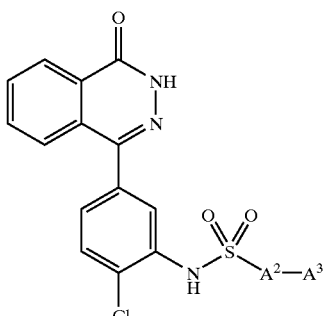
(I-C-2)
| No. | —A²—A³ | No. | —A²—A³ |
|---|---|---|---|
| 4 | 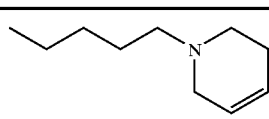 | 19 | 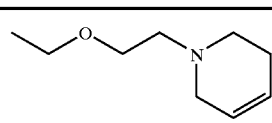 |
| 5 | 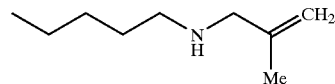 | 20 | 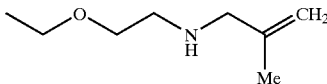 |
| 6 | 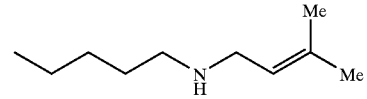 | 21 | 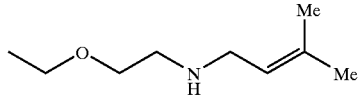 |
| 7 | 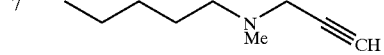 | 22 | 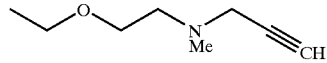 |
| 8 | 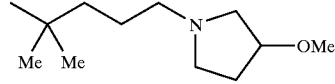 | 23 | 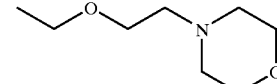 |
| 9 | 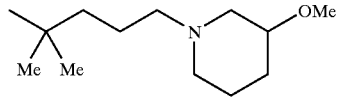 | 24 | 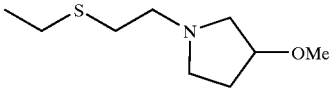 |
| 10 | 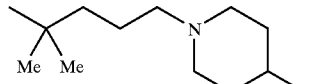 | 25 | 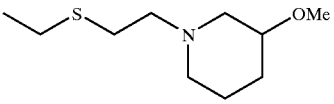 |
| 11 | 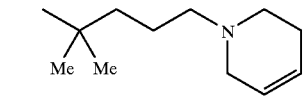 | 26 | 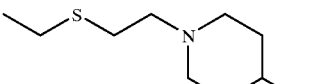 |
| 12 | 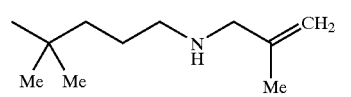 | 27 | 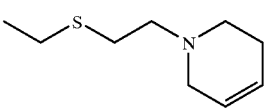 |
| 13 | 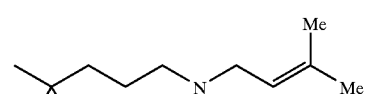 | 28 | 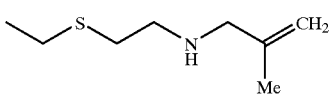 |

TABLE 19-continued
(I-C-2)
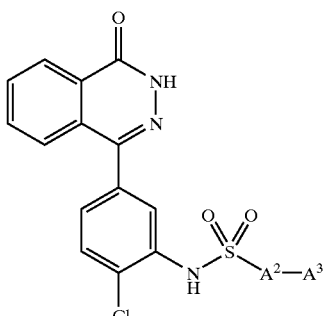
| No. | —A²—A³ | No. | —A²—A³ |
|---|---|---|---|
| 14 | 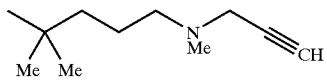 | 29 | 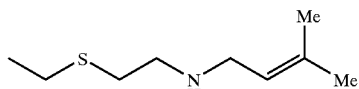 |
| 15 | 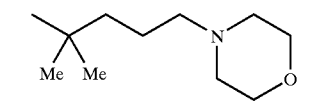 | 30 | 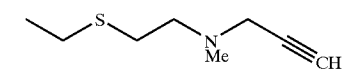 |
|  |  | 31 | 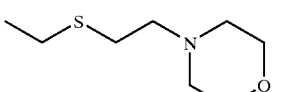 |
TABLE 20
(I-H-2)
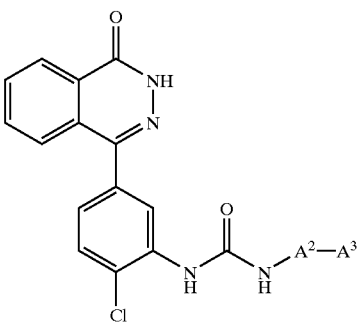
| No. | —A²—A³ | No. | —A²—A³ |
|---|---|---|---|
| 1 | 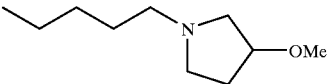 | 16 | 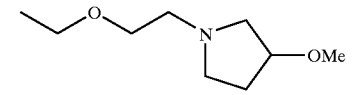 |
| 2 | 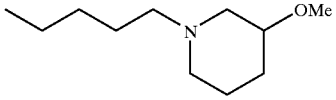 | 17 | 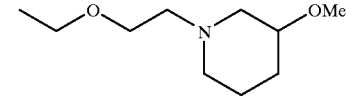 |
| 3 | 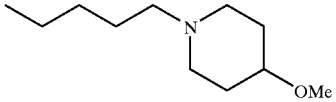 | 18 | 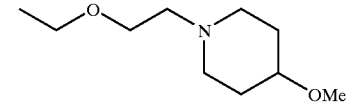 |

TABLE 20-continued
(I-H-2)
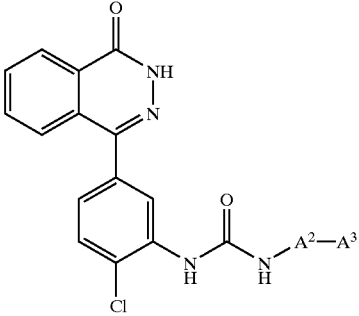
| No. | —A²—A³ | No. | —A²—A³ |
|---|---|---|---|
| 4 | 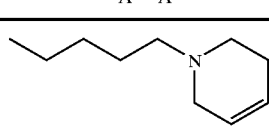 | 19 | 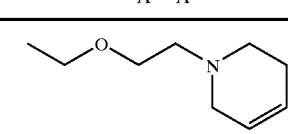 |
| 5 | 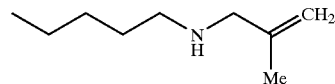 | 20 | 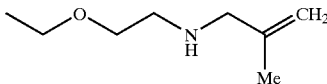 |
| 6 | 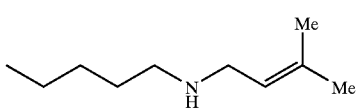 | 21 | 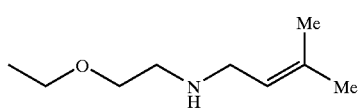 |
| 7 | 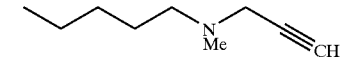 | 22 | 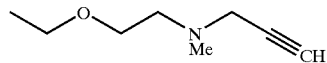 |
| 8 | 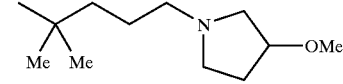 | 23 | 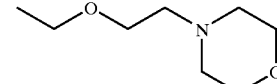 |
| 9 | 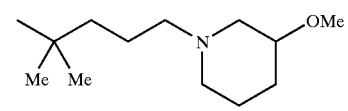 | 24 | 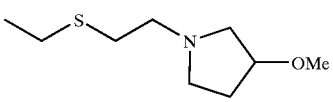 |
| 10 | 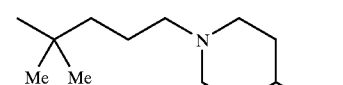 | 25 | 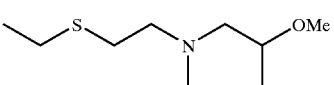 |
| 11 | 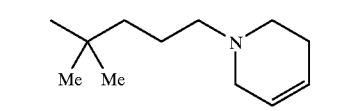 | 26 | 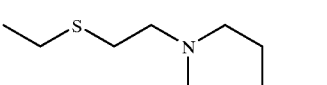 |
| 12 | 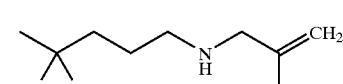 | 27 | 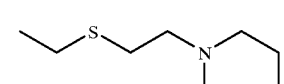 |
| 13 | 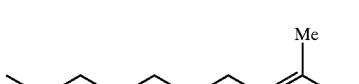 | 28 | 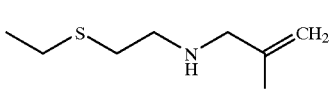 |

TABLE 20-continued (I-H-2)

| No. | —A²—A³ | No. | —A²—A³ |
|---|---|---|---|
| 14 | Me₂C(Me)-CH₂CH₂CH₂-N(Me)-CH₂-C≡CH | 29 | EtS-CH₂CH₂-NH-CH₂-CH=C(Me)₂ |
| 15 | Me₂C(Me)-CH₂CH₂CH₂-morpholine | 30 | EtS-CH₂CH₂-N(Me)-CH₂-C≡CH |
|  |  | 31 | EtS-CH₂CH₂-morpholine |

TABLE 21

(I-J-2)

| No. | —A²—A³ | No. | —A²—A³ |
|---|---|---|---|
| 1 | pentyl-(3-OMe-pyrrolidin-1-yl) | 16 | MeOCH₂CH₂-(3-OMe-pyrrolidin-1-yl) |
| 2 | pentyl-(3-OMe-piperidin-1-yl) | 17 | MeOCH₂CH₂-(3-OMe-piperidin-1-yl) |
| 3 | pentyl-(4-OMe-piperidin-1-yl) | 18 | MeOCH₂CH₂-(4-OMe-piperidin-1-yl) |

TABLE 21-continued
(I-J-2)
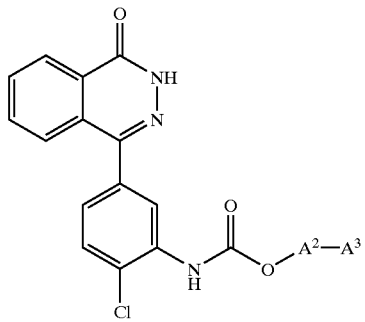
| No. | —A²—A³ | No. | —A²—A³ |
|---|---|---|---|
| 4 | | 19 | |
| 5 | | 20 | |
| 6 | | 21 | |
| 7 | | 22 | |
| 8 | | 23 | |
| 9 | | 24 | |
| 10 | | 25 | |
| 11 | | 26 | |
| 12 | | 27 | |
| 13 | | 28 | |

TABLE 21-continued
(I-J-2)
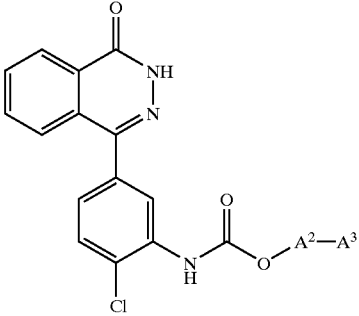
| No. | —A²—A³ | No. | —A²—A³ |
|---|---|---|---|
| 14 | 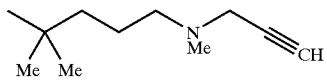 | 29 | 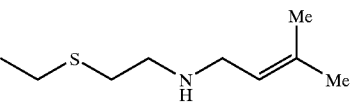 |
| 15 | 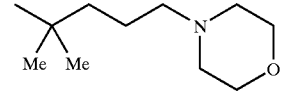 | 30 |  |
|  |  | 31 | 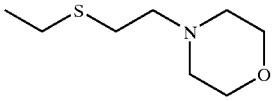 |
TABLE 22
(I-K-2)
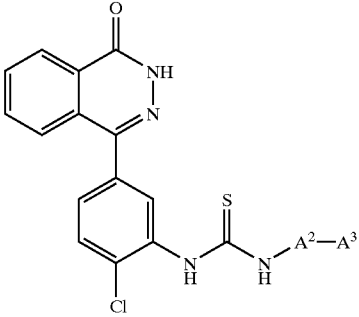
| No. | —A²—A³ | No. | —A²—A³ |
|---|---|---|---|
| 1 | 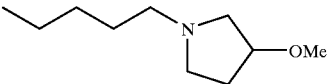 | 16 | 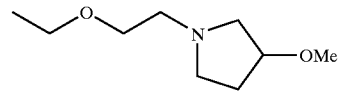 |
| 2 | 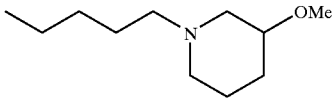 | 17 | 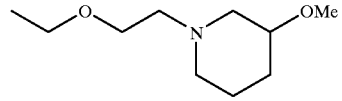 |
| 3 | 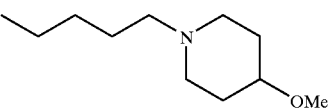 | 18 | 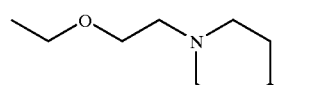 |

TABLE 22-continued

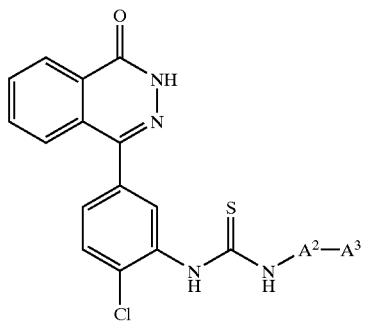

(I-K-2)

| No. | —A²—A³ | No. | —A²—A³ |
|---|---|---|---|
| 4 | pentyl-tetrahydropyridin-1-yl | 19 | ethoxyethyl-tetrahydropyridin-1-yl |
| 5 | pentyl-NH-CH₂-C(Me)=CH₂ | 20 | ethoxyethyl-NH-CH₂-C(Me)=CH₂ |
| 6 | pentyl-NH-CH₂-CH=C(Me)Me | 21 | ethoxyethyl-NH-CH₂-CH=C(Me)Me |
| 7 | pentyl-N(Me)-CH₂-C≡CH | 22 | ethoxyethyl-N(Me)-CH₂-C≡CH |
| 8 | Me₂C-propyl-(3-methoxypyrrolidin-1-yl) | 23 | ethoxyethyl-morpholin-4-yl |
| 9 | Me₂C-propyl-(3-methoxypiperidin-1-yl) | 24 | ethylthioethyl-(3-methoxypyrrolidin-1-yl) |
| 10 | Me₂C-propyl-(4-methoxypiperidin-1-yl) | 25 | ethylthioethyl-(3-methoxypiperidin-1-yl) |
| 11 | Me₂C-propyl-tetrahydropyridin-1-yl | 26 | ethylthioethyl-(4-methoxypiperidin-1-yl) |
| 12 | Me₂C-propyl-NH-CH₂-C(Me)=CH₂ | 27 | ethylthioethyl-tetrahydropyridin-1-yl |
| 13 | Me₂C-propyl-NH-CH₂-CH=C(Me)Me | 28 | ethylthioethyl-NH-CH₂-C(Me)=CH₂ |

TABLE 22-continued
(I-K-2)
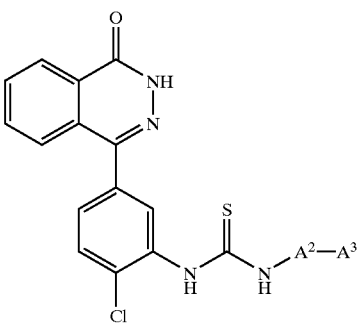
| No. | —A²—A³ | No. | —A²—A³ |
|---|---|---|---|
| 14 | 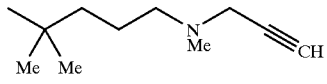 | 29 | 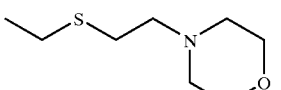 |
| 15 | 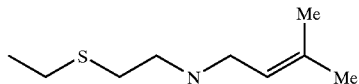 | 30 | 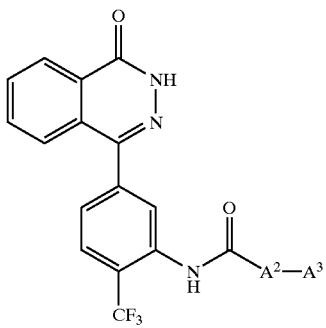 |
|  |  | 31 | 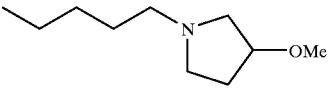 |
TABLE 23
(I-A-3)
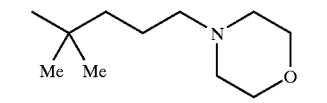
| No. | —A²—A³ | No. | —A²—A³ |
|---|---|---|---|
| 1 | 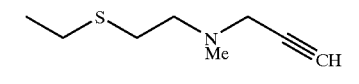 | 16 | 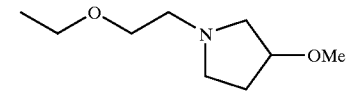 |
| 2 | 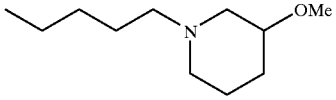 | 17 | 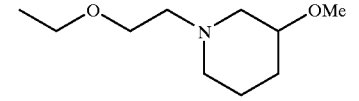 |
| 3 | 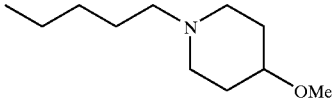 | 18 | 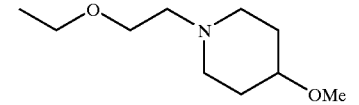 |

TABLE 23-continued
(I-A-3)
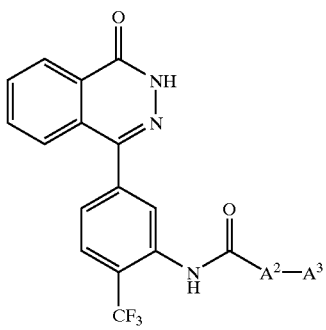
| No. | —A²—A³ | No. | —A²—A³ |
|---|---|---|---|
| 4 | 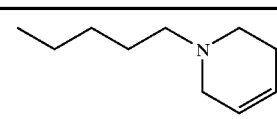 | 19 | 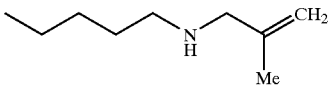 |
| 5 | 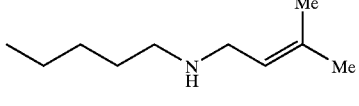 | 20 | 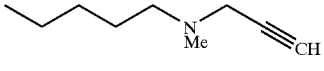 |
| 6 | 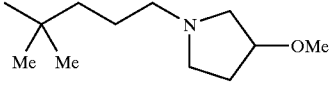 | 21 | 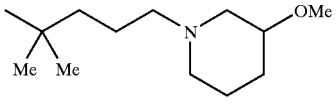 |
| 7 | 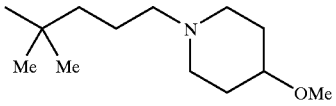 | 22 | 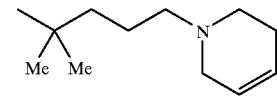 |
| 8 | 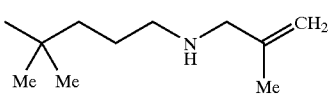 | 23 | 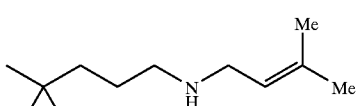 |
| 9 | 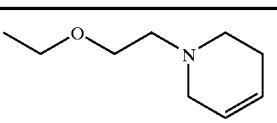 | 24 | 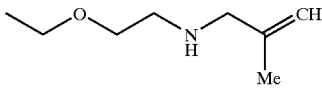 |
| 10 | 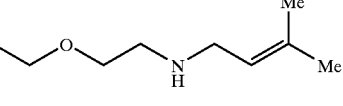 | 25 | 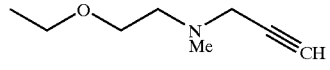 |
| 11 | 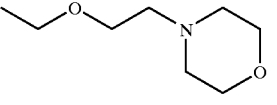 | 26 | 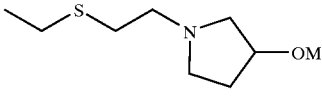 |
| 12 | 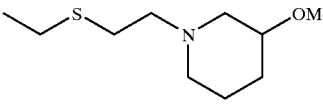 | 27 | 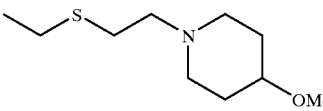 |
| 13 | 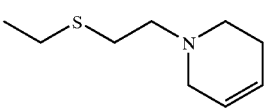 | 28 | 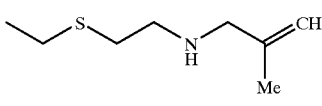 |

TABLE 23-continued
(I-A-3)
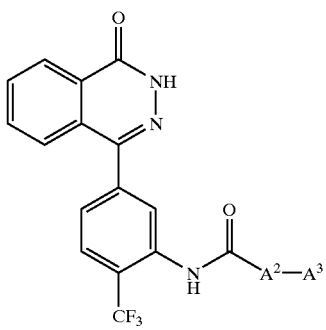
| No. | —A²—A³ | No. | —A²—A³ |
|---|---|---|---|
| 14 | 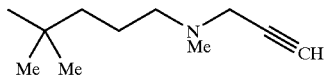 | 29 | 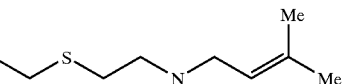 |
| 15 | 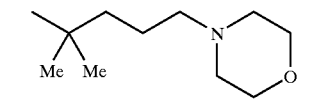 | 30 | 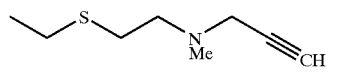 |
|  |  | 31 | 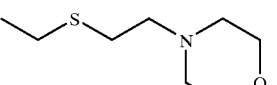 |
TABLE 24
(I-C-3)
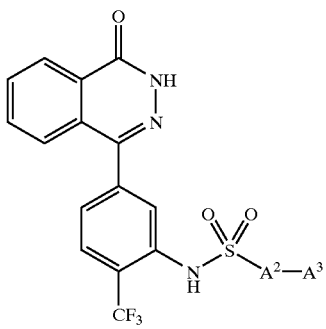
| No. | —A²—A³ | No. | —A²—A³ |
|---|---|---|---|
| 1 | 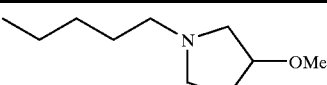 | 16 | 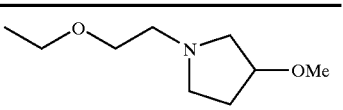 |
| 2 | 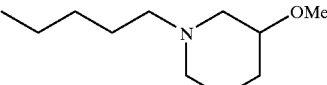 | 17 | 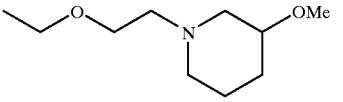 |
| 3 | 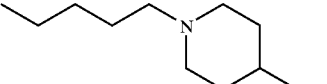 | 18 | 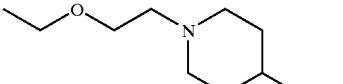 |

TABLE 24-continued
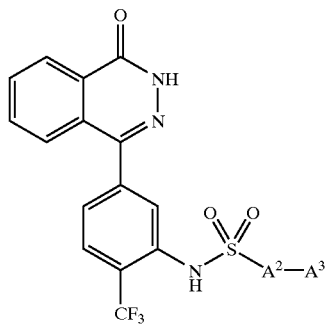
(I-C-3)
| No. | —A²—A³ | No. | —A²—A³ |
|---|---|---|---|
| 4 | | 19 | |
| 5 | | 20 | |
| 6 | | 21 | |
| 7 | | 22 | |
| 8 | | 23 | |
| 9 | | 24 | |
| 10 | | 25 | |
| 11 | | 26 | |
| 12 | | 27 | |
| 13 | | 28 | |

TABLE 24-continued
(I-C-3)
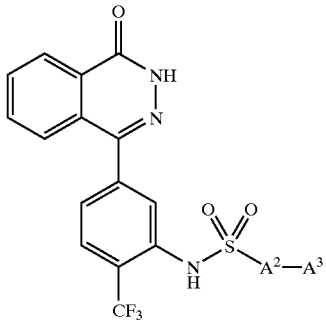
| No. | —A²—A³ | No. | —A²—A³ |
|---|---|---|---|
| 14 | 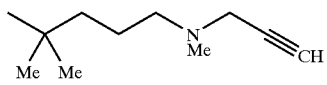 | 29 | 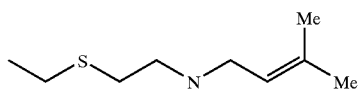 |
| 15 | 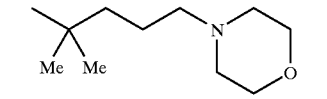 | 30 | 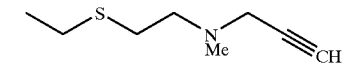 |
|  |  | 31 | 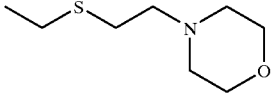 |
TABLE 25
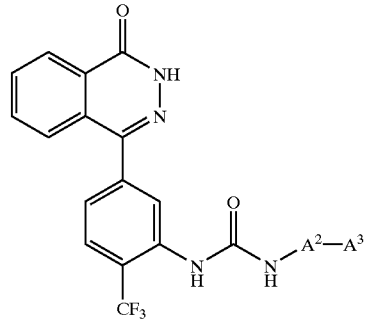
| No. | —A²—A³ | No. | —A²—A³ |
|---|---|---|---|
| 1 | 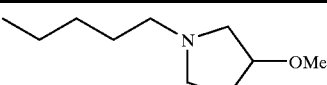 | 16 | 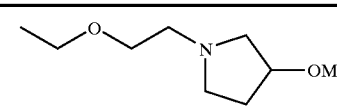 |
| 2 | 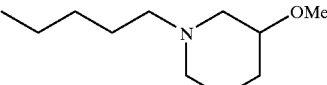 | 17 | 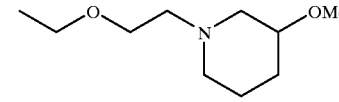 |
| 3 | 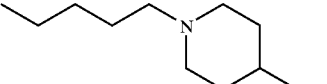 | 18 | 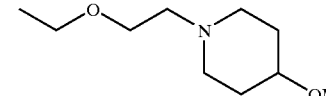 |

TABLE 25-continued
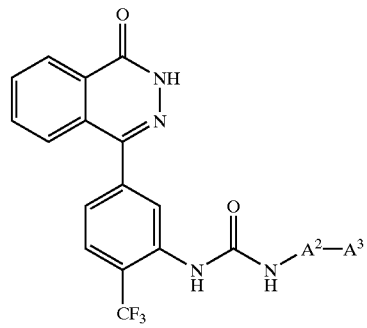
| No. | —A²—A³ | No. | —A²—A³ |
|---|---|---|---|
| 4 | 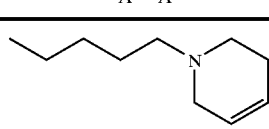 | 19 | 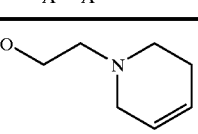 |
| 5 | 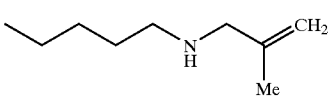 | 20 | 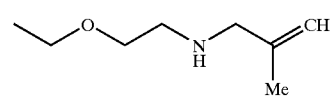 |
| 6 | 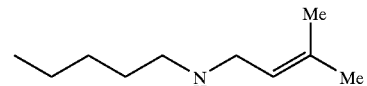 | 21 | 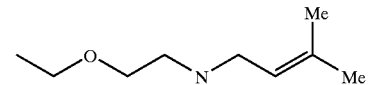 |
| 7 | 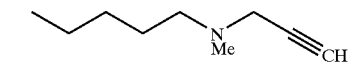 | 22 | 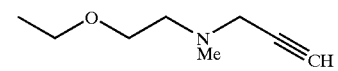 |
| 8 | 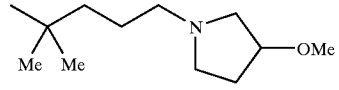 | 23 | 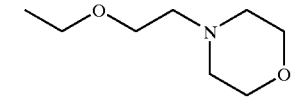 |
| 9 | 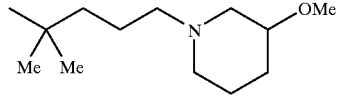 | 24 | 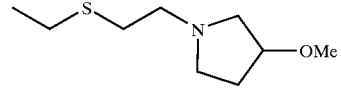 |
| 10 | 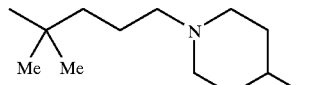 | 25 | 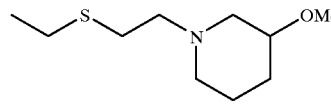 |
| 11 | 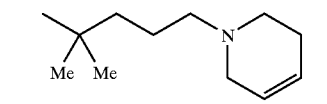 | 26 | 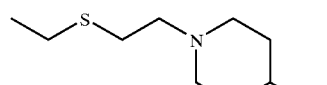 |
| 12 | 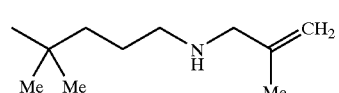 | 27 | 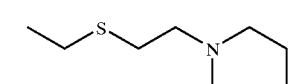 |
| 13 | 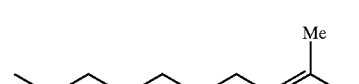 | 28 | 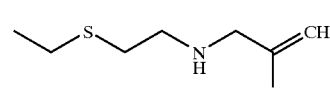 |

TABLE 25-continued
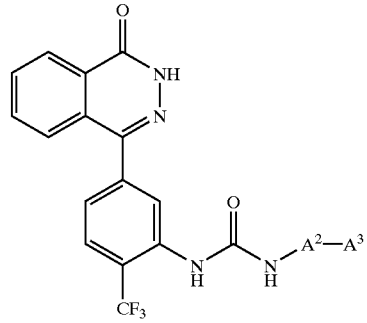
| No. | —A²—A³ | No. | —A²—A³ |
|---|---|---|---|
| 14 | 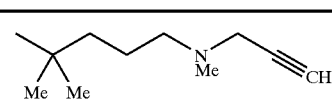 | 29 | 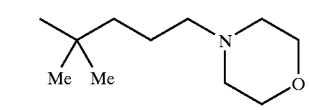 |
| 15 | 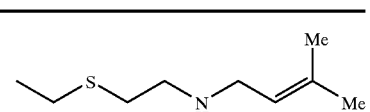 | 30 | 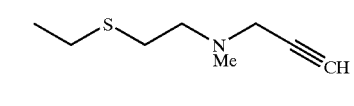 |
|  |  | 31 | 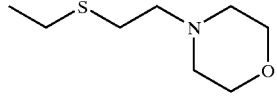 |
TABLE 26
(I-J-3)
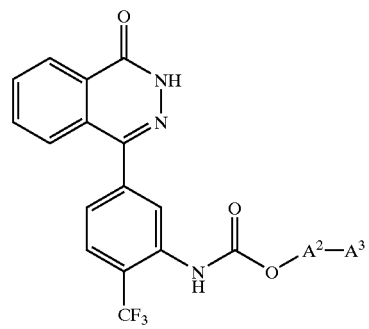
| No. | —A²—A³ | No. | —A²—A³ |
|---|---|---|---|
| 1 | 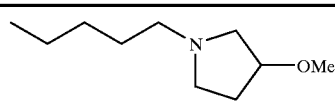 | 16 | 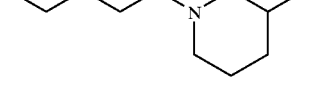 |
| 2 | 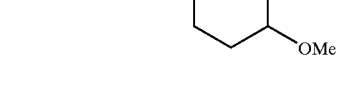 | 17 | 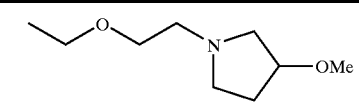 |
| 3 | 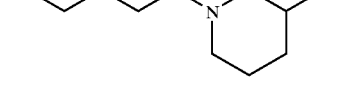 | 18 | 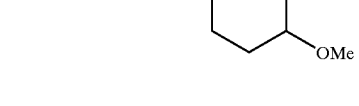 |

TABLE 26-continued
(I-J-3)
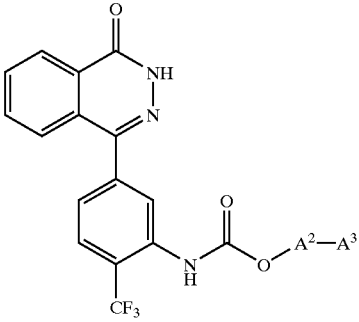
| No. | —A²—A³ | No. | —A²—A³ |
|---|---|---|---|
| 4 | 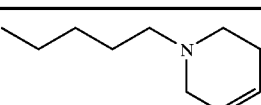 | 19 | 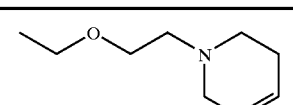 |
| 5 | 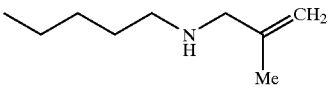 | 20 | 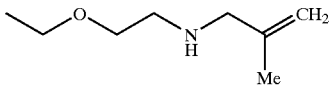 |
| 6 | 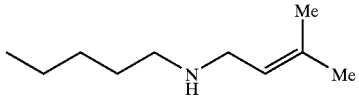 | 21 | 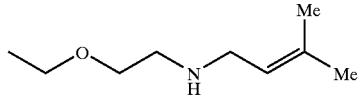 |
| 7 | 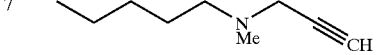 | 22 | 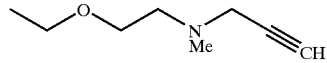 |
| 8 | 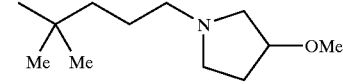 | 23 | 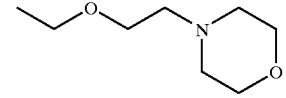 |
| 9 | 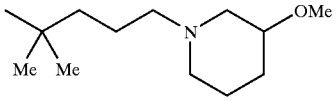 | 24 | 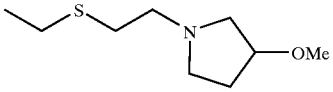 |
| 10 | 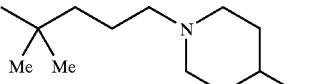 | 25 | 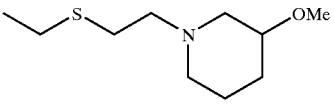 |
| 11 | 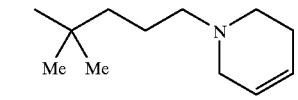 | 26 | 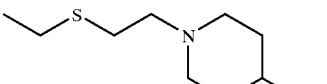 |
| 12 | 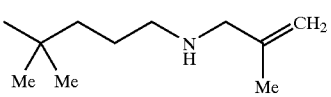 | 27 | 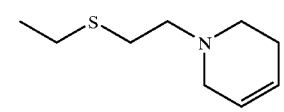 |
| 13 | 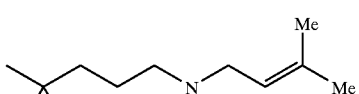 | 28 | 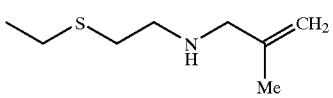 |

TABLE 26-continued
(I-J-3)
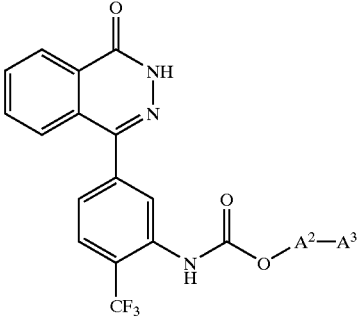
| No. | —A²—A³ | No. | —A²—A³ |
|---|---|---|---|
| 14 | 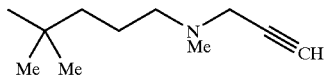 | 29 | 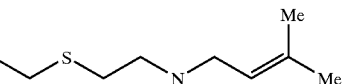 |
| 15 | 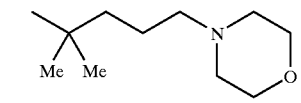 | 30 | 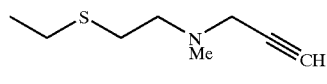 |
|  |  | 31 | 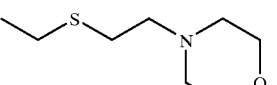 |
TABLE 27
(I-K-3)
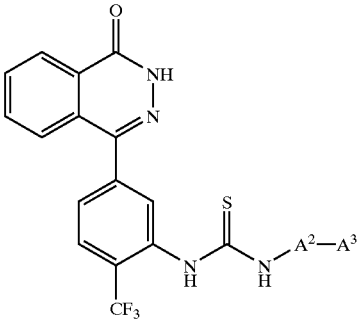
| No. | —A²—A³ | No. | —A²—A³ |
|---|---|---|---|
| 1 | 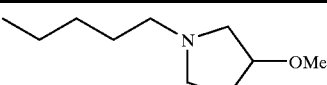 | 16 | 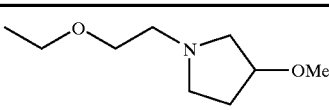 |
| 2 | 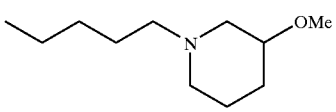 | 17 | 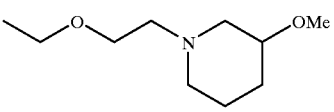 |
| 3 | 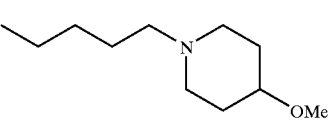 | 18 | 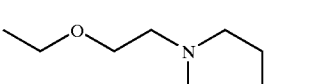 |

TABLE 27-continued
(I-K-3)
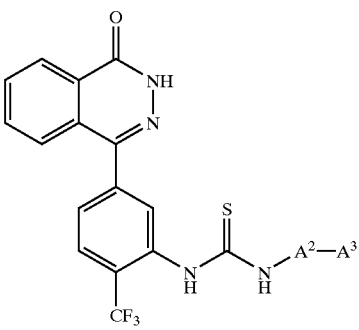
| No. | —A²—A³ | No. | —A²—A³ |
|---|---|---|---|
| 4 | 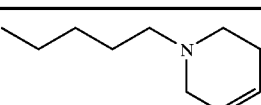 | 19 | 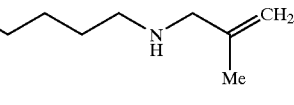 |
| 5 | 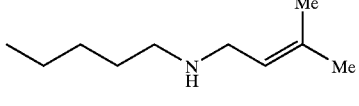 | 20 | 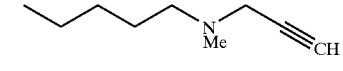 |
| 6 | 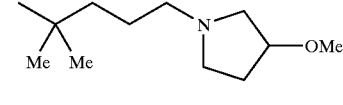 | 21 | 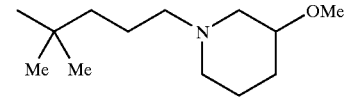 |
| 7 | 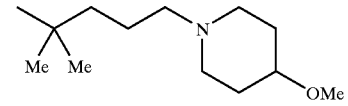 | 22 | 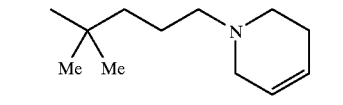 |
| 8 | 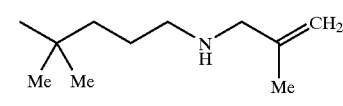 | 23 | 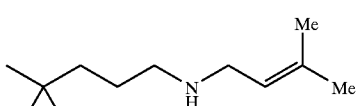 |
| 9 | 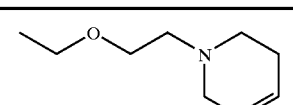 | 24 | 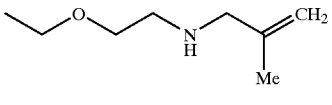 |
| 10 | 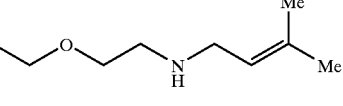 | 25 | 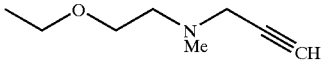 |
| 11 | 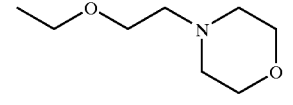 | 26 | 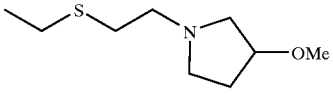 |
| 12 | 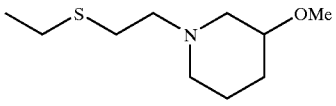 | 27 | 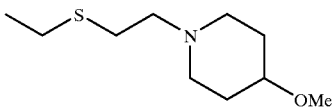 |
| 13 | 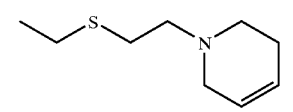 | 28 | 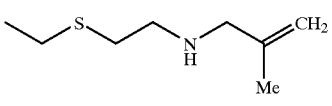 |

TABLE 27-continued (I-K-3)

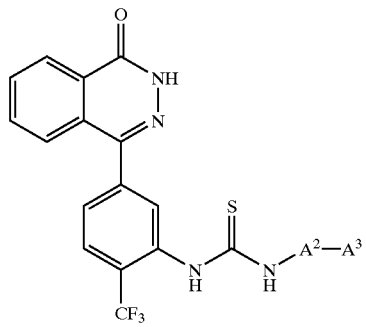

| No. | —A²—A³ | No. | —A²—A³ |
|---|---|---|---|
| 14 | 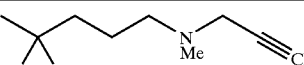 | 29 |  |
| 15 |  | 30 | 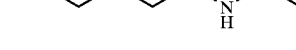 |
|  |  | 31 | 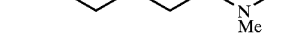 |

Processes for the Preparation of the Compound of the Present Invention

The compounds of formula (I) of the present invention may be prepared by following, described in example or known methods.

[1] In the compounds of formula (I) of the present invention, the compound in which $A^1$ is —$NR^3C(O)$— or —$CH_2$—$NR^7C(O)$, that is the compounds of the formula (I-1)

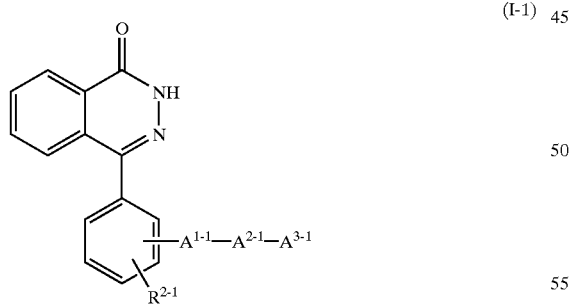

wherein $A^{1-1}$ is —$NR^3C(O)$— or —$CH_2$—$NR^7C(O)$—, $A^{2-1}, A^{3-1}$ and $R^{2-1}$ are the same meaning as $A^2, A^3$ and $R^2$ respectively, with the proviso that the amino group included in the group represented by $A^{2-1}$ is protected if necessary, —COOH, hydroxy, amino, amidino or guanidino group included in the group represented by $A^{3-1}$ is protected if necessary, the amino group included in the group represented by $R^{2-1}$ is protected if necessary, protective group for —COOH means, for example, methyl, ethyl, t-butyl, benzyl, etc., protective group for hydroxy means, for example, methoxymethyl, tetrahydropyranyl, t-butyldimethylsilyl, acetyl, benzyl etc., protective group for amino means, for example, benzyloxycarbonyl, t-butoxycarbonyl, trifluoroacetyl, etc., the other symbols are the same meaning as hereinbefore defined may be prepared by amidation of the compound of the formula (II)

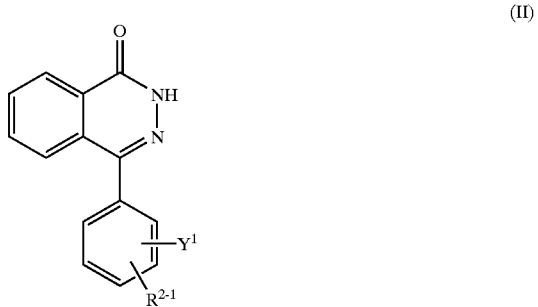

wherein $Y^1$ is —$NHR^3$ or —$CH_2$—$NHR^7$, the other symbols are the same meaning as hereinbefore defined with the compound of the formula (III)

$$HOOC—A^{2-1}—A^{3-1}$$ (III)

wherein all symbols are the same meaning as hereinbefore defined.

The amidation is known per se and can be carried out by methods for example:

(1) using an acid halide,
(2) using a mixed acid anhydride,
(3) using a condensing agent, etc.
These methods are explained as follows.

1) The method using an acid halide may be carried out, for example, by reacting a carboxylic acid with an acid halide (oxalyl chloride or thionyl chloride, etc.) in an inert organic solvent (chloroform, methylene chloride, diethyl ether or tetrahydrofuran, etc.) or without a solvent at from −20° C. to the reflux temperature of the solvent, and then by reacting the acid halide obtained with a corresponding amine in the presence of a tertiary amine (pyridine, triethylamine, dimethylaniline or dimethylaminopyridine, etc.) in an inert organic solvent (chloroform, methylene chloride, diethyl ether or tetrahydrofuran, etc.), at a temperature of from 0° C. to 40° C.

2) The method using a mixed acid anhydride may be carried out, for example, by reacting a carboxylic acid and an acid halide (pivaloyl chloride, tosyl chloride or mesyl chloride, etc.) or an acid derivative (ethyl chloroformate or isobutyl chloroformate, etc.) in the presence of a tertiary amine (pyridine, triethylamine, dimethylaniline or dimethylaminopyridine, etc.) in an inert organic solvent (chloroform, methylene chloride, diethyl ether or tetrahydrofuran, etc.) or without a solvent at a temperature of from 0° C. to 40° C., and then by reacting the mixture of acid anhydride obtained with a corresponding amine in an inert organic solvent (chloroform, methylene chloride, diethyl ether or tetrahydrofuran, etc.), at a temperature of from 0° C. to 40° C.

3) The method using a condensing agent (1,3-dicyclohexyl carbodiimide (DCC), 1-ethyl-3-[3-(dimethylamino)propyl]carbodiimide (EDC), 1,1'-carbonyidiimidazole (CDI) or 2-chloro-1-methylpyridinium iodide, etc.) may be carried out, for example, by reacting a carboxylic acid with a corresponding amine using a condensing agent in the presence or absence of a tertiary amine (pyridine, triethylamine, dimethylaniline or dimethylaminopyridine, etc.) in an inert organic solvent (chloroform, methylene chloride, dimethyl formamide or diethyl ether, etc.) or without a solvent, in the presence or absence of 1-hydroxybenztriazole (HOBt) at a temperature of from 0° C. to 40° C.

These reactions 1), 2) and 3) hereinbefore described may be, preferably carried out in an atmosphere of inert gas (argon or nitrogen, etc.) under anhydrous conditions.

[2] In the compounds of formula (I) of the present invention, the compound in which $A^1$ is —$NR^5SO_2$—, that is the compounds of the formula (I-2)

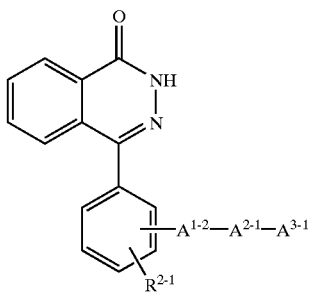

(I-2)

wherein $A^{1-2}$ is —$NR^5SO_2$—, the other symbols are the same meaning as hereinbefore defined
may be prepared by sulfonamidation of the compound of the formula (IV)

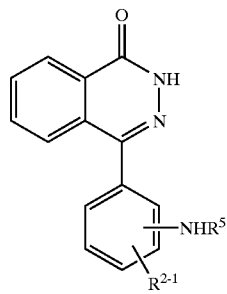

(IV)

wherein all symbols are the same meaning as hereinbefore defined
with the compound of the formula (V)

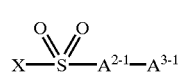

(V)

wherein X is a halogen atom, the other symbols are the same meaning as hereinbefore defined.

The sulfonamidation is known per se and can be carried out in the presence of a tertiary amine (pyridine, triethylamine, dimethylaniline or dimethylaminopyridine, etc.) in an inert organic solvent (chloroform, methylene chloride, diethyl ether or tetrahydrofuran, etc.) at a temperature of from 0° C. to 40° C.

[3] In the compounds of formula (I) of the present invention, the compound in which $A^1$ is —OC(O)—, that is the compounds of the formula (I-3)

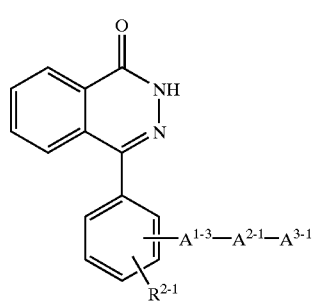

(I-3)

wherein $A^{1-3}$ is —OC(O)—, the other symbols are the same meaning as hereinbefore defined
may be prepared by esterification of the compound of the formula (VI)

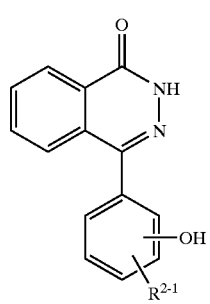

(VI)

wherein all symbols are the same meaning as hereinbefore defined with the compound of the formula (III) hereinbefore described

   (III)

wherein all symbols are the same meaning as hereinbefore defined.

The esterification is known per se and can be carried out by methods for example:

1) using an acid halide,
2) using a mixed acid anhydride,
3) using a condensing agent, etc.

These methods are explained as follows.

1) The method using an acid halide may be carried out, for example, by reacting a carboxylic acid with an acid halide (oxalyl chloride or thionyl chloride, etc.) in an inert organic solvent (chloroform, methylene chloride, diethyl ether or tetrahydrofuran, etc.) or without a solvent at from −20° C. to the reflux temperature of the solvent, and then by reacting the acid halide obtained with a corresponding alcohol in the presence of a tertiary amine (pyridine, triethylamine, dimethylaniline or dimethylaminopyridine, etc.) in an inert organic solvent (chloroform, methylene chloride, diethyl ether or tetrahydrofuran, etc.), at a temperature of from 0° C. to 40° C.

2) The method using a mixed acid anhydride may be carried out, for example, by reacting a carboxylic acid and an acid halide (pivaloyl chloride, tosyl chloride or mesyl chloride, etc.) or an acid derivative (ethyl chloroformate or isobutyl chloroformate, etc.) in the presence of a tertiary amine (pyridine, triethylamine, dimethylaniline or dimethylaminopyridine, etc.) in an inert organic solvent (chloroform, methylene chloride, diethyl ether or tetrahydrofuran, etc.) or without a solvent at a temperature of from 0° C. to 40° C., and then by reacting the mixture of acid anhydride obtained with a corresponding alcohol in an inert organic solvent (chloroform, methylene chloride, diethyl ether or tetrahydrofuran, etc.), at a temperature of from 0° C. to 40° C.

3) The method using a condensing agent (1,3-dicyclohexyl carbodiimide (DCC), 1-ethyl-3-[3-(dimethylamino)propyl]carbodiimide (EDC), 1,1'-carbonyldiimidazole (CDI) or 2-chloro-1-methylpyridinium iodide, etc.) may be carried out, for example, by reacting a carboxylic acid with a corresponding alcohol using a condensing agent in the presence or absence of a tertiary amine (pyridine, triethylamine, dimethylaniline or dimethylaminopyridine, etc.) in an inert organic solvent (chloroform, methylene chloride, dimethyl formamide or diethyl ether, etc.) or without a solvent, in the presence or absence of 1-hydroxybenztriazole (HOBt) at a temperature of from 0° C. to 40° C.

These reactions 1), 2) and 3) hereinbefore described may be preferably carried out in an atmosphere of inert gas (argon or nitrogen, etc.) under anhydrous conditions.

[4] In the compounds of formula (I) of the present invention, the compound in which $A^1$ is —$CH_2$—O—, that is the compounds of the formula (I-4)

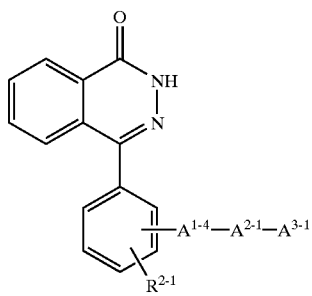

wherein $A^{1-4}$ is —$CH_2$—O—, the other symbols are the same meaning as hereinbefore defined (a) may be prepared by etherification of the compound of the formula (VII-a)

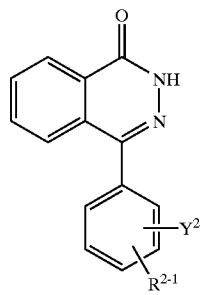

wherein $Y^2$ is —$CH_2$—OH, the other symbols are the same meaning as hereinbefore defined
with the compound of the formula (VIII-a)

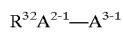   (VIII-a)

wherein $R^{32}$ is leaving group (for example, a halogen atom, mesyl or tosyl, etc.), the other symbols are the same meaning as hereinbefore defined, (b) may be prepared by etherification of the compound of the formula (VII-b)

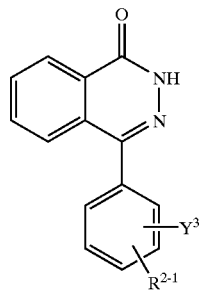

wherein $Y^3$ is —$CH_2$—$R^{32}$, the other symbols are the same meaning as hereinbefore defined
with the compound of the formula (VIII-b)

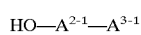   (VIII-b)

wherein all the symbols are the same meaning as hereinbefore defined, or (c) may be prepared by etherication of the compound of the formula (VII-a) hereinbefore described with the compound of the formula (VIII-b) hereinbefore described.

The etherication of a compound of formula (VII-a) and a compound of formula (VIII-a), and a compound of formula (VII-b) and a compound of formula (VIII-b) is known per se and can be carried out, for example, in an inert organic solvent (dimethylformamide, dimethylsulfoxide, chloroform, methylene chloride, diethyl ether or tetrahydrofuran, etc.) using hydroxide of alkali metal (sodium hydroxide, potassium hydroxide, lithium hydroxide, etc.), hydroxide of alkaline earth metal (barium hydroxide, calcium hydroxide, etc.) or carbonate (sodium carbonate, potassium carbonate, etc.) or an aqueous solution thereof or a mixture thereof at a temperature of from 0° C. to 100° C.

The etherication of a compound of formula (VII-a) and a compound of formula (VII-a), and a compound of formula (VII-b) and a compound of formula (VIII-b) is known per se and can be carried out, for example, in an organic solvent (dichloromethane, ether, tetrahydrofuran, acetonitrile, benzene, toluene, etc.) in the presence of azo compound (azodicarboxylic acid diethyl, azodicarboxylic acid diisopropyl, 1,1'-(azodicarbonyl)dipiperidine, 1,1'-azobis(N,N-dimethylformamide), etc.) and phosphine compound (triphenylphosphine, tributylphosphine, trimethylphosphine, etc.) with a corresponding alcohol compound at a temperature of from 0° C. to 60° C.

[5] In the compounds of formula (I) of the present invention, the compound in which $A^1$ is —$NR^{13}$—, that is the compounds of the formula (I-5)

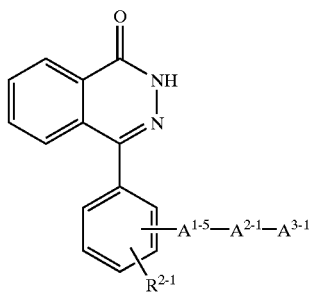

(I-5)

wherein $A^{1-5}$ is —$NR^{13}$—, the other symbols are the same meaning as hereinbefore defined (a) may be prepared by reacting the compound of the formula (IV) hereinbefore described with the compound of the formula (IX)

$Y^4$—$A^{2-1}$—$A^{3-1}$ (IX)

wherein $Y^4$ is leaving group (for example, a halogen atom, etc.), the other symbols are the same meaning as hereinbefore defined, or (b) the compound of the formula (X)

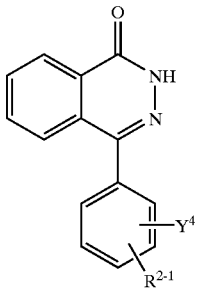

(X)

wherein all symbols are the same meaning as hereinbefore defined with the compound of the formula (XI)

$R^{13}HN$—$A^{2-1}$—$A^{3-1}$ (XI)

wherein all symbols are the same meaning as hereinbefore defined.

The reaction of the compound of the formula (IV) with the compound of the formula (IX) and the reaction of the compound of the formula (X) with the compound of the formula (XI) are known per se and can be carried out in the presence or absence of a base (triethylamine, pyridine, etc.) in an inert organic solvent (dimethyl formamide, dimethylsulfoxide, chloroform, methylene chloride, diethyl ether, tetrahydrofuran, acetonitrile, etc.) at a temperature of from 0° C. to 100° C.

(c) In the compounds of formula (I-5) of the present invention, the compound in which $A^{2-1}$ is C1–8 alkylene, C2–8 alkenylene, —(C1–4 alkylene)—O—(C1–4 alkylene)—, —(C1–4 alkylene)—S—(C1–4 alkylene)—, —(C1–4 alkylene)—$NR^{14}$—(C1–4 alkylene)—, —(C1–8 alkylene)—(Cyc$^1$)—, or —(C1–4 alkylene)—(Cyc$^1$)—(C1–4 alkylene), that is the compounds of the formula (I-5')

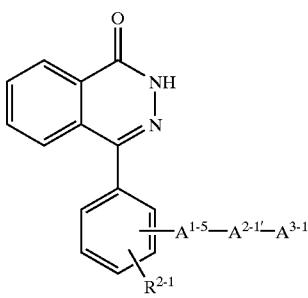

(I-5')

wherein $A^{2-1}$ is C1–8 alkylene, C2–8 alkenylene, —(C1–4 alkylene)—O—(C1–4 alkylene)—, —(C1–4 alkylene)—S—(C1–4 alkylene)—, —(C1–4 alkylene)—$NR^{14}$—(C1–4 alkylene)—, —(C1–8 alkylene)—(Cyc$^1$), or —(C1–4 alkylene)—(Cyc$^1$)—(C1–4 alkylene), the other symbols are the same meaning as hereinbefore defined may be prepared by reductive amination of the compound of the formula (IV)

hereinbefore described with the compound of the formula (XI)

OHC—A$^{2\text{-}1''}$—A$^{3\text{-}1}$ (XII)

wherein A$^{2\text{-}1''}$ is C1–7 alkylene, C2–7 alkenylene, —(C1–3 alkylene)—O—(C1–4 alkylene)—, —(C1–3 alkylene)—S—(C1–4 alkylene)—, —(C1–3 alkylene)—NR$^{14}$—(C1–4 alkylene)—, —(C1–7 alkylene)—(Cyc$^1$)—, or —C1–3 alkylene)—(Cyc$^1$)—(C1–4 alkylene)—, the other symbols are the same meaning as hereinbefore defined.

The reductive amination is known per se and can be carried out, for example, in an organic solvent (methanol, ethanol, etc.), using reductive agent (sodium cyanoborohydride, sodium borohydride, sodium triacetoxyborohydride, etc.), if necessary, in the presence of an acid (acetic acid, hydrochloric acid, etc.) at a temperature of from −20° C. to 60° C.

[6] In the compounds of formula (I) of the present invention, the compound in which A$^1$ is —CH$_2$—NR$^6$—, that is the compounds of the formula (I-6)

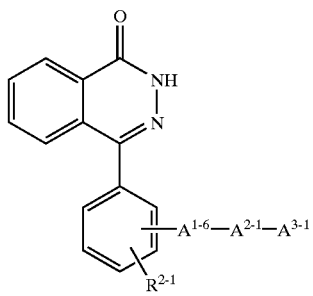
(I-6)

wherein A$^{1\text{-}6}$ is —CH$_2$—NR$^6$—, the other symbols are the same meaning as hereinbefore defined (a) may be prepared by reacting the compound of the formula (XIII)

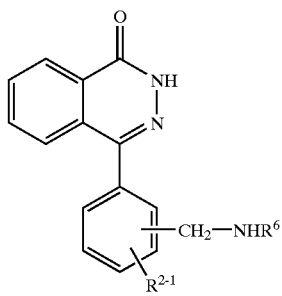
(XIII)

wherein all symbols are the same meaning as hereinbefore defined with the compound of the formula (IX) hereinbefore described, (b) may be prepared by reacting the compound of the formula (X) hereinbefore described with the compound of the formula (XIV)

Y$^4$—CH$_2$—A$^{2\text{-}1}$—A$^{3\text{-}1}$ (XIV)

wherein all symbols are the same meaning as hereinbefore defined, or (c) may be prepared by reductive amination of the compound of the formula (XV)

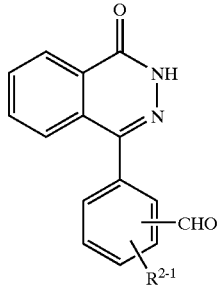
(XV)

wherein all symbols are the same meaning as hereinbefore defined with the compound of the formula (XI) hereinbefore described.

The reaction of the compound of the formula (XIII) with the compound of the formula (IX) and the reaction of the compound of the formula (X) with the compound of the formula (XIV) are known per se and can be carried out by the same method as the reaction of the compound of the formula (IV) hereinbefore described and the compound of the formula (IX).

The reductive amination of the compound of the formula (XV) with the compound of the formula (XI) can be carried out by the same method as the reaction of the compound of the formula (IV) hereinbefore described and the compound of the formula (XII).

[7] In the compounds of formula (I) of the present invention, the compound in which A$^1$ is —NR$^8$C(O)NR$^9$—, that is the compounds of the formula (I-7)

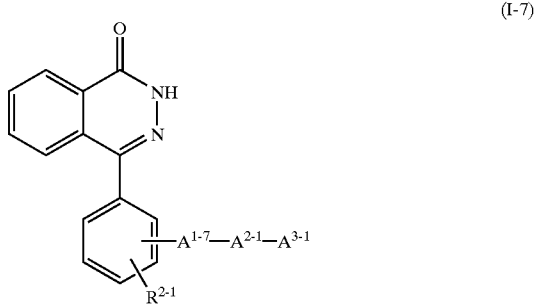
(I-7)

wherein A$^{1\text{-}7}$ is —NR$^8$C(O)NR$^9$—, the other symbols are the same meaning as hereinbefore defined may be prepared by reacting the compound of the formula (IV) hereinbefore described with the compound of the formula (XVI)

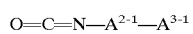
O=C=N—A$^{2\text{-}1}$—A$^{3\text{-}1}$ (XVI)

wherein all symbols are the same meaning as hereinbefore defined.

The reaction is known per se and can be carried out in an organic solvent (tetrahydrofuran, methylene chloride, diethyl ether, etc.) at a temperature of from 0° C. to 100° C.

[8] In the compounds of formula (I) of the present invention, the compound in which A$^1$ is —NR$^{11}$C(S)NR$^{12}$—, that is the compounds of the formula (I-8)

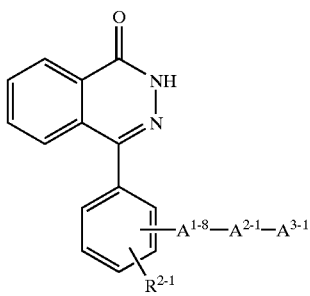

(I-8)

wherein $A^{1-7}$ is —$NR^{11}C(S)NR^{12}$—, the other symbols are the same meaning as hereinbefore defined may be prepared by reacting the compound of the formula (IV) hereinbefore described with the compound of the formula (XVII)

$$S=C=N-A^{2-1}-A^{3-1} \quad (XVII)$$

wherein all symbols are the same meaning as hereinbefore defined.

The reaction can be carried out by the same method as the reaction of the compound of the formula (IV) hereinbefore described and the compound of the formula (XVI).

[9] In the compounds of formula (I) of the present invention, the compound in which $A^1$ is —$NR^{10}OC(O)O$—, that is the compounds of the formula (I-9)

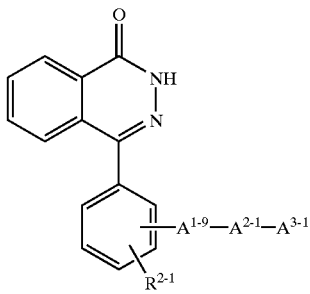

(I-9)

wherein $A^{1-9}$ is —$NR^{10}OC(O)O$—, the other symbols are the same meaning as hereinbefore defined may be prepared by reacting the compound of the formula (IV) hereinbefore described with the compound of the formula (XVIII)

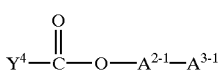

(XVIII)

wherein all symbols are the same meaning as hereinbefore defined.

The reaction is known per se and can be carried out, for example, in an organic solvent (tetrahydrofuran, methylene chloride, diethyl ether, etc.) at a temperature of from −78° C. to 40° C.

[10] In the compounds of formula (I) of the present invention, the compound in which $A^1$ is —$NR^4C(S)$—, that is the compounds of the formula (I-10)

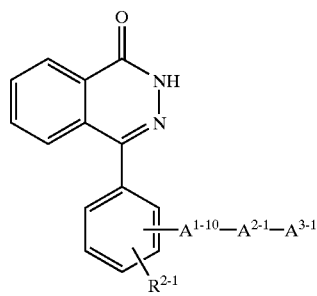

(I-10)

wherein $A^{1-10}$ is —$NR^4C(S)$—, the other symbols are the same meaning as hereinbefore defined may be prepared by thiocarbonylation of the compound of the formula (I-1')

(I-1')

wherein $A^{1-1'}$ is —$NR^3C(O)$—, the other symbols are the same meaning as hereinbefore defined.

The reaction is known per se and can be carried out in an organic solvent (dioxane, benzene, toluene, xylene, tetrahydrofuran, etc.), using Lawesson's reagent at a temperature of from 20° C. to 150° C.

[11] In the compounds of formula (I) of the present invention, the compound in which $A^1$ is

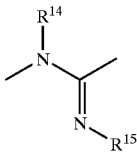

that is the compounds of the formula (I-11)

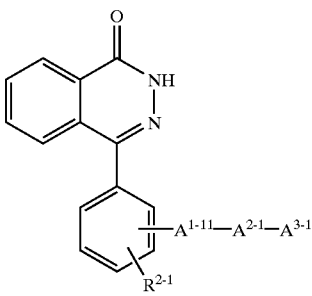

(I-11)

wherein $A^{1-11}$ is

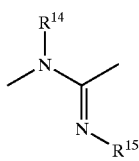

the other symbols are the same meaning as hereinbefore defined may be prepared by reacting the compound of the formula (IV) hereinbefore described with the compound of the formula (XIX)

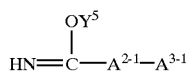 (XIX)

wherein $Y^5$ is C1–4 alkyl, the other symbols are the same meaning as hereinbefore defined.

The reaction is known per se and can be carried out, for example, in an organic solvent (methanol, ethanol, etc.) at a temperature of from 0° C. to 50° C.

[12] In the compounds of formula (I) of the present invention, the compound in which $A^3$ is —$NR^{17}R^{18}$ or hetero ring as shown by

wherein the ring represents $Cyc^2$, which comprises at least one nitrogen atom (the nitrogen atom is connected to $A^2$), that is the compounds of the formula (I-12)

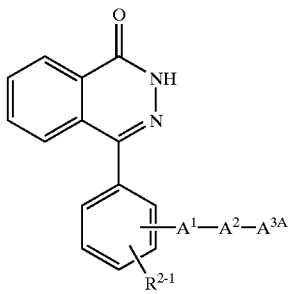 (I-12)

wherein $A^3$ is —$NR^{17}R^{18}$ or hetero ring as show

, the other symbols are the same meaning as hereinbefore defined may be prepared by reacting the compound of the formula (I-12')

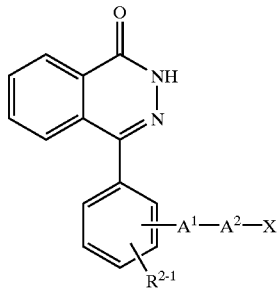 (I-12')

wherein all symbols are the same meaning as hereinbefore defined with the compound of the formula (XX)

H—$NR^{17}R^{18}$ (XX)

wherein all symbols are the same meaning as hereinbefore defined, or the compound of the formula (YY)

 (YY)

wherein all symbols are the same meaning as hereinbefore defined.

The reaction of the compound of the formula (I-12') with the compound of the formula (XX) or the compound of the formula (YY) may be carried out by the same method as [5] (a) hereinbefore described.

[13] In the compounds of formula (I) of the present invention, the compound wherein at least one of $A^2$, $A^3$ or $R^2$ is —COOH, hydroxy, amino, amidino guanidino, or a group including —COOH, hydroxy, amino, amidino or guanidino, that is the compounds of the formula (I-13)

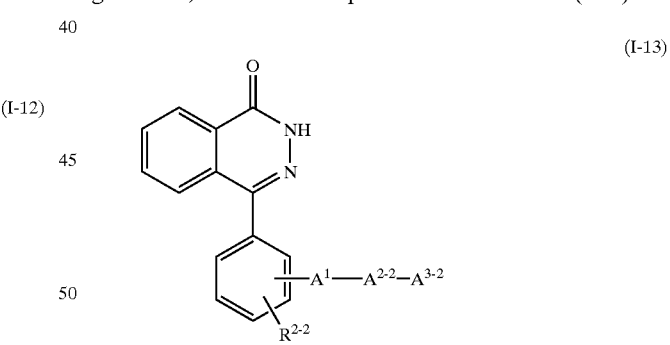 (I-13)

wherein $A^{2-2}$, $A^{3-2}$ or $R^{2-2}$ are the same meaning as $A^2$, $A^3$ or $R^2$, with the proviso that at least one of $A^2$, $A^3$ or $R^2$ is —COOH, hydroxy, amino, amidino, guanidino, or the group including —COOH, hydroxy, amino, amidino or guanidino, and the other symbols are the same meaning as hereinbefore defined may be prepared by subjecting to a deprotection reaction a compound of the formula (I-1), (I-2), (I-3), (I-4), (I-5), (I-6), (I-7), (I-8), (I-9), (I-10), (I-11) and (I-12) hereinbefore described by alkali hydrolysis, deprotection reaction under acidic conditions, deprotection reaction of silyl group or deprotection reaction by hydrogenation.

Deprotection reaction by alkali hydrolysis is known, for example, it is carried out in an organic solvent (methanol, tetrahydrofuran, dioxane, etc.) using hydroxide of alkali metal (sodium hydroxide, potassium hydroxide, lithium hydroxide, etc.), hydroxide of alkaline earth metal (barium hydroxide, calcium hydroxide, etc.) or carbonate (sodium carbonate, potassium carbonate, etc.) or an aqueous solution thereof or a mixture thereof at a temperature of from 0° C. to 40° C.

Deprotection reaction under acidic conditions is known, for example, it is carried out in an organic solvent (dichloromethane, chloroform, dioxane, ethyl acetate, anisole, etc.), in organic acid (acetic acid, trifluoroacetic acid, methanesulfonic acid, trimethylsilyl iodide etc.) or inorganic acid (hydrochloric acid, sulfuric acid, etc.) or a mixture thereof (hydrobromic acid-acetic acid etc.) at a temperature of from 0° C. to 100° C.

Deprotection reaction of silyl group is known, for example, it is carried out in a water-soluble organic solvent (tetrahydrofuran, acetonitrile, etc.), using tetrabutylammonium fluoride at a temperature of from 0° C. to 40° C.

Deprotection reaction by hydrogenation is known, for example, it is carried out in an inert solvent [ether (e.g. tetrahydrofuran, dioxane, dimethoxyethane, diethyl ether, etc.), ketone (e.g. acetone, methylethylketone, etc.), nitrile (e.g. acetonitrile etc.), amide (e.g. dimethylformamide etc.), water, ethyl acetate, acetic acid or a mixture of two or more thereof], in the presence of hydrogenating catalyst (e.g. palladium-carbon, palladium black, palladium, palladium hydroxide, platinum hydroxide, platinum dioxide, nickel, Raney-nickel, ruthenium chloride, etc.) in the presence or absence of inorganic acid (e.g. hydrochloric acid, sulfuric acid, hypochlorous acid, boronic acid, tetrafluoroboronic acid, etc.) or organic acid (e.g. acetic acid, p-toluenesulfonic acid, oxalic acid, trifluoroacetic acid, formic acid etc.), under normal atmosphere or suppressed atmosphere of hydrogen or in the presence of ammonium formate, at a temperature of from 0° C. to 200° C. In use of acid, its salt may be used.

In the present invention deprotection reaction means a comprehensive deprotection reaction easily understood by those skilled in the art, for example, alkali hydrolysis, deprotection reaction under acidic condition, deprotection reaction by hydrogenation. The desired compounds of the present invention can be easily prepared by these reactions.

As should be easily understood by those skilled in the art, methyl, ethyl, t-butyl and benzyl are included in the protective groups for carboxyl, but other groups that can be easily and selectively eliminated may also be used instead. For example, the groups described in T. W. Greene, Protective Groups in Organic Synthesis, Wiley, New York, 1991 may be used.

Methoxymethyl, tetrahydropyranyl, t-butyldimethylsilyl, acetyl and benzyl are included in the protective groups for hydroxy, but other groups that can be easily and selectively eliminated may also be used instead. For example, the groups described in T. W. Greene, Protective Groups in Organic Synthesis, Wiley, New York, 1991 may be used.

Benzyloxycarbonyl, t-butoxycarbonyl and trifluoroacetyl are included in the protective groups for amino, amidino and guanidino but other groups that can be easily and selectively eliminated may also be used instead. For example, the groups described in T. W. Greene, Protective Groups in Organic Synthesis, Wiley, New York, 1991 may be used.

The compounds of formula (II), (III), (IV), (V), (VI), (VII-a), (VII-b), (VIII-a), (VIII-b), (IX), (X), (XI), (XII), (XIII), (XIV), (XV), (XVI), (XVII), (XVIII), (XIX) and (XX) are known per se or may be easily prepared by known methods.

For example, the compounds of formula (XIX) may be prepared by the method described in the following reaction schemes.

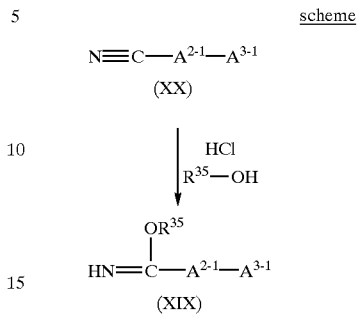

scheme

The all symbols in the reaction schemes are as hereinbefore described.

The compounds of the formula (XX) in the reaction schemes are known per se or may be prepared by known methods.

In each reaction described in the present specification, reaction products may be purified by conventional techniques. For example, purification may be carried out by distillation at atmospheric or reduced pressure, by high performance liquid chromatography, thin layer chromatography or column chromatography using silica gel or magnesium silicate, by washing or by recrystallization, etc. Purification may be carried out after each reaction, or after a series of reactions.

Pharmacological Activities

It has been confirmed that the compounds of the present invention of the formula (I) possess an inhibitory activity against PARP by the following experimental results.

1) Enzyme Assay In Vitro

Methods

The below procedure was carried out with 96 well plate. The reaction mixture contained 50 mM Tris/HCl (pH 8.0, WAKO), 10 mM $MgCl_2$, 5 mM dithiothreitol (sigma), and 0.5 mg/mL activated DNA in 80 $\mu$L. The 10 $\mu$L of test compound was added to the reaction mixture and the reaction was started by addition of 10 $\mu$L of 0.01 $\mu$L PARP (TREVIGEN). The reaction was terminated at 10 minutes by addition of 100 $\mu$L of 20% trichloroacetic acid. The reaction product was collected on a glass fiber filter (GF/C, PACKARD). The radioactivity was measured by topcount (PACKARD). Inhibitory activity of the compound was represented by 50% inhibitory concentration (IC50) calculated 100% of control (distilled water). The results were shown in Table 28.

TABLE 28

| Example No | $IC_{50}$ (nM) |
|---|---|
| 5 | 42 |
| 4 (14) | 88 |
| 5 (10) | 50 |

*The compound as example 5 is trifluoro acetate.

2) Ischemia-reperfusion Injury Model (Brain and Heart)

Model of cerebral or coronary ischemia-reperfusion was prepared according to procedures described previously (Jpn. J. Stroke, 8, 1 (1986), Stroke, 27, 1624–1628 (1996) and Eur. J. Pharmacol., 270, 45 (1994)). This invention compound was effective in ischemia-reperfusion injury model.

Toxicity

The toxicity of the compounds of the present invention is very low and therefore compounds may be considered safe for pharmaceutical use.

Application for Pharmaceuticals

Inhibition of PARP is useful for prevention and/or treatment of various diseases, for example, ischemic diseases (cerebral, myocardial, intestinal, skeletal muscular or retinal ischemia etc.), inflammatory diseases (inflammatory bowel disease, multiple sclerosis or arthritis etc.), neurodegenerative disorders (extrapyramidal disease, Alzheimer's disease or muscular dystrophy etc.), diabetes, shock, head trauma, reanal insufficiency or hyperalgesia etc. Also it is increased the effects of antiretroviral (HIV etc.) or anticancer drugs.

For the purpose above described, the compounds of formula (I) of the present invention and non-toxic salts thereof, acid addition salts thereof and hydrates thereof may normally be administered systemically or locally, usually by oral or parenteral administration.

The doses to be administered are determined depending upon age, body weight, symptom, the desired therapeutic effect, the route of administration, and the duration of the treatment etc. In the human adult, the doses per person per dose are generally between 1 mg and 1000 mg, by oral administration, up to several times per day, and between 0.1 mg and 100 mg, by parenteral administration (preferred into vein) up to several times per day, or continuous administration between 1 and 24 hrs. per day into vein.

As mentioned above, the doses to be used depend upon various conditions. Therefore, there are cases in which doses lower than or greater than the ranges specified above may be used.

The compounds of the present invention may be administered as inner solid compositions or inner liquid compositions for oral administration, or as injections, liniments or suppositories etc. for parenteral administration.

Inner solid compositions for oral administration include compressed tablets, pills, capsules, dispersible powders and granules etc. Capsules contain hard capsules and soft capsules.

In such inner solid compositions, one or more of the active compound(s) is or are, admixed with at least one inert diluent (lactose, mannitol, glucose, $\mu$crystalline cellulose, starch etc.), connecting agents (hydroxypropyl cellulose, polyvinylpyrrolidone, magnesium metasilicate aluminate etc.), disintegrating agents (cellulose calcium glycolate etc.), lubricating agents (magnesium stearate etc.), stabilizing agents, assisting agents for dissolving (glutamic acid, asparaginic acid etc.) etc. to prepare pharmaceuticals by known methods. The pharmaceuticals may, if desired, be coated with material such as sugar, gelatin, hydroxypropyl cellulose or hydroxypropyl cellulose phthalate etc., or be coated with two or more films. And further, coating may include containment within capsules of absorbable materials such as gelatin.

Inner liquid compositions for oral administration include pharmaceutically-acceptable water-agents, suspensions, emulsions, syrups and elixirs etc. In such liquid compositions, one or more of the active compound(s) is or are comprised in inert diluent(s) commonly used in the art (purified water, ethanol or mixture thereof etc.). Besides inert diluents, such compositions may also comprise adjuvants such as wetting agents, suspending agents, emulsifying agents, sweetening agents, flavouring agents, perfuming agents, preserving agents and buffer agents etc.

Injections for parenteral administration include solutions, suspensions and emulsions and solid injections which are dissolved or suspended in solvent when it is used. One or more active compound(s) is or are dissolved, suspended or emulsified in a solvent when such compositions are used. Aqueous solutions or suspensions include distilled water for injection and physiological salt solution, plant oil, propylene glycol, polyethylene glycol and alcohol such as ethanol etc., and mixture thereof. Such compositions may comprise additional diluents such as stabilizing agent, assisting agents for dissolving (glutamic acid, asparaginic acid, POLYSOLBATE80 (registered trade mark) etc.), suspending agents, emulsifying agents, dispersing agents, buffer agents, preserving agents etc. They may be sterilized for example, by filtration through a bacteria-retaining filter, by incorporation of sterilizing agents in the compositions or by irradiation. They may also be manufactured in the form of sterile solid compositions and which can be dissolved in sterile water or some other sterile diluent for injection immediately before use.

Other compositions for parenteral administration include liquids for external use, ointments, endermic liniments, aerosols, spray compositions, suppositories and pessaries for vaginal administration etc. which comprise one or more of the active compound(s) and may be prepared by known methods.

Spray compositions may comprise additional substances other than inert diluents: e.g. stabilizing agents such as sodium hydrogen sulfate, stabilizing agents to give isotonicity, isotonic buffer such as sodium chloride, sodium citrate, citric acid. For preparation of such spray compositions, for example, the method described in the U.S. Pat. No. 2,868,691 or 3,095,355 may be used.

BEST MODE FOR CARRYING OUT THE INVENTION

The following reference examples and examples illustrate the present invention, but do not limit the present invention.

The solvents in the parentheses show the developing or eluting solvents and the ratios of the solvents used are by volume in chromatographic separations or TLC.

The solvents in the parentheses in NMR show the solvents used in measurement.

REFERENCE EXAMPLE 1

3-t-Butyidimethylsilyloxymethyl-1-bromobenzene

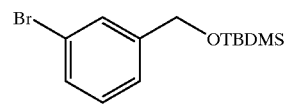

To a solution of 3-bromobenzylalcohol (18.7 g) in dimethylformamide (100 ml) was added imidazole (13.6 g) and t-butyidimethylsilylchloride (15.8 g). The mixture was stirred for 2 hours at room temperature. The reaction mixture was poured into water (300 ml) and then extracted with a mixture of hexane and ethyl acetate (1:1, 100 ml×2). The extract was washed with 0.5N hydrochloric acid, water and a saturated aqueous solution of sodium chloride, successively, dried over anhyrous sodium sulfate and concentrated to give the title compound (30.1 g) having the following physical data.

TLC: Rf 0.69 (Hexane:Ethyl acetate=19:1); NMR (CDCl$_3$): δ 7.37 (br-s, 1H), 7.26 (m, 1H), 7.16–7.06 (m, 2H), 4.60 (s, 2H), 0.84 (s, 9H), 0.00 (s, 6H).

EXAMPLE 1

4-(3-(Hydroxymethyl)phenyl)-2H-phthalazin-1-one

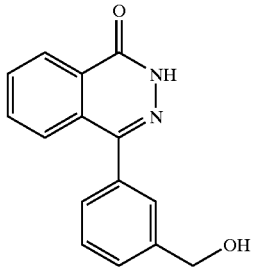

To a suspension of magnesium chip (2.55 g) in tetrahydrofuran (100 ml) was added 1,2-dibromoethane (a few drops). To the mixture was added the compound prepared in reference example 1 (30.1 g) dropwise in order to keep the reflux condition, and then the mixture was refluxed for 1 hour. After cooling the reaction mixture to room temperature, a solution of phthalic anhydride (14.8 g) in tetrahydrofuran (100 ml) was added to the reaction mixture at 15° C. The mixture was stirred for 30 minutes at room temperature. 6N hydrochloric acid (100 ml) was added to the reaction mixture and the mixture was stirred at room temperature overnight. The reaction mixture was saturated with sodium chloride and then the organic layer was separated. The aqueous layer was extracted with ethyl acetate. The combined organic layer was washed with a saturated aqueous solution of sodium chloride, dried over anhydrous magnesium sulfate and concentrated. The residue was dissolved into 2N aqueous solution of sodium hydroxide and washed with ether (50 ml). The aqueous layer was acidified by adding 12N hydrochloric acid (25 ml) and extracted with ethyl acetate (200 ml). The extract was washed with a saturated aqueous solution of sodium chloride, dried over anhydrous sodium sulfate and concentrated. The residue was suspended in chloroform. The insoluble phthalic acid was filtered off and the filtrate was concentrated. To a solution of the residue (20.5 g) in ethanol (300 ml) was added 80% hydrazine monohydrate (4 ml) and the mixture was refluxed for 5 hours. The reaction mixture was cooled with ice. The precipitate was washed with ethanol to give the compound of the present invention (7.45 g) having the following physical data.

TLC: Rf 0.50 (Chloroform:Methanol=9:1); NMR (DMSO-d$_6$): δ 12.83 (br-s, 1H), 8.33 (m, 1H), 7.92–7.84 (m, 2H), 7.68 (m, 1H), 7.54–7.42 (m, 4H), 5.29 (t, J=5.4 Hz, 1H), 4.59 (d, J=5.4 Hz, 2H).

REFERENCE EXAMPLE 2

4-(3-(Chloromethyl)phenyl)-2H-phthalazin-1-one

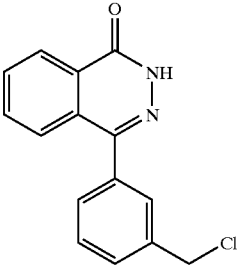

To a solution of the compound prepared in example 1 (2.52 g) in dimethylformamide (30 ml) were added 2,4,6-collidine (3.96 ml), mesyl chloride (929 μl) and lithium chloride (593 mg). The mixture was stirred for 2 hours at room temperature. The reaction mixture was poured into water and the precipitate was collected by filtration. The precipitate was washed with water, methanol and ether to give the title compound (2.50 g) having the following physical data.

TLC: Rf 0.44 (Chloroform:Methanol=10:1); NMR (DMSO-d$_6$): δ 12.87 (s, 1H), 8.34 (m, 1H), 7.94–7.84 (m, 2H), 7.70–7.54 (m, 5H), 4.87 (s, 2H).

REFERENCE EXAMPLE 3

4-(3-(Azidomethyl)phenyl)-2H-phthalazin-1-one

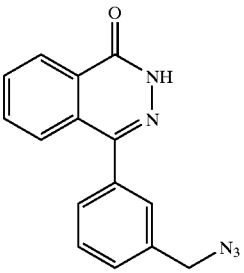

To a solution of the compound prepared in reference example 2 (1.00 g) in dimethylformamide (30 ml) was added sodium azide (722 mg) and the mixture was stirred for 1 hours at 90° C. The reaction mixture was poured into water (200 ml) and the precipitate was collected by filtration. The precipitate was washed with water, methanol and ether to give the title compound (945 mg) having the following physical data.

TLC: Rf 0.44 (Chloroform:Methanol=10:1); NMR (DMSO-d$_6$): δ 12.87 (s, 1H), 8.34 (m, 1H), 7.92–7.86 (m, 2H), 7.67 (m, 1H), 7.62–7.52 (m, 4H), 4.57 (s, 2H).

EXAMPLE 2

4-(3-(Aminomethyl)phenyl)-2H-phthalazin-1-one Hydrochloride

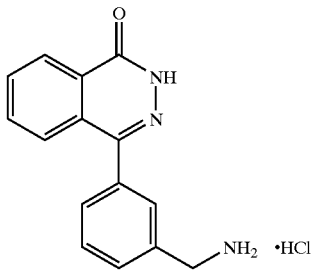

A suspension of the compound prepared in reference example 3 (707 mg) and platinum(IV) oxide (70 mg) in tetrahydrofuran (30 ml) and ehanol (7.5 ml) was stirred for 1 hour under an atmosphere of hydrogen. The catalyst was filtered off and filtrate was concentrated. The residue was dissolved into tetrahydrofuran (15 ml) and added 4N solution of hydrochloric acid in ethyl acetate (2 ml) and the precipitate was collected by filtration. The precipitate was washed with ethyl acetate to give the present invention (725 mg) having the following physical data.

TLC: Rf 0.22 (Chloroform:Methanol:28% Ammonia water=100:10:1); NMR (DMSO-$d_6$): δ 12.91 (s, 1H), 8.46 (br, 3H), 8.35 (m, 1H), 7.94–7.87 (m, 2H), 7.78–7.70 (m, 2H), 7.68–7.58 (m, 3H), 4.12 (br-q, J=5.4 Hz, 2H).

EXAMPLE 3

4-(3-(Dimethylaminomethyl)phenyl)-2H-phthalazin-1-one Hydrochloride

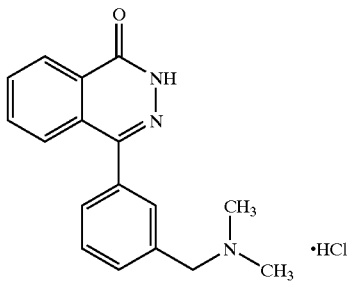

To a solution of the compound prepared in reference example 2 (135 mg) in dimethylformamide (3 ml) was added 2.0M solution of dimethylamine in methanol (750 μl) and the mixture was stirred for 30 minutes at 90° C. The reaction mixture was diluted with ethyl acetate and washed with water, a saturated aqueous solution of sodium bicarbonate and a saturated aqueous solution of sodium chloride, successively, dried over anhydrous sodium sulfate and concentrated. To a solution of the residue in ethyl acetate was added 4N solution of hydrochloric acid in ethyl acetate (0.5 ml) and the precipitate was collected by filtration. The precipitate was washed with ethyl acetate to give the compound of the present invention (139 mg) having the following physical data.

TLC: Rf 0.35 (Chloroform:Methanol=9:1); NMR (DMSO-$d_6$): δ 12.92 (s, 1H), 10.64 (br, 1H), 8.34 (m, 1H), 7.94–7.87 (m, 2H), 7.79–7.61 (m, 5H), 4.36 (d, J=5.1 Hz, 2H), 2.73 (d, J=5.1 Hz, 6H).

REFERENCE EXAMPLE 4

4-(3-Formylphenyl)-2H-phthalazin-1-one

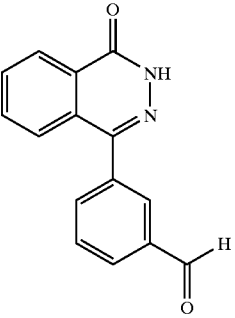

To a solution of the compound prepared in reference example 1 (1.01 g) in dimethylformamide (40 ml) was added manganese(IV) oxide (6.96 g) and the mixture was stirred for 1 hour at room temperature. The catalyst was filtered off and the filtrate was concentrated The residue was washed with ethanol to give the title compound (830 mg) having the following physical data.

TLC: Rf 0.54 (Chloroform:Methanol=9:1); NMR (DMSO-$d_6$): δ 12.93 (br-s, 1H), 10.11 (s, 1H), 8.35 (m, 1H), 8.11 (s, 1H), 8.06 (d, J=7.5 Hz, 1H), 7.96–7.88 (m, 3H), 7.78 (t, J=7.5 Hz, 1H), 7.68 (m, 1H).

EXAMPLE 4

4-(3-(5-(t-Butoxycarbonylamino)valerylamino)phenyl)-2H-phthalazin-1-one

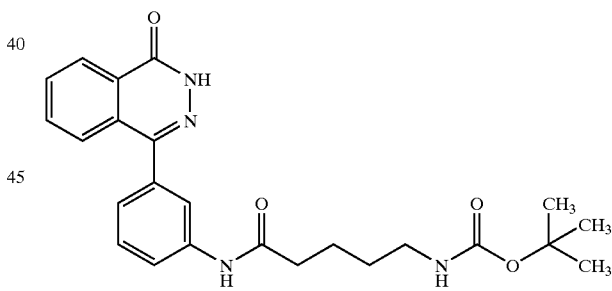

To a solution of 4-(3-aminophenyl)-2H-phthalazin-1-one (825 mg) in dimethylformamide (9.00 ml) were added 5-t-butoxycarbonylaminopentanoic acid (755 mg), 1-hydroxybenzotriazole (470 mg), triethylamine (0.53 ml) and 1-ethyl-3-(3-dimethylaminopropyl)carbodiimide hydrochloride (734 mg) at room temperature and the mixture was stirred for 4 hours. The reaction mixture was concentrated. Water was added to the residue and the mixture was extracted with methylene chloride. The extract was washed with water and a saturated aqueous solution of sodium chloride, successively, dried over anhydrous magnesium sulfate and concentrated. The residue was recrystallized from methanol-methylene chloride-hexane and dried under reduced pressure to give the compound of the present invention (976 mg) having the following physical data.

TLC: Rf 0.31 (Methanol:Chloroform=1:10); NMR (DMSO-$d_6$): δ 12.83 (s, 1H), 10.04 (s, 1H), 8.35–8.32 (m, 1H), 7.94–7.86 (m, 3H), 7.73–7.69 (m, 2H), 7.46 (t, J=7.8 Hz, 1H), 7.23 (d, J=7.8 Hz, 1H), 6.79 (brt, J=5.2 Hz, 1H), 2.91 (q, J=6.9 Hz, 2H), 2.31 (t, J=7.4 Hz, 2H), 1.58–1.37 (m, 4H), 1.35 (s, 9H).

EXAMPLE 4(1)~4(27)

The following compounds of the present invention were obtained by the same procedure as a series of reactions of Example 4, if necessary, by converting to corresponding salts by conventional method, using 4-(3-aminophenyl)-2H-phthalazin-1-one or amino derivative corresponding the compound prepared in Example 2 and carboxylic acid corresponding 5-t-butoxycarbonylaminopentanoic acid.

In case of preparation of the compound in Example 4(20), 4-(3-hydroxyphenyl)-2H-phthalazin-1-one and 5-t-butoxycarbonylaminopentanoic acid were used.

EXAMPLE 4(1)

4-(3-(2-(t-Butoxycarbonylamino)acetylamino)phenyl)-2H-phthalazin-1-one

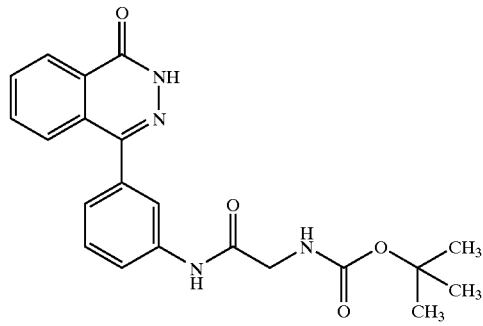

TLC: Rf 0.35 (Methanol:Chloroform=1:10); NMR (DMSO-$d_6$): δ 12.85 (s, 1H), 10.10 (s, 1H), 8.34 (m, 1H), 7.90 (m, 3H), 7.72 (d, J=8.0 Hz, 2H), 7.48 (t, J=8.0 Hz, 1H), 7.26 (d, J=8.0 Hz, 1H), 7.05 (t, J=5.9 Hz, 1H), 3.73 (d, J=5.9 Hz, 2H), 1.38 (s, 9H).

EXAMPLE 4(2)

4-(3-(2-(Benzyloxycarbonylamino)butyrylamino)phenyl)-2H-phthalazin-1-one

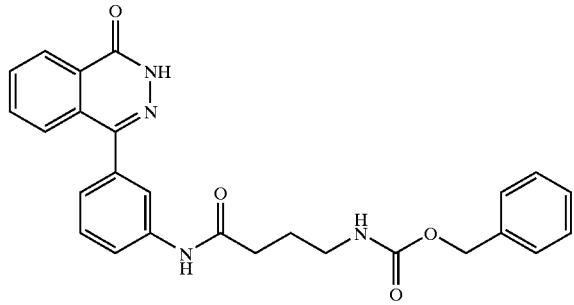

TLC: Rf 0.45 (Methanol:Chloroform=1:10); NMR (DMSO-$d_6$): δ 12.84 (s, 1H), 10.07 (s, 1H), 8.34 (m, 1H), 7.89 (m, 3H), 7.72 (m, 2H), 7.46 (t, J=7.8 Hz, 1H), 7.27 (m, 6H), 4.99 (s, 2H), 3.05 (m, 2H), 2.34 (t, J=7.4 Hz, 2H), 1.72 (m, 2H).

EXAMPLE 4(3)

4-(3-(6-(t-Butoxycarbonylamino)hexanoylamino)phenyl)-2H-phthalazin-1-one

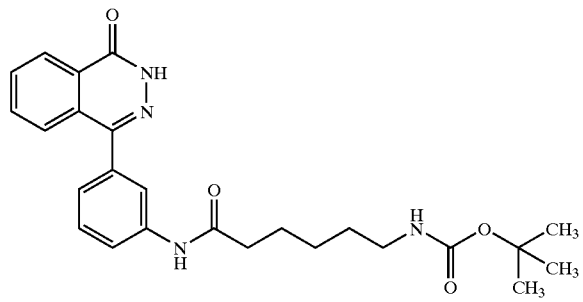

TLC: Rf 0.42 (Methanol:Chloroform=1:10); NMR (DMSO-$d_6$): δ 12.84 (s, 1H), 10.04 (s, 1H), 8.34 (m, 1H), 7.91 (m, 3H), 7.72 (m, 2H), 7.46 (t, J=8.0 Hz, 1H), 7.23 (d, J=8.0 Hz, 1H), 6.75 (m, 1H), 2.89 (q, J=6.8 Hz, 2H), 2.30 (t, J=7.4 Hz, 2H), 1.43 (m, 6H), 1.34 (s, 9H).

EXAMPLE 4(4)

4-(3-(3-(Benzyloxycarbonylamino)propionylamino)phenyl)-2H-phthalazin-1-one

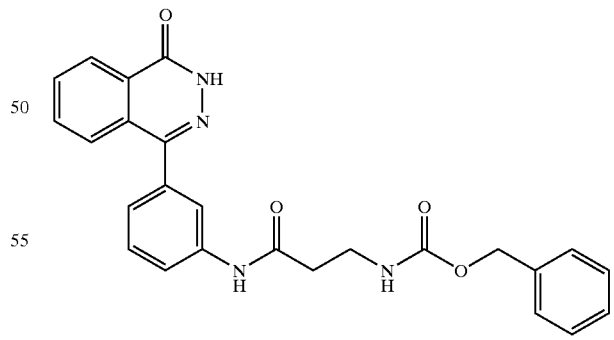

TLC: Rf 0.43 (Methanol:Chloroform=1 10); NMR (DMSO-$d_6$): δ 12.84 (s, 1H), 10.13 (s, 1H), 8.34 (m, 1H), 7.89 (m, 3H), 7.71 (m, 2H), 7.43 (t, J=8.0 Hz, 1H), 7.29 (m, 6H), 5.00 (s, 2H), 3.22 (m, 2H), 2.52 (t, J=6.8 Hz, 2H).

EXAMPLE 4(5)

4-(3-(2-(t-Butoxycarbonylamino)acetylaminomethyl)phenyl)-2H-phthalazin-1-one

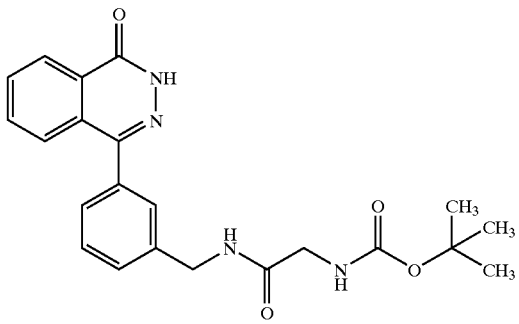

TLC: Rf 0.44 (Chloroform:Methanol=9:1); NMR (DMSO-$d_6$): δ 12.82 (s, 1H), 8.38–8.31 (m, 2H), 7.92–7.84 (m, 2H), 7.66 (m, 1H), 7.51–7.38 (m, 4H), 6.97 (t, J=6.0 Hz, 1H), 4.37 (d, J=6.0 Hz, 2H), 3.55 (d, J=6.0 Hz, 2H), 1.31 (s, 9H).

EXAMPLE 4(6)

4-(3-(3-(t-Butoxycarbonylamino)propionylaminomethyl)phenyl)-2H-phthalazin-1-one

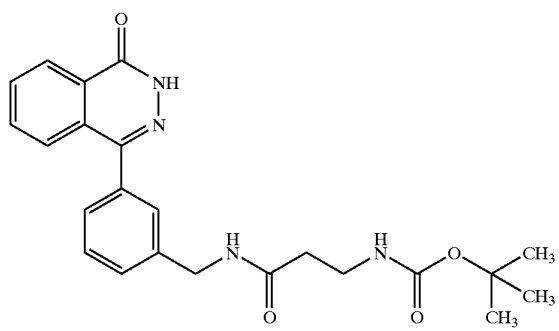

TLC: Rf 0.44 (Chloroform:Methanol=9:1); NMR (DMSO-$d_6$): δ 12.83 (s, 1H), 8.43 (t, J=6.0 Hz, 1H), 8.33 (m, 1H), 7.92–7.85 (m, 2H), 7.67 (m, 1H), 7.52–7.38 (m, 4H), 6.74 (t, J=6.0 Hz, 1H), 4.35 (d, J=6.0 Hz, 2H), 3.13 (m, 2H), 2.29 (t, J=7.2 Hz, 2H), 1.31 (s, 9H).

EXAMPLE 4(7)

4-(3-(1-t-Butoxycarbonylpiperidin-4-ylcarbonylamino)phenyl)-2H-phthalazin-1-one

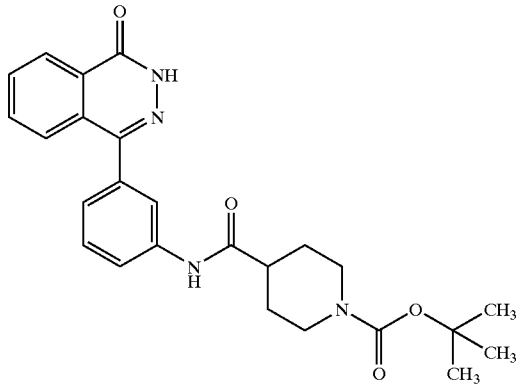

TLC: Rf 0.31 (Methanol:Chloroform=1:10); NMR (DMSO-$d_6$): δ 12.84 (s, 1H), 10.10 (s, 1H), 8.34 (m, 1H), 7.90 (m, 3H), 7.72 (m, 2H), 7.46 (t, J=7.8 Hz, 1H), 7.25 (d, J=7.8 Hz, 1H), 3.99 (brd, 2H), 2.80 (m, 3H), 1.78 (brd, 2H), 1.49 (m, 2H), 1.39 (s, 9H).

EXAMPLE 4(8)

4-(3-(4-(t-Butoxycarbonylamino)butyrylaminomethyl)phenyl)-2H-phthalazin-1-one

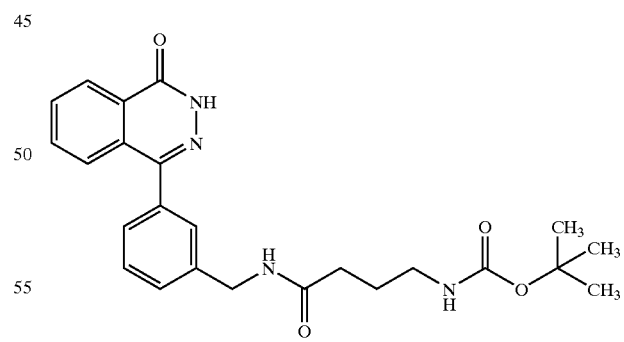

TLC: Rf 0.45 (Chloroform:Methanol=9:1); NMR (DMSO-$d_6$): δ 12.83 (s, 1H), 8.40–8.30 (m, 2H), 7.92–7.84 (m, 2H), 7.67 (m, 1H), 7.52–7.38 (m, 4H), 6.78 (t, J=5.5 Hz, 1H), 4.34 (d, J=5.5 Hz, 2H), 2.89 (m, 2H), 2.12 (t, J=7.5 Hz, 2H), 1.60 (quint, J=7.5 Hz, 2H), 1.31 (s, 9H).

EXAMPLE 4(9)

4-(3-(5-(t-Butoxycarbonylamino)valerylaminomethyl)phenyl)-2H-phthalazin-1-one

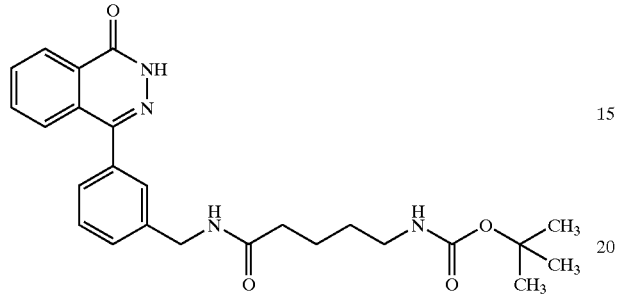

TLC: Rf 0.45 (Chloroform:Methanol=9:1); NMR (DMSO-d$_6$): δ 12.83 (s, 1H), 8.38–8.30 (m, 2H), 7.92–7.84 (m, 2H), 7.67 (m, 1H), 7.52–7.37 (m, 4H), 6.74 (t, J=5.5 Hz, 1H), 4.34 (d, J=5.5 Hz, 2H), 2.86 (m, 2H), 2.12 (t, J=7.2 Hz, 2H), 1.48 (m, 2H), 1.38–1.27 (m, 11H).

EXAMPLE 4(10)

4-(2-(5-(t-Butoxycarbonylamino)valerylamino)phenyl)-2H-phthalazin-1-one

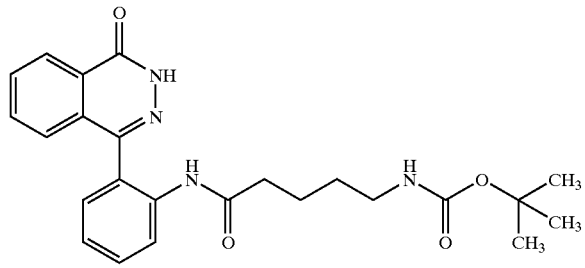

TLC: Rf 0.42 (Methanol:Chloroform=1:20); NMR (DMSO-d$_6$): δ 12.80 (s, 1H), 9.20 (s, 1H), 8.31–8.26 (m, 1H), 7.84–7.75 (m, 3H), 7.49 (ddd, J=7.0, 7.0, 1.5 Hz, 1H), 7.40 (dd, J=7.0, 1.5 Hz, 1H), 7.28 (ddd, J=7.0, 7.0, 1.5 Hz, 1H), 7.21 (dd, J=7.0, 1.5 Hz, 1H), 6.67 (brt, 1H), 2.73 (brq, 2H), 1.92 (brt, 2H), 1.35 (s, 9H), 1.23–1.56 (m, 4H).

EXAMPLE 4(11)

4-(3-(3-(Indol-3-yl)propionylamino)phenyl)-2H-phthalazin-1-one

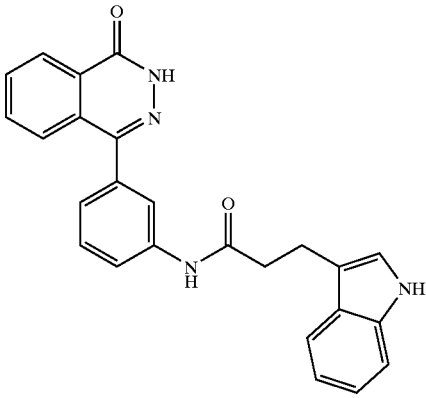

TLC: Rf 0.42 (Methanol:Chloroform=1:10); NMR (DMSO-d$_6$): δ 12.84 (s, 1H), 10.75 (s, 1H), 10.10 (s, 1H), 8.35–8.32 (m, 1H), 7.92–7.88 (m, 3H), 7.74–7.71 (m, 2H), 7.55 (d, J=7.8 Hz, 1H), 7.49 (t, J=7.8 Hz, 1H), 7.31 (d, J=7.8 Hz, 1H), 7.24 (d, J=7.8 Hz, I1H), 7.12 (d, J=1.8 Hz, 1H), 7.05 (t, J=7.8 Hz, 1H), 6.95 (t, J=7.8 Hz, 1H), 3.02 (t, J=7.2 Hz, 2H), 2.70 (t, J=7.2 Hz, 2H).

EXAMPLE 4(12)

4-(3-(5-Morpholinovalerylamino)phenyl)-2H-phthalazin-1-one

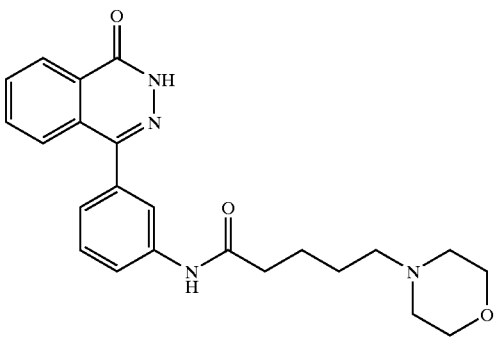

Salt-free:
TLC: Rf 0.22 (Chloroform:Methanol:Acetic acid=8:1:1); NMR (DMSO): δ 12.83 (s, 1H), 10.04 (s, 1H), 8.35–8.32 (m, 1H), 7.92–7.85 (m, 3H), 7.74–7.69 (m, 2H), 7.46 (t, J=7.8 Hz, 1H), 7.25–7.22 (m, 1H), 3.56–3.50 (m, 4H), 2.38–2.22 (m, 8H), 1.66–1.38 (m, 4H).

Hydrochloride:
TLC: Rf 0.55 (Chloroform:Methanol=8:2); NMR (DMSO-d$_6$): δ 12.85 (s, 1H), 10.44 (brs, 1H), 10.22 (s, 1H), 8.34 (m, 1H), 7.94–7.84 (m, 3H), 7.76–7.68 (m, 2H), 7.46 (t, J=7.8 Hz, 1H), 7.24 (d, J=7.8 Hz, 1H), 4.00–3.60 (m, 4H), 3.50–3.24 (m, 2H, overlapped with H$_2$O), 3.20–2.90 (m, 4H), 2.40 (t, J=7.2 Hz, 2H), 1.80–1.60 (m, 4H).

Methanesulfonate:

TLC: Rf 0.60 (Methylele chloride:Methanol:Acetic acid= 8:1:1); NMR (DMSO): δ 12.85 (s, 1H), 10.13 (s, 1H), 9.46 (brs, 1H), 8.35–8.32 (m, 1H), 7.93–7.88 (m, 3H), 7.72–7.69 (m, 2H), 7.47 (t, J=7.8 Hz, 1H), 7.26 (d, J=7.8 Hz, 1H), 3.97–3.93 (m, 2H), 3.70–3.58 (m, overlapped H$_2$O, 2H), 3.43–3.39 (m, 2H), 3.16–2.98 (m, 4H), 2.42–2.38 (m, 2H), 2.33 (s, 3H), 1.78–1.60 (m, 4H).

½ Sulfate:

TLC: Rf 0.61 (Chloroform:Methanol:Acetic acid=8:2:1); NMR (DMSO-d$_6$, DMSO=2.49 ppm): δ 12.84 (s, 1H), 10.08 (s, 1H), 9.57 (brs, 1H), 8.35–8.32 (m, 1H), 7.91–7.87 (m, 3H), 7.73–7.70 (m, 2H), 7.46 (t, J=7.8 Hz, 1H), 7.24 (d, J=7.8 Hz, 1H), 3.65–3.15 (m, 6H), 2.72 (m, 4H), 2.36 (t, J=6.6 Hz, 2H), 1.58 (brs, 4H).

p-Toluenesulfonate:

TLC: Rf 0.36 (Chloroform:Methanol=8:2); NMR (DMSO-d$_6$, DMSO=2.49 ppm): δ 12.85 (s, 1H), 10.12 (s, 1H), 9.42 (brs, 1H), 8.35–8.32 (m, 1H), 7.91–7.88 (m, 3H), 7.72–7.69 (m, 2H), 7.50–7.44 (m, 3H), 7.25 (d, J=7.8 Hz, 1H), 7.09 (d, J=8.1 Hz, 2H), 3.98–3.93 (m, 2H), 3.65–3.57 (m, 2H), 3.443.39 (m, 2H), 3.11–3.01 (m, 4H), 2.40 (t, J=6.6 Hz, 2H), 2.27 (s, 3H), 1.64 (m, 4H).

Maleate:

TLC: Rf 0.78 (Chloroform:Methanol=8:2); NMR (DMSO-d$_6$, DMSO=2.49 ppm): δ 12.85 (s, 1H), 10.11 (s, 1H), 8.35–8.32 (m, 1H), 7.91–7.88 (m, 3H), 7.71–7.69 (m, 2H), 7.47 (t, J=7.8 Hz, 1H), 7.25 (d, J=7.8 Hz, 1H), 6.02 (s, 2H), 3.75–3.02 (m, 10H), 2.39 (brs, 2H), 1.63 (brs, 4H).

EXAMPLE 4(13)

4-(3-(2-(Pyridin-4-yl)acetylamino)phenyl)-2H-phthalazin-1-one

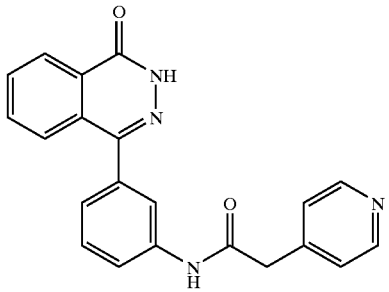

TLC: Rf 0.31 (Methanol:Chloroform=1:10); NMR (DMSO-d$_6$): δ 12.84 (s, 1H), 10.46 (s, 1H), 8.49 (d, J=6.3 Hz, 2H), 8.34–8.31 (m, 1H), 7.91–7.86 (m, 3H), 7.72–7.69 (m, 2H), 7.48 (t, J=7.8 Hz, 1H), 7.34 (d, J=6.3 Hz, 2H), 7.27 (d, J=7.8 Hz, 1H), 3.73 (s, 2H).

EXAMPLE 4(14)

4-(3-(5-(Pyrrolidin-1-yl)valerylamino)phenyl)-2H-phthalazin-1-one

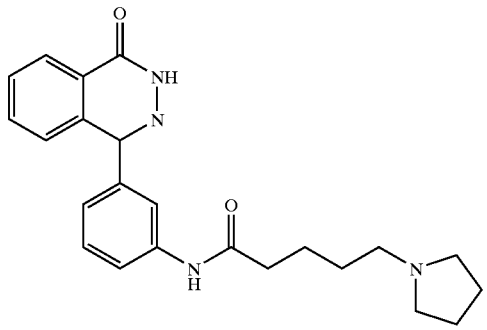

Hydrochloride:

TLC: Rf 0.39 (Chloroform:Methanol:28% Ammonia water=40:10:1); NMR (DMSO-d$_6$): δ 12.85 (s, 1H), 10.22 (s, 1H), 10.14 (br-s, 1H), 8.34 (m, 1H), 7.94–7.86 (m, 3H), 7.74–7.68 (m, 2H), 7.46 (t, J=7.8 Hz, 1H), 7.24 (d, J=7.8 Hz, 1H), 3.60–2.80 (m, 6H, overlapped with H$_2$O), 2.39 (t, J=6.5 Hz, 2H), 2.00–1.80 (m, 4H), 1.74–1.58 (m, 4H).

Methanesulfonate:

TLC: Rf 0.28 (Methanol:Chloroform:Acetic acid=1:9:1); NMR (DMSO-d$_6$): δ 12.85 (s, 1H), 10.12 (s, 1H), 9.34 (brs, 1H), 8.36–8.31 (m, 1H), 7.94–7.86 (m, 3H), 7.74–7.67 (m, 2H), 7.47 (t, J=7.8 Hz, 1H), 7.25 (d, J=7.8 Hz, 1H), 3.56–3.46 (m, 2H), 3.18–3.08 (m, 2H), 3.04–2.90 (m, 2H), 2.39 (t, J=6.3 Hz, 2H), 2.30 (s, 3H), 2.05–1.76 (m, 4H), 1.74–1.56 (m, 4H).

EXAMPLE 4(15)

4-(3-(5-(Dimethylamino)valerylamino)phenyl)-2H-phthalazin-1-one Hydrochloride

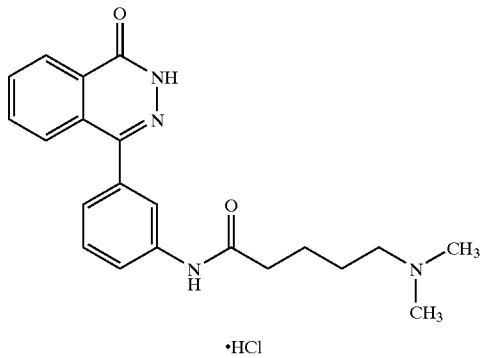

TLC: Rf 0.39 (Chloroform:Methanol:28% Ammonia water=40:10:1); NMR (DMSO-d$_6$): δ 12.85 (s, 1H), 10.25 (s, 1H), 10.02 (br-s, 1H), 8.34 (m, 1H), 7.94–7.84 (m, 3H), 7.76–7.68 (m, 2H), 7.46 (t, J=7.8 Hz, 1H), 7.24 (d, J=7.8 Hz, 1H), 3.07–3.00 (m, 2H), 2.72 (d, J=4.8 Hz, 6H), 2.40 (t, J=6.8 Hz, 2H), 1.72–1.58 (m, 4H).

EXAMPLE 4(16)

4-(3-(3-(Pyridin-3-yl)propionylamino)phenyl)-2H-phthalazin-1-one

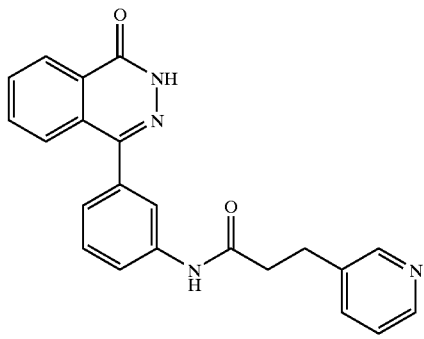

TLC: Rf 0.33 (Methanol:Chloroform=1:10); NMR (DMSO-$d_6$): δ 12.84 (s, 1H), 10.10 (s, 1H), 8.47 (d, J=1.8 Hz, 1H), 8.39 (dd, J=4.8,1.8 Hz, 1H), 8.35–8.32 (m, 1H), 7.91–7.84 (m, 3H), 7.72–7.65 (m, 3H), 7.46 (t, J=7.8 Hz, 1H), 7.29 (dd, J=7.8,4.8 Hz, 1H), 7.24 (d, J=7.8 Hz, 1H), 2.95–2.88 (m, 2H), 2.72–2.65 (m, 2H).

EXAMPLE 4(17)

4-(3-(5-(N-Methyl-N-t-butoxycarbonylamino)valerylamino)phenyl)-2H-phthalazin-1-one

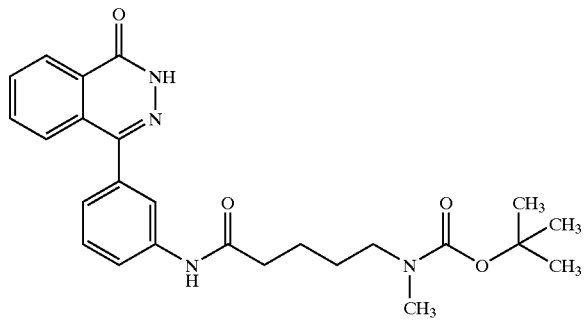

TLC: Rf 0.57 (Chloroform:Methanol=9:1); NMR (DMSO-$d_6$): δ 12.83 (s, 1H), 10.05 (s, 1H), 8.34 (m, 1H), 7.94–7.84 (m, 3H), 7.74–7.66 (m, 2H), 7.46 (t, J=7.8 Hz, 1H), 7.23 (d, J=7.8 Hz, 1H), 3.15 (t, J=6.6 Hz, 2H), 2.74 (s, 3H), 2.34 (t, J=6.8 Hz, 2H), 1.60–1.42 (m, 4H), 1.36 (s, 9H).

EXAMPLE 4(18)

4-(3-(2-(2-(t-Butoxycarbonylamino)ethylthio)acetylamino)phenyl)-2H-phthalazin-1-one

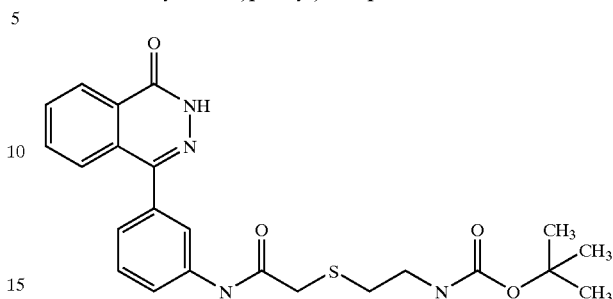

TLC: Rf 0.57 (Chloroform:Methanol=9:1); NMR (DMSO-$d_6$): δ 12.84 (s, 1H), 10.25 (s, 1H), 8.34 (m, 1H), 7.94–7.85 (m, 3H), 7.74–7.66 (m, 2H), 7.48 (t, J=7.8 Hz, 1H), 7.27 (d, J=7.8 Hz, 1H), 6.91 (m, 1H), 3.33 (s, 2H), 3.13 (m, 2H), 2.65 (t, J=7.2 Hz, 2H), 1.34 (s, 9H).

EXAMPLE 4(19)

4-(3-(2-(N-(2-(t-Butoxycarbonylamino)ethyl)-N-tbutoxycarbonylamino)acetylamino)phenyl)-2H-phthalazin-1-one

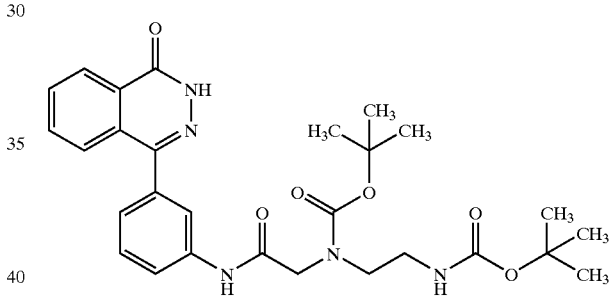

TLC: Rf 0.57 (Chloroform:Methanol=9:1); NMR (DMSO-$d_6$): δ 12.83 (s, 1H), 10.19 and 10.17 (each s, total 1H), 8.34 (m, 1H), 7.94–7.85 (m, 3H), 7.74–7.66 (m, 2H), 7.49 (t, J=7.8 Hz, 1H), 7.27 (d, J=7.8 Hz, 1H), 6.73 (m, 1H), 3.98 and 3.93 (each s, total 2H), 3.30–3.24 (m, 2H, S overlapped with $H_2O$), 3.06 (m, 2H), 1.40–1.26 (m, 18H).

EXAMPLE 4(20)

4-(3-(5-(t-Butoxycarbonylamino)valeryloxy)phenyl)-2H-phthalazin-1-one

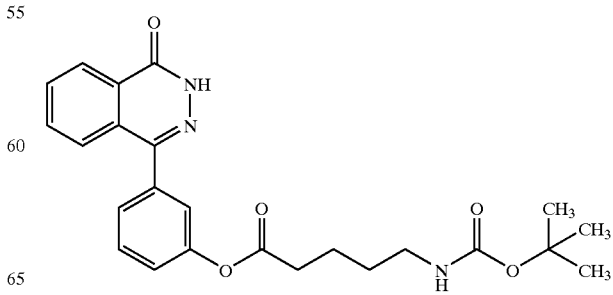

TLC: Rf 0.36 (Methanol:Chloroform=1:20); NMR (DMSO-d$_6$): δ 12.89 (s, 1H), 8.36–8.32 (m, 1H), 7.96–7.85 (m, 2H), 7.70–7.66 (m, 1H), 7.60 (t, J=7.6 Hz, 1H), 7.48 (d, J=7.6 Hz, 1H), 7.36 (m, 1H), 7.31–7.27 (m, 1H), 6.82 (brt, 1H), 2.94 (q, J=6.2 Hz, 2H), 2.60 (t, J=7.0 Hz, 2H), 1.66–1.42 (m, 4H), 1.34 (s, 9H).

EXAMPLE 4(21)

4-(3-(2-(3-(t-Butoxycarbonylamino)phenyl)acetylamino)phenyl)-2H-phthalazin-1-one

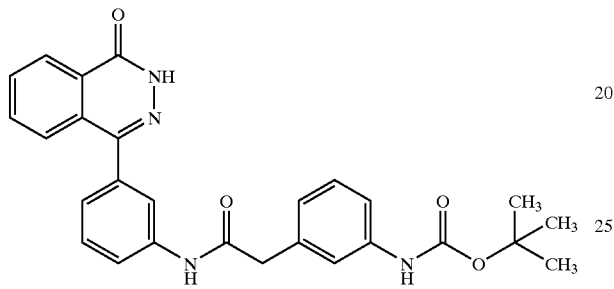

TLC: Rf 0.27 (Methanol:Chloroform=1:20); NMR (DMSO-d$_6$): δ 12.84 (s, 1H), 10.34 (s, 1H), 9.30 (s, 1H), 8.35–8.31 (m, 1H), 7.94–7.87 (m, 3H), 7.74–7.69 (m, 2H), 7.51–7.43 (m, 2H), 7.26 (d, J=7.8 Hz, 1H), 7.25 (d, J=9.2 Hz, 1H), 7.17 (t, J=7.2 Hz, 1H), 6.93 (d, J=7.2 Hz, 1H), 3.59 (s, 2H), 1.44 (s, 9H).

EXAMPLE 4(22)

4-(3-(3-(t-Butoxycarbonylaminomethyl)benzoylamino)phenyl)-2H-phthalazin-1-one

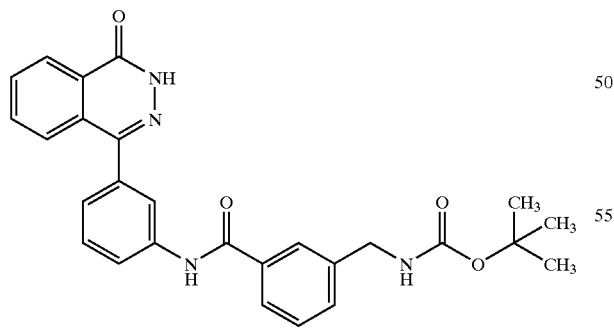

TLC: Rf 0.48 (Methanol:Chloroform=1:10); NMR (DMSO-d$_6$): δ 12.87 (s, 1H), 10.42 (s, 1H), 8.37–8.33 (m, 1H), 8.04–7.76 (m, 6H), 7.58–7.45 (m, 5H), 7.32 (d, J=8.0 Hz, 1H), 4.20 (d, J=6.0 Hz, 2H), 1.38 (s, 9H).

EXAMPLE 4(23)

4-(3-(trans-4-(t-Butoxycarbonylaminomethyl)cyclohexylcarbonylamino)phenyl)-2H-phthalazin-1-one

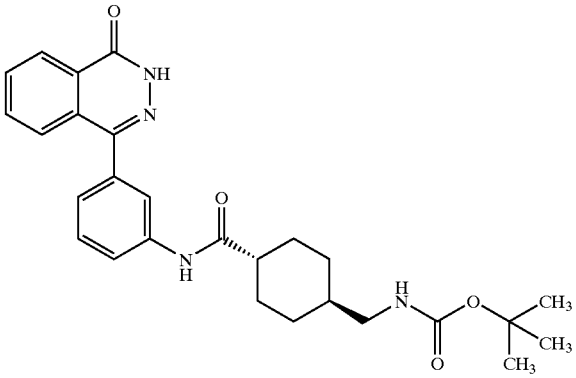

TLC: Rf 0.62 (Hexane:Ethyl acetate=1:4); NMR (DMSO-d$_6$): δ 12.83 (s, 1H), 9.98 (s, 1H), 8.34 (m, 1H), 7.94–7.84 (m, 3H), 7.74–7.70 (m, 2H), 7.45 (t, J=7.8 Hz, 1H), 7.22 (d, J=7.8 Hz, 1H), 6.80 (t, J=5.7 Hz, 1H), 2.78 (m, 2H), 2.27 (m, 1H), 1.90–1.70 (m, 4H), 1.50–1.20 (m, 12H), 0.98–0.82 (m, 2H).

EXAMPLE 4(24)

4-(3-(4-(t-Butoxycarbonylamino)cyclohexylcarbonylamino)phenyl)-2H-phthalazin-1-one

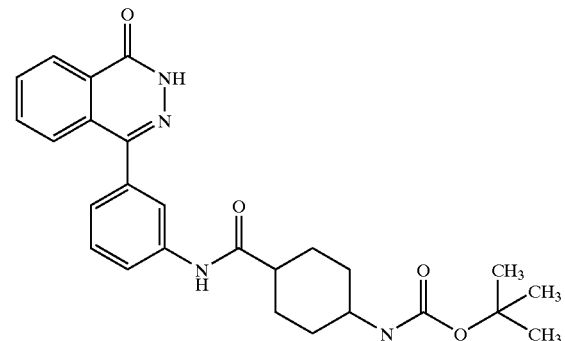

TLC: Rf 0.62 (Hexane:Ethyl acetate=1:4); NMR (DMSO-d$_6$): δ 12.83 (s, 1H), 9.99 and 9.91 (each s, total 1H), 8.34 (m, 1H), 7.94–7.84 (m, 3H), 7.74–7.68 (m, 2H), 7.45 (t, J=7.8 Hz, 1H), 7.23 (d, J=7.8 Hz, 1H), 6.74 (m, 1H), 3.48 (m, 1H), 2.40 (m, 1H), 1.92–1.26 (m, 17H).

EXAMPLE 4(25)

4-(3-(4-(t-Butoxycarbonylaminomethyl)benzoylamino)phenyl)-2H-phthalazin-1-one

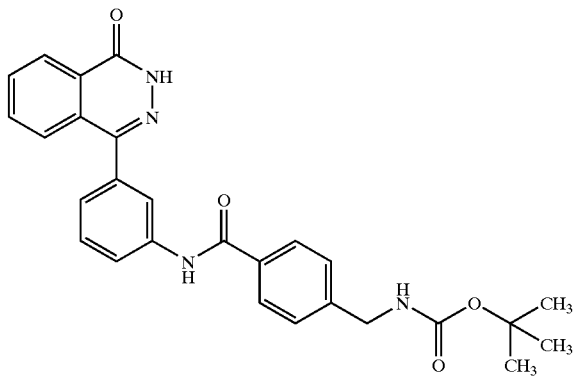

TLC: Rf 0.48 (Hexane:Ethyl acetate=1:4); NMR (DMSO-$d_6$): δ 12.86 (s, 1H), 10.36 (s, 1H), 8.34 (m, 1H), 8.04 (t, J=1.8 Hz, 1H), 7.96–7.86 (m, 5H), 7.78 (m, 1H), 7.55–7.44 (m, 2H), 7.37 (t, J=8.4 Hz, 2H), 7.32 (d, J=7.8 Hz, 1H), 4.19 (d, J=6.3 Hz, 1H), 1.39 (s, 9H).

EXAMPLE 4(26)

4-(3-(2-(4-(t-Butoxycarbonylamino)phenyl)acetylamino)phenyl)-2H-phthalazin-1-one

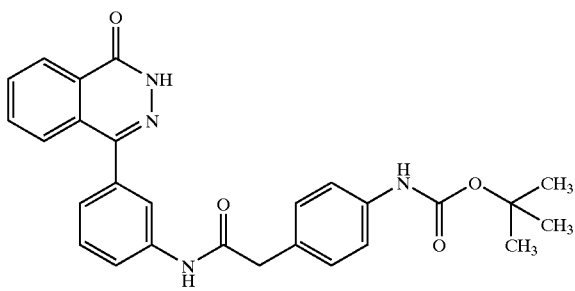

TLC: Rf 0.48 (Hexane:Ethyl acetate=1:4); NMR (DMSO-$d_6$): δ 12.83 (s, 1H), 10.28 (s, 1H), 9.26 (s, 1H), 8.33 (m, 1H), 7.94–7.84 (m, 3H), 7.74–7.68 (m, 2H), 7.46 (t, J=7.8 Hz, 1H), 7.37 (d, J=8.4 Hz, 2H), 7.25 (d, J=7.8 Hz, 1H), 7.19 (d, J=8.4 Hz, 2H), 3.56 (s, 2H), 1.45 (s, 9H).

EXAMPLE 4(27)

4-(3-((E)-3-(1-(t-Butoxycarbonyl)imidazol-4-yl)propenoylamino)phenyl)-2H-phthalazin-1-one

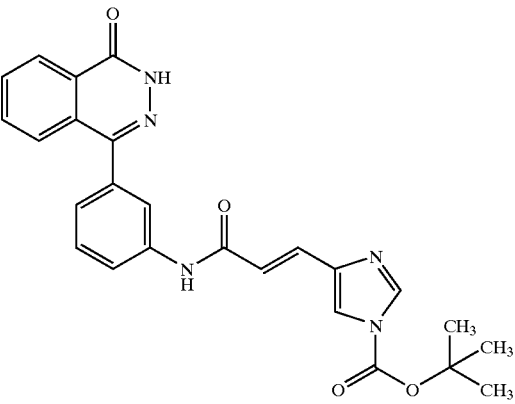

TLC: Rf 0.52 (Methanol:Chloroform=1:10); NMR (DMSO-$d_6$): δ 12.85 (s, 1H), 10.39 (s, 1H), 8.36–8.33 (m, 1H), 8.27 (s, 1H), 7.97–7.74 (m, 6H), 7.50 (t, J=7.8 Hz, 1H), 7.47 (d, J=15.6 Hz, 1H), 7.27 (d, J=7.8 Hz, 1H), 6.93 (d, J=15.6 Hz, 1H), 1.57 (s, 9H).

EXAMPLE 5

4-(3-(5-Aminovalerylamino)phenyl)-2H-phthalazin-1-one

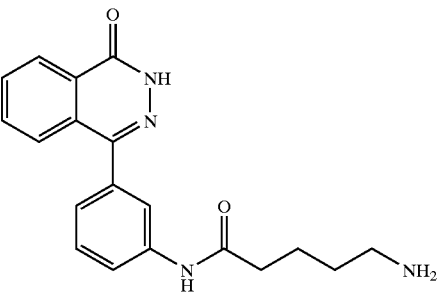

To a solution of the compound prepared in example 4 (850 mg) in methanol (6.00 ml) was added 4N solution of hydrochloric acid in dioxane (3.00 ml) under cooling with ice and the mixture was stirred for 2 hours at room temperature. The precipitated crystal was collected by filtration. The crystal was washed with hexane and dried under reduced pressure to give the compound of the present invention (hydrochloride: 478 mg) having the following physical data. Furthermore, the following compounds of the present invention (trifluoroacetate, methanesulfonate) were obtained by using trifluoroacetic acid or methanesulfonic acid instead of 4N solution of hydrochloric acid in dioxane.

Hydrochloride:

TLC: Rf 0.35 (Chloroform:Methanol:Acetic acid=8:2:0.5); NMR (DMSO-$d_6$, DMSO=2.49 ppm): δ 12.85 (s, 1H), 10.32 (s, 1H), 8.36–8.32 (m, 1H), 7.95–7.85 (m, 3H), 7.77–7.70 (m, 2H), 7.46 (t, J=8.0 Hz, 1H), 7.24 (d, J=8.0 Hz, 1H), 2.80–2.76 (m, 2H), 2.38 (t, J=7.0 Hz, 2H), 1.64–1.62 (m, 4H).

Trifloroacetate:

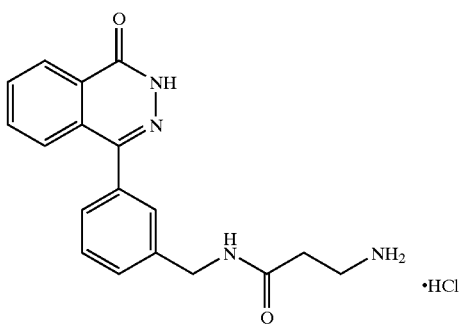

TLC: Rf 0.12 (Chloroform:Methanol=8:2); NMR (DMSO-$d_6$, DMSO=2.49 ppm): δ 12.85 (s, 1H), 10.13 (s, 1H), 8.34 (m, 1H), 7.89 (m, 3H), 7.72 (m, 4H), 7.47 (t, J=7.8 Hz, 1H), 7.25 (d, J=7.8 Hz, 1H), 2.80 (m, 2H), 2.37 (t, J=6.0 Hz, 2H), 1.60 (m, 4H).

Methanesulfonate:

TLC: Rf 0.17 (Chloroform:Methanol:Acetic acid=8:2:0.5); NMR (DMSO-$d_6$, DMSO=2.49 ppm): δ 12.84 (brs, 1H), 10.18 (s, 1H), 8.35–8.32 (m, 1H), 7.92–7.86 (m, 3H), 7.73–7.70 (m, 5H), 7.46 (t, J=7.8 Hz, 1H), 7.24 (d, J=7.8 Hz, 1H), 2.79 (t, J=6.9 Hz, 2H), 2.37 (t, J=6.9 Hz, 2H), 2.29 (s, 3H), 1.62 (m, 4H).

EXAMPLE 5(1)–EXAMPLE 5(19)

The following compounds of the present invention were obtained by the same procedure as a series of reactions of Example 5 using the compound prepared in Example 4(1), Example 4(3), Example 4(5)–Example 4(10) and Example 4(17)–Example 4(27) in place of the compound prepared in Example 4, or using trifluoroacetic acid instead of 4N solution of hydrochloric acid in dioxane.

EXAMPLE 5(1)

4-(3-(2-Aminoacetylamino)phenyl)-2H-phthalazin-1-one Trifluoroacetate

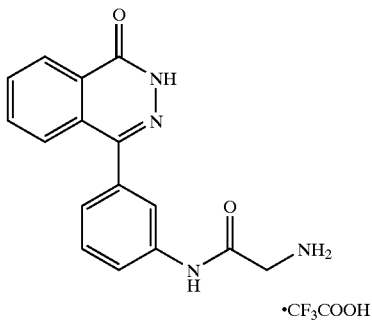

TLC: Rf 0.22 (Methanol:Chloroform=2:8); NMR (DMSO-$d_6$): δ 12.88 (s, 1H), 10.63 (s, 1H), 8.35 (m, 1H), 8.13 (brs, 2H), 7.89 (m, 3H), 7.72 (m, 2H), 7.54 (t, J=7.8 Hz, 1H), 7.34 (d, J=7.8 Hz, 1H), 3.81 (s, 2H).

EXAMPLE 5(2)

4-(3-(6-Aminohexanoylamino)phenyl)-2H-phthalazin-1-one Trifluoroacetate

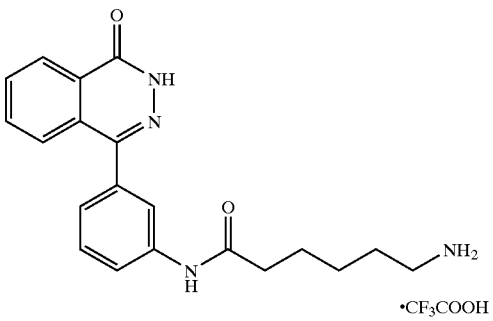

TLC: Rf 0.13 (Methanol:Chloroform=2:8); NMR (DMSO-$d_6$): δ 12.85 (s, 1H), 10.09 (s, 1H), 8.34 (m, 1H), 7.83 (m, 2H), 7.71 (m, 3H), 7.47 (t, J=7.8 Hz, 1H), 7.24 (d, J=7.8 Hz, 1H), 2.76 (m, 2H), 2.33 (t, J=7.0 Hz, 2H), 1.61 (m, 4H), 1.34 (m, 2H).

EXAMPLE 5(3)

4-(3-(2-Aminoacetylaminomethyl)phenyl)-2H-phthalazin-1-one Hydrochloride

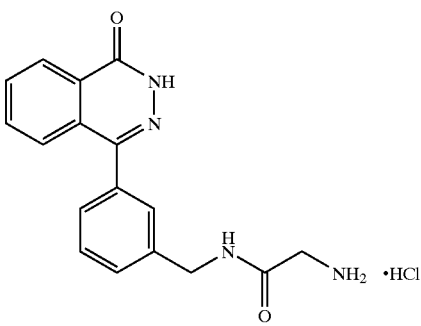

TLC: Rf 0.40 (Chloroform:Methanol:28% Ammonia water=100:20:1); NMR (DMSO-$d_6$): δ 12.86 (s, 1H), 8.98 (t, J=6.0 Hz, 1H), 8.34 (m, 1H), 8.09 (br, 3H), 7.94–7.86 (m, 2H), 7.67 (m, 1H), 7.55–7.44 (m, 4H), 4.44 (d, J=6.0 Hz, 2H), 3.60 (m, 2H).

EXAMPLE 5(4)

4-(3-(2-Aminopropionylaminomethyl)phenyl)-2H-phthalazin-1-one Hydrochloride

TLC. Rf 0.14 (Chloroform:Methanol:28% Ammonia water=100:20:1); NMR (DMSO-$d_6$): δ 12.85 (s, 1H), 8.71 (t, J=5.8 Hz, 1H), 8.34 (m, 1H), 7.94–7.76 (m, 5H), 7.67 (m, 1H), 7.53–7.41 (m, 4H), 4.39 (d, J=5.8 Hz, 2H), 2.99 (t, J=6.8 Hz, 2H), 2.54 (t, J=6.8 Hz, 2H).

EXAMPLE 5(5)

4-(3-(Piperidin-4-ylcarbonylamino)phenyl)-2H-phthalazin-1-one Trifluoroacetate

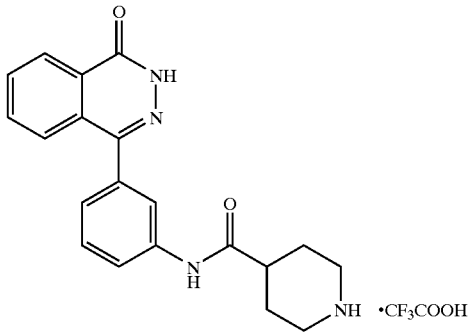

TLC: Rf 0.22 (Methanol:Chloroform=2:8); NMR (DMSO-$d_6$): δ 12.86 (s, 1H), 10.24 (s, 1H), 8.62 (brs, 1H), 8.34 (m, 1H), 7.90 (m, 3H), 7.71 (m, 2H), 7.48 (t, J=7.8 Hz, 1H), 7.27 (d, J=7.8 Hz, 1H), 3.34 (m, 2H), 2.93 (m, 2H), 2.66 (m, 1H), 1.88 (m, 4H).

EXAMPLE 5(6)

4-(3-(4-Aminobutyrylaminomethyl)phenyl)-2H-phthalazin-1-one Hydrochloride

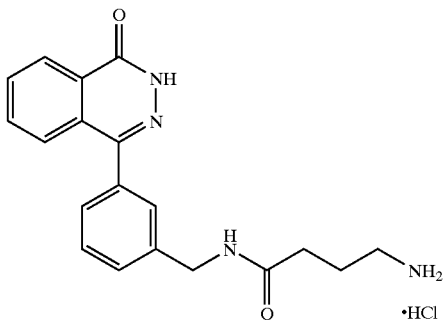

TLC: Rf 0.12 (Chloroform:Methanol:28% Ammonia water=100:20:1); NMR (DMSO-$d_6$): δ 12.85 (s, 1H), 8.54 (t, J=6.0 Hz, 1H), 8.34 (m, 1H), 7.93–7.86 (m, 2H), 7.81 (br, 3H), 7.67 (m, 1H), 7.53–7.39 (m, 4H), 4.36 (d, J=6.0 Hz, 2H), 2.78 (m, 2H), 2.26 (t, J=7.0 Hz, 2H), 1.78 (m, 2H).

EXAMPLE 5(7)

4-(3-(5-Aminovalerylaminomethyl)phenyl)-2H-phthalazin-1-one Hydrochloride

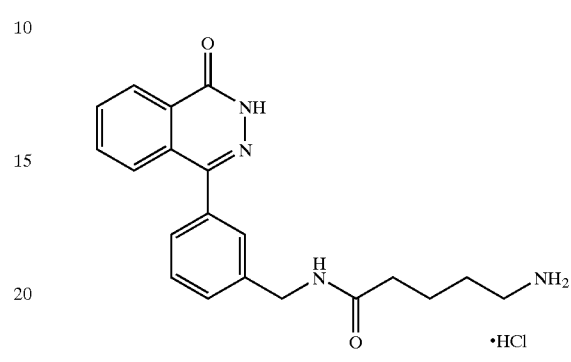

TLC: Rf 0.11 (Chloroform:Methanol:28% Ammonia water=100:20:1); NMR (DMSO-$d_6$): δ 12.85 (s, 1H), 8.46 (t, J=6.0 Hz, 1H), 8.34 (m, 1H), 7.92–7.86 (m, 2H), 7.77 (br, 3H), 7.67 (m, 1H), 7.53–7.38 (m, 4H), 4.36 (d, J=6.0 Hz, 2H), 2.74 (m, 2H), 2.17 (t, J=6.8 Hz, 2H), 1.60–1.48 (m, 4H).

EXAMPLE 5(8)

4-(2-(5-Aminovalerylamino)phenyl)-2H-phthalazin-1-one Hydrochloride

TLC: Rf 0.53 (Methanol:Chloroform:Acetic acid= 2:8:0.5); NMR (DMSO-$d_6$): δ 12.81 (s, 1H), 9.29 (s, 1H), 8.32–8.27 (m, 1H), 7.86–7.76 (m, 4H), 7.53–7.20 (m, 3H), 2.63–2.51 (m, 2H), 1.96 (m, 2H), 1.55–1.22 (m, 4H).

EXAMPLE 5(9)

4-(3-(5-(Methylamino)valerylamino)phenyl)-2H-phthalazin-1-one Hydrochloride

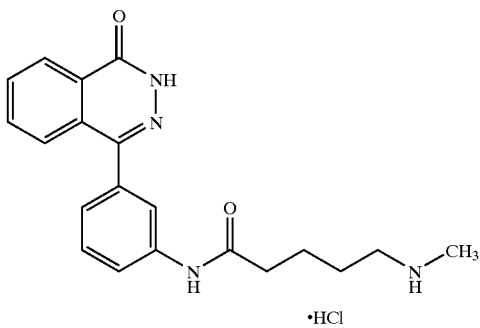

TLC: Rf 0.26 (Chloroform:Methanol:28% Ammonia water=65:25:4); NMR (DMSO-$d_6$): δ 12.85 (s, 1H), 10.20 (s, 1H), 8.52 (br-s, 2H), 8.34 (m, 1H), 7.94–7.84 (m, 3H), 7.73–7.68 (m, 2H), 7.46 (t, J=7.8 Hz, 1H), 7.24 (d, J=7.8 Hz, 1H), 2.88 (m, 2H), 2.52 (m, 3H, overlapped with DMSO), 2.38 (m, 2H), 1.70–1.58 (m, 4H).

EXAMPLE 5(10)

4-(3-(2-(2-Aminoethylthio)acetylamino)phenyl)-2H-phthalazin-1-one Hydrochloride

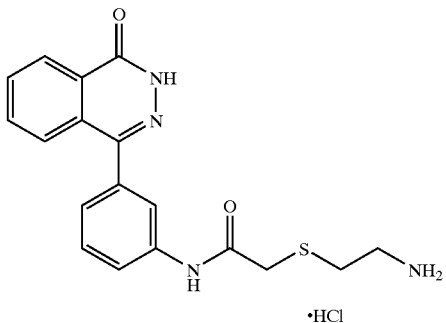

TLC: Rf 0.42 (Chloroform:Methanol:28% Ammonia water=40:10:1); NMR (DMSO-$d_6$): δ 12.86 (s, 1H), 10.54 (s, 1H), 8.34 (m, 1H), 8.00–7.86 (m, 6H), 7.74–7.68 (m, 2H), 7.49 (t, J=7.8 Hz, 1H), 7.28 (d, J=7.8 Hz, 1H), 3.45 (s, 2H), 3.05 (m, 2H), 2.87 (t, J=7.1 Hz, 2H).

EXAMPLE 5(11)

4-(3-(2-(2-Aminoethylamino)acetylamino)phenyl)-2H-phthalazin-1-one Dihydrochloride

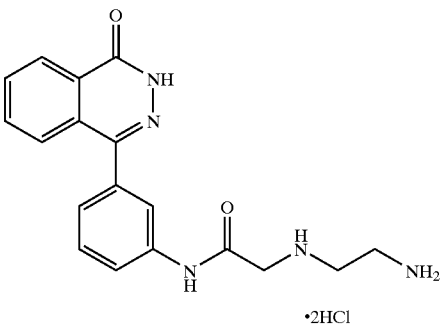

TLC: Rf 0.31 (Chloroform:Methanol:28% Ammonia water=65:25:4); NMR (DMSO-$d_6$): δ 12.87 (s, 1H), 10.92 (s, 1H), 9.50 (br-s, 2H), 8.34 (m, 1H), 8.20 (br-s, 3H), 7.94–7.86 (m, 3H), 7.76–7.70 (m, 2H), 7.54 (t, J=7.8 Hz, 1H), 7.35 (d, J=7.8 Hz, 1H), 4.05 (s, 2H), 3.28 (m, 2H), 3.18 (m, 2H).

EXAMPLE 5(12)

4-(3-5-Aminovaleryloxy)phenyl)-2H-phthalazin-1-one Hydrochloride

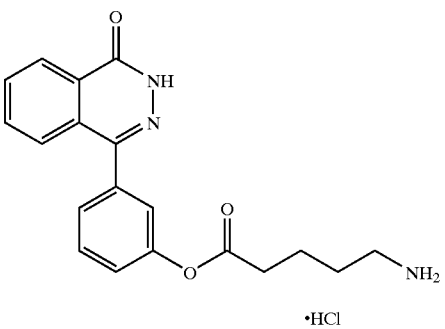

TLC: Rf 0.45 (Methanol:Chloroform=1:10); NMR (DMSO-$d_6$): δ 12.90 (s, 1H), 8.35–8.32 (m, 1H), 7.92–7.88 (m, 2H), 7.86 (brs, 2H), 7.69–7.66 (m, 1H), 7.60 (t, J=7.8 Hz, 1H), 7.49 (d, J=7.8 Hz, 1H), 7.36 (m, 1H), 7.32–7.28 (m, 1H), 2.81 (q, J=6.2 Hz, 2H), 2.66 (t, J=6.8 Hz, 2H), 1.67 (m, 4H).

EXAMPLE 5(13)

4-(3-(2-(3-Aminophenyl)acetylamino)phenyl)-2H-phthalazin-1-one Hydrochloride

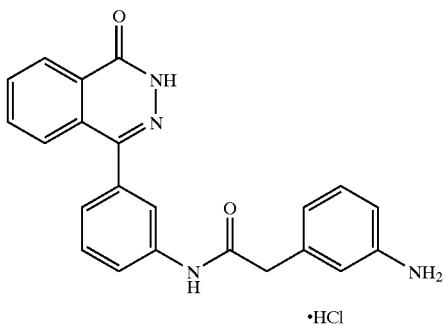

TLC: Rf 0.56 (Methanol:Chloroform=1:10); NMR (DMSO-$d_6$): δ 12.84 (s, 1H), 10.52 (s, 1H), 9.58 (brs, 2H), 8.35–8.32 (m, 1H), 7.91–7.87 (m, 3H), 7.74–7.69 (m, 2H), 7.47 (t, J=7.8 Hz, 1H), 7.38 (t, J=7.8 Hz, 1H), 7.27–7.25 (m, 3H), 7.14 (d, J=7.8 Hz, 1H), 3.71 (s, 2H).

EXAMPLE 5(14)

4-(3-(3-(Aminomethyl)benzoylamino)phenyl)-2H-phthalazin-1-one Hydrochloride

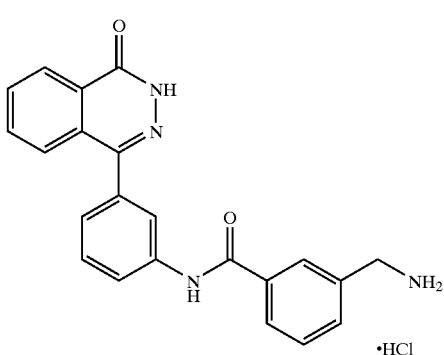

TLC: Rf 0.23 (Methanol:Chloroform:Acetic acid= 2:8:0.5); NMR (DMSO-$d_6$): δ 12.88 (s, 1H), 10.54 (s, 1H), 8.36–8.33 (m, 3H), 8.15 (s, 1H), 8.07 (s, 1H), 8.02–7.89 (m, 4H), 7.79–7.76 (m, 1H), 7.69 (d, J=7.8 Hz, 1H), 7.58 (t, J=7.8 Hz, 1H), 7.54 (t, J=7.8 Hz, 1H), 7.34 (d, J=7.8 Hz, 1H), 4.12 (s, 2H).

EXAMPLE 5(15)

4-(3-trans-4-(Aminomethyl)cyclohexylcarbonylamino)phenyl)-2H-phthalazin-1-one Hydrochloride

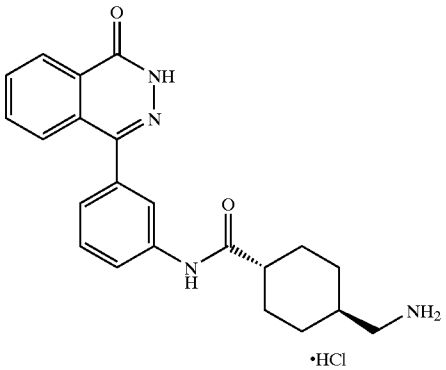

TLC: Rf 0.49 (Chloroform Methanol:28% Ammonia water=65:25:4); NMR (DMSO-$d_6$): δ 12.84 (s, 1H), 10.10 (s, 1H), 8.34 (m, 1H), 7.94–7.80 (m, 6H), 7.74–7.70 (m, 2H), 7.45 (t, J=7.8 Hz, 1H), 7.23 (d, J=7.8 Hz, 1H), 2.66 (m, 2H), 2.32 (m, 1H), 1.92–1.80 (m, 4H), 1.64–1.32 (m, 3H), 1.06–0.96 (m, 2H).

EXAMPLE 5(16)

4-(3-(4-Aminocyclohexylcarbonylamino)phenyl)-2H-phthalazin-1-one Hydrochloride

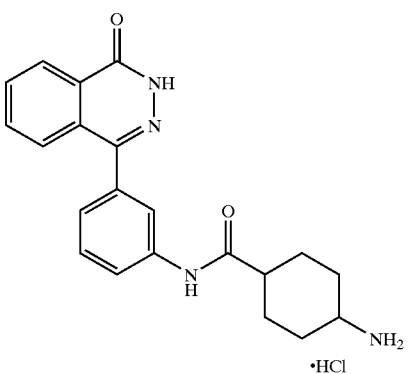

TLC: Rf 0.50 and 0.44 (Chloroform:Methanol:28% Ammonia water=65:25:4); NMR (DMSO-$d_6$): δ 12.84 (s, 1H), 10.15 and 10.11 (eachs, total 1H), 8.34 (m, 1H), 8.00–7.86 (m, 6H), 7.75–7.70 (m, 2H), 7.46 (t, J=7.8 Hz, 1H), 7.24 (d, J=7.8 Hz, 1H), 3.18 (m, 1H), 2.56 (m, 1H), 2.06–1.30 (m, 8H).

EXAMPLE 5(17)

4-(3-(4-(Aminomethyl)benzoylamino)phenyl)-2H-phthalazin-1-one Hydrochloride

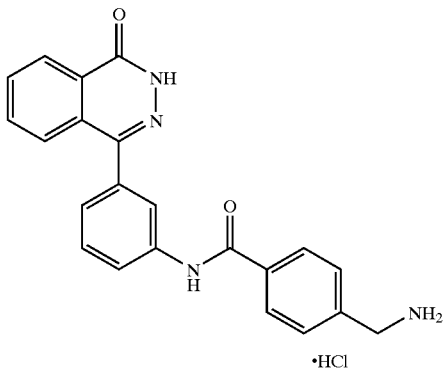

TLC: Rf 0.49 (Chloroform:Methanol:28% Ammonia water=40:10:1); NMR (DMSO-$d_6$): δ 12.87 (s, 1H), 10.49 (s, 1H), 8.45 (br-s, 3H), 8.34 (m, 1H), 8.06–7.86 (m, 6H), 7.77 (m, 1H), 7.63 (d, J=8.4 Hz, 2H), 7.54 (t, J=7.8 Hz, 1H), 7.33 (d, J=7.8 Hz, 1H), 4.11 (m, 2H).

EXAMPLE 5(18)

4-(3-(2-(4-Aminophenyl)acetylamino)phenyl)-2H-phthalazin-1-one Hydrochloride

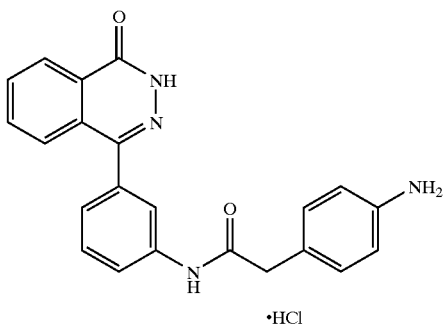

TLC: Rf 0.41 (Chloroform:Methanol:28% Ammonia water=100:10:1); NMR (DMSO-$d_6$): δ 12.84 (s, 1H), 10.49 (s, 1H), 9.80 (br-s, 3H), 8.33 (m, 1H), 7.92–7.84 (m, 3H), 7.74–7.68 (m, 2H), 7.47 (t, J=7.8 Hz, 1H), 7.40 (d, J=8.4 Hz, 2H), 7.28–7.22 (m, 3H), 3.70 (s, 2H).

EXAMPLE 5(19)

4-(3-((E)-3-(Imidazol-4-yl)propenoylamino)phenyl)-2H-phthalazin-1-one Hydrochloride

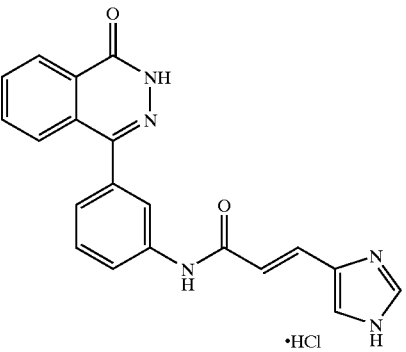

TLC: Rf 0.47 (Methanol:Chloroform=2:8); NMR (DMSO-$d_6$): δ 12.86 (s, 1H), 10.62 (s, 1H), 9.04 (s, 1H), 8.36–8.33 (m, 1H), 7.98–7.85 (m, 6H), 7.76–7.73 (m, 1H), 7.54–7.49 (m, 2H), 7.31 (d, J=7.5 Hz, 1H), 6.85 (d, J=15.9 Hz, 1H).

4-(3-(Acetylamino)phenyl)-2H-phthalazin-1-one

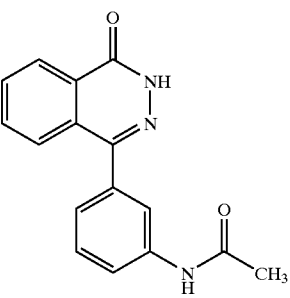

To a suspension of 4-(3-aminophenyl)-2H-phthalazin-1-one (50.0 mg) in pyridine (0.5 ml) was added dropwise acetyl chloride (16.5 μl) under cooling with ice, and the mixture was stirred for 2 hours. To the reaction mixture was added water, and the mixture was stirred for 1 hour. The appeared crystal was collected by filtration. The crystal was washed with water and hexane, and then dried under reduced pressure to give the compound of the present invention (16.5 mg) having the following physical data.

TLC: Rf 0.36 (Methanol:Chloroform=1:10); NMR (DMSO-$d_6$): δ 12.83 (s, 1H), 10.11 (s, 1H), 8.33 (m, 1H), 7.88 (m, 3H), 7.70 (m, 2H), 7.46 (t, J=7.8 Hz, 1H), 7.25 (d, J=6.6 Hz, 1H), 2.06 (s, 3H).

EXAMPLE 6(1)~EXAMPLE 6(10)

The following compounds of the present invention were obtained by the same procedure as a series of reactions of Example 6, using corresponding amine derivative instead of 4-(3-aminophenyl)-2H-phthalazin-1-one and corresponding halide compound instead of acetyl chloride. In case of preparation of the compound in Example 6(10), 4-(3-hydroxyphenyl)-2H-phthalazin-1-one and acetyl chloride were used.

EXAMPLE 6(1)

4-(3-(Hexanoylamino)phenyl)-2H-phthalazin-1-one

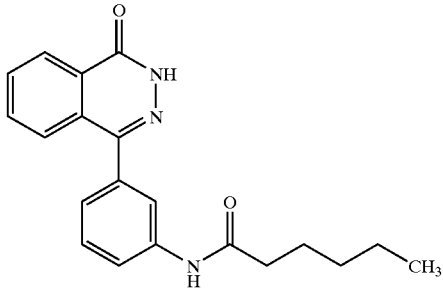

TLC: Rf 0.40 (Methanol:Chloroform=1:10); NMR (DMSO-$d_6$): δ 12.83 (s, 1H), 10.04 (s, 1H), 8.33 (m, 1H), 7.88 (m, 3H), 7.71 (m, 2H), 7.45 (t, J=8.0 Hz, 1H), 7.23 (d, J=8.0 Hz, 1H), 2.31 (t, J=7.5 Hz, 2H), 1.59 (m, 2H), 1.28 (m, 4H), 0.86 (t, J=6.9 Hz, 3H).

EXAMPLE 6(2)

4-(3-(Benzoylamino)phenyl)-2H-phthalazin-1-one

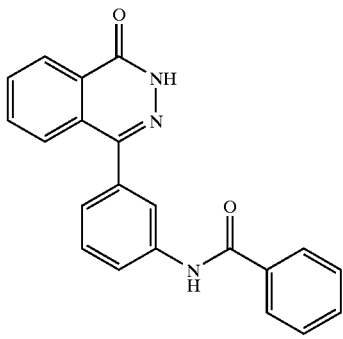

TLC: Rf 0.30 (Methanol:Chloroform=1:10); NMR (DMSO-$d_6$): δ 12.87 (s, 1H), 10.43 (s, 1H), 8.35 (m, 1H), 7.91 (m, 7H), 7.47 (m, 4H), 7.33 (d, J=8.0 Hz, 1H).

EXAMPLE 6(3)

4-(3-(Butyrylamino)phenyl)-2H-phthalazin-1-one

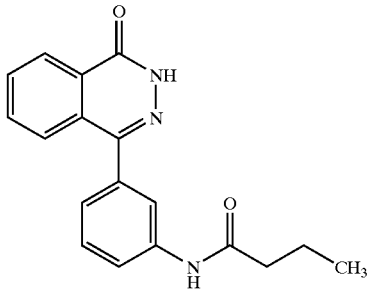

TLC: Rf 0.42 (Methanol:Chloroform=1:10); NMR (DMSO-$d_6$): δ 12.84 (s, 1H), 10.04 (s, 1H), 8.34 (m, 1H), 7.90 (m, 3H), 7.72 (m, 2H), 7.46 (t, J=7.8 Hz, 1H), 7.24 (d, J=7.8 Hz, 1H), 2.30 (t, J=7.1 Hz, 2H), 1.61 (m, 2H), 0.91 (t, J=7.3 Hz, 3H).

EXAMPLE 6(4)

4-(3-(Valerylamino)phenyl)-2H-phthalazin-1-one

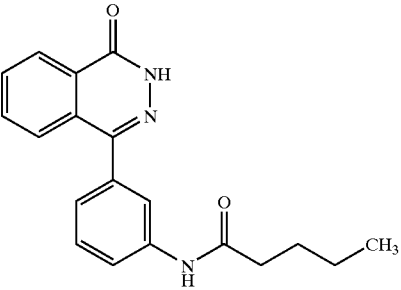

TLC: Rf 0.50 (Methanol:Chloroform=1:10); NMR (DMSO-$d_6$): δ 12.84 (s, 1H), 10.04 (s, 1H), 8.34 (m, 1H), 7.90 (m, 3H), 7.71 (m, 2H), 7.46 (t, J=7.8 Hz, 1H), 7.24 (d, J=7.8 Hz, 1H), 2.32 (t, J=7.4 Hz, 2H), 1.57 (m, 2H), 1.32 (m, 2H), 0.88 (t, J=7.4 Hz, 3H).

EXAMPLE 6(5)

4-(3-(Mesylamino)phenyl)-2H-phthalazin-1-one

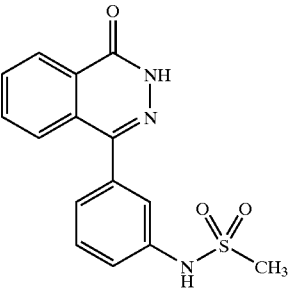

TLC: Rf 0.33 (Methanol:Chloroform=1:10); NMR (DMSO-$d_6$): δ 12.86 (s, 1H), 9.95 (s, 1H), 8.36–8.32 (m, 1H), 7.92–7.88 (m, 2H), 7.74–7.69 (m, 1H), 7.52 (t, J=8.0 Hz, 1H), 7.41–7.30 (m, 3H), 3.04 (s, 3H).

EXAMPLE 6(6)

4-(3-(Butylsulfonylamino)phenyl)-2H-phthalazin-1-one

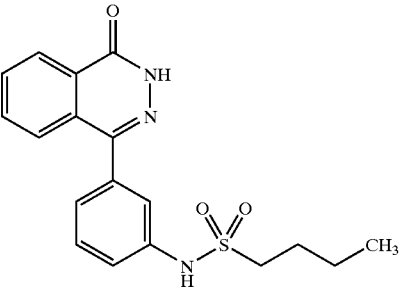

TLC: Rf 0.76 (Methanol:Chloroform=1:10); NMR (DMSO-$d_6$): δ 12.85 (s, 1H), 9.98 (s, 1H), 8.35–8.32 (m, 1H), 7.91–7.88 (m, 2H), 7.70–7.67 (m, 1H), 7.50 (t, J=7.8 Hz, 1H), 7.40 (s, 1H), 7.36 (d, J=7.8 Hz, 1H), 7.30 (d, J=7.8 Hz, 1H), 3.13 (t, J=7.6 Hz, 2H), 1.68–1.63 (m, 2H), 1.39–1.31 (m, 2H), 0.82 (t, J=7.4 Hz, 3H).

EXAMPLE 6(7)

4-(2-(Acetylamino)phenyl)-2H-phthalazin-1-one

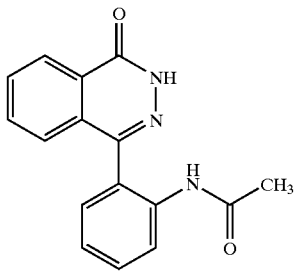

TLC: Rf 0.71 (Methanol:Chloroform=1:10); NMR (DMSO-$d_6$): δ 12.80 (s, 1H), 9.25 (s, 1H), 8.29 (d, J=7.8 Hz, 1H), 7.84–7.77 (m, 3H), 7.49 (dd, J=8.1, 7.5 Hz, 1H), 7.39 (d, J=7.5 Hz, 1H), 7.28 (t, J=7.5 Hz, 1H), 7.22 (d, J=8.1 Hz, 1H), 1.68 (s, 3H).

EXAMPLE 6(8)

4-(4-Chloro-3-(acetylamino)phenyl)-2H-phthalazin-1-one

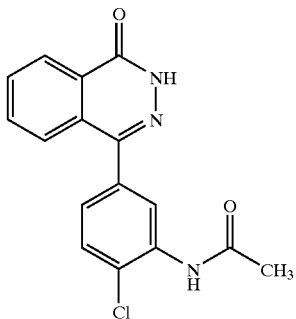

TLC: Rf 0.38 (Methanol:Chloroform=1:10); NMR (DMSO-$d_6$): δ 12.89 (s, 1H), 9.69 (s, 1H), 8.34 (ddd, J=6.8, 4.6, 2.0 Hz, 1H), 7.98 (d, J=2.0 Hz, 1H), 7.92–7.88 (m, 2H), 7.74 (ddd, J=6.8, 4.6, 2.0 Hz, 1H), 7.66 (d, J=8.2 Hz, 1H), 7.40 (dd, J=8.2, 2.0 Hz, 1H), 2.11 (s, 3H).

EXAMPLE 6(9)

4-(3-(4-(Methoxycarbonyl)butyrylamino)phenyl)-2H-phthalazin-1-one

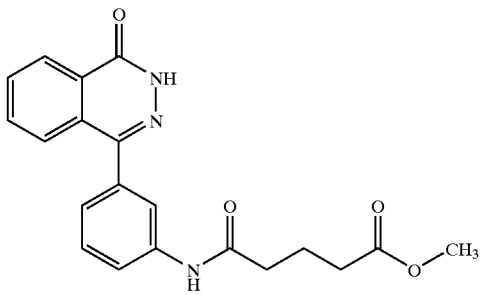

TLC: Rf 0.39 (Methanol:Chloroform=1:0); NMR (DMSO-$d_6$): δ 12.83 (s, 1H), 10.08 (s, 1H), 8.35–8.32 (m, 1H), 7.93–7.86 (m, 3H), 7.73–7.69 (m, 2H), 7.46 (t, J=7.8 Hz, 1H), 7.24 (d, J=7.8 Hz, 1H), 3.58 (s, 3H), 2.36 (t, J=7.4 Hz, 4H), 1.88–1.78 (m, 2H).

EXAMPLE 6(10)

4-(3-(Acetoxy)phenyl)-2H-phthalazin-1-one

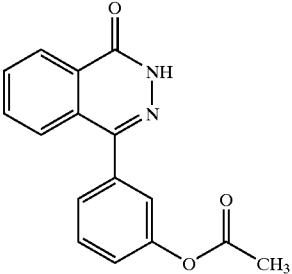

TLC: Rf 0.48 (Methanol:Chloroform=1:10); NMR (DMSO-$d_6$): δ 12.88 (s, 1H), 8.35–8.32 (m, 1H), 7.92–7.88 (m, 2H), 7.70–7.67 (m, 1H), 7.59 (t, J=7.8 Hz, 1H), 7.48 (d, J=7.8 Hz, 1H), 7.37 (s, 1H), 7.32–7.28 (m, 1H), 2.29 (s, 3H).

EXAMPLE 7

4-(3-(4-Aminobutyrylamino)phenyl)-2H-phthalazin-1-one

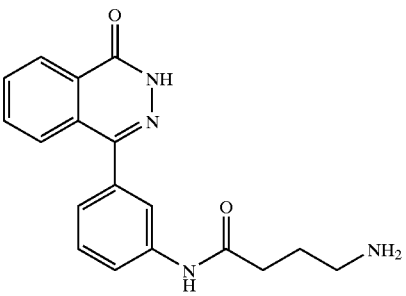

A suspension of the compound prepared in example 4(2) (228 mg) and 10% palladium carbon (23.0 mg) in dimethylformamide (1.50 ml) was stirred for 3 hours at 50° C. under an atmosphere of hydrogen. The reaction mixture was filtered, and the filtrate was concentrated. The residue was recrystallized from methanol-methylene chloride-hexane and dried under reduced pressure to give the compound of the present invention (112 mg) having the following physical data.

TLC: Rf 0.45 (Methanol:Chloroform=1:10); NMR (DMSO-$d_6$): δ 10.11 (brs, 1H), 8.34 (m, 1H), 7.90 (m, 3H), 7.72 (m, 2H), 7.46 (t, J=7.8 Hz, 1H), 7.23 (d, J=7.8 Hz, 1H), 2.56 (t, J=7.0 Hz, 2H), 2.35 (t, J=7.6 Hz, 2H), 1.65 (m, 2H).

EXAMPLE 7(1)

4-(3-(3-Aminopropionylamino)phenyl)-2H-phthalazin-1-one

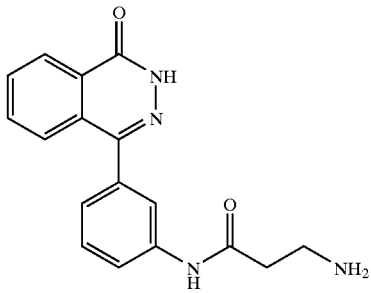

The compound having the following physical data was obtained by the same procedure as a series of reactions of Example 7, using the compound prepared in example 4(4) instead of the compound prepared in example 4(2).

TLC: Rf 0.22 (Methanol:Chloroform=1:10); NMR (DMSO-$d_6$): δ 10.19 (s, 1H), 8.34 (m, 1H), 7.90 (m, 3H), 7.72 (m, 2H), 7.46 (t, J=7.8 Hz, 1H), 7.24 (d, J=7.8 Hz, 1H), 2.85 (t, J=6.3 Hz, 2H), 2.42 (t, J=6.3 Hz, 2H).

EXAMPLE 8

4-(3-(4-Carboxybutyrylamino)phenyl)-2H-phthalazin-1-one

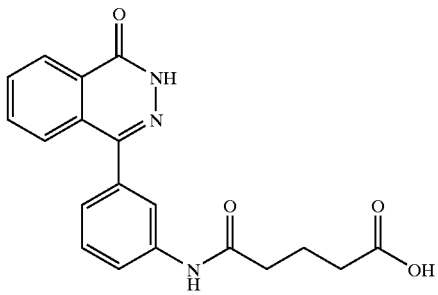

To a suspension of the compound prepared in example 6(9) (100 mg) in methanol (5.00 ml) was added dropwise 2N aqueous solution of sodium hydroxide (0.410 ml) at room temperature, and the mixture was stirred for 2 hours. To the reaction mixture was added 2N hydrochloric acid (0.410 ml), the mixture was stirred for 1 hour and then concentrated. The residue was dissolved into methylene chloride and the precipitate was filtered off. The filtrate was concentrated. The residue was recrystallized from methanolmethylene chloride-hexane and dried under reduced pressure to give the compound of the present invention (96.0 mg) having the following physical data.

TLC: Rf 0.30 (Methanol:Chloroform=2:8); NMR (DMSO-$d_6$): δ 12.83 (s, 1H), 12.06 (brs, 1H), 10.10 (s, 1H), 8.35–8.30 (m, 1H), 7.93–7.87 (m, 3H), 7.73–7.70 (m, 2H), 7.48–7.43 (m, 1H), 7.24 (d, J=7.2 Hz, 1H), 2.37 (t, J=7.2 Hz, 2H), 2.27 (t, J=7.2 Hz, 2H), 1.85–1.75 (m, 2H).

EXAMPLE 9

4-(3-(5-Hydroxyvalerylamino)phenyl)-2H-phthalazin-1-one

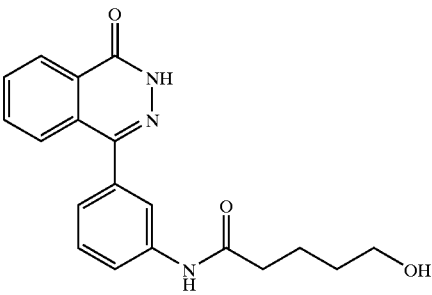

To a suspension of the compound prepared in example 6(9) (100 mg) in tetrahydrofuran (5.00 ml) was added lithium aluminium hydride (10.4 mg) at room temperature. The reaction mixture was stirred for 2 hours. To the reaction mixture was added lithium aluminium hydride (10.4 mg) and the mixture was stirred for 1 hour. To the reaction mixture was added lithium aluminium hydride (3.0 mg) and the mixture was stirred for 1 hour. To the reaction mixture was added water and the mixture was filtered. The filtrate was concentrated. The residue was purified by column chromatography on silica gel (methanol:chloroform= 1:20→1:10) to give the compound (22.7 mg) of the present invention having the following physical data.

TLC: Rf 0.31 (Methanol:Chloroform=1:10); NMR (DMSO-$d_6$): δ 12.83 (s, 1H), 10.04 (s, 1H), 8.35–8.32 (m, 1H), 7.93–7.86 (m, 3H), 7.73–7.69 (m, 2H), 7.46 (t, J=7.8 Hz, 1H), 7.23 (d, J=7.8 Hz, 1H), 4.38 (t, J=5.1 Hz, 1H), 3.43–3.37 (m, 2H), 2.32 (t, J=7.5 Hz, 2H), 1.64–1.49 (m, 2H), 1.47–1.40 (m, 2H).

EXAMPLE 10

4-(3-(4-(t-Butoxycarbonylamino)butylaminomethyl) phenyl)-2H-phthalazin-1-one

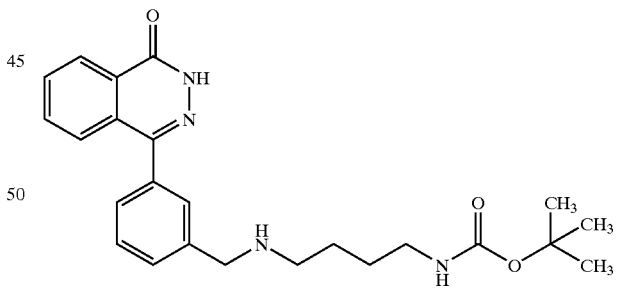

A suspension of the compound prepared in reference example 4 (250 mg) and 4-(t-butoxycarbonylamino) butylamine (188 mg) in tetrahydrofuran (10 ml) was refluxed for 1 hour. The reaction mixture was cooled to 0° C. and then diluted with methanol (10 ml), added acetic acid (57 μl) and sodium cyanoborohydride (63 mg). The reaction mixture was stirred for 1 hour at 0° C. and then stirred overnight at room temperature. Water was added to the reaction mixture and then extracted with ethyl acetate. The extract was washed with water and a saturated aqueous solution of sodium chloride, successively, dried over anhydrous sodium sulfate and concentrated. The residue was purified by column chromatography on silica gel (chloroform methanol=50:1→10:1) to give the compound (314 mg) of the present invention having the following physical data.

TLC: Rf 0.32 (Chloroform:Methanol=9:1); NMR (DMSO-$d_6$): δ 12.82 (s, 1H), 8.33 (m, 1H), 7.91–7.84 (m, 2H), 7.68 (m, 1H), 7.55 (s, 1H), 7.49–7.42 (m, 3H), 6.77 (t, J=5.4 Hz, 1H), 3.81 (s, 2H), 2.88 (m, 2H), 2.54 (m, 2H), 1.42–1.38 (m, 4H), 1.33 (s, 9H).

EXAMPLE 11

4-(3-(4-Aminobutylaminomethyl)phenyl)-2H-phthalazin-1-one Dihydrochloride

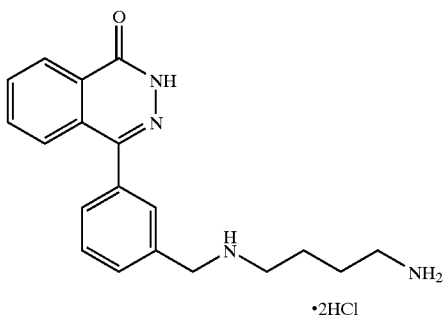

The compound having the following physical data was obtained by the same procedure as a series of reactions of Example 5, using the compound prepared in example 10 instead of the compound prepared in example 4.

TLC: Rf 0.26 (Chloroform:Methanol:28% Ammonia water=65:25:4); NMR (DMSO-$d_6$): δ 12.91 (s, 1H), 9.40 (br-s, 2H), 8.35 (m, 1H), 8.10–7.86 (m, 5H), 7.80–7.72 (m, 3H), 7.64–7.58 (m, 2H), 4.21 (s, 2H), 2.94 (t, J=7.4 Hz, 2H), 2.79 (t, J=7.4 Hz, 2H), 1.78–1.55 (m, 4H).

EXAMPLE 12

4-(3-(3-Ethyl-2-thioureido)phenyl)-2H-phthalazin-1-one

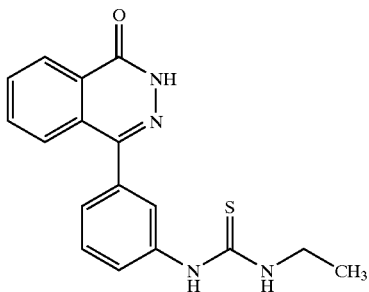

To a solution of 4-(3-aminophenyl)-2H-phthalazin-1-one (119 mg) in tetrahydrofuran (4 ml) was added ethyl isothiocyanate (44 μl). The mixture was refluxed for 4 hours. The reaction mixture was cooled to room temperature, and then the precipitate was washed with tetrahydrofuran and ether to give the compound (61.0 mg) of the present invention having the following physical data.

TLC: Rf 0.57 (Chloroform:Methanol=9:1); NMR (DMSO-$d_6$): δ 12.84 (s, 1H), 9.60 (br-s, 1H), 8.33 (m, 1H), 7.94–7.84 (m, 4H), 7.70 (s, 1H), 7.54–7.44 (m, 2H), 7.30 (m, 1H), 3.48 (m, 2H), 1.12 (t, J=7.2 Hz, 3H).

EXAMPLE 12(1)

4-(3-(3-Ethylureido)phenyl)-2H-phthalazin-1-one

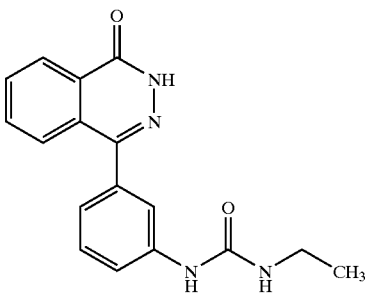

The compound of the present invention having the following physical data was obtained by the same procedure as a series of reactions of example 12, using ethyl isocyanate instead of ethyl isothiocyanate.

TLC: Rf 0.42 (Methanol:Chloroform=1:10); NMR (DMSO-$d_6$): δ 12.80 (s, 1H), 8.60 (s, 1H), 8.34–8.31 (m, 1H), 7.92–7.85 (m, 2H), 7.74–7.71 (m, 1H), 7.68 (s, 1H), 7.47 (d, J=8.4 Hz, 1H), 7.37 (m, 1H), 7.08 (d, J=7.8 Hz, 1H), 6.14 (t, J=5.6 Hz, 1H), 3.14–3.05 (m, 2H), 1.04 (t, J=7.2 Hz, 3H).

EXAMPLE 13

4-(3-(Ethoxycarbonylamino)phenyl)-2H-phthalazin-1-one

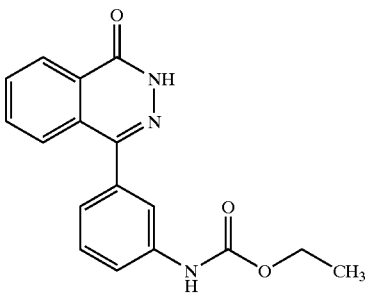

To a solution of 4-(3-aminophenyl)-2H-phthalazin-1-one (119 mg) in pyridine (2 ml) was added ethyl chloroformate (48 μl) under cooling with ice. The mixture was stirred for 2 hours. The reaction mixture was diluted with ethyl acetate, washed with 1N hydrochloric acid, water and a saturated aqueous solution of sodium chloride, successively, dried over anhydrous sodium sulfate and concentrated. The residue was washed with ether to give the compound (89.4 mg) of the present invention having the following physical data.

TLC: Rf 0.49 (Hexane:Ethyl acetate=1:2); NMR (DMSO-$d_6$): δ 12.83 (s, 1H), 9.80 (s, 1H), 8.33 (m, 1H), 7.94–7.84 (m, 2H), 7.74–7.68 (m, 2H), 7.60 (d, J=8.0 Hz, 1H), 7.44 (t, J=8.0 Hz, 1H), 7.19 (d, J=8.0 Hz, 1H), 4.12 (q, J=7.0 Hz, 2H), 1.24 (t, J=7.0 Hz, 3H).

EXAMPLE 14

4-(3-(5-(t-Butoxycarbonylamino)pentylamino)phenyl)-2H-phthalazin-1-one

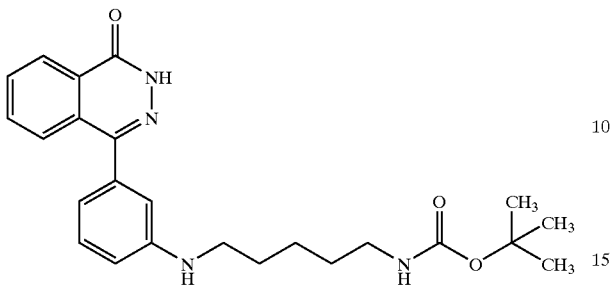

To a solution of 4-(3-aminophenyl)-2H-phthalazin-1-one (200 mg) and 1-t-butoxycarbonyl-2-hydroxypiperidine (170 mg, see J Org. Chem., 61, 4180 (1996)) in dimethylformamide (4 ml) were added acetic acid (98 μl) and sodium triacetoxyborohydride (358 mg) and then the mixture was stirred overnight at room temperature. The reaction mixture was diluted with ethyl acetate, washed with a saturated aqueous solution of sodium bicarbonate and a saturated aqueous solution of sodium chloride, successively, dried over anhydrous sodium sulfate and concentrated. The residue was purified by column chromatography on silica gel (methylene chloride:ethyl acetate=4:1). Further the obtained residue was purified by column chromatography on silica gel (hexane:ethyl acetate=1:2) to give the compound (106 mg) of the present invention having the following physical data.

TLC: Rf 0.50 (Methylene chloride:Ethyl acetate=1:2); NMR (DMSO-$d_6$): δ 12.73 (s, 1H), 8.31 (m, 1H), 7.91–7.83 (m, 2H), 7.74 (m, 1H), 7.21 (t, J=7.7 Hz, 1H), 6.78–6.54 (m, 4H), 5.77 (t, J=5.3 Hz, 1H), 3.00 (m, 2H), 2.90 (m, 2H), 1.54 (m, 2H), 1.50–1.18 (m, 13H).

EXAMPLE 15

4-(3-(5-Aminopentylamino)phenyl)-2H-phthalazin-1-one Dihydrochloride

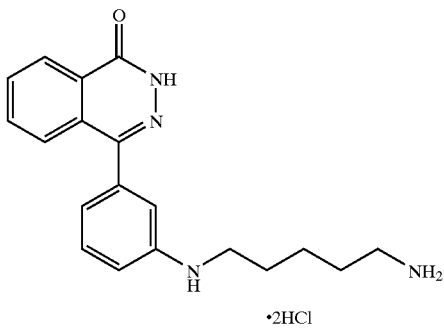

The compound of the present invention having the following physical data was obtained by the same procedure as a series of reactions of example 5, using the compound prepared in example 14 instead of the compound prepared in example 4.

TLC: Rf 0.44 (Chloroform:Methanol:28% Ammonia water=65:25:4); NMR (DMSO-$d_6$): δ 12.83 (s, 1H), 8.33 (m, 1H), 8.04–7.76 (m, 6H), 7.72 (m, 1H), 7.42 (m, 1H), 7.22–7.02 (m, 2H), 3.14 (t, J=7.2 Hz, 2H), 2.75 (m, 2H), 1.70–1.50 (m, 4H), 1.46–1.34 (m, 2H).

EXAMPLE 16

4-(3-(Propylthiocarbonylamino)phenyl)-2H-phthalazin-1-one

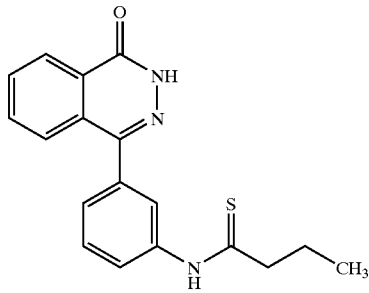

A solution of the compound prepared in example 6(3) (70.0 mg) and Lawesson's reagent (96.4 mg) in dioxane (3.00 ml) was refluxed for 3 hours. The reaction mixture was cooled to room temperature and concentrated. The residue was purified by column chromatography on silica gel (methanol:chloroform=1:20) to give the compound (6.1 mg) of the present invention having the following physical data.

TLC: Rf 0.24 (Methanol:Chloroform=1:20); NMR (DMSO-$d_6$): δ 12.87 (s, 1H), 11.66 (s, 1H), 8.36–8.32 (m, 1H), 8.08 (s, 1H), 7.91–7.84 (m, 4H), 7.57 (t, J=7.8 Hz, 1H), 7.45 (d, J=7.8 Hz, 1H), 2.73 (t, J=7.4 Hz, 2H), 1.82–1.75 (m, 2H), 0.94 (t, J=7.4 Hz, 3H).

EXAMPLE 17

4-(3-(5-(Acetylamino)valerylamino)phenyl)-2H-phthalazin-1-one

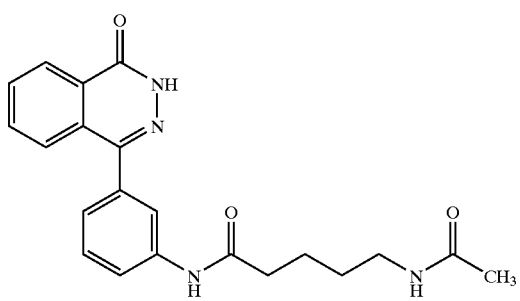

The compound of the present invention having the following physical data was obtained by the same procedure as a series of reactions of example 4, using 5-acetylaminopentanoic acid instead of 5-t-butoxycarbonylaminopentanoic acid.

TLC: Rf 0.18 (Methanol:Chloroform=1:9); NMR (DMSO-$d_6$): δ 12.83 (s, 1H), 10.05 (s, 1H), 8.35–8.32 (m, 1H), 7.93–7.86 (m, 3H), 7.82–7.78 (m, 1H), 7.74–7.69 (m, 2H), 7.46 (t, J=8.1 Hz, 1H), 7.24 (d, J=7.2 Hz, 1H), 3.06–3.00 (m, 2H), 2.32 (t, J=7.2 Hz, 2H), 1.77 (s, 3H), 1.63–1.53 (m, 2H), 1.46–1.36 (m, 2H).

EXAMPLE 18

4-(3-(3-(3-t-Butoxycarbonylaminopropyl)-2-thioureido)phenyl)-2H-phthalazin-1-one

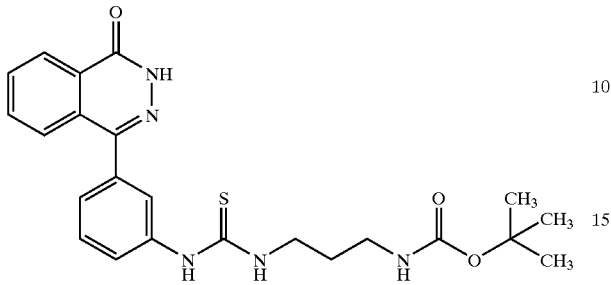

The compound of the present invention having the following physical data was obtained by the same procedure as a series of reactions of example 12, using 3-t-butoxycarbonylaminopropyl isothiocyanate instead of ethyl isothiocyanate.

TLC: Rf 0.46 (Chloroform:Methanol=9:1); NMR (DMSO-$d_6$): δ 12.84 (s, 1H), 9.68 (br-s, 1H), 8.33 (m, 1H), 7.90–7.60 (m, 4H), 7.69 (s, 1H), 7.53–7.45 (m, 2H), 7.32 (m, 1H), 6.83 (m, 1H), 3.46 (m, 2H), 2.95 (m, 2H), 1.63 (m, 2H), 1.35 (s, 9H).

EXAMPLE 19

4-(3-(3-(3-Aminopropyl)-2-thioureido)phenyl)-2H-phthalazin-1-one Hydrochloride

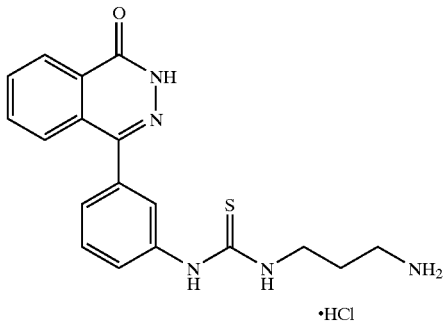

The compound of the present invention having the following physical data was obtained by the same procedure as a series of reactions of example 5, using the compound prepared in example 18 instead of the compound prepared in example 4.

TLC: Rf 0.48 (Chloroform:Methanol:28% Ammonia water=65:25:4); NMR (DMSO-$d_6$): δ 12.85 (s, 1H), 10.18 (br-s, 1H), 8.34 (m, 2H), 8.16–7.80 (m, 6H), 7.76 (s, 1H), 7.58 (d, J=8.1 Hz, 1H), 7.48 (t, J=7.8 Hz, 1H), 7.31 (d, J=7.8 Hz, 1H), 3.55 (m, 2H), 2.84 (m, 2H), 1.84 (m, 2H).

EXAMPLE 20

4-(3-(5-Bromovalerylamino)phenyl)-2H-phthalazin-1-one

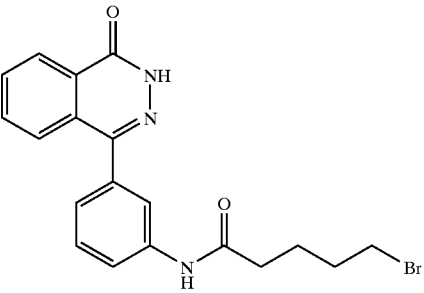

To a solution of 4-(3-aminophenyl)-2H-phthalazin-1-one (7.00 g) in pyridine (40.0 ml) was added a solution of 5-bromovaleryl chloride (6.00 ml) in methylene chloride (3.00 ml) under cooling with ice and then the mixture was stirred for 20 minutes at room temperature. The reaction mixture was concentrated and the residue was extracted with ethyl acetate. The organic layer was washed with a saturated aqueous solution of sodium bicarbonate and a saturated aqueous solution of sodium chloride, successively, dried over anhydrous magnesium sulfate and concentrated. The residue was washed with a mixture of ethanol and methylene chloride (7:3) by heating to give the compound (8.21 g) of the present invention having the following physical data.

TLC: Rf 0.38 (Methylene chloride:Methanol=20:1); NMR (DMSO-$d_6$): δ 12.84 (s, 1H), 10.08 (s, 1H), 8.35–8.32 (m, 1H), 7.91–7.69 (m, 5H), 7.46 (t, J=7.8 Hz, 1H), 7.25 (d, J=7.8 Hz, 1H), 3.55 (t, J=6.0 Hz, 2H), 2.36 (t, J=7.2 Hz, 2H), 1.87–1.68 (m, 4H).

EXAMPLE 20(1)

4-(3-(5-Bromovalerylamino)-4-chlorophenyl)-2H-phthalazin-1-one

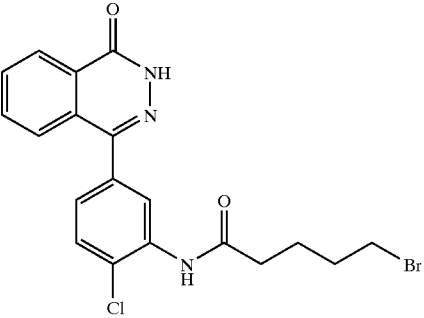

The compound of the present invention having the following physical data was obtained by the same procedure as a series of reactions of example 20, using 4-(3-amino-4-chlorophenyl)-2H-phthalazin-1-one instead of 4-(3-aminophenyl)-2H-phthalazin-1-one.

TLC: Rf 0.52 (Methylene chloride:Methanol=9:1); NMR (DMSO-$d_6$): δ 12.90 (s, 1H), 9.65 (s, 1H), 8.36–8.32 (m, 1H), 7.93–7.89 (m, 3H), 7.76–7.64 (m, 2H), 7.43–7.38 (m, 1H), 3.56 (t, J=6.8 Hz, 2H), 2.50–2.44 (m, 2H), 1.90–1.60 (m, 4H).

EXAMPLE 21

4-(3-(5-Cyclohexylaminovalerylamino)-4-chlorophenyl)-2H-phthalazin-1-one Hydrochloride

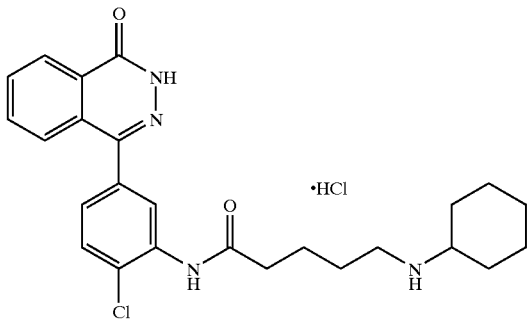

A mixture of the compound prepared in example 20(1) (200 mg) and cyclohexylamine (3.00 ml) was stirred for 1 hour at 80° C. The reaction mixture was concentrated and the residue was dissolved into ethyl acetate, washed with a saturated aqueous solution of sodium bicarbonate and a saturated aqueous solution of sodium chloride, successively, dried over anhydrous magnesium sulfate and concentrated. To a solution of the residue in methanol (2.00 ml) was added 4N solution of hydrochloric acid in ethyl acetate (1.00 ml) under cooling with ice, and the mixture was stirred for 15 minutes at room temperature. The reaction mixture was concentrated and the residue was recrystallized from methanol-hexane to give the compound (72.5 mg) of the present invention having the following physical data.

TLC: Rf 0.70 (Methylene chloride:Methanol:Acetic acid=8:1:1); NMR (DMSO-$d_6$): δ 12.90 (s, 1H), 9.72 (s, 1H), 8.53 (brs, 2H), 8.35–8.32 (m, 1H), 7.94–7.89 (m, 3H), 7.75–7.71 (m, 1H), 7.68 (d, J=8.1 Hz, 1H), 7.42 (dd, J=8.1, 1.8 Hz, 1H), 2.90 (brs, 3H), 2.01–1.98 (m, 2H), 1.74–1.57 (m, 8H), 1.281.22 (m, 6H).

EXAMPLE 21(1)–EXAMPLE 21(97)

The following compounds of the present invention were obtained by the same procedure as a series of reactions of example 21, using corresponding amine derivative instead of cyclohexylamine and the compound prepared in example 20, example 20(1) or corresponding halide compound.

EXAMPLE 21(1)

4-(3-(5-Cyclopentylaminovalerylamino)phenyl)-2H-phthalazin-1-one Hydrochloride

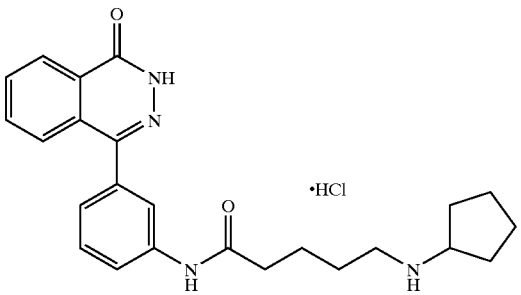

TLC: Rf 0.43 (Chloroform:Methanol:Acetic acid=8:2:1); NMR (DMSO-$d_6$): δ 12.85 (s, 1H), 10.27 (s, 1H), 8.72 (brs, 2H), 8.37–8.30 (m, 1H), 7.95–7.85 (m, 3H), 7.76–7.68 (m, 2H), 7.46 (t, J=7.8 Hz, 1H), 7.24 (d, J=7.5 Hz, 1H), 3.60–3.33 (m, 1H), 2.93–2.80 (m, 2H), 2.43–2.34 (m, 2H), 2.02–1.28 (m, 12H).

EXAMPLE 21(2)

4-(3-(5-Cyclohexylaminovalerylamino)phenyl)-2H-phthalazin-1-one Hydrochloride

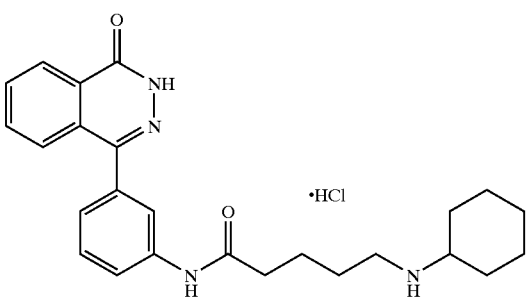

TLC: Rf 0.48 (Chloroform:Methanol:Acetic acid=8:2:1); NMR (DMSO-$d_6$): δ 12.85 (s, 1H), 10.25 (s, 1H), 8.59 (brs, 2H), 8.36–8.31 (m, 1H), 7.96–7.85 (m, 3H), 7.75–7.68 (m, 2H), 7.46 (t, J=7.8 Hz, 1H), 7.24 (d, J=7.5 Hz, 1H), 3.60–3.17 (m, 1H), 2.98–2.83 (m, 2H), 2.44–2.32 (m, 2H), 2.05–1.95 (m, 2H), 1.77–1.47 (m, 6H), 1.35–0.99 (m, 6H).

EXAMPLE 21(3)

4-(3-(6-Dimethylaminohexanoylamino)phenyl)-2H-phthalazin-1-one Hydrochloride

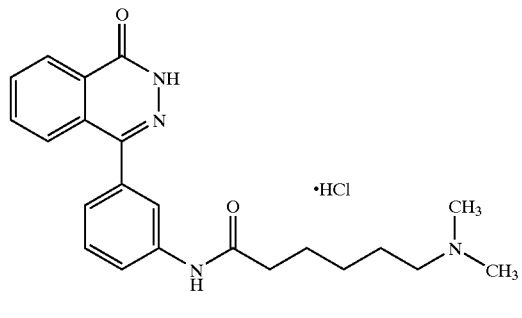

TLC: Rf 0.35 (Chloroform:Methanol:Acetic acid= 8:2:0.5); NMR (DMSO-d$_6$): δ 12.85 (s, 1H), 10.18 (s, 1H), 9.97 (brs, 1H), 8.36–8.32 (m, 1H), 7.91–7.89 (m, 3H), 7.74–7.70 (m, 2H), 7.46 (t, J=7.8 Hz, 1H), 7.24 (d, J=7.8 Hz, 1H), 3.05–2.95 (m, 2H), 2.71 (d, J=4.8 Hz, 6H), 2.35 (t, J=7.2 Hz, 2H), 1.72–1.52 (m, 4H), 1.39–1.22 (m, 2H).

EXAMPLE 21(4)

4-(3-(5-(Thiazolidin-3-yl)valerylamino)phenyl)-2H-phthalazin-1-one

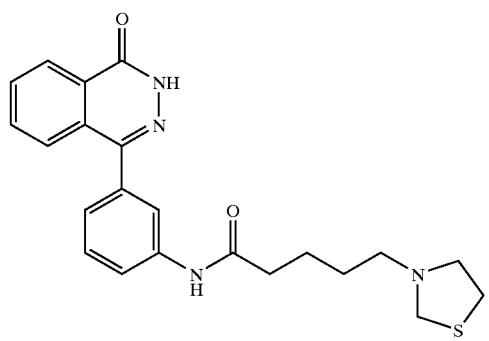

TLC: Rf 0.50 (Chloroform:Methanol=9:1); NMR (DMSO-d$_6$): δ 12.83 (s, 1H), 10.05 (s, 1H), 8.35–8.30 (m, 1H), 7.94–7.86 (m, 3H), 7.75–7.69 (m, 2H), 7.46 (t, J=7.8 Hz, 1H), 7.23 (d, J=7.8 Hz, 1H), 3.99 (s, 2H), 2.97 (t, J=6.3 Hz, 2H), 2.75 (t, J=6.3 Hz, 2H), 2.36–2.26 (m, 4H), 1.68–1.58 (m, 2H), 1.51–1.41 (m, 2H).

EXAMPLE 21(5)

4-(3-(5-(Furan-2-ylmethylamino)valerylamino)phenyl)-2H-phthalazin-1-one Hydrochloride

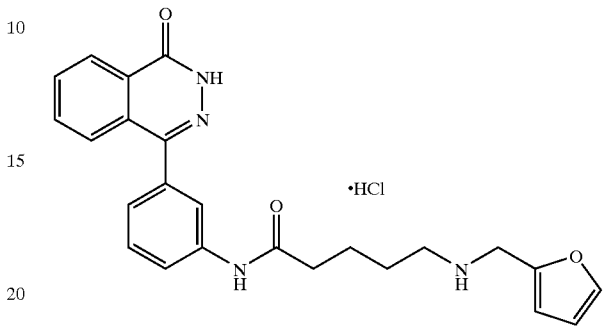

TLC: Rf 0.33 (Chloroform:Methanol:28% Ammonia water=9:1:0.1); NMR (DMSO-d$_6$): δ 12.84 (s, 1H), 10.30 (s, 1H), 9.37–9.20 (br, 2H), 8.35–8.30 (m, 1H), 7.94–7.83 (m, 3H), 7.74–7.68 (m, 3H), 7.45 (t, J=7.8 Hz, 1H), 7.23 (d, J=7.8 Hz, 1H), 6.62–6.61 (m, 1H), 6.50–6.48 (m, 1H), 4.17 (t, J=5.0 Hz, 2H), 2.95–2.79 (br, 2H), 2.42–2.30 (br, 2H), 1.74–1.51 (br, 4H).

EXAMPLE 21(6)

4-(3-(5-(N-Methyl-N-propylamino)valerylamino)phenyl)-2H-phthalazin-1-one Hydrochloride

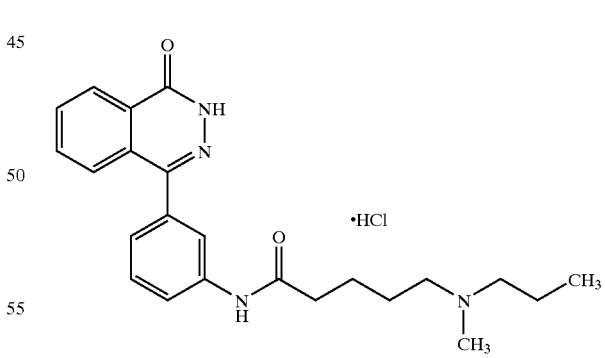

TLC: Rf 0.32 (Chloroform:Methanol:Acetic acid= 8:2:0.5); NMR (DMSO-d$_6$): δ 12.84 (s, 1H), 10.26 (s, 1H), 9.98 (brs, 1H), 8.35–8.32 (m, 1H), 7.89 (m, 3H), 7.72 (m, 2H), 7.46 (t, J=7.2 Hz, 1H), 7.24 (d, J=7.2 Hz, 1H), 2.98 (m, 4H), 2.68 (s, 3H), 2.40 (m, 2H), 1.65 (m, 6H), 0.87 (t, J=7.2 Hz, 3H).

EXAMPLE 21(7)

4-(3-(5-(2-Dimethylaminoethylamino)valerylamino)phenyl)-2H-phthalazin-1-one Dihydrochloride

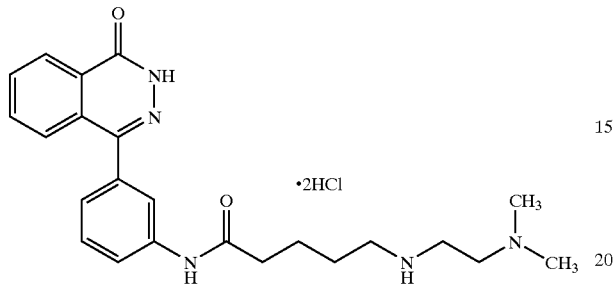

TLC: Rf 0.10 (Acetic acid); NMR (DMSO-d$_6$): δ 12.85 (s, 1H), 10.72 (brs, 1H), 10.24 (s, 1H), 9.19 (brs, 2H), 8.35–8.32 (m, 1H), 7.92–7.88 (m, 3H), 7.74-7.70 (m, 2H), 7.46 (t, J=7.8 Hz, 1H), 7.24 (d, J=7.8 Hz, 1H), 3.42 (m, 4H), 2.98 (brs, 2H), 2.82 (s, 6H), 2.39 (m, 2H), 1.67 (brs, 4H).

EXAMPLE 21(8)

4-(3-(5-Diethylaminovalerylamino)phenyl)-2H-phthalazin-1-one Hydrochloride

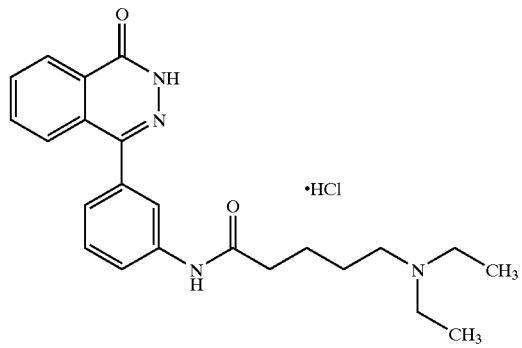

TLC: Rf 0.17 (Chloroform:Methanol:28% Ammonia water=9:1:0.1); NMR (DMSO-d$_6$): δ 12.84 (s, 1H), 10.30 (s, 1H), 10.15–9.99 (br, 1H), 8.35–8.30 (m, 1H), 7.89–7.83 (m, 3H), 7.75–7.68 (m, 2H), 7.45 (t, J=7.8 Hz, 1H), 7.23 (d, J=7.8 Hz, 1H), 3.08–2.99 (m, 6H), 2.44–2.32 (br, 2H), 1.77–1.48 (br, 4H), 1.18 (t, J=7.2 Hz, 6H).

EXAMPLE 21(9)

4-(3-(5-(Azetidine-1-yl)valerylamino)phenyl)-2H-phthalazin-1-one Hydrochloride

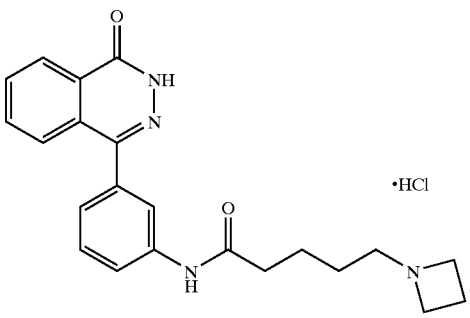

TLC: Rf 0.37 (Chloroform:Methanol:Acetic acid=8:2:1); NMR (DMSO-d$_6$): δ 12.84 (s, 1H), 10.21 (s, 2H), 8.36–8.31 (m, 1H), 7.94–7.86 (m, 3H), 7.74–7.69 (m, 2H), 7.46 (t, J=7.8 Hz, 1H), 7.24 (d, J=7.5 Hz, 1H), 4.10–3.86 (m, 4H), 3.15–3.07 (m, 2H), 2.50–2.16 (m, 4H), 1.68–1.44 (m, 4H).

EXAMPLE 21(10)

4-(3-(5-Benzylaminovalerylamino)phenyl)-2H-phthalazin-1-one Hydrochloride

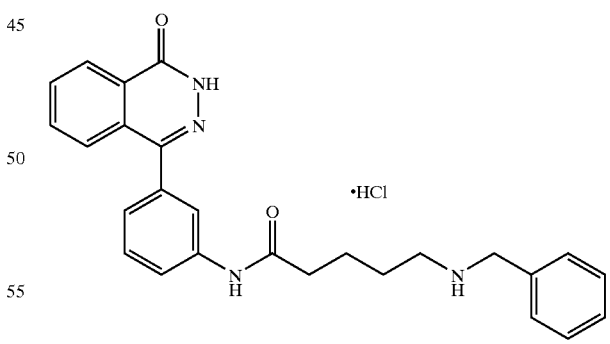

TLC: Rf 0.33 (Chloroform:Methanol:28% Ammonia water=9:10.1); NMR (DMSO-d$_6$): δ 12.84 (s, 1H), 10.28 (s, 1H), 9.33–9.11 (br, 2H), 8.35–8.30 (m, 1H), 7.93–7.83 (m, 3H), 7.74–7.68 (m, 2H), 7.55–7.35 (m, 6H), 7.23 (d, J=7.6 Hz, 1H), 4.09 (t, J=5.8 Hz, 2H), 2.98–2.79 (br, 2H), 2.36 (t, J=7.0 Hz, 2H), 1.79–1.52 (br, 4H).

EXAMPLE 21(11)

4-(3-(5-(N-(Furan-2-yl)methyl-N-methylamino)valerylamino)phenyl)-2H-phthalazin-1-one Hydrochloride

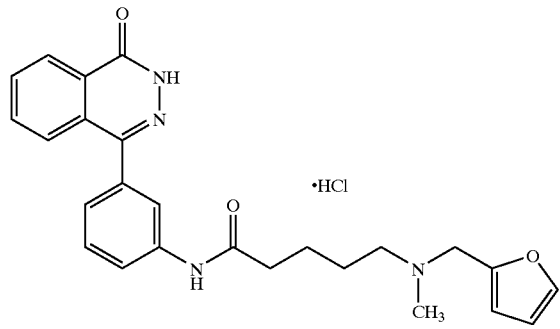

TLC: Rf 0.49 (Chloroform:Methanol:Acetic acid=8:2:1); NMR (DMSO-$d_6$): δ 12.85 (s, 1H), 10.40 (s, 1H), 10.24 (s, 1H), 8.35–8.31 (m, 1H), 7.93–7.86 (m, 3H), 7.23 (d, J=1.5 Hz, 1H), 7.74–7.70 (m, 2H), 7.46 (t, J=8.1 Hz, 1H), 7.24 (d, J=7.8 Hz, 1H), 6.73 (d, J=3.3 Hz, 1H), 6.55–6.53 (m, 1H), 4.44–4.30 (m, 2H), 3.14–2.90 (m, 2H), 2.65 (d, J=4.5 Hz, 3H), 2.39 (t, J=7.5 Hz, 2H), 1.80–1.54 (m, 4H).

EXAMPLE 21(12)

4-(3-(5-(N-methylamino)valerylamino)phenyl)-2H-phthalazin-1-one Hydrochloride

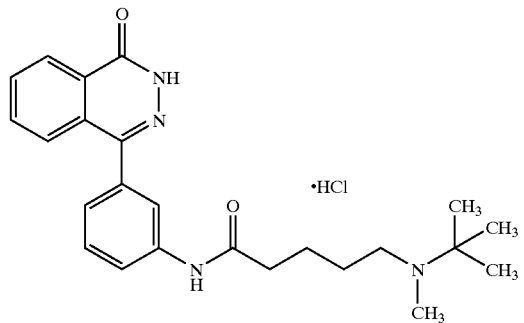

TLC: Rf 0.49 (Chloroform:Methanol:28% Ammonia water=9:1:0.1); NMR (DMSO-$d_6$): δ 12.85 (s, 1H), 10.30 (s, 1H), 9.88–9.69 (br, 1H), 8.35–8.30 (m, 1H), 7.94–7.83 (m, 3H), 7.76–7.68 (m, 2H), 7.45 (t, J=7.8 Hz, 1H), 7.23 (d, (d, J=7.8 Hz, 1H), 3.29–3.18 (m, 1H), 2.81–2.60 (m, 4H), 2.40 (t, J=6.8 Hz, 2H), 1.87–1.52 (br, 4H), 1.31 (s, 9H).

EXAMPLE 21(13)

4-(3-(5-(N-Methy-N-2-propynylamino)valerylamino)phenyl)-2H-phthalazin-1-one Hydrochloride

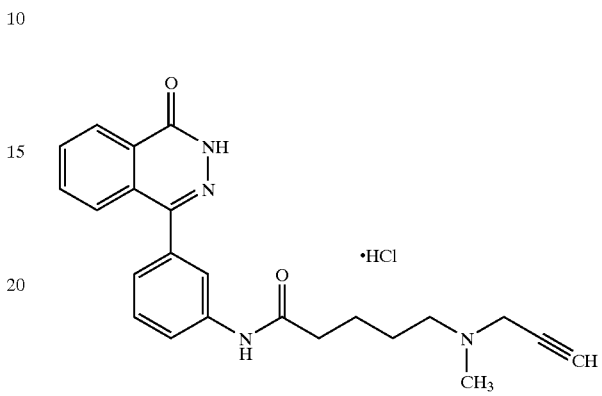

TLC: Rf 0.34 (Chloroform:Methanol:Acetic acid=8:2:0.5); NMR (DMSO-$d_6$): δ 12.84 (s, 1H), 10.56 (brs, 1H), 10.21 (s, 1H), 8.33 (m, 1H), 7.86 (m, 3H), 7.72 (m, 2H), 7.46 (t, J=7.8 Hz, 1H), 7.24 (d, J=7.8 Hz, 1H), 4.09 (s, 2H), 3.84 (s, 1H), 3.10 (m, 2H), 2.77 (s, 3H), 2.39 (m, 2H), 1.65 (m, 4H).

EXAMPLE 21(14)

4-(3-(5-(N-Isobutyl-N-methylamino)valerylamino)phenyl)-2H-phthalazin-1-one Hydrochloride

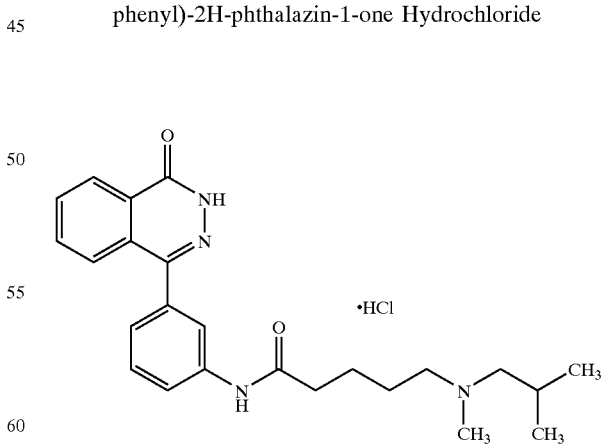

TLC: Rf 0.22 (Chloroform:Methanol:Acetic acid=8:2:0.5); NMR (DMSO-$d_6$): δ 12.85 (s, 1H), 10.24 (s, 1H), 9.25 (brs, 1H), 8.35–8.32 (m, 1H), 7.91–7.88 (m, 3H), 7.74–7.70 (m, 2H), 7.46 (t, J=7.8 Hz, 1H), 7.24 (d, J=7.8 Hz, 1H), 3.08–2.81 (m, 4H), 2.71 (d, J=4.8 Hz, 3H), 2.40 (t, J=6.6 Hz, 2H), 2.05–1.98 (m, 1H), 1.70–1.62 (m, 4H), 0.95–0.91 (m, 6H).

EXAMPLE 21(15)

4-(3-(4-Morpholinobutyrylamino)phenyl)-2H-phthalazin-1-one

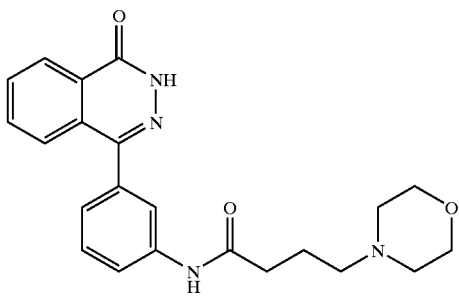

Hydrochloride:
TLC: Rf 0.27 (Chloroform:Methanol:Acetic acid=8:2:1); NMR (DMSO): δ 12.85 (s, 1H), 10.60 (brs, 1H), 10.31 (s, 1H), 8.36–8.30 (m, 1H), 7.94–7.85 (m, 3H), 7.76–7.68 (m, 2H), 7.47 (t, J=7.8 Hz, 1H), 7.26 (d, J=7.8 Hz, 1H), 3.98–3.88 (m, 2H), 3.80–3.68 (m, 2H), 3.48–3.38 (m, 2H, overlapped with H$_2$O), 3.16–2.98 (m, 4H), 2.52–2.42 (m, 2H overlapped with DMSO), 2.06–1.94 (m, 2H).
Methanesulfonate:
TLC: Rf 0.46 (Chloroform:Methanol=10:1); NMR (DMSO-d$_6$, DMSO=2.49 ppm): δ 12.85 (s, 1H), 10.22 (s, 1H), 9.68 (brs, 1H), 8.35–8.32 (m, 1H), 7.92–7.88 (m, 3H), 7.72–7.68 (m, 2H), 7.48 (t, J=7.8 Hz, 1H), 7.26 (d, J=7.8 Hz, 1H), 3.98–3.95 (m, 2H), 3.69–3.61 (m, 2H), 3.47–3.34 (m, 2H), 3.16–3.04 (m, 4H), 2.48–2.43 (m, 2H), 2.32 (s, 3H), 2.00–1.94 (m, 2H).

EXAMPLE 21(16)

4-(3-(5-(N-Ethyl-N-methylamino)valerylamino)phenyl)-2H-phthalazin-1-one Hydrochloride

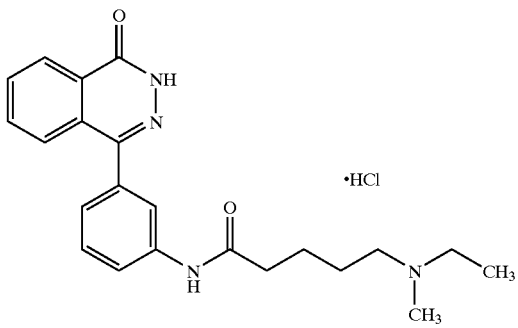

TLC: Rf 0.23 (Chloroform:Methanol:Acetic acid=8:2:1); NMR (DMSO-d$_6$): δ 12.85 (s, 1H), 10.25 (s, 1H), 9.93 (brs, 1H), 8.35–8.32 (m, 1H), 7.93–7.86 (m, 3H), 7.75–7.69 (m, 2H), 7.46 (t, J=7.8 Hz, 1H), 7.24 (d, J=7.5 Hz, 1H), 3.18–2.92 (m, 4H), 2.67 (d, J=5.1 Hz, 3H), 2.40 (t, J=6.6 Hz, 2H), 1.76–1.56 (m, 4H), 1.20 (t, J=7.5 Hz, 3H).

EXAMPLE 21(17)

4-(3-(5-(2,2,2-Trifluoroethylamino)valerylamino)phenyl)-2H-phthalazin-1-one Hydrochloride

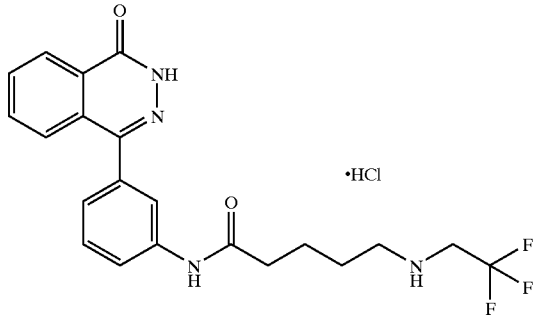

TLC: Rf 0.35 (Chloroform:Methanol=9:1); NMR (DMSO-d$_6$): δ 12.85 (s, 1H), 10.24 (s, 1H), 9.71 (brs, 2H), 8.35–8.32 (m, 1H), 7.94–7.85 (m, 3H), 7.75–7.69 (m, 2H), 7.46 (t, J=7.8 Hz, 1H), 7.24 (d, J=7.8 Hz, 1H), 4.05 (q, J=9.6 Hz, 2H), 3.01 (t, J=7.8 Hz, 2H), 2.38 (t, J=6.6 Hz, 2H), 1.78–1.58 (m, 4H).

EXAMPLE 21(18)

4-(3-(5-Cyclopropylaminovalerylamino)phenyl)-2H-phthalazin-1-one Hydrochloride

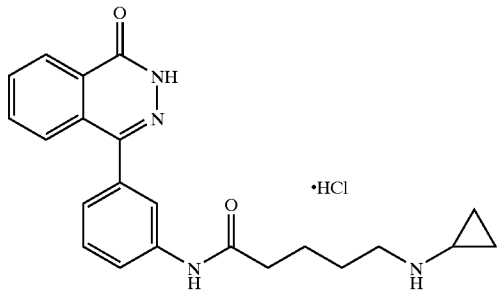

TLC: Rf 0.56 (Chloroform:Methanol:Acetic acid=9:1:0.5); NMR (DMSO-d$_6$): δ 12.84 (s, 1H), 10.26 (s, 1H), 9.07–8.94 (br, 2H), 8.35–8.30 (m, 1H), 7.95–7.85 (m, 3H), 7.75–7.69 (m, 2H), 7.45 (t, J=8.0 Hz, 1H), 7.23 (d, J=8.0 Hz, 1H), 3.02–2.90 (m, 2H), 2.70–2.58 (m, 1H), 2.44–2.32 (m, 2H), 1.72–1.58 (m, 4H), 0.88–0.82 (m, 2H), 0.73–0.66 (m, 2H).

EXAMPLE 21(19)

4-(3-(5-(Cyclohexylmethylamino)valerylamino)phenyl)-2H-phthalazin-1-one Hydrochloride

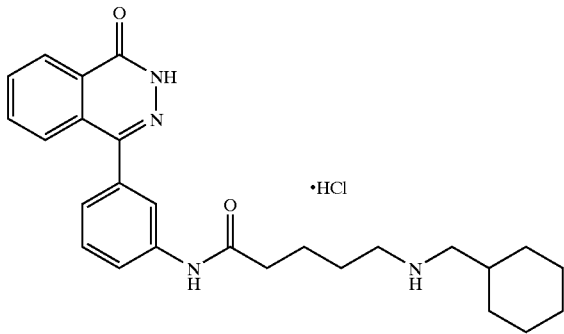

TLC: Rf 0.31 (Chloroform:Methanol:Acetic acid= 9:1:0.2); NMR (DMSO-$d_6$): δ 12.84 (s, 1H), 10.26 (s, 1H), 8.60–8.47 (br, 2H), 8.36–8.30 (m, 1H), 7.94–7.85 (m, 3H), 7.75–7.68 (m, 2H), 7.46 (t, J=7.5 Hz, 1H), 7.24 (d, J=7.5 Hz, 1H), 2.93–2.82 (m, 2H), 2.75–2.66 (m, 2H), 2.43–2.33 (m, 2H), 1.78–1.50 (m, 10H), 1.25–1.00 (m, 3H), 0.98–0.83 (m, 2H).

EXAMPLE 21(20)

4-(3-(5-(N,N-Bis(2-methoxyethyl)amino)valerylamino)phenyl)-2H-phthalazin-1-one Hydrochloride

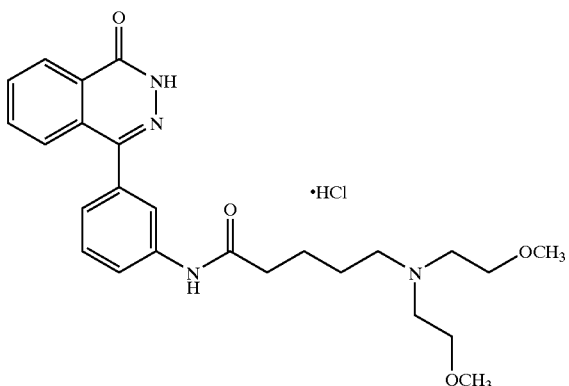

TLC: Rf 0.24 (Chloroform:Methanol:Acetic acid= 8:2:0.5); NMR (DMSO-$d_6$): δ 12.86 (s, 1H), 10.28 (s, 1H), 9.84 (brs, 1H), 8.36–8.32 (m, 1H), 7.90 (m, 3H), 7.71 (m, 2H), 7.46 (t, J=7.8 Hz, 1H), 7.24 (d, J=7.8 Hz, 1H), 3.67 (t, J=5.0 Hz, 4H), 3.46 (m, 4H), 3.27 (s, 6H), 3.13 (m, 2H), 2.39 (m, 2H), 1.65 (m, 4H).

EXAMPLE 21(21)

4-(3-(5-(Thiophen-2-ylmethylamino)valerylamino)phenyl)-2H-phthalazin-1-one Hydrochloride

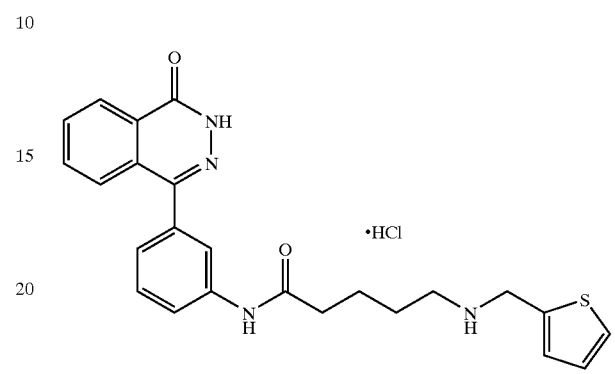

TLC: Rf 0.53 (Chloroform:Methanol:Acetic acid= 8:2:0.5); NMR (DMSO-$d_6$): δ 12.85 (s, 1H), 10.21 (s, 1H), 9.04 (brs, 2H), 8.36–8.32 (m, 1H), 7.92–7.88 (m, 3H), 7.74–7.70 (m, 2H), 7.62 (dd, J=5.2,1.2 Hz, 1H), 7.47 (t, J=7.8 Hz, 1H), 7.30–7.23 (m, 2H), 7.08 (dd, J=5.2, 3.4 Hz, 1H), 4.35 (m, 2H), 2.91 (m, 2H), 2.37 (m, 2H), 1.65 (m, 4H).

EXAMPLE 21(22)

4-(3-(5-(N-Methyl-N-isopropylamino)valerylamino)phenyl)-2H-phthalazin-1-one Hydrochloride

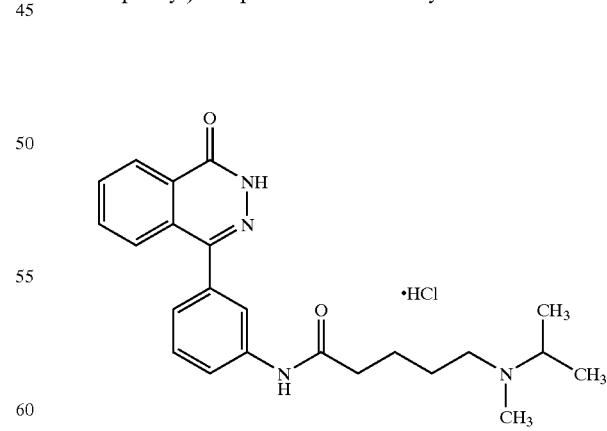

TLC: Rf 0.23 (Chloroform:Methanol:Acetic acid= 8:2:0.5); NMR (DMSO-$d_6$): δ 12.85 (s, 1H), 10.18 (s, 1H), 9.34 (brs, 1H), 8.35–8.32 (m, 1H), 7.92–7.86 (m, 3H), 7.71 (m, 2H), 7.47 (t, J=7.8 Hz, 1H), 7.25 (d, J=7.8 Hz, 1H), 3.50 (m, 1H), 3.08–2.95 (m, 2H), 2.62 (d, J=4.8 Hz, 3H), 2.40 (t, J=6.9 Hz, 2H), 1.65 (m, 4H), 1.22 (d, J=6.6 Hz, 3H), 1.18 (d, J=6.6 Hz, 3H).

EXAMPLE 21(23)

4-(3-(5-(Tetrahydrofuran-2-ylmethylamino)valerylamino)phenyl)-2H-phthalazin-1-one Hydrochloride

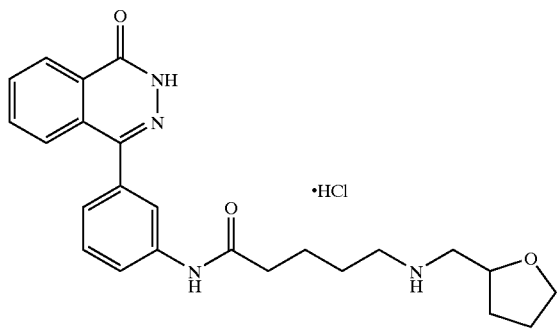

TLC: Rf 0.50 (Chloroform:Methanol:Acetic acid=8:2 0.3); NMR (DMSO-$d_6$): δ 12.85 (s, 1H), 10.28 (s, 1H), 8.94–8.80 (br, 1H), 8.72–8.58 (br, 1H), 8.35–8.31 (m, 1H), 7.95–7.86 (m, 3H), 7.76–7.69 (m, 2H), 7.46 (t, J=8.0 Hz, 1H), 7.24 (d, J=8.0 Hz, 1H), 4.17–4.07 (m, 1H), 3.80–3.75 (m, 1H), 3.72–3.64 (m, 1H), 3.08–2.80 (m, 4H), 2.40–2.35 (m, 2H), 2.05–1.48 (m, 8H).

EXAMPLE 21(24)

4-(3-(5-t-Butylaminovalerylamino)phenyl)-2H-phthalazin-1-one Hydrochloride

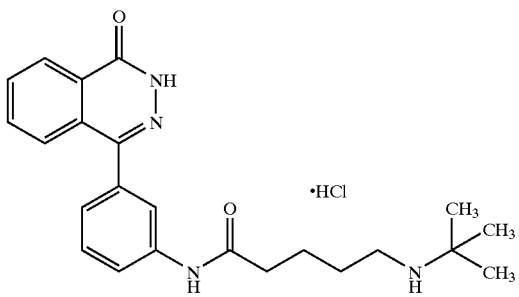

TLC: Rf 0.55 (Chloroform:Methanol:Acetic acid= 8:2:0.3); NMR (DMSO-$d_6$): δ 12.85 (s, 1H), 10.29 (s, 1H), 8.70–8.60 (br, 2H), 8.36–8.31 (m, 1H), 7.94–7.86 (m, 3H), 7.76–7.70 (m, 2H), 7.46 (t, J=8.0 Hz, 1H), 7.24 (d, J=8.0 Hz, 1H), 2.90–2.78 (m, 2H), 2.45–2.38 (m, 2H), 1.75–1.60 (m, 4H), 1.26 (s, 9H).

EXAMPLE 21(25)

4-(3-(5-Neopentylaminovalerylamino)phenyl)-2H-phthalazin-1-one Hydrochloride

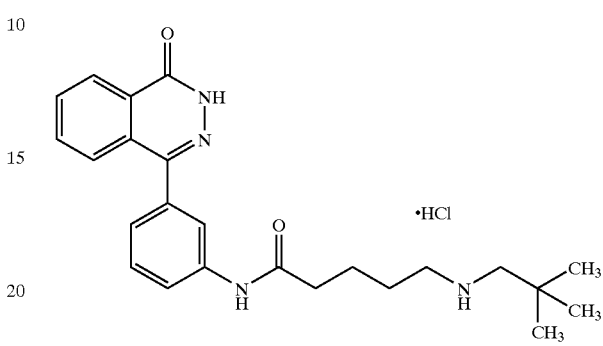

TLC: Rf 0.49 (Chloroform:Methanol:Acetic acid= 8:2:0.5); NMR (DMSO-$d_6$): δ 12.85 (s, 1H), 10.26 (s, 1H), 8.35–8.32 (m, 1H), 8.26 (brs, 2H), 7.91–7.88 (m, 3H), 7.75–7.70 (m, 2H), 7.47 (t, J=7.8 Hz, 1H), 7.24 (d, J=7.8 Hz, 1H), 2.90 (m, 2H), 2.72 (m, 2H), 2.39 (t, J=6.9 Hz, 2H), 1.72–1.62 (m, 4H), 0.96 (s, 9H).

EXAMPLE 21(26)

4-(3-(5-(2-Propynylamino)valerylamino)phenyl)-2H-phthalazin-1-one Hydrochloride

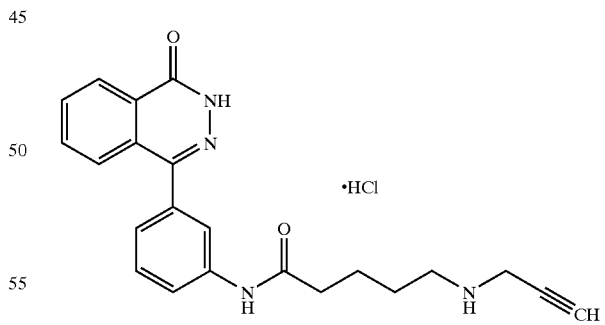

TLC: Rf 0.33 (Chloroform:Methanol:28% Ammonia water=9:1:0.1); NMR (DMSO-$d_6$): δ 12.84 (s, 1H), 10.27 (s, 1H), 9.46–9.24 (br, 2H), 8.35–8.30 (m, 1H), 7.94–7.83 (m, 3H), 7.75–7.68 (m, 2H), 7.45 (t, J=7.8 Hz, 1H), 7.23 (d, J=7.8 Hz, 1H), 3.92–3.79 (br, 2H), 3.6 8 (t, J=2.4 Hz, 1H), 3.04–2.96 (br, 2H), 2.43–2.31 (br, 2H), 1.79–1.50 (br, 4H).

EXAMPLE 21(27)

4-(3-(5-sec-Butylaminovalerylamino)phenyl)-2H-phthalazin-1-one Hydrochloride

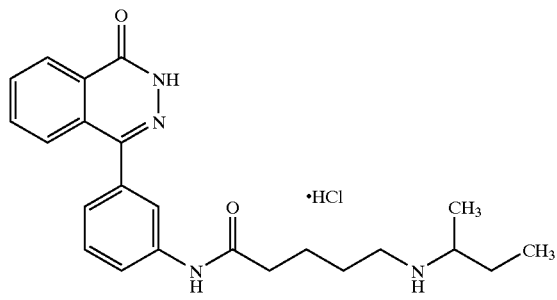

TLC: Rf 0.48 (Chloroform:Methanol:28% Ammonia water=4:1:0.1); NMR (DMSO-$d_6$): δ 12.84 (s, 1H), 10.28 (s, 1H), 8.77–8.43 (br, 2H), 8.35–8.30 (m, 1H), 7.94–7.84 (m, 3H), 7.75–7.68 (m, 2H), 7.45 (t, J=7.8 Hz, 1H), 7.23 (d, J=7.8 Hz, 1H), 3.11–2.78 (br, 3H), 2.43–2.32 (br, 2H), 1.82–1.32 (m, 6H), 1.17 (d, J=6.6 Hz, 3H), 0.86 (t, J=7.4 Hz, 3H).

EXAMPLE 21(28)

4-(3-(5-Ethylaminovalerylamino)-4-chlorophenyl)-2H-phthalazin-1-one Hydrochloride

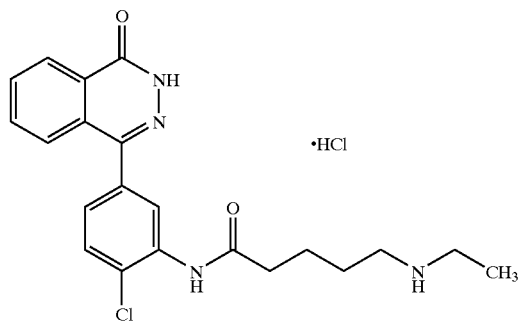

TLC: Rf 0.54 (Chloroform:Methanol:Acetic acid=8:2:1); NMR (DMSO-$d_6$): δ 12.90 (s, 1H), 9.72 (s, 1H), 8.54 (brs, 2H), 8.35–8.32 (m, 1H), 7.94–7.89 (m, 3H), 7.76–7.72 (m, 1H), 7.66 (d, J=8.1 Hz, 1H), 7.41 (dd, J=8.1, 1.8 Hz, 1H), 2.94–2.82 (m, 4H), 2.52–2.42 (m, 2H), 1.66–1.58 (m, 4H), 1.16 (t, J=7.5 Hz, 3H).

EXAMPLE 21(29)

4-(3-(5-Butylaminovalerylamino)-4-chlorophenyl)-2H-phthalazin-1-one Hydrochloride

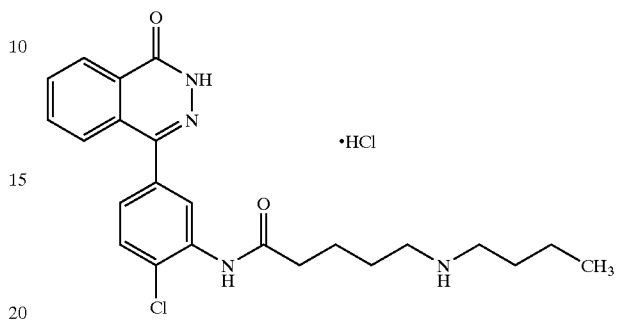

TLC: Rf 0.33 (Chloroform:Methanol:Acetic acid=8:1:1); NMR (DMSO-$d_6$): δ 12.90 (s, 1H), 9.73 (s, 1H), 8.60 (brs, 2H), 8.35–8.32 (m, 1H), 7.94–7.88 (m, 3H), 7.75–7.72 (m, 1H), 7.66 (d, J=8.1 Hz, 1H), 7.41 (dd, J=8.4, 2.1 Hz, 1H), 2.94–2.78 (m, 4H), 2.51–2.42 (m, 2H), 1.68–1.50 (m, 6H), 1.36–1.24 (m, 2H), 0.86 (t, J=7.2 Hz, 3H).

EXAMPLE 21(30)

4-(3-(5-Cyclopropylmethylaminovalerylamino)phenyl)-2H-phthalazin-1-one Hydrochloride

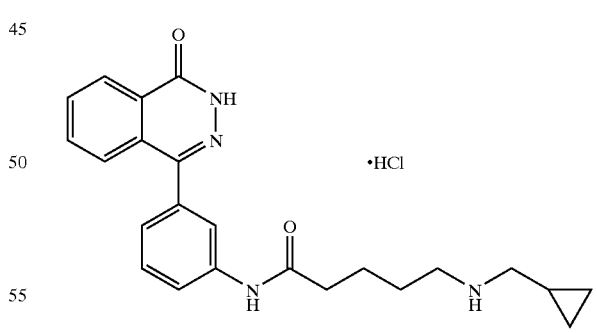

TLC: Rf 0.77 (Chloroform:Methanol:Acetic acid=8:2:0.5); NMR (DMSO-$d_6$): δ 12.85 (s, 1H), 10.25 (s, 1H), 8.67 (brs, 2H), 8.35–8.32 (m, 1H), 7.92–7.88 (m, 3H), 7.74–7.70 (m, 2H), 7.46 (t, J=7.8 Hz, 1H), 7.24 (d, J=7.8 Hz, 1H), 2.89 (m, 2H), 2.76 (m, 2H), 2.38 (m, 2H), 1.65 (brs, 4H), 1.02 (m, 1H), 0.54 (m, 2H), 0.33 (m, 2H).

EXAMPLE 21(31)

4-(3-(5-Cyclopentylmethylaminovalerylamino)phenyl)-2H-phthalazin-1-one Hydrochloride

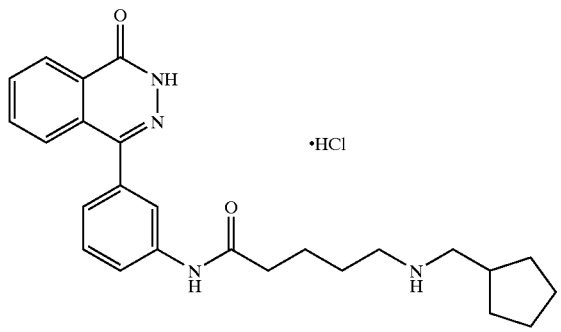

TLC: Rf 0.59 (Chloroform:Methanol:Acetic acid=8:2:0.2); NMR (DMSO-$d_6$): δ 12.85 (s, 1H), 10.24 (s, 1H), 8.55–8.43 (br, 2H), 8.36–8.31 (m, 1H), 7.94–7.86 (m, 3H), 7.75–7.69 (m, 2H), 7.46 (t, J=7.8 Hz, 1H), 7.24 (d, J=7.8 Hz, 1H), 2.94–2.77 (m, 4H), 2.43–2.35 (m, 2H), 2.20–2.06 (m, 1H), 1.80–1.40 (m, 10H), 1.26–1.13 (m, 2H).

EXAMPLE 21(32)

4-(3-(5-Cyclobutylaminovalerylamino)phenyl)-2H-phthalazin-1-one Hydrochloride

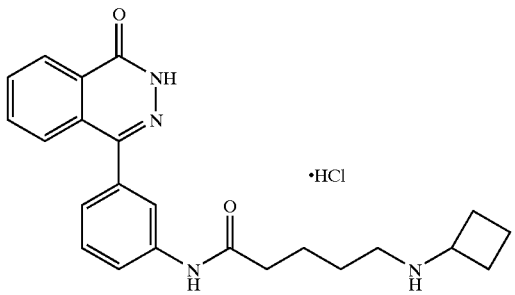

TLC: Rf 0.59 (Chloroform:Methanol:Acetic acid=8:2:0.2); NMR (DMSO-$d_6$): δ 12.85 (s, 1H), 10.25 (s, 1H), 9.01–8.86 (br, 2H), 8.36–8.30 (m, 1H), 7.95–7.85 (m, 3H), 7.76–7.68 (m, 2H), 7.46 (t, J=7.8 Hz, 1H), 7.24 (d, J=7.8 Hz, 1H), 3.70–3.50 (m, 1H), 2.82–2.68 (m, 2H), 2.42–2.32 (m, 2H), 2.20–2.06 (m, 4H), 1.82–1.55 (m, 6H).

EXAMPLE 21(33)

4-(3-(5-(2-Fluoroethylamino)valerylamino)phenyl)-2H-phthalazin-1-one Hydrochloride

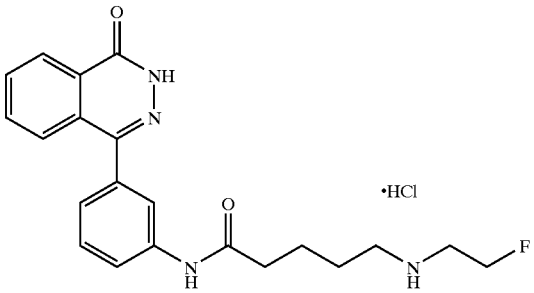

TLC: Rf 0.35 (Chloroform:Methanol:Acetic acid=8:2:1); NMR (DMSO-$d_6$): δ 12.85 (s, 1H), 10.24 (s, 1H), 8.99 (brs, 2H), 8.35–8.32 (m, 1H), 7.94–7.85 (m, 3H), 7.74–7.70 (m, 2H), 7.46 (t, J=8.1 Hz, 1H), 7.24 (d, J=9.3 Hz, 1H), 4.72 (dt, J=46.8, 4.8 Hz, 2H), 3.26–3.18 (m, 2H), 3.02–2.90 (m, 2H), 2.41–2.36 (m, 2H), 1.78–1.58 (m, 4H).

EXAMPLE 21(34)

4-(3-(5-Morpholinovalerylamino)-4-chlorophenyl)-2H-phthalazin-1-one Hydrochloride

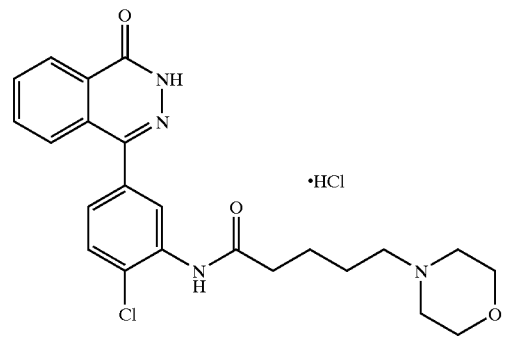

TLC: Rf 0.23 (Chloroform:Methanol=9:1); NMR (DMSO-$d_6$): δ 12.90 (s, 1H), 10.41 (brs, 1H), 9.72 (s, 1H), 8.38–8.31 (m, 1H), 7.96–7.86 (m, 3H), 7.76–7.71 (m, 1H), 7.66 (d, J=8.4 Hz, 1H), 7.41 (dd, J=8.4, 2.1 Hz, 1H), 3.98–3.90 (m, 2H), 3.76–3.68 (m, 2H), 3.42–3.30 (m, 2H), 3.14–2.94 (m, 4H), 2.50–2.41 (m, 2H), 1.80–1.56 (m, 4H).

EXAMPLE 21(35)

4-(3-(5-Dimethylaminovalerylamino)-4-methoxyphenyl)-2H-phthalazin-1-one Hydrochloride

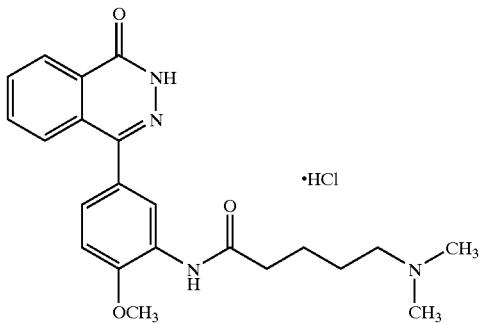

TLC: Rf 0.28 (Chloroform:Methanol:Acetic acid= 8:2:0.5); NMR (DMSO-$d_6$): δ 12.78 (s, 1H), 10.20–10.03 (br, 1H), 9.30 (s, 1H), 8.35–8.30 (m, 1H), 8.21 (d, J=2.0 Hz, 1H), 7.94–7.83 (m, 2H), 7.80–7.73 (m, 1H), 7.30 (dd, J=8.5, 2.0 Hz, 1H), 7.20 (d, J=8.5 Hz, 1H), 3.92 (s, 3H), 3.07–2.97 (m, 2H), 2.70 (d, J=4.8 Hz, 6H), 2.49–2.40 (m, 2H), 1.74–1.50 (m, 4H).

EXAMPLE 21(36)

4-(3-(5-(2-Methyl-2-propenylamino)valerylamino)phenyl)-2H-phthalazin-1-one Hydrochloride

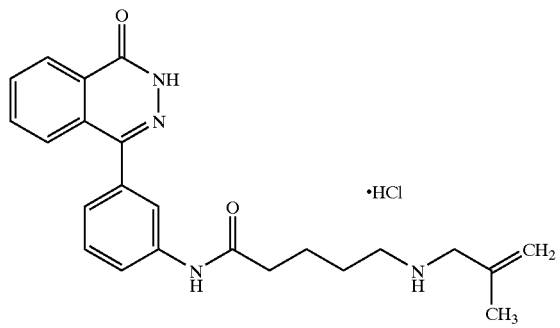

TLC: Rf 0.43 (Chloroform:Methanol:28% Ammonia water=9:1:0.1); NMR (DMSO-$d_6$): δ 12.84 (s, 1H), 10.29 (s, 1H), 9.02–8.83 (br, 2H), 8.35–8.30 (m, 1H), 7.94–7.84 (m, 3H), 7.75–7.68 (m, 2H), 7.45 (t, J=7.8 Hz, 1H), 7.23 (d, J=7.8 Hz, 1H), 5.07 (s, 2H), 3.61–3.37 (br, 2H), 2.94–2.88 (br, 2H), 2.43–2.32 (br, 2H), 1.77–1.65 (m, 7H).

EXAMPLE 21(37)

4-(3-(5-(2-(1-Cyclohexen-1-yl)ethylamino)valerylamino)phenyl)-2H-phthalazin-1-one Hydrochloride

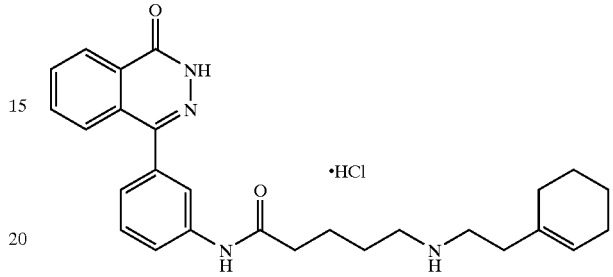

TLC: Rf 0.40 (Chloroform:Methanol:28% Ammonia water=9:1:0.1); NMR (DMSO-$d_6$): δ 12.91–12.76 (br, 1H), 10.28 (s, 1H), 7.35–7.68 (m, 8H), 7.45 (t, J=7.6 Hz, 1H), 7.23 (d, J=7.6 Hz, 1H), 5.47–5.39 (br, 1H), 2.97–2.74 (br, 4H), 2.43–2.10 (br, 4H), 1.99.1.79 (br, 4H), 1.74–1.48 (br, 8H).

EXAMPLE 21(38)

4-(3-(5-Dimethylaminovalerylamino)-4-hydroxyphenyl)-2H-phthalazin-1-one Hydrochloride

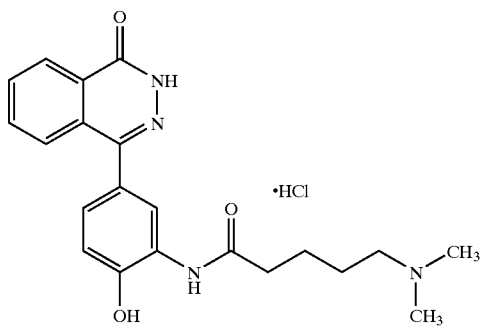

TLC: Rf 0.26 (Chloroform:Methanol:Acetic acid=6:4:1); NMR (DMSO-$d_6$): δ 12.74 (s, 1H), 10.26 (s, 1H), 9.58–9.43 (br, 1H), 9.35 (s, 1H), 8.36–8.30 (m, 1H), 8.07 (d, J=1.8 Hz, 1H), 7.93–7.74 (m, 3H), 7.16 (dd, J=8.1, 1.8 Hz, 1H), 7.02 (d, J=8.1 Hz, 1H), 3.10–3.00 (m, 2H), 2.73 (d, J=3.3 Hz, 6H), 2.50–2.45 (m, 2H), 1.72–1.53 (m, 4H).

EXAMPLE 21(39)

4-(3-(5-(1,2-Dimethylpropylamino)valerylamino)phenyl)-2H-phthalazin-1-one Hydrochloride

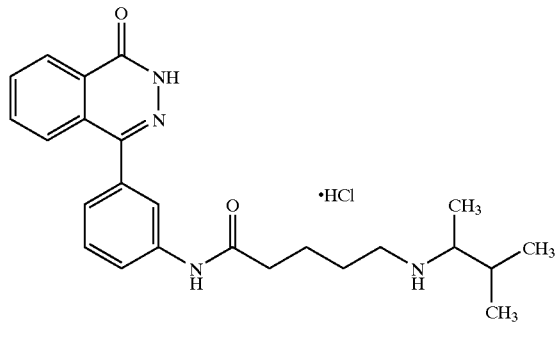

TLC: Rf 0.54 (Chloroform:Methanol:Acetic acid= 8:2:0.5); NMR (DMSO-$d_6$): δ 12.85 (s, 1H), 10.21 (s, 1H), 8.39 (brs, 1H), 8.35–8.32 (m, 1H), 8.16 (brs, 1H), 7.93–7.86 (m, 3H), 7.73–7.70 (m, 2H), 7.47 (t, J=7.8 Hz, 1H), 7.25 (d, J=7.8 Hz, 1H), 3.06–2.92 (m, 3H), 2.39 (t, J=6.3 Hz, 2H), 2.04 (m, 1H), 1.66 (m, 4H), 1.09 (d, J=6.6 Hz, 3H), 0.89 (d, J=8.7 Hz, 3H), 0.86 (d, J=8.7 Hz, 3H).

EXAMPLE 21(40)

4-(3-(5-Thiomorpholinovalerylamino)phenyl)-2H-phthalazin-1-one Hydrochloride

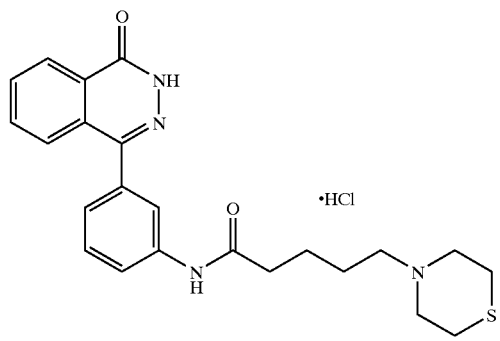

TLC: Rf 0.38 (Chloroform:Methanol:28% Ammonia water=9:1:0.1); NMR (DMSO-$d_6$): δ 12.84 (s, 1H), 10.75–10.52 (br, 1H), 10.26 (s, 1H), 8.358.30 (m, 1H), 7.94–7.84 (m, 3H), 7.75–7.68 (m, 2H), 7.45 (t, J=7.8 Hz, 1H), 7.23 (d, J=7.8 Hz, 1H), 3.72–3.59 (m, 2H), 3.23–2.97 (m, 6H), 2.88–2.72 (m, 2H), 2.39 (t, J=7.0 Hz, 2H), 1.81–1.53 (m, 4H).

EXAMPLE 21(41)

4-(3-(5-(4-Methylpiperazin-1-yl)valerylamino)phenyl)-2H-phthalazin-1-one Dihydrochloride

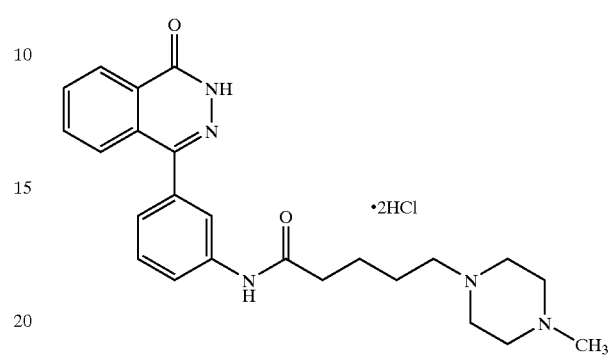

TLC: Rf 0.13 (Chloroform:Methanol:28% Ammonia water=9:1:0.1); NMR (DMSO-$d_6$): δ 12.84 (s, 1H), 12.00–11.40 (br, 2H), 10.27 (s, 1H), 8.35–8.30 (m, 1H), 7.94–7.83 (m, 3H), 7.75–7.68 (m, 2H), 7.45 (t, J=7.8 Hz, 1H), 7.23 (d, J=7.8 Hz, 1H), 3.85–2.98 (br, 10H), 2.79 (s, 3H), 2.39 (t, J=6.8 Hz, 2H), 1.83–1.52 (br, 4H).

EXAMPLE 21(42)

4-(3-(5-Dimethylaminovalerylamino)-4-fluorophenyl)-2H-phthalazin-1-one Hydrochloride

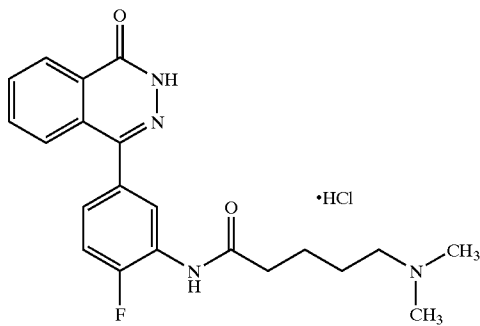

TLC: Rf 0.41 (Chloroform:Methanol:28% Ammonia water=9:1:0.2); NMR (DMSO-$d_6$): δ 12.86 (s, 1H), 10.10–9.95 (br, 1H), 9.95 (s, 1H), 8.35–8.31 (m, 1H), 8.16–8.11 (m, 1H), 7.95–7.85 (m, 2H), 7.74–7.68 (m, 1H), 7.46–7.32 (m, 2H), 3.06–3.00 (m, 2H), 2.71 (s, 6H), 2.49–2.43 (m, 2H), 1.741.50 (m, 4H).

EXAMPLE 21(43)

4-(3-(5-Cyclopropylaminovalerylamino)-4-chlorophenyl)-2H-phthalazin-1-one Hydrochloride

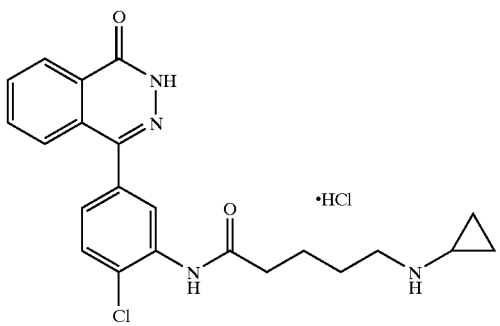

TLC: Rf 0.43 (Chloroform:Methanol:28% Ammonia water=9:1:0.2); NMR (DMSO-d$_6$): δ 12.90 (s, 1H), 9.70 (s, 1H), 8.73–8.57 (br, 2H), 8.37–8.31 (m, 1H), 7.96–7.86 (m, 3H), 7.76–7.69 (m, 1H), 7.66 (d, J=8.1 Hz, 1H), 7.41 (dd, J=8.1, 2.0 Hz, 1H), 3.06–2.90 (m, 2H), 2.74–2.60 (m, 1H), 2.50–2.40 (m, 2H), 1.76–1.56 (m, 4H), 0.85–0.65 (m, 4H).

EXAMPLE 21(44)

4-(3-(5-(2-Fluoroethylamino)valerylamino)-4-chlorophenyl)-2H-phthalazin-1-one Hydrochloride

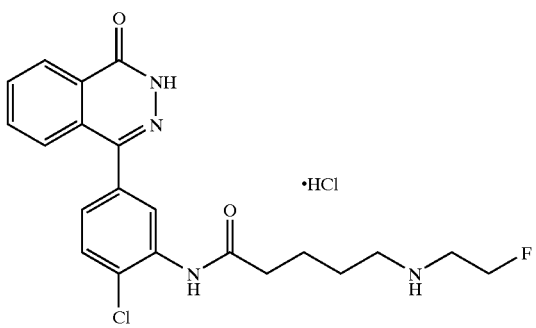

TLC: Rf 0.51 (Chloroform:Methanol:28% Ammonia water=9:1:0.2); NMR (DMSO-d$_6$): δ 12.90 (s, 1H), 9.71 (s, 1H), 8.97–8.84 (br, 2H), 8.37–8.31 (m, 1H), 7.95–7.86 (m, 3H), 7.76–7.70 (m, 1H), 7.66 (d, J=8.4 Hz, 1H), 7.41 (dd, J=8.4, 2.1 Hz, 1H), 4.71 (dt, J=47.0, 4.5 Hz, 2H), 3.37–3.18 (m, 2H), 3.02–2.90 (m, 2H), 2.50–2.40 (m, 2H), 1.75–1.60 (m, 4H).

EXAMPLE 21(45)

4-(3-(5-Dimethylaminovalerylamino)-4-methylphenyl)-2H-phthalazin-1-one Hydrochloride

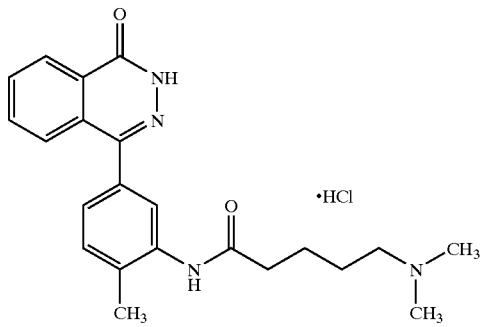

TLC: Rf 0.25 (Chloroform:Methanol:28% Ammonia water=9:1:0.2); NMR (DMSO-d$_6$): δ 12.82 (s, 1H), 10.25–10.06 (br, 1H), 9.53 (s, 1H), 8.36–8.30 (m, 1H), 7.93–7.84 (m, 2H), 7.79–7.73 (m, 1H), 7.66 (s, 1H), 7.37 (d, J=7.7 Hz, 1H), 7.29 (d, J=7.7 Hz, 1H), 3.09–2.97 (m, 2H), 2.71 (d, J=4.5 Hz, 6H), 2.46–2.40 (m, 2H), 2.31 (s, 3H), 1.76–1.56 (m, 4H).

EXAMPLE 21(46)

4-(3-(5-(2-Methyl-2-propenylamino)valerylamino)-4-chlorophenyl)-2H-phthalazin-1-one Hydrochloride

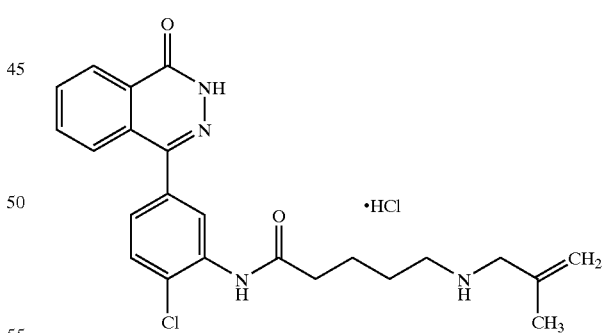

TLC: Rf 0.50 (Chloroform:Methanol:28% Ammonia water=9:1:0.2); NMR (DMSO-d$_6$): δ 12.90 (s, 1H), 9.71 (s, 1H), 8.80–8.67 (br, 2H), 8.36–8.31 (m, 1H), 7.95–7.86 (m, 3H), 7.76–7.70 (m, 1H), 7.66 (d, J=8.1 Hz, 1H), 7.41 (dd, J=8.1, 2.0 Hz, 1H), 5.07 (s, 2H), 3.49 (t, J=5.4 Hz, 2H), 2.94–2.82 (m, 2H), 2.48–2.43 (m, 2H), 1.77 (s, 3H), 1.77–1.58 (m, 4H).

EXAMPLE 21(47)

4-(3-(5-(2-Propenylamino)valerylamino)phenyl)-2H-phthalazin-1-one Hydrochloride

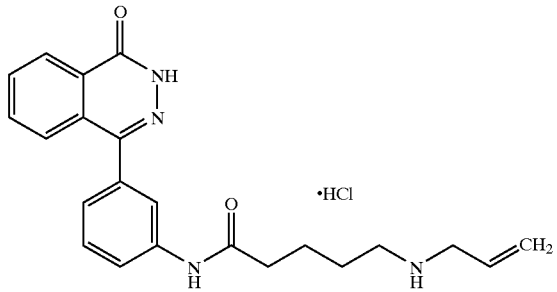

TLC: Rf 0.56 (Chloroform:Methanol:Acetic acid=8:2:1); NMR (DMSO-$d_6$): δ 12.85 (s, 1H), 10.25 (s, 1H), 8.91 (brs, 2H), 8.36–8.31 (m, 1H), 7.93–7.85 (m, 3H), 7.76–7.68 (m, 2H), 7.46 (t, J=8.1 Hz, 1H), 7.24 (d, J=7.5 Hz, 1H), 5.95–5.82 (m, 1H), 5.44 (dd, J=17.4, 1.2 Hz, 1H), 5.37 (d, J=10.2 Hz, 1H), 3.57–3.51 (m, 2H), 2.92–2.80 (m, 2H), 2.41–2.34 (m, 2H), 1.69–1.60 (m, 4H).

EXAMPLE 21(48)

4-(3-(5-(2-Propynylamino)valerylamino)-4-chlorophenyl)-2H-phthalazin-1-one Hydrochloride

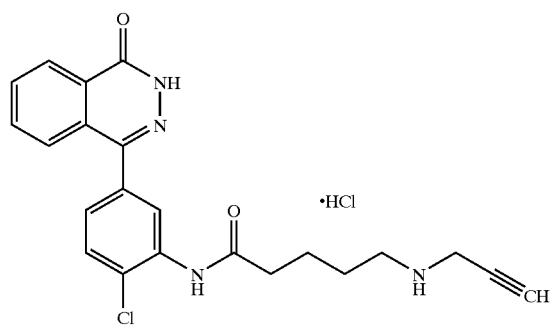

TLC: Rf 0.41 (Chloroform:Methanol:28% Ammonia water=9:1:0.2); NMR (DMSO-$d_6$): δ 12.90 (s, 1H), 9.73 (s, 1H), 9.40.9.25 (br, 2H), 8.37–8.30 (m, 1H), 7.96–7.86 (m, 3H), 7.76–7.70 (m, 1H), 7.66 (d, J=8.4 Hz, 1H), 7.40 (dd, J=8.4, 2.0 Hz, 1H), 3.91–3.83 (m, 2H), 3.69 (t, J=2.3 Hz, 1H), 3.00–2.88 (m, 2H), 2.49–2.40 (m, 2H), 1.74–1.57 (m, 4H).

EXAMPLE 21(49)

4-(3-(5-(N-Methyl-N-propylamino)valerylamino)-4-chlorophenyl)-2H-phthalazin-1-one Hydrochloride

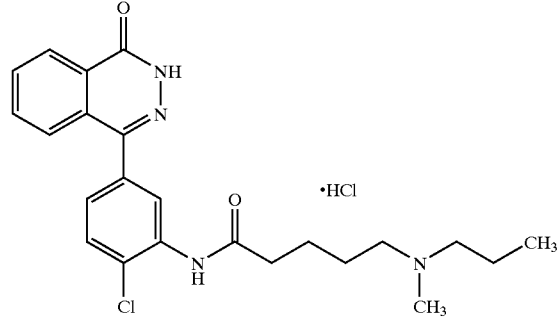

TLC: Rf 0.29 (Chloroform:Methanol:Acetic acid=8:2:0.5); NMR (DMSO-$d_6$): δ 12.90 (s, 1H), 10.01 (brs, 1H), 9.74 (s, 1H), 8.36–8.32 (m, 1H), 7.93–7.88 (m, 3H), 7.75–7.71 (m, 1H), 7.67 (d, J=8.2 Hz, 1H), 7.41 (m, 1H), 2.98 (m, 4H), 2.68 (d, J=4.8 Hz, 3H), 2.48 (m, 2H), 1.70–1.59 (m, 6H), 0.87 (t, J=7.0 Hz, 3H).

EXAMPLE 21(50)

4-(3-(5-Isobutylaminovalerylamino)phenyl)-2H-phthalazin-1-one Hydrochloride

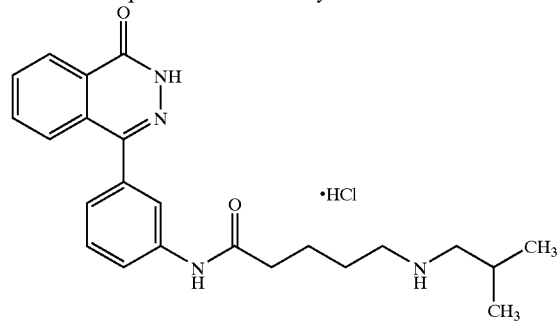

TLC: Rf 0.70 (Chloroform:Methanol:Acetic acid=8:2:0.5); NMR (DMSO-$d_6$): δ 12.85 (s, 1H), 10.22 (s, 1H), 8.36–8.32 (m, 3H), 7.89 (m, 3H), 7.74–7.70 (m, 2H), 7.51–7.19 (m, 2H), 2.88 (m, 2H), 2.70 (m, 2H), 2.38 (m, 2H), 1.65 (m, 5H), 0.92 (d, J=6.6 Hz, 6H).

EXAMPLE 21(51)

4-(3-(5-(2-Propenyloxyamino)valerylamino)phenyl)-2H-phthalazin-1-one Hydrochloride

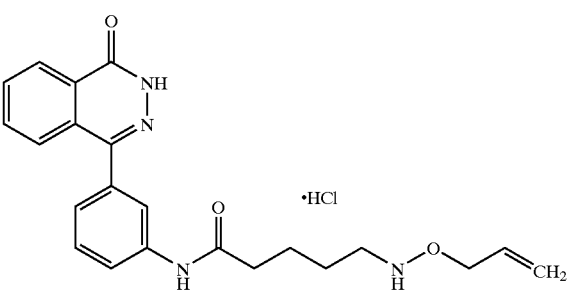

TLC: Rf 0.46 (Chloroform:Methanol=9:1); NMR (DMSO-d₆): δ 12.84 (s, 1H), 11.53 (brs, 1H), 10.18 (s, 1H), 8.36–8.30 (m, 1H), 7.94–7.85 (m, 3H), 7.75–7.68 (m, 3H), 7.46 (t, J=7.8 Hz, 1H), 7.24 (d, J=7.8 Hz, 1H), 5.97–5.84 (m, 1H), 5.40 (dd, J=17.1, 1.5 Hz, 1H), 5.32 (d, J=10.2 Hz, 1H), 4.54 (d, J=5.7 Hz, 2H), 3.20–3.14 (m, 2H), 2.40–2.35 (m, 2H), 1.69–1.63 (m, 4H).

EXAMPLE 21(52)

4-(3-(5-Cycloheptylaminovalerylamino)phenyl)-2H-phthalazin-1-one Hydrochloride

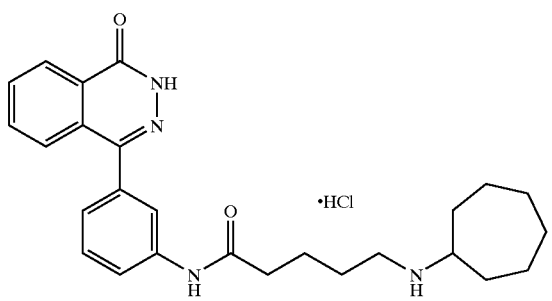

TLC: Rf 0.34 (Chloroform:Methanol:Acetic acid=8:2:0.1); NMR (DMSO-d₆): δ 12.85 (s, 1H), 10.24 (s, 1H), 8.51 (m, 2H), 8.33 (m, 1H), 7.90 (m, 3H), 7.72 (m, 2H), 7.46 (t, J=7.6 Hz, 1H), 7.24 (m, 1H), 3.10 (m, 1H), 2.90 (m, 2H), 2.38 (m, 2H), 1.56 (m, 16H).

EXAMPLE 21(53)

4-(3-(5-(Piperidin-1-yl)valerylamino)phenyl)-2H-phthalazin-1-one Hydrochloride

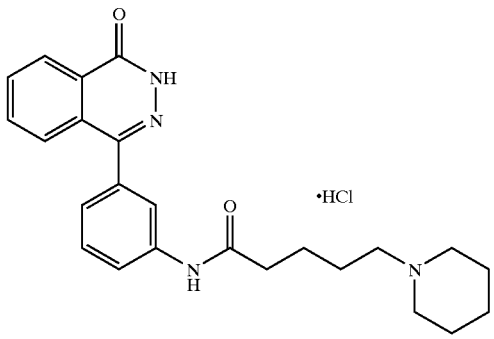

TLC: Rf 0.38 (Chloroform:Methanol:Acetic acid=8:2:1); NMR (DMSO-d₆): δ 12.85 (s, 1H), 10.24 (s, 1H), 9.73 (brs, 1H), 8.35–8.32 (m, 1H), 7.93–7.86 (m, 3H), 7.74–7.70 (m, 2H), 7.46 (t, J=7.8 Hz, 1H), 7.24 (d, J=7.5 Hz, 1H), 3.58–3.34 (m, 2H), 3.04–2.97 (m, 2H), 2.88–2.70 (m, 2H), 2.40 (t, J=6.9 Hz, 2H), 1.84–1.55 (m, 9H), 1.44–1.26 (m, 1H).

EXAMPLE 21(54)

4-(3-(5-(2-Cyanoethylamino)valerylamino)phenyl)-2H-phthalazin-1-one Hydrochloride

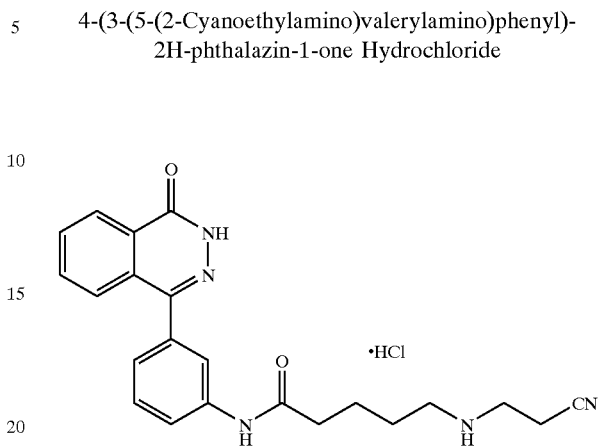

TLC: Rf 0.45 (Methylene chloride:Methanol:Acetic acid=8:1:1); NMR (DMSO-d₆): δ 12.84 (s, 1H), 10.29 (s, 1H), 9.24 (brs, 2H), 8.35–8.32 (m, 1H), 7.91–7.88 (m, 3H), 7.73–7.72 (m, 2H), 7.46 (t, J=8.0 Hz, 1H), 7.25 (d, J=8.0 Hz, 1H), 3.27–3.16 (m, 2H), 2.99 (t, J=7.5 Hz, 2H), 2.99–2.87 (m, 2H), 2.40–2.36 (m, 2H), 1.65 (s, 4H).

EXAMPLE 21(55)

4-(3-(5-(Perhydroazepin-1-yl)valerylamino)phenyl)-2H-phthalazin-1-one Hydrochloride

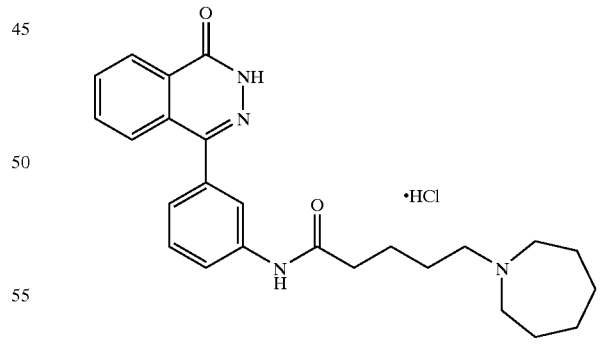

TLC: Rf 0.61 (Methylene chloride:Methanol:Acetic acid=8:1:1); NMR (DMSO-d₆): δ 12.85 (s, 1H), 10.20 (s, 1H), 9.66 (brs, 1H), 8.35–8.32 (m, 1H), 7.93–7.91 (m, 3H), 7.73–7.71 (m, 2H), 7.47 (t, J=7.5 Hz, 1H), 7.24 (d, J=7.5 Hz, 1H), 3.09–3.05 (m, 6H), 2.39 (t, J=6.3 Hz, 2H), 1.78–1.55 (m, 12H).

EXAMPLE 21(56)

4-(3-(5-Cyclobutylaminovalerylamino)-4-chlorophenyl)-2H-phthalazin-1-one Hydrochloride

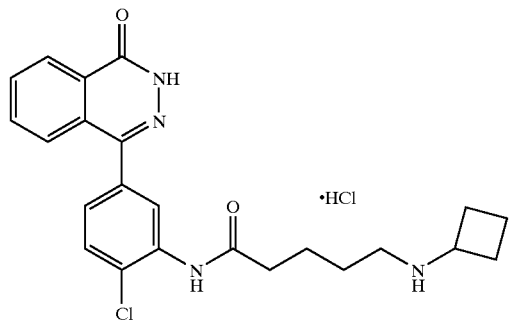

TLC: Rf 0.23 (Methylene chloride:Methanol=5:1); NMR (DMSO-$d_6$): δ 12.90 (s, 1H), 9.72 (s, 1H), 8.90 (brs, 2H), 8.35–8.32 (m, 1H), 7.94–7.87 (m, 3H), 7.75–7.72 (m, 1H), 7.65 (d, J=8.4 Hz, 1H), 7.43–7.39 (m, 1H), 3.65–3.60 (m, 1H), 2.80–2.72 (m, 2H), 2.54–2.46 (m, 2H), 2.17–2.10 (m, 4H), 1.79–1.56 (m, 6H).

EXAMPLE 21(57)

4-(3-(5-(2,6-Dimethylmorpholin-4-yl)valerylamino) phenyl)-2H-phthalazin-1-one Hydrochloride

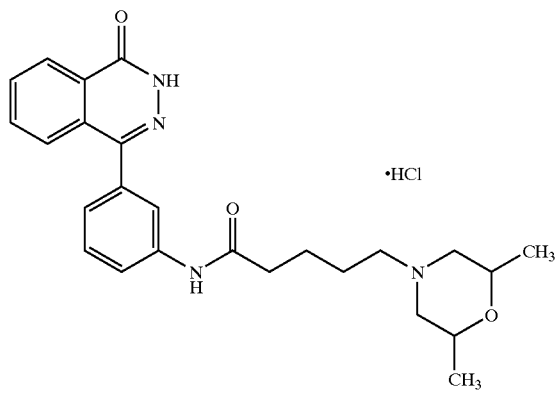

TLC: Rf 0.51, 0.70 (Methylene chloride:Methanol:Acetic acid=8:1:1); NMR (DMSO-$d_6$): δ 12.85 (s, 1H), 10.58 (brs, 1H), 10.22 (s, 1H), 8.35–8.32 (m, 1H), 7.92–7.90 (m, 3H), 7.73–7.70 (m, 2H), 7.47 (t, J=7.5 Hz, 1H), 7.26 (d, J=7.5 Hz, 1H), 3.92–3.87 (m, 2H), 3.50–3.16 (m, 4H), 3.10–3.00 (m, 2H), 2.59 (t, J=10.8 Hz, 2H 3/10), 2.40 (t, J=7.5 Hz, 2H 7/10), 1.74–1.62 (m, 4H), 1.40 (d, J=7.2 Hz, 3H 3/10), 1.12 (d, J=6.6 Hz, 6H 7/10), 1.08 (d, J=6.0 Hz, 3H 3/10).

EXAMPLE 21(58)

4-(3-(5-(N-Ethyl-N-2-methoxyethylamino) valerylamino)phenyl)-2H-phthalazin-1-one Hydrochloride

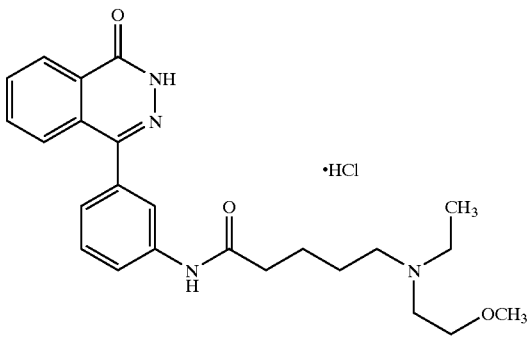

TLC: Rf 0.50 (Methylene chloride:Methanol:Acetic acid=8:1:1); NMR (DMSO-$d_6$): δ 12.85 (s, 1H), 10.23 (s, 1H), 9.62 (brs, 1H), 8.35–8.32 (m, 1H), 7.93–7.86 (m, 3H), 7.74–7.71 (m, 2H), 7.46 (t, J=7.8 Hz, 1H), 7.26 (d, J=7.8 Hz, 1H), 3.65 (t, J=4.5 Hz, 2H), 3.30–3.24 (m, 2H), 3.28 (s, 3H), 3.13–3.10 (m, 4H), 2.40 (t, J=6.9 Hz, 2H), 1.64 (brs, 4H), 1.19 (t, J=7.5 Hz, 3H).

EXAMPLE 21(59)

4-(3-(5-(2-Ethyl-4-methylimidazol-1-yl) valerylamino)phenyl)-2H-phthalazin-1-one Hydrochloride

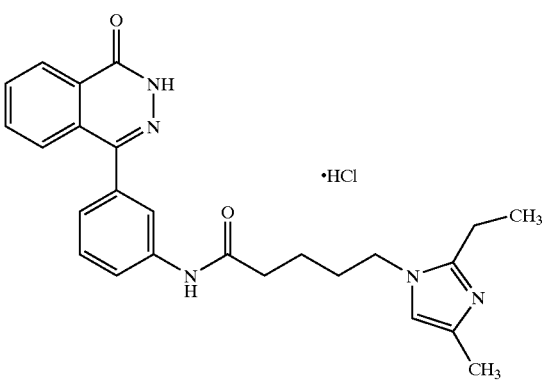

TLC: Rf 0.60 (Methylene chloride:Methanol:Acetic acid=8:1:1); NMR (DMSO-$d_6$): δ 12.85 (s, 1H), 10.38 (s, 1H), 8.35–8.32 (m, 1H), 7.89–7.88 (m, 3H), 7.75–7.69 (m, 2H), 7.45 (t, J=7.8 Hz, 1H), 7.36–7.33 (m, 1H), 7.24 (d, J=7.8 Hz, 1H), 4.07 (t, J=6.9 Hz, 2H), 2.94–2.88 (m, 2H), 2.43–2.38 (m, 2H), 2.21 (s, 3H), 1.76–1.58 (m, 4H), 1.25 (t, J=7.5 Hz, 3H).

EXAMPLE 21(60)

4-(3-(5-Morpholinovalerylamino)-4-fluorophenyl)-2H-phthalazin-1-one Hydrochloride

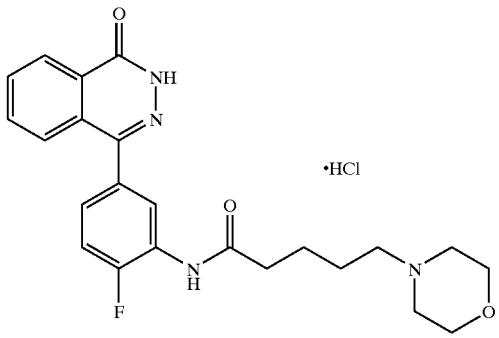

TLC: Rf 0.37 (Chloroform:Methanol:Acetic acid=9:1:1); NMR (DMSO-$d_6$): δ 12.86 (s, 1H), 10.38 (brs, 1H), 9.94 (s, 1H), 8.36–8.31 (m, 1H), 8.15 (dd, J=7.8, 1.8 Hz, 1H), 7.94–7.85 (m, 2H), 7.73–7.68 (m, 1H), 7.46–7.33 (m, 2H), 3.96–3.91 (m, 2H), 3.71 (t, J=11.7 Hz, 2H), 3.42–3.27 (m, 2H), 3.14–2.93 (m, 4H), 2.52–2.42 (m, 2H), 1.78–1.54 (m, 4H).

EXAMPLE 21(61)

4-(3-(5-(1,2,5,6-Tetrahydropyridin-1-yl)valerylamino)phenyl)-2H-phthalazin-1-one Hydrochloride

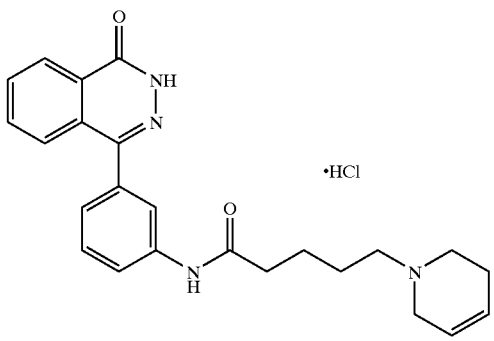

TLC: Rf 0.40 (Chloroform:Methanol:Acetic acid=9:1:1); NMR (DMSO-$d_6$): δ 12.85 (s, 1H), 10.25 (s, 1H), 10.13 (brs, 1H), 8.35–8.31 (m, 1H), 7.94–7.85 (m, 3H), 7.75–7.70 (m, 2H), 7.46 (t, J=7.8 Hz, 1H), 7.24 (d, J=7.8 Hz, 1H), 5.93–5.84 (m, 1H), 5.72–5.63 (m, 1H), 3.83–3.70 (m, 1H), 3.59–3.32 (m, 2H), 3.14–2.98 (m, 3H), 2.52–2.35 (m, 3H), 2.32–2.18 (m, 1H), 1.80–1.54 (m, 4H).

EXAMPLE 21(62)

4-(3-(5-(Pyrrolidin-1-yl)valerylamino)-4-chlorophenyl)-2H-phthalazin-1-one Hydrochloride

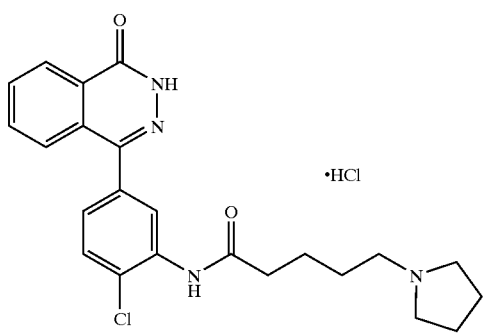

TLC: Rf 0.58 (Methylene chloride:Methanol:Acetic acid=8:1:1); NMR (DMSO-$d_6$): δ 12.90 (s, 1H), 10.19 (brs, 1H), 9.72 (s, 1H), 8.35–8.32 (m, 1H), 7.94–7.87 (m, 3H), 7.75–7.72 (m, 1H), 7.65 (d, J=8.1 Hz, 1H), 7.43 (dd, J=8.1, 2.1 Hz, 1H), 3.59–3.52 (m, 2H), 3.16–3.07 (m, 2H), 2.96–2.93 (m, 2H), 2.50–2.44 (m, 2H), 1.97–1.83 (m, 4H), 1.76–1.60 (m, 4H).

EXAMPLE 21(63)

4-(3-(5-((2S)-2-Methoxymethylpyrrolidin-1-yl)valerylamino)phenyl)-2H-phthalazin-1-one Hydrochloride

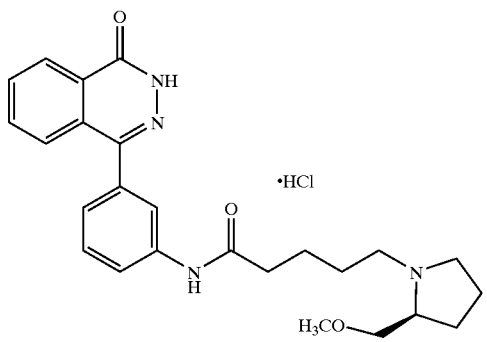

TLC: Rf 0.20 (Chloroform:Methanol:Acetic acid=8:2:0.1); NMR (DMSO-$d_6$): δ 12.85 (s, 1H), 10.26 (s, 1H), 9.89 (brs, 1H), 8.35–8.32 (m, 1H), 7.91–7.88 (m, 3H), 7.74–7.70 (m, 2H), 7.46 (t, J=7.8 Hz, 1H), 7.24 (d, J=7.8 Hz, 1H), 3.68–3.29 (m, 5H), 3.29 (s, 3H), 3.05 (m, 2H), 2.39 (m, 2H), 2.13–1.63 (m, 8H).

EXAMPLE 21(64)

4-(3-(5-(1,2,3-Triazol-1-yl)valerylamino)phenyl)-2H-phthalazin-1-one Hydrochloride

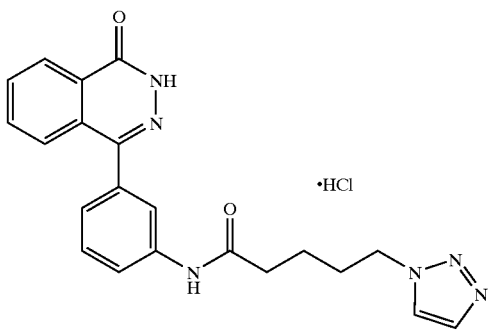

TLC: Rf 0.44 (Methylene chloride;Methanol=9:1); NMR (DMSO-$d_6$): δ 12.83 (s, 1H), 10.09 (s, 1H), 8.35–8.32 (m, 1H), 8.12 (s, 1H), 7.91–7.86 (m, 3H), 7.73–7.68 (m, 3H), 7.46 (t, J=8.1 Hz, 1H), 7.25–7.22 (m, 1H), 4.40 (t, J=6.9 Hz, 2H), 2.36 (t, J=7.5 Hz, 2H), 1.88–1.83 (m, 2H), 1.56–1.51 (m, 2H).

EXAMPLE 21(65)

4-(3-(5-Cyclopentylaminovalerylamino)-4-chlorophenyl)-2H-phthalazin-1-one Hydrochloride

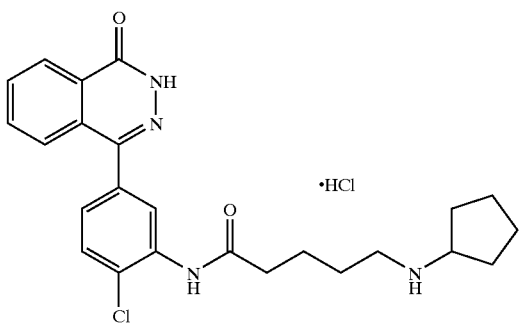

TLC: Rf 0.27 (Methylene chloride:Methanol=5:1); NMR (DMSO-$d_6$): δ 12.90 (s, 1H), 9.72 (s, 1H), 8.58 (brs, 2H), 8.36–8.33 (m, 1H), 7.94–7.89 (m, 3H), 7.75–7.72 (m, 1H), 7.65 (d, J=8.4 Hz, 1H), 7.43–7.40 (m, 1H), 3.40–3.39 (m, 1H), 2.95–2.85 (m, 2H), 2.49–2.40 (m, 2H), 1.98–1.90 (m, 2H), 1.66–1.50 (m, 10H).

EXAMPLE 21(66)

4-(3-(5-(N-2-Methoxyethyl-N-methylamino)valerylamino)-4-chlorophenyl)-2H-phthalazin-1-one Hydrochloride

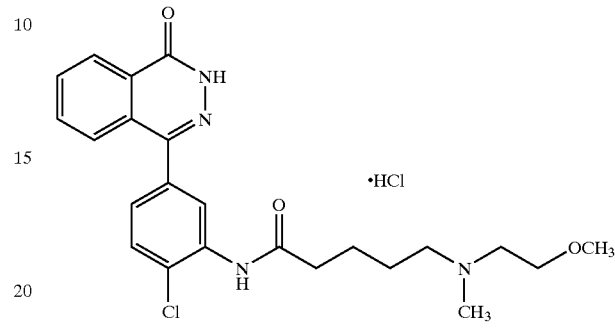

TLC: Rf 0.51 (Methylene chloride:Methanol:Acetic acid=8:1:1); NMR (DMSO-$d_6$): δ 12.90 (s, 1H), 9.86 (brs, 1H), 9.74 (s, 1H), 8.35–8.32 (m, 1H), 7.94–7.87 (m, 3H), 7.75–7.72 (m, 1H), 7.65 (d, J=8.4 Hz, 1H), 7.43–7.39 (m, 1H), 3.64 (t, J=5.1 Hz, 2H), 3.30–3.05 (m, 7H), 2.74 (d, J=4.5 Hz, 3H), 2.54–2.49 (m, 2H), 1.70–1.62 (m, 4H).

EXAMPLE 21(67)

4-(3-(5-(2-Methylthioethylamino)valerylamino)phenyl)-2H-phthalazin-1-one Hydrochloride

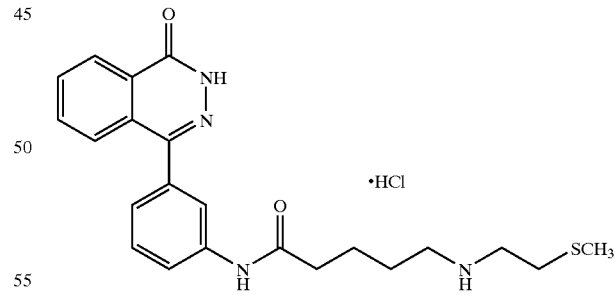

TLC: Rf 0.56 (Methylene chloride:Methanol:Acetic acid=8:1:1); NMR (DMSO-$d_6$): δ 12.84 (s, 1H), 10.24 (s, 1H), 8.76 (brs, 2H), 8.35–8.32 (m, 1H), 7.92–7.88 (m, 3H), 7.74–7.70 (m, 2H), 7.46 (t, J=8.1 Hz, 1H), 7.25 (d, J=8.1 Hz, 1H), 3.12–3.04 (m, 2H), 2.98–2.88 (m, 2H), 2.73 (t, J=6.9 Hz, 2H), 2.42–2.35 (m, 2H), 2.08 (s, 3H), 1.68–1.62 (m, 4H).

EXAMPLE 21(68)

4-(3-(5-Morpholinovalerylamino)-4-methylphenyl)-2H-phthalazin-1-one Hydrochloride

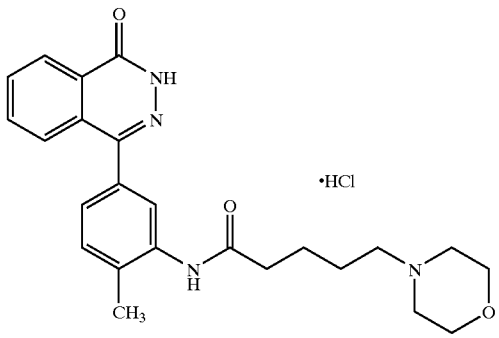

TLC: Rf 0.51 (Chloroform:Methanol:28% Ammonia water=9:1:0.2); NMR (DMSO-$d_6$): δ 12.81 (s, 1H), 10.56–10.40 (br, 1H), 9.49 (s, 1H), 8.35–8.30 (m, 1H), 7.92–7.84 (m, 2H), 7.78–7.71 (m, 1H), 7.66 (d, J=1.5 Hz, 1H), 7.37 (d, J=7.8 Hz, 1H), 7.28 (dd, J=7.8, 1.5 Hz, 1H), 3.96–3.89 (m, 2H), 3.78–3.67 (m, 2H), 3.40–3.34 (m, 2H), 3.15–2.93 (m, 4H), 2.43 (t, J=6.9 Hz, 2H), 2.30 (s, 3H), 1.80–1.55 (m, 4H).

EXAMPLE 2(69)

4-(3-(5-(Imidazol-1-yl)valerylamino)phenyl)-2H-phthalazin-1-one Hydrochloride

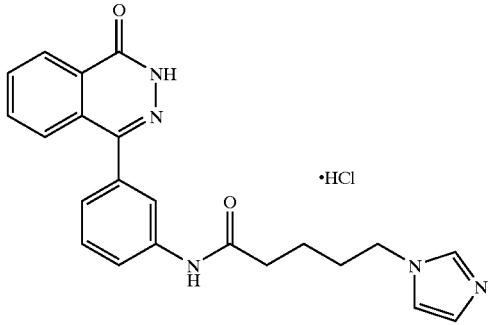

TLC: Rf 0.36 (Methylene chloride:Methanol:Acetic acid=8:1:1); NMR (DMSO-$d_6$): δ 12.85 (s, 1H), 10.25 (s, 1H), 9.18 (s, 1H), 8.38–8.32 (m, 1H), 7.96–7.86 (m, 3H), 7.84–7.78 (m, 1H), 7.76–7.68 (m, 3H), 7.52–7.42 (m, 1H), 7.30–7.22 (m, 1H), 4.25–4.19 (m, 2H), 2.44–2.36 (m, 2H), 1.88–1.80 (m, 2H), 1.62–1.50 (m, 2H).

EXAMPLE 21(70)

4-(3-(5-(3-Methoxypyrrolidin-1-yl)valerylamino)phenyl)-2H-phthalazin-1-one Hydrochloride

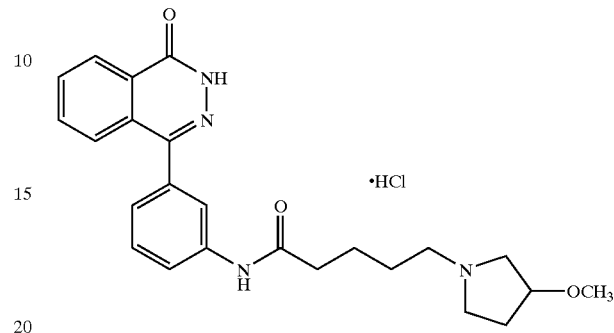

TLC: Rf 0.36 (Chloroform:Methanol:Acetic acid= 8:2:0.1); NMR (DMSO-$d_6$): δ 12.84 (s, 1H), 10.63 (brs, 1H×½), 10.25 (s, 1H×½), 10.22 (s, 1H×½), 10.14 (brs, 1H×½), 8.35–8.32 (m, 1H), 7.89 (m, 3H), 7.73–7.71 (m, 2H), 7.46 (t, J=7.8 Hz, 1H), 7.24 (d, J=7.8 Hz, 1H), 4.09 (m, 1H), 3.56 (m, 2H), 3.22 (s, 3H), 3.10 (m, 4H), 2.38 (t, J=6.3 Hz, 2H), 2.25–1.91 (m, 2H), 1.65 (m, 4H).

EXAMPLE 21(71)

4-(3-(5-(N-Methyl-N-2-propynylamino)valerylamino)-4-chlorophenyl)-2H-phthalazin-1-one Hydrochloride

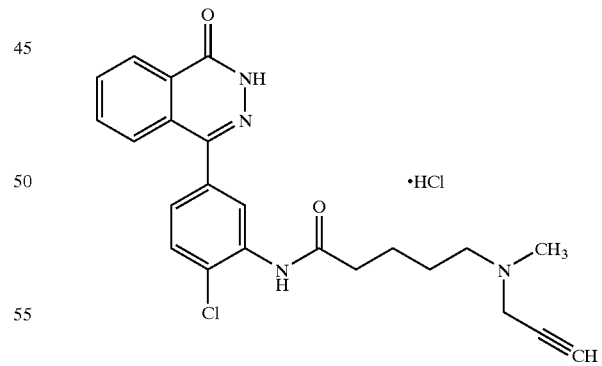

TLC: Rf 0.43 (Methylene chloride:Methanol=10:1); NMR (DMSO-$d_6$): δ 12.90 (s, 1H), 11.03 (brs, 1H), 9.75 (s, 1H), 8.35–8.32 (m, 1H), 7.94–7.89 (m, 3H), 7.75–7.72 (m, 1H), 7.65 (d, J=8.1 Hz, 1H), 7.42 (d, J=8.1 Hz, 1H), 4.06 (s, 2H), 3.82 (s, 1H), 3.14–3.04 (m, 2H), 2.74 (s, 3H), 2.54–2.44 (m, 2H), 1.73–1.63 (m, 4H).

EXAMPLE 21(72)

4-(3-(5-(1-Methoxymethylcyclopentylamino)valerylamino)phenyl)-2H-phthalazin-1-one Hydrochloride

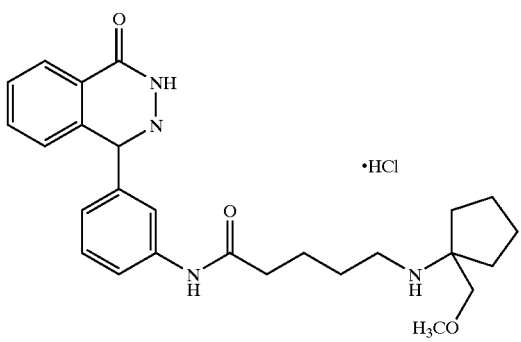

TLC: Rf 0.36 (Chloroform:Methanol:28% Ammonia water=9:1:0.2); NMR (DMSO-d$_6$): δ 12.85 (s, 1H), 10.24 (s, 1H), 8.64–8.52 (br, 2H), 8.36–8.31 (m, 1H), 7.95．7.85 (m, 3H), 7.76–7.69 (m, 2H), 7.47 (t, J=8.0 Hz, 1H), 7.25 (d, J=8.0 Hz, 1H), 3.38 (s, 2H), 3.33 (s, 3H), 2.90–2.76 (m, 2H), 2.45–2.35 (m, 2H), 1.80–1.47 (m, 12H).

EXAMPLE 21(73)

4-(3-(5-(Tetrahydropyran-4-ylamino)valerylamino)phenyl)-2H-phthalazin-1-one Hydrochloride

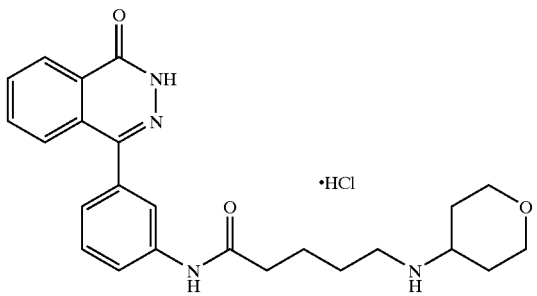

TLC: Rf 0.32 (Chloroform:Methanol:28% Ammonia water=9:1:0.2); NMR (DMSO-d$_6$): δ 12.85 (s, 1H), 10.26 (s, 1H), 8.92–8.77 (br, 2H), 8.36–8.30 (m, 1H), 7.95–7.85 (m, 3H), 7.77–7.68 (m, 2H), 7.46 (t, J=8.0 Hz, 1H), 7.24 (d, J=8.0 Hz, 1H), 3.94–3.83 (m, 2H), 3.38–3.14 (m, 3H), 2.99–2.83 (m, 2H), 2.45–2.34 (m, 2H), 2.00–1.87 (m, 2H), 1.77–1.48 (m, 6H).

EXAMPLE 21(74)

4-(3-(5-(3-Methoxypiperidin-1-yl)valerylamino)phenyl)-2H-phthalazin-1-one Hydrochloride

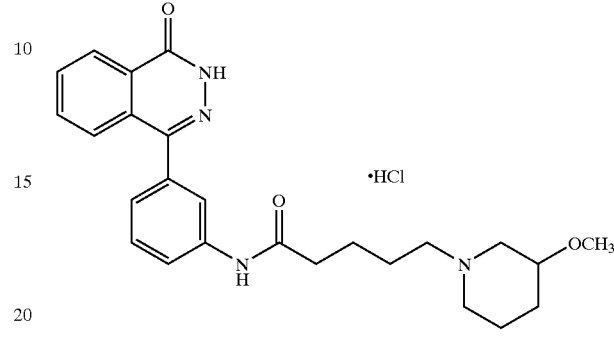

TLC: Rf 0.49 (Chloroform:Methanol:Acetic acid= 8:2:0.1); NMR (DMSO-d$_6$): δ 12.85 (s, 1H), 10.58 (brs, 1H×½), 10.34 (s, 1H×½), 10.29 (s, 1H×½), 9.12 (brs, 1H×½), 8.35–8.32 (m, 1H), 7.91–7.88 (m, 3H), 7.75–7.70 (m, 2H), 7.46 (t, J=7.8 Hz, 1H), 7.24 (d, J=7.8 Hz, 1H), 3.66–3.03 (m, 7H), 3.28 (s, 3H), 2.40–2.30 (m, 2H), 2.09–1.50 (m, 8H).

EXAMPLE 21(75)

4-(3-(5-(2-Methoxycyclohexylamino)valerylamino)phenyl)-2H-phthalazin-1-one Hydrochloride

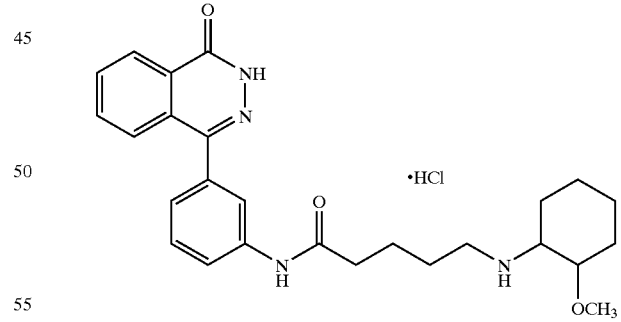

TLC: Rf 0.44 (Chloroform:Methanol:28% Ammonia water=9:1:0.2); NMR (DMSO-d$_6$): δ 12.85 (s, 1H), 10.29 (s, 1H), 8.93–8.76 (br, 1H), 8.48–8.31 (m, 2H), 7.95–7.86 (m, 3H), 7.76–7.69 (m, 2H), 7.46 (t, J=7.8 Hz, 1H), 7.24 (d, J=7.8 Hz, 1H), 3.30–3.22 (m, 1H), 3.29 (s, 3H), 3.00–2.80 (m, 3H), 2.43–2.35 (m, 2H), 2.23–2.02 (m, 2H), 1.80–0.95 (m, 10H).

EXAMPLE 21(76)

4-(3-(5-((1S,2S)-2-Methoxycyclopentylamino)valerylamino)phenyl)-2H-phthalazin-1-one Hydrochloride

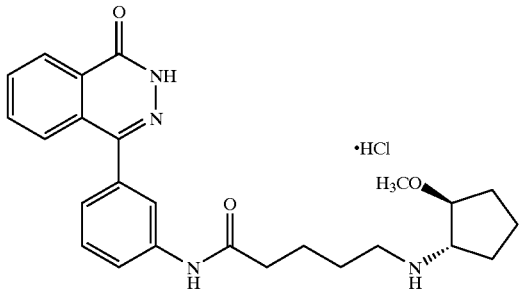

TLC: Rf 0.68 (Chloroform:Methanol:Acetic acid=9:1:1); NMR (DMSO-d$_6$): δ 12.85 (s, 1H), 10.24 (s, 1H), 8.89 (brs, 2H), 8.35–8.32 (m, 1H), 7.94–7.85 (m, 3H), 7.74–7.70 (m, 2H), 7.46 (t, J=7.8 Hz, 1H), 7.24 (d, J=7.8 Hz, 1H), 3.88–3.82 (m, 1H), 3.38–3.24 (m, 1H), 3.23 (s, 3H), 3.03–2.86 (m, 2H), 2.42–2.34 (m, 2H), 2.10–1.86 (m, 2H), 1.76–1.49 (m, 8H).

EXAMPLE 21(77)

4-(3-(5-((2R)2-Methoxymethylpyrrolidin-1-yl)valerylamino)phenyl)-2H-phthalazin-1-one Hydrochloride

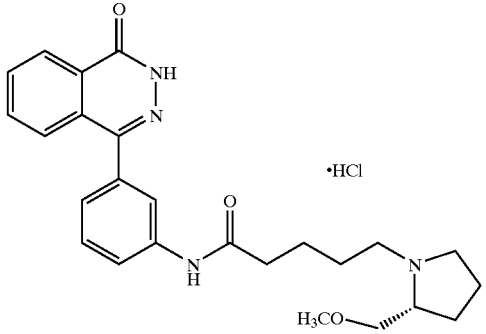

TLC: Rf 0.64 (Methylene chloride:Methanol:Acetic acid=8:1:1); NMR (DMSO-d$_6$): δ 12.85 (s, 1H), 10.24 (s, 1H), 9.80 (brs, 1H), 8.35–8.32 (m, 1H), 7.93–7.86 (m, 3H), 7.74–7.70 (m, 2H), 7.46 (t, J=7.8 Hz, 1H), 7.26 (d, J=7.8 Hz, 1H), 3.69–3.23 (m, 8H), 3.12–3.01 (m, 2H), 2.41–2.37 (m, 2H), 2.131.66 (m, 8H).

EXAMPLE 21(78)

4-(3-(5-(2-Propenylamino)valerylamino)-4-chlorophenyl)-2H-phthalazin-1-one Hydrochloride

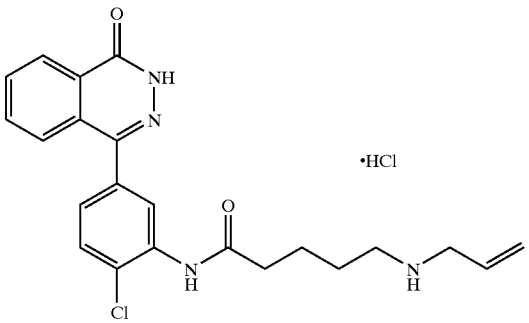

TLC: Rf 0.77 (Chloroform:Methanol:Acetic acid=8:2:1); NMR (DMSO-d$_6$): δ 12.90 (s, 1H), 9.72 (s, 1H), 8.81 (brs, 2H), 8.35–8.32 (m, 1H), 7.94–7.86 (m, 3H), 7.76–7.71 (m, 1H), 7.66 (d, J=8.4 Hz, 1H), 7.41 (dd, J=8.4, 2.1 Hz, 1H), 5.94–5.81 (m, 1H), 5.44 (d, J=17.1 Hz, 1H), 5.37 (d, J=10.2 Hz, 1H), 3.57–3.51 (m, 2H), 2.93–2.80 (m, 2H), 2.52–2.40 (m, 2H), 1.70–1.60 (m, 4H).

EXAMPLE 21(79)

4-(3-(5-(4-Methoxypiperidin-1-yl)valerylamino)phenyl)-2H-phthalazin-1-one

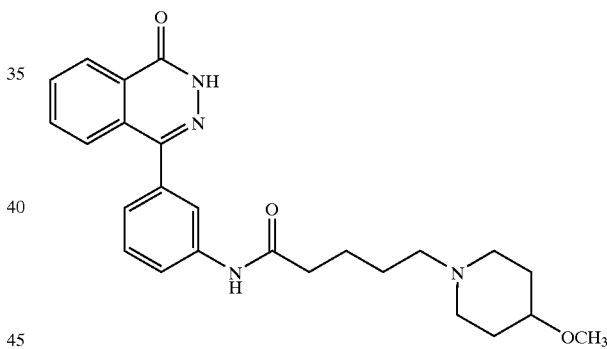

Hydrochloride:
TLC: Rf 0.36 (Chloroform:Methanol:Acetic acid=9:1:1); NMR (DMSO-d$_6$): δ 12.85 (s, 1H), 10.24 and 10.22 (s, 1H), 9.94 (brs, 1H), 8.36–8.31 (m, 1H), 7.94–7.85 (m, 3H), 7.75–7.68 (m, 2H), 7.46 (t, J=7.8 Hz, 1H), 7.24 (d, J=7.8 Hz, 1H), 3.55–3.22 (m, 6H, overlapped with H$_2$O), 3.08–2.82 (m, 4H), 2.39 (t, J=6.6 Hz, 2H), 2.14–2.04 (m, 1H), 1.96–1.82 (m, 2H), 1.78–1.52 (m, 5H).

½ Sulfate:
TLC: Rf 0.42 (Chloroform:Methanol:28% Ammonia water=9:1:0.2); NMR (DMSO-d$_6$): δ 12.84 (s, 1H), 10.08 (s, 1H), 8.36–8.30 (m, 1H), 7.94–7.85 (m, 3H), 7.75–7.68 (m, 2H), 7.46 (t, J=7.8 Hz, 1H), 7.24 (d, J=7.8 Hz, 1H), 3.54–3.20 (m, 6H, overlapped H$_2$O), 2.98–2.84 (m, 2H), 2.74–2.32 (m, 5H, overlapped DMSO), 1.93–1.78 (m, 2H), 1.67–1.46 (m, 5H).

p-Toluenesulfonate:
TLC: Rf 0.40 (Chloroform:Methanol:28% Ammonia water=9:1:0.2); NMR (DMSO-d$_6$): δ 12.85 (s, 1H), 10.12 (s, 1H), 9.02–8.85 (br, 1H), 8.36–8.31 (m, 1H), 7.94–7.85 (m, 3H), 7.75–7.68 (m, 2H), 7.50–7.44 (m, 3H), 7.25 (d, J=7.5 Hz, 1H), 7.09 (d, J=8.1 Hz, 2H), 3.60–3.20 (m, 6H, overlapped H₂O), 3.12–2.83 (m, 4H), 2.39 (t, J=6.5 Hz, 2H), 2.27 (s, 3H), 2.18–2.07 (m, 1H), 2.02–1.90 (m, 1H), 1.84–1.40 (m, 6H).

Methanesulfonate:

TLC: Rf 0.40 (Chloroform:Methanol:28% Ammonia water=9:1:0.2); NMR (DMSO-d₆): δ 12.85 (s, 1H), 10.14 (s, 1H), 9.10–8.92 (br, 1H), 8.36–8.31 (m, 1H), 7.94–7.85 (m, 3H), 7.75–7.68 (m, 2H), 7.47 (t, J=7.8 Hz, 1H), 7.25 (d, J=7.8 Hz, 1H), 3.57–3.23 (m, 6H, overlapped H₂O), 3.12–2.84 (m, 4H), 2.39 (t, J=6.6 Hz, 2H), 2.32 (s, 3H), 2.18–2.07 (m, 1H), 2.02–1.90 (m, 1H), 1.85–1.42 (m, 6H).

EXAMPLE 21(80)

4-(3-(5-Isobutylaminovalerylamino)-4-chlorophenyl)-2H-phthalazin-1-one Hydrochloride

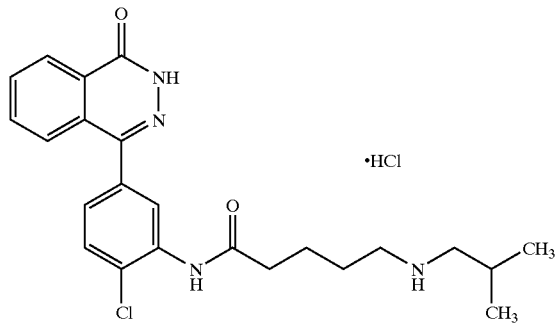

TLC: Rf 0.69 (Methylene chloride:Methanol:Acetic acid=8:1:1); NMR (DMSO-d₆): δ 12.90 (s, 1H), 9.76 (s, 1H), 8.72 (brs, 2H), 8.35–8.32 (m, 1H), 7.94–7.87 (m, 3H), 7.75–7.72 (m, 1H), 7.65 (d, J=8.1 Hz, 1H), 7.42–7.39 (m, 1H), 2.94–2.80 (m, 2H), 2.72–2.64 (m, 2H), 2.50–2.46 (m, 2H), 2.05–1.92 (m, 1H), 1.78–1.60 (m, 4H), 0.91 (d, J=6.6 Hz, 6H).

EXAMPLE 21(81)

4-(3-(5-(Pyrrolidin-1-yl)valerylamino)-4-fluorophenyl)-2H-phthalazin-1-one Hydrochloride

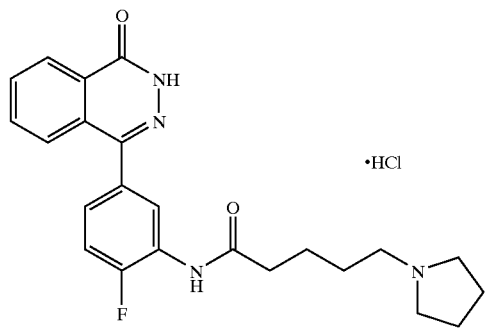

TLC: Rf 0.43 (Chloroform:Methanol:28% Ammonia water=9:1:0.2); NMR (DMSO-d₆): δ 12.86 (s, 1H), 9.93 (s, 1H), 9.93–9.72 (br, 1H), 8.36–8.30 (m, 1H), 8.16–8.12 (m, 1H), 7.94–7.86 (m, 2H), 7.74–7.68 (m, 1H), 7.47–7.33 (m, 2H), 3.55–3.43 (m, 2H), 3.16–3.04 (m, 2H), 3.01–2.88 (m, 2H), 2.50–2.44 (m, 2H), 2.05–1.55 (m, 8H).

EXAMPLE 21(82)

4-(3-(6-Morpholinohexanoylamino)phenyl)-2H-phthalazin-1-one Hydrochloride

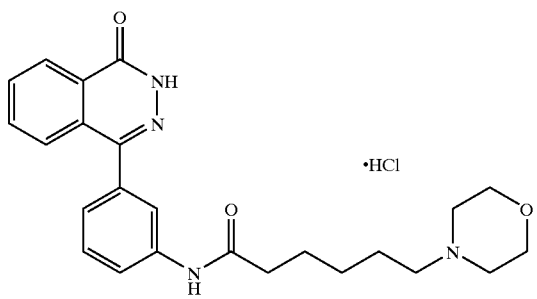

TLC: Rf 0.43 (Chloroform:Methanol=8:2); NMR (DMSO-d₆): δ 12.84 (s, 1H), 10.48 (brs, 1H), 10.17 (s, 1H), 8.35–8.32 (m, 1H), 7.92–7.88 (m, 3H), 7.73–7.70 (m, 2H), 7.46 (t, J=7.8 Hz, 1H), 7.24 (d, J=7.8 Hz, 1H), 3.95–3.69 (m, 4H), 3.36 (m, 2H), 3.09–2.98 (m, 4H), 2.36 (t, J=7.6 Hz, 2H), 1.73–1.60 (m, 4H), 1.35–1.30 (m, 2H).

EXAMPLE 21(83)

4-(3-(5-(Perhydroazepin-1-yl)valerylamino)-4-chlorophenyl)-2H-phthalazin-1-one Hydrochloride

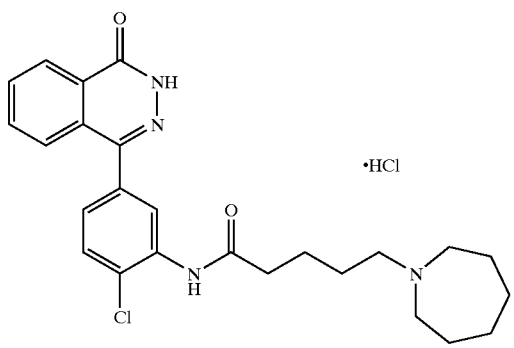

TLC: Rf 0.65 (Chloroform:Methanol:Acetic acid=8:1:1); NMR (DMSO-d₆): δ 12.90 (s, 1H), 10.04 (brs, 1H), 9.73 (s, 1H), 8.35–8.32 (m, 1H), 7.94–7.86 (m, 3H), 7.75–7.65 (m, 2H), 7.42–7.39 (m, 1H), 3.36–3.29 (m, 2H), 3.09–2.99 (m, 4H), 2.60–2.45 (m, 2H), 1.80–1.54 (m, 12H).

EXAMPLE 21(84)

4-(3-(5-(2-Fluoroethylamino)valerylamino)-4-fluorophenyl)-2H-phthalazin-1-one Hydrochloride

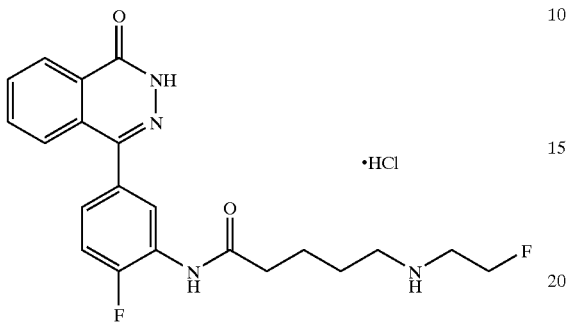

TLC: Rf 0.45 (Chloroform:Methanol:28% Ammonia water=9:1:0.2); NMR (DMSO-$d_6$): δ 12.86 (s, 1H), 9.94 (s, 1H), 9.10–8.90 (br, 2H), 8.36–8.30 (m, 1H), 8.18–8.12 (m, 1H), 7.95–7.86 (m, 2H), 7.74–7.68 (m, 1H), 7.47–7.33 (m, 2H), 4.72 (dt, J=47.0, 4.5 Hz, 2H), 3.30–3.16 (m, 2H), 3.00–2.88 (m, 2H), 2.50–2.44 (m, 2H), 1.76–1.50 (m, 4H).

EXAMPLE 21(85)

4-(3-(5-(Tetrahydropyran-4-ylamino)valerylamino)-4-chlorophenyl)-2H-phthalazin-1-one Hydrochloride

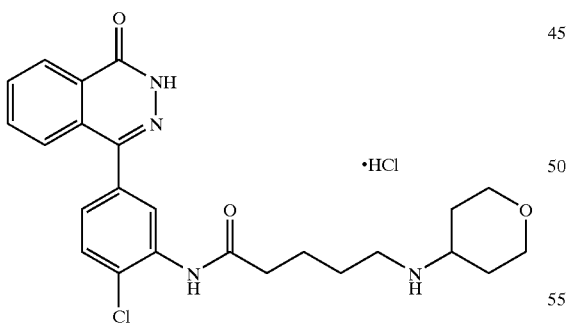

TLC: Rf 0.45 (Chloroform:Methanol:28% Ammonia water=9:1:0.2); NMR (DMSO-$d_6$): δ 12.90 (s, 1H), 9.73 (s, 1H), 8.90–8.75 (br, 2H), 8.36–8.32 (m, 1H), 7.97–7.87 (m, 3H), 7.76–7.70 (m, 1H), 7.66 (d, J=8.4 Hz, 1H), 7.41 (dd, J=8.4, 2.0 Hz, 1H), 3.92–3.85 (m, 2H), 3.40–3.15 (m, 3H), 2.98–2.85 (m, 2H), 2.50–2.45 (m, 2H), 1.96–1.87 (m, 2H), 1.75–1.48 (m, 6H).

EXAMPLE 21(86)

4-(3-(5-(2-Hydroxyethylamino)valerylamino)phenyl)-2H-phthalazin-1-one Hydrochloride

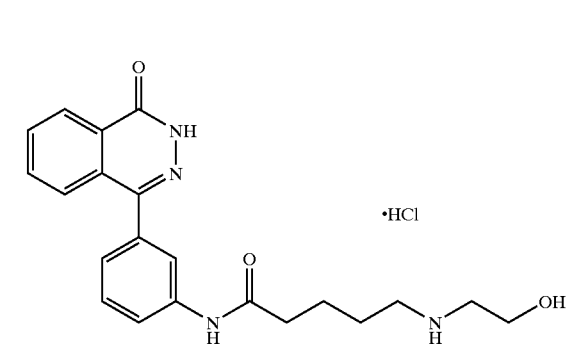

TLC: Rf 0.40 (Chloroform:Methanol:Acetic acid=8:2:1); NMR (DMSO-$d_6$): δ 12.85 (s, 1H), 10.24 (s, 1H), 8.63 (brs, 2H), 8.37–8.30 (m, 1H), 7.94–7.85 (m, 3H), 7.76–7.69 (m, 2H), 7.46 (t, J=8.1 Hz, 1H), 7.26–7.22 (m, 1H), 5.18 (brs, 1H), 3.64 (t, J=5.4 Hz, 2H), 3.00–2.85 (m, 4H), 2.38 (t, J=6.3 Hz, 2H), 1.74–1.56 (m, 4H).

EXAMPLE 21(87)

4-(3-(5-(3-Methylbutylamino)valerylamino)phenyl)-2H-phthalazin-1-one Hydrochloride

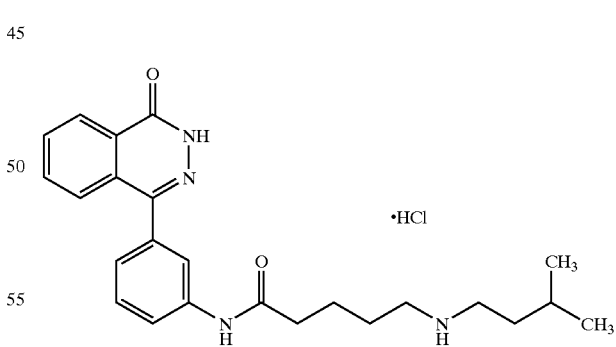

TLC: Rf 0.81 (Chloroform:Methanol:Acetic acid=8:1:1); NMR (DMSO-$d_6$): δ 12.85 (s, 1H), 10.27 (s, 1H), 8.64 (brs, 2H), 8.35–8.32 (m, 1H), 7.91–7.88 (m, 3H), 7.74–7.70 (m, 2H), 7.46 (t, J=7.8 Hz, 1H), 7.25 (d, J=7.8 Hz, 1H), 2.96–2.80 (m, 4H), 2.44–2.34 (m, 2H), 1.68–1.44 (m, 7H), 0.87 (d, J=6.3 Hz, 6H).

EXAMPLE 21(88)

4-(3-(5-(3-Methoxypiperidin-1-yl)valerylamino)-4-chlorophenyl)-2H-phthalazin-1-one Hydrochloride

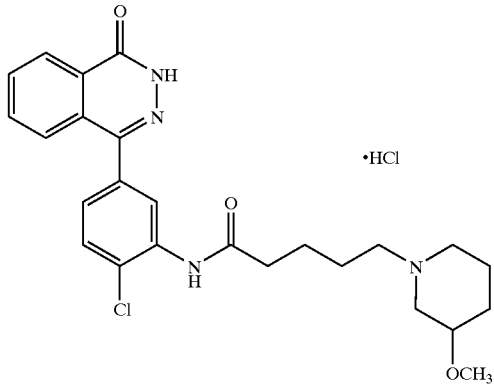

TLC: Rf 0.57 (Chloroform:Methanol:Acetic acid=8:1:1); NMR (DMSO-d$_6$): δ 12.90 (s, 1H), 10.22 (brs, 1H×½), 9.72 (s, 1H), 9.06 (brs, 1H×½), 8.35–8.32 (m, 1H), 7.95–7.88 (m, 3H), 7.74–7.65 (m, 2H), 7.42 (d, J=7.8 Hz, 1H), 3.67 (brs, 1H), 3.60–3.45 (m, 2H), 3.28 (s, 3H), 3.15–2.98 (m, 4H), 2.50–2.40 (m, 2H), 2.00–1.40 (m, 8H).

EXAMPLE 21(89)

4-(3-(5-(N-Methyl-N-tetrahydropyran-4-yl)aminovalerylamino)phenyl)-2H-phthalazin-1-one Hydrochloride

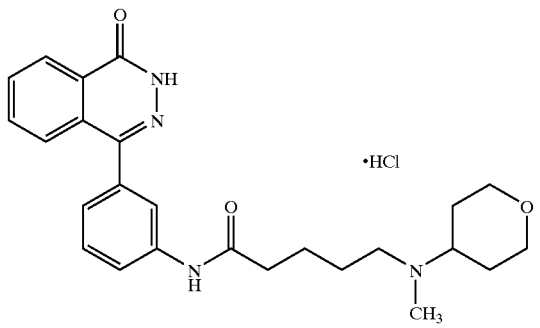

TLC: Rf 0.33 (Chloroform:Methanol:Acetic acid=8:1:1); NMR (DMSO-d$_6$): δ 12.85 (s, 1H), 10.23 (s, 1H), 10.04 (brs, 1H), 8.35–8.32 (m, 1H), 7.91–7.88 (m, 3H), 7.73–7.71 (m, 2H), 7.47 (t, J=7.5 Hz, 1H), 7.26 (d, J=7.5 Hz, 1H), 3.95–3.91 (m, 2H), 3.40–3.24 (m, 4H), 3.06–2.94 (m, 1H), 2.66 (d, J=4.8 Hz, 3H), 2.46–2.36 (m, 2H), 1.98–1.84 (m, 2H), 1.76–1.58 (m, 6H).

EXAMPLE 21(90)

4-(3-(5-((3R)-3-Methoxypiperidin-1-yl)valerylamino)phenyl)-2H-phthalazin-1-one Hydrochloride

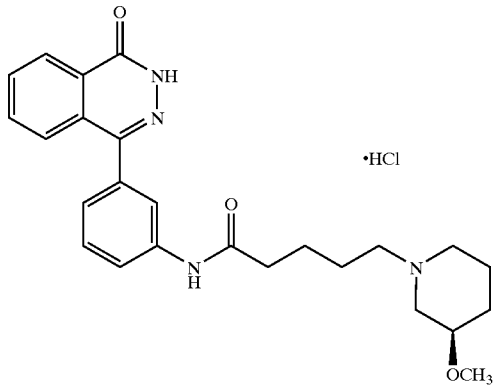

TLC: Rf 0.58 (Chloroform:Methanol:28% Ammonia water=9:1:0.1); NMR (DMSO-d$_6$): δ 12.86 (s, 1H), 10.45–10.22 (m, 1.5H), 9.19–8.93 (m, 0.5H), 8.39–8.30 (m, 1H), 7.96–7.85 (m, 3H), 7.77–7.68 (m, 2H), 7.47 (t, J=7.8 Hz, 1H), 7.25 (d, J=7.8 Hz, 1H), 3.72–3.22 (m, 6H), 3.15–2.56 (m, 4H), 2.40 (t, J=6.8 Hz, 2H), 2.18–1.10 (m, 8H).

EXAMPLE 21(91)

4-(3-(5-((3S)-3-Methoxypiperidin-1-yl)valerylamino)phenyl)-2H-phthalazin-1-one Hydrochloride

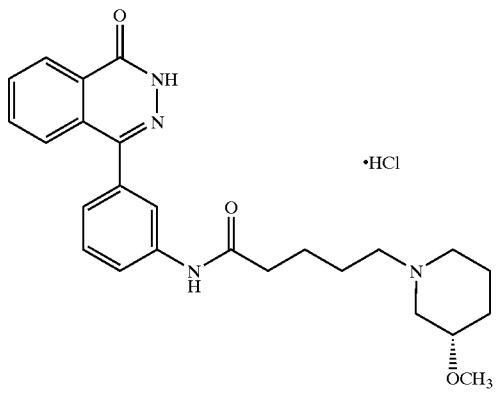

TLC: Rf 0.51 (Chloroform:Methanol:28% Ammonia water=9:1:0.2); NMR (DMSO-d$_6$): δ 12.85 (s, 1H), 10.37–10.24 (br, ½H), 10.26 and 10.24 (s, 1H), 9.14–8.97 (br, ½H), 8.36–8.31 (m, 1H), 7.94–7.85 (m, 3H), 7.75–7.69 (m, 2H), 7.46 (t, J=8.0 Hz, 1H), 7.24 (d, J=8.0 Hz, 1H), 3.70–1.10 (m, 17H), 3.28 (s, 3H).

EXAMPLE 21(92)

4-(3-(5-(3-Methoxypiperidin-1-yl)valerylamino)-4-fluorophenyl)-2H-phthalazin-1-one Hydrochloride

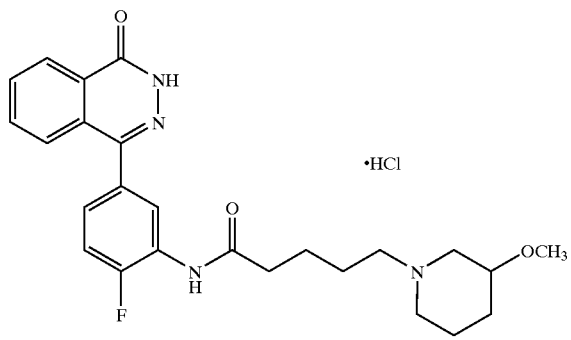

TLC: Rf 0.43 (Chloroform:Methanol:28% Ammonia water=9:1:0.2); NMR (DMSO-$d_6$): δ 12.86 (s, 1H), 10.45–10.29 (br, ½H), 9.95 (s, 1H), 9.16–8.98 (br, ½H), 8.36–8.30 (m, 1H), 8.17–8.11 (m, 1H), 7.95–7.85 (m, 2H), 7.74–7.67 (m, 1H), 7.47–7.32 (m, 2H), 3.70–1.10 (m, 17H), 3.28 (s, 3H).

EXAMPLE 21(93)

4-(3-(5-(Piperidin-4-one-1-yl)valerylamino)phenyl)-2H-phthalazin-1-one Hydrochloride

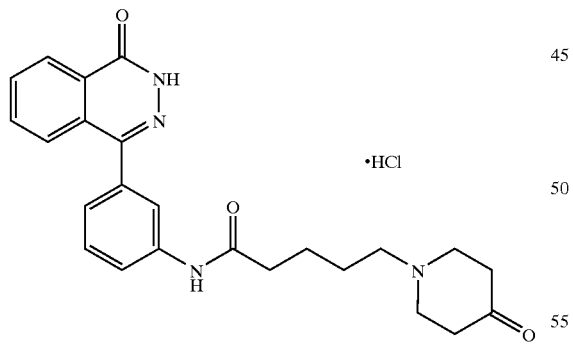

TLC: Rf 0.41 (Chloroform:Methanol:Acetic acid= 8:2:0.5); NMR (DMSO-$d_6$): δ 12.84 (s, 1H), 11.04 (brs, 1H×½), 10.25 (s, 1H), 10.17 (brs, 1H×½), 8.35–8.32 (m, 1H), 7.92–7.88 (m, 3H), 7.74–7.70 (m, 2H), 7.46 (t, J=7.8 Hz, 1H), 7.24 (d, J=7.8 Hz, 1H), 3.66–2.87 (m, 6H), 2.44–2.37 (m, 4H), 1.94–1.60 (m, 6H).

EXAMPLE 21(94)

4-(3-(5-((3R)-Tetrahydrofuran-3-ylamino)valerylamino)phenyl)-2H-phthalazin-1-one Hydrochloride

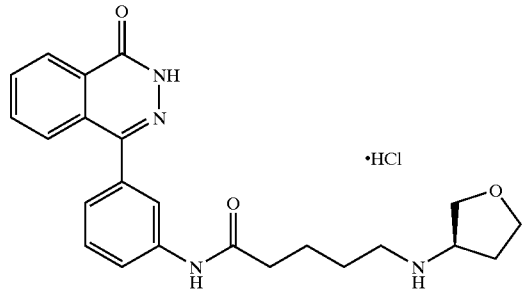

$[\alpha]_D$=+5.10° (c=0.95, Methanol); TLC: Rf 0.39 (Chloroform:Methanol:28% Ammonia water=9:1:0.2); NMR (DMSO-$d_6$): δ 12.85 (s, 1H), 10.24 (s, 1H), 8.98–8.83 (br, 2H), 8.36–8.30 (m, 1H), 7.94–7.85 (m, 3H), 7.75–7.68 (m, 2H), 7.46 (t, J=7.8 Hz, 1H), 7.24 (d, J=7.8 Hz, 1H), 3.92–3.57 (m, 5H), 2.98–2.85 (m, 2H), 2.44–2.34 (m, 2H), 2.25–2.12 (m, 2H), 2.03–1.91 (m, 2H), 1.74–1.58 (m, 4H).

EXAMPLE 21(95)

4-(3-(5-((3S)-Tetrahydrofuran-3-ylamino)valerylamino)phenyl)-2H-phthalazin-1-one Hydrochloride

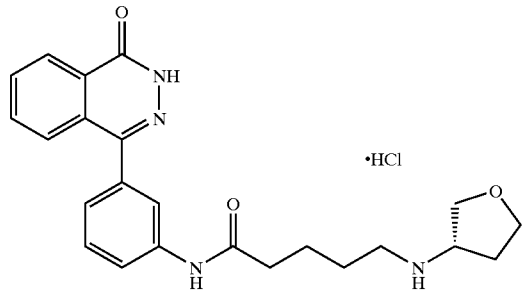

$[\alpha]_D$=−=4.83° (c=1.03, Methanol); TLC: Rf 0.39 (Chloroform:Methanol:28% Ammonia water=9:1:0.2); NMR (DMSO-$d_6$): δ 12.85 (s, 1H), 10.24 (s, 1H), 8.98–8.83 (br, 2H), 8.36–8.30 (m, 1H), 7.94–7.85 (m, 3H), 7.75–7.68 (m, 2H), 7.46 (t, J=7.8 Hz, 1H), 7.24 (d, J=7.8 Hz, 1H), 3.92–3.57 (m, 5H), 2.98–2.85 (m, 2H), 2.44–2.34 (m, 2H), 2.25–2.12 (m, 2H), 2.03–1.91 (m, 2H), 1.74–1.58 (m, 4H).

EXAMPLE 21(96)

4-(3-(5-(3-Methoxymethylpiperidin-1-yl)valerylamino)phenyl)-2H-phthalazin-1-one Hydrochloride

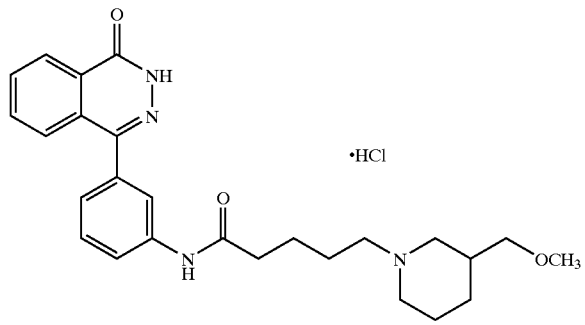

TLC: Rf 0.58 (Chloroform:Methanol:Acetic acid=8:1:1); NMR (DMSO-$d_6$): δ 12.84 (s, 1H), 10.23 (s, 1H), 9.92 (brs, 1H), 8.35–8.32 (m, 1H), 7.93–7.86 (m, 3H), 7.73–7.70 (m, 2H), 7.46 (t, J=8.1 Hz, 1H), 7.25 (d, J=8.1 Hz, 1H), 3.60–3.38 (m, 4H), 3.28–3.00 (m, 7H), 2.42–2.36 (m, 2H), 1.80–1.58 (m, 8H), 1.18–1.12 (m, 1H).

EXAMPLE 21(97)

4-(3-(5-(3-Methoxypiperidin-1-yl)valerylamino)-4-methylphenyl)-2H-phthalazin-1-one Hydrochloride

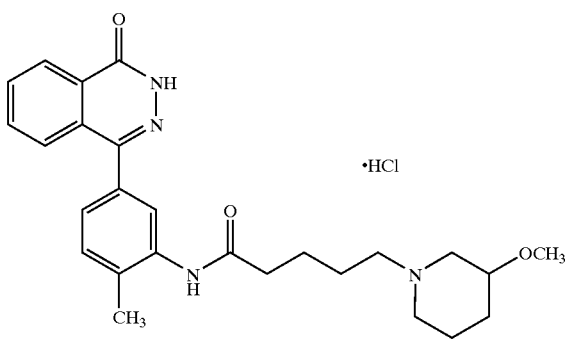

TLC: Rf 0.59 (Chloroform:Methanol=8:1); NMR (DMSO-$d_6$): δ 12.82–12.81 (m, 1H), 10.48 (brs, 1H×½), 9.54–9.52 (m, 1H), 9.10 (brs, 1H×½), 8.34–8.31 (m, 1H), 7.92–7.85 (m, 2H), 7.76–7.74 (m, 1H), 7.66 (s, 1H), 7.39–7.27 (m, 2H), 3.70–3.44 (m, 4H), 3.27 (s, 3H), 3.10–2.96 (m, 2H), 2.46–2.38 (m, 2H), 2.31 (s, 3H), 1.94–1.48 (m, 8H), 1.30–1.20 (m, 1H).

EXAMPLE 22~EXAMPLE 22(13)

The following compounds of the present invention were obtained by the same procedure as a series of reactions of example 6, if necessary, by converting to corresponding salts by conventional method, using 4-(3-aminophenyl)-2H-phthalazin-1-one or corresponding amine derivative and corresponding halide compound instead of acetyl chloride.

EXAMPLE 22

4-(3-(4-Dimethylaminobutyrylamino)-4-chlorophenyl)-2H-phthalazin-1-one Hydrochloride

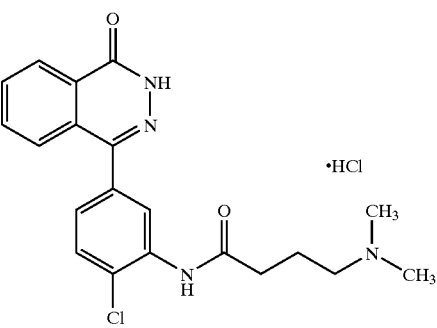

TLC: Rf 0.25 (Chloroform:Methanol:28% Ammonia water=9:1:0.1); NMR (DMSO-$d_6$): δ 12.90 (s, 1H), 10.66–10.11 (br, 1H), 9.83 (s, 1H), 8.35–8.30 (m, 1H), 7.94–7.87 (m, 3H), 7.74–7.64 (m, 2H), 7.43–7.38 (m, 1H), 3.05 (t, J=8.0 Hz, 2H), 2.71 (s, 6H), 2.52 (t, J=7.4 Hz, 2H), 2.02–1.87 (m, 2H).

EXAMPLE 22(1)

4-(3-(4-Dimethylaminobutyrylamino)phenyl)-2H-phthalazin-1-one Hydrochloride

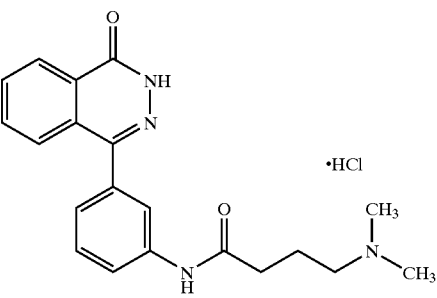

TLC: Rf 0.23 (Chloroform:Methanol:28% Ammonia water=9:1:0.1); NMR (DMSO-$d_6$): δ 12.85 (s, 1H), 10.47–10.33 (br, 2H), 8.36–8.28 (m, 1H), 7.94–7.83 (m, 3H), 7.74–7.68 (m, 2H), 7.46 (t, J=7.8 Hz, 1H), 7.24 (d, J=7.8 Hz, 1H), 3.09–3.01 (m, 2H), 2.72 (s, 6H), 2.45 (t, J=7.2 Hz, 2H), 2.03–1.88 (m, 2H).

EXAMPLE 22(2)

4-(4-Dimethylamino-3-(5-dimethylaminovalerylamino)phenyl)-2H-phthalazin-1-one Dihydrochloride

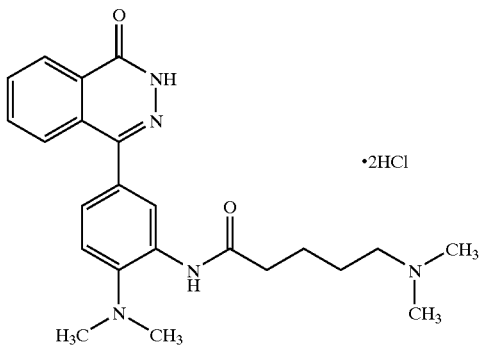

TLC: Rf 0.36 (Chloroform:Methanol:28% Ammonia water=9:1:0.1); NMR (DMSO-d$_6$): δ 12.88 (s, 1H), 10.61–10.38 (br, 1H), 10.13–9.88 (br, 1H), 8.35–8.30 (m, 1H), 7.96–7.84 (m, 3H), 7.77–7.68 (m, 2H), 7.48 (d, J=7.8 Hz, 1H), 3.09–2.92 (br, 8H), 2.68 (d, J=5.0 Hz, 6H), 2.52 (t, J=6.4 Hz, 2H), 1.79–1.52 (br, 4H).

EXAMPLE 22(3)

4-(3-(5-Dimethylaminovalerylamino)-4-chlorophenyl)-2H-phthalazin-1-one

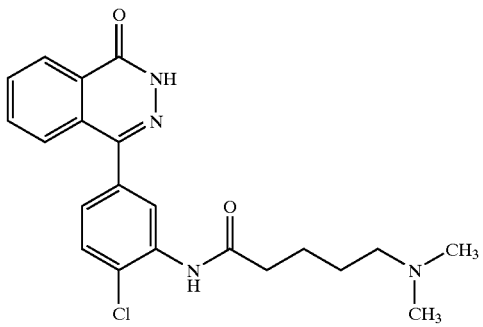

Hydrochloride:
TLC: Rf 0.28 (Chloroform:Methanol:Acetic acid=8:2:1); NMR (DMSO): δ 12.90 (s, 1H), 10.08 (s, 1H), 9.73 (s, 1H), 8.35–8.32 (m, 1H), 7.94–7.88 (m, 3H), 7.75–7.72 (m, 1H), 7.66 (d, J=7.8 Hz, 1H), 7.41 (dd, J=8.1, 1.8 Hz, 1H), 3.07–3.00 (m, 2H), 2.72 (s, 3H), 2.70 (s, 3H), 2.50–2.42 (m, 2H, overlapped with solvent), 1.74–1.56 (m, 2H).
Methanesulfonate:
TLC: Rf 0.22 (Chloroform:Methanol:Acetic acid= 8:2:0.1); NMR (DMSO-d$_6$, DMSO=2.49 ppm): δ 12.90 (s, 1H), 9.70 (s, 1H), 9.37 (brs, 1H), 8.35–8.32 (m, 1H), 7.94–7.89 (m, 3H), 7.74–7.71 (m, 1H), 7.67 (d, J=8.2 Hz, 1H), 7.41 (dd, J=8.2, 2.1 Hz, 1H), 3.06–3.02 (m, 2H), 2.74 (d, J=5.1 Hz, 6H), 2.49–2.45 (m, 2H), 2.29 (s, 3H), 1.68–1.63 (m, 4H).

EXAMPLE 22(4)

4-(3-(4-Cyanobutyrylamino)-4-dimethylaminophenyl)-2H-phthalazin-1-one Hydrochloride

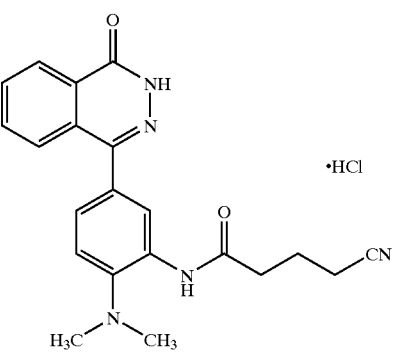

TLC: Rf 0.41 (Chloroform:Methanol=19:1); NMR (DMSO-d$_6$): δ 12.86 (s, 1H), 9.98–9.75 (br, 1H), 8.35–8.30 (m, 1H), 7.92–7.84 (m, 3H), 7.77–7.60 (m, 2H), 7.47 (d, J=7.8 Hz, 1H), 2.95 (s, 6H), 2.62–2.50 (m, 4H), 1.95–1.80 (m, 2H).

EXAMPLE 22(5)

4-(3-(4-Cyanobutyrylamino)phenyl)-2H-phthalazin-1-one

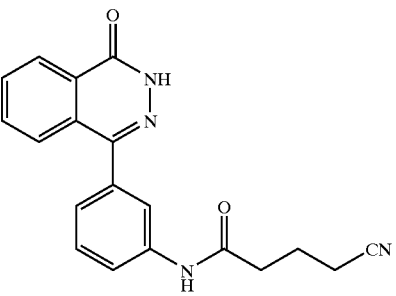

TLC: Rf 0.40 (Chloroform:Methanol=9:1); NMR (DMSO-d$_6$): δ 12.84 (s, 1H), 10.17 (s, 1H), 8.36–8.30 (m, 1H), 7.94–7.85 (m, 3H), 7.76–7.67 (m, 2H), 7.47 (t, J=7.8 Hz, 1H), 7.27–7.23 (m, 1H), 2.56 (t, J=6.9 Hz, 2H), 2.53–2.44 (m, 2H), 1.92–1.82 (m, 2H).

EXAMPLE 22(6)

4-(3-(3-Morpholinopropylsulfonylamino)phenyl)-2H-phthalazin-1-one Hydrochloride

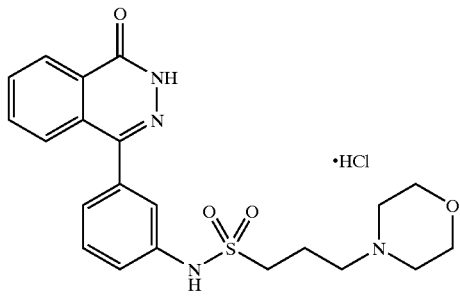

TLC: Rf 0.55 (Chloroform:Methanol:28% Ammonia water=9:1:0.1); NMR (DMSO-$d_6$): δ 12.87 (s, 1H), 10.95 (brs, 1H), 10.19 (s, 1H), 8.36–8.32 (m, 1H), 7.95–7.86 (m, 2H), 7.75–7.70 (m, 1H), 7.51 (t, J=8.1 Hz, 1H), 7.45–7.38 (m, 2H), 7.35–7.31 (m, 1H), 3.96–3.88 (m, 2H), 3.75 (t, J=11.7 Hz, 2H), 3.37–3.27 (m, 4H), 3.22–3.14 (m, 2H), 3.06–2.94 (m, 2H), 2.20–2.10 (m, 2H).

EXAMPLE 22(7)

4-(3-(4-Morpholinobutylsulfonylamino)phenyl)-2H-phthalazin-1-one Hydrochloride

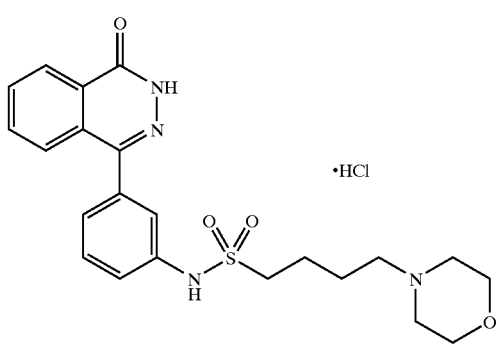

TLC: Rf 0.45 (Chloroform:Methanol:28% Ammonia water=9:1:0.1); NMR (DMSO-$d_6$): δ 12.87 (s, 1H), 10.64 (brs, 1H), 10.10 (s, 1H), 8.35–8.32 (m, 1H), 7.95–7.86 (m, 2H), 7.73–7.67 (m, 1H), 7.51 (t, J=8.1 Hz, 1H), 7.43–7.36 (m, 2H), 7.31 (d, J=7.2 Hz, 1H), 3.95–3.88 (m, 2H), 3.72 (t, J=11.7 Hz, 2H), 3.36–3.27 (m, 2H), 3.21 (t, J=7.2 Hz, 2H), 3.09–2.87 (m, 4H), 1.86–1.66 (m, 4H).

EXAMPLE 22(8)

4-(3-(5-Morpholino-2,2-dimethylvalerylamino)phenyl)-2H-phthalazin-1-one Hydrochloride

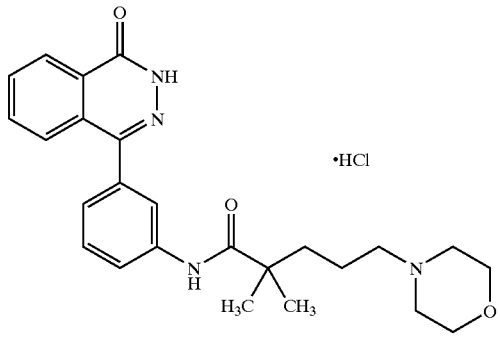

TLC: Rf 0.57 (Chloroform:Methanol:28% Ammonia water=9:1:0.1); NMR (DMSO-$d_6$): δ 12.86 (s, 1H), 10.34 (brs, 1H), 9.45 (s, 1H), 8.37–8.32 (m, 1H), 7.94–7.88 (m, 3H), 7.86–7.80 (m, 1H), 7.76–7.70 (m, 1H), 7.47 (t, J=7.8 Hz, 1H), 7.30–7.23 (m, 1H), 3.98–3.84 (m, 2H), 3.77–3.62 (m, 2H), 3.44–3.26 (m, 2H), 3.10–2.89 (m, 4H), 1.76–1.52 (m, 4H), 1.24 (s, 6H).

EXAMPLE 22(9)

4-(3-(4-Dimethylaminobutylsulfonylamino)phenyl)-2H-phthalazin-1-one Hydrochloride

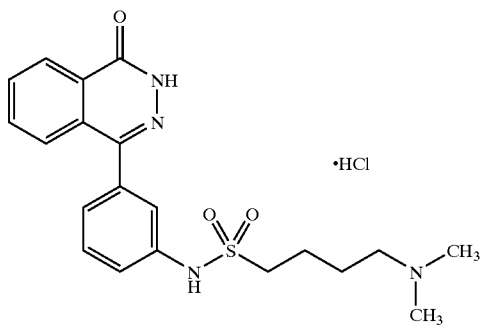

TLC: Rf 0.48 (Chloroform:Methanol:Acetic acid=8:2:1); NMR (DMSO-$d_6$): δ 12.87 (s, 1H), 10.09 (s, 1H), 9.94 (s, 1H), 8.37–8.31 (m, 1H), 7.95–7.86 (m, 2H), 7.73–7.67 (m, 1H), 7.51 (t, J=7.8 Hz, 1H), 7.43–7.29 (m, 3H), 3.23–3.17 (m, 2H), 3.04–2.94 (m, 2H), 2.68 (d, J=4.5 Hz, 6H), 1.75–1.68 (m, 4H).

EXAMPLE 22(10)

4-(3-(4-Morpholinobutylsulfonylamino)-4-methoxyphenyl)-2H-phthalazin-1-one Hydrochloride

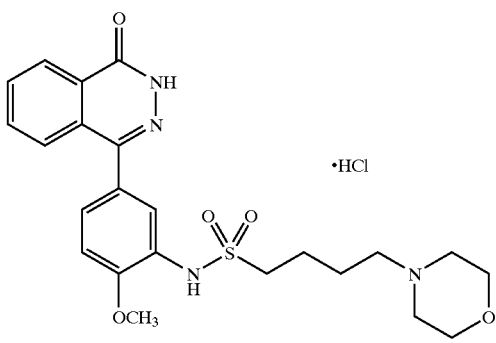

TLC: Rf 0.46 (Chloroform:Methanol=8:1); NMR (DMSO-d$_6$): δ 12.81 (s, 1H), 11.60 (brs, 1H), 9.23 (s, 1H), 8.34–8.31 (m, 1H), 7.91–7.87 (m, 2H), 7.76–7.73 (m, 1H), 7.48–7.42 (m, 2H), 7.25 (d, J=8.4 Hz, 1H), 3.93 (s, 3H), 3.92–3.78 (m, 4H), 3.14–2.92 (m, 8H), 1.88–1.74 (m, 4H).

EXAMPLE 22(11)

4-(3-(4-Morpholinobutylsulfonylamino)-4-fluorophenyl)-2H-phthalazin-1-one Hydrochloride

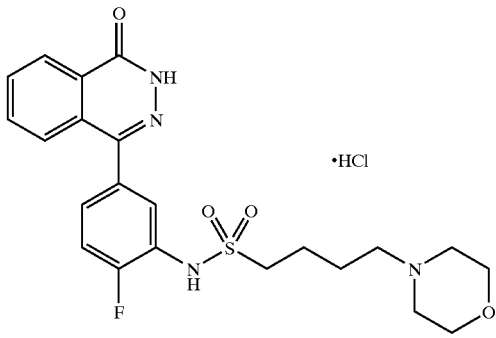

TLC: Rf 0.53 (Chloroform:Methanol=8:2); NMR (DMSO-d$_6$): δ 12.88 (s, 1H), 10.33 (brs, 1H), 9.93 (s, 1H), 8.35–8.32 (m, 1H), 7.92–7.89 (m, 2H), 7.71–7.68 (m, 1H), 7.61 (d, J=7.5 Hz, 1H), 7.49–7.46 (m, 2H), 3.95–3.92 (m, 2H), 3.78–3.66 (m, 4H), 3.23 (brt, 2H), 3.09–2.96 (m, 4H), 1.79 (brs, 4H).

EXAMPLE 22(12)

4-(3-(4-Morpholinobutylsulfonylamino)-4-methylphenyl)-2H-phthalazin-1-one Hydrochloride

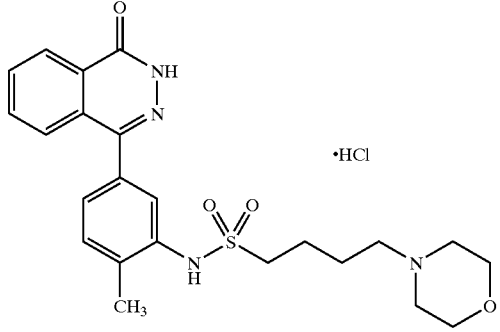

TLC: Rf 0.22 (Chloroform:Methanol=8:1); NMR (DMSO-d$_6$): δ 12.85 (s, 1H), 10.62 (brs, 1H), 9.35 (s, 1H), 8.35–8.31 (m, 1H), 7.93–7.86 (m, 3H), 7.76–7.70 (m, 1H), 7.44–7.32 (m, 2H), 4.00–2.90 (m, 12H), 2.41 (s, 3H), 1.84–1.72 (m, 4H).

EXAMPLE 22(13)

4-(3-(4-(3-Methoxypiperidin-1-yl)butylsulfonylamino)phenyl)-2H-phthalazin-1-one Hydrochloride

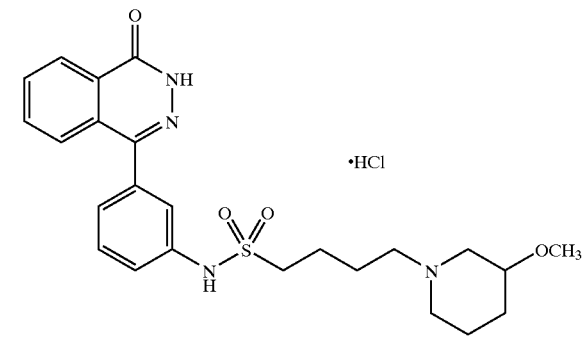

TLC: Rf 0.33 (Chloroform:Methanol=9:1); NMR (DMSO-d$_6$): δ 12.87 (s, 1H), 10.32 (br.s, 0.5H), 10.10 and 10.09 (s, 1H), 9.07 (br.s, 0.5H), 8.37–8.31 (m, 1H), 7.96–7.85 (m, 2H), 7.74–7.67 (m, 1H), 7.51 (t, J=7.8 Hz, 1H), 7.44–7.29 (m, 3H), 3.66–2.42 (m, 12H), 2.14–1.14 (m, 8H).

EXAMPLE 23~EXAMPLE 23(21)

The following compounds of the present invention were obtained by the same procedure as a series of reactions of example 4, if necessary, by converting to corresponding salts by conventional method, using 4-(3-aminophenyl)-2H-phthalazin-1-one or corresponding amine derivative and a corresponding carboxylic acid instead of 5-t-butoxycarbonylaminopentanoic acid.

EXAMPLE 23

4-(3-(5-(N-t-Butoxycarbonyl-N-ethylamino)
valerylamino)phenyl)-2H-phthalazin-1-one

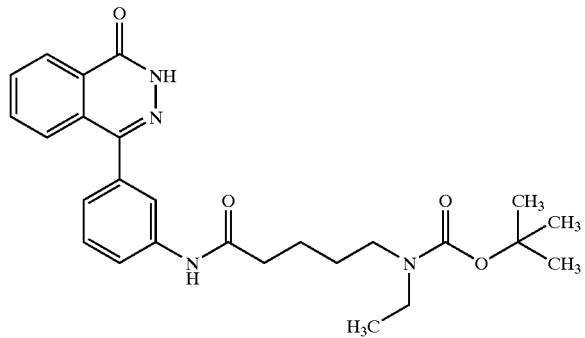

TLC: Rf 0.56 (Chloroform:Methanol=9:1); NMR (DMSO-$d_6$): δ 12.84 (s, 1H), 10.05 (s, 1H), 8.36–8.30 (m, 1H), 7.95–7.84 (m, 3H), 7.74–7.66 (m, 2H), 7.46 (t, J=7.8 Hz, 1H), 7.26–7.21 (m, 1H), 3.18–3.05 (m, 4H), 2.34 (t, J=6.4 Hz, 2H), 1.64–1.44 (m, 4H), 1.35 (s, 9H), 1.00 (t, J=6.8 Hz, 3H).

EXAMPLE 23(1)

4-(3-(5-(N-t-Butoxycarbonyl-N-propylamino)
valerylamino)phenyl)-2H-phthalazin-1-one

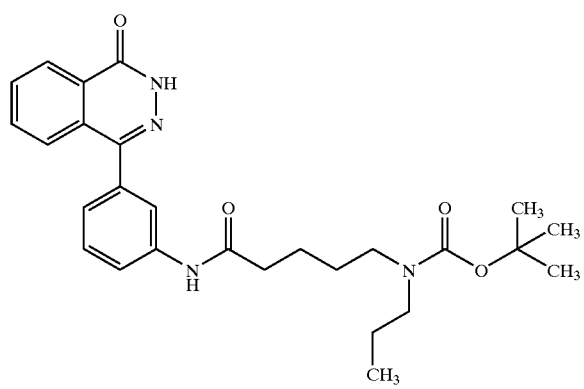

TLC: Rf 0.54 (Chloroform:Methanol=9:1); NMR (DMSO-$d_6$): δ 12.84 (s, 1H), 10.05 (s, 1H), 8.36–8.32 (m, 1H), 7.94–7.84 (m, 3H), 7.76–7.66 (m, 2H), 7.46 (t, J=8.2 Hz, 1H), 7.24 (d, J=7.8 Hz, 1H), 3.15–3.01 (m, 4H), 2.33 (t, J=7.0 Hz, 2H), 1.62–1.45 (m, 6H), 1.35 (s, 9H), 0.78 (t, J=7.2 Hz, 3H).

EXAMPLE 23(2)

4-(3-(5-(N-Isopropyl-N-t-butoxycarbonylamino)
valerylamino)phenyl)-2H-phthalazin-1-one

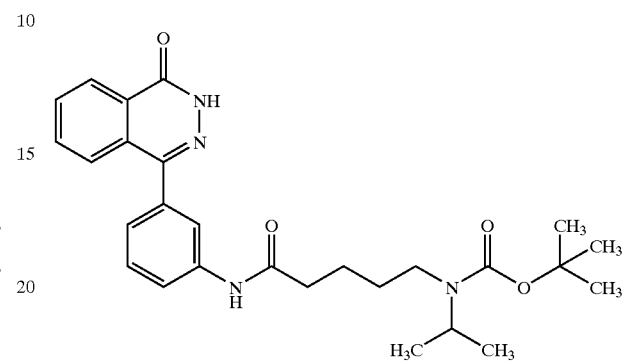

TLC: Rf 0.58 (Chloroform:Methanol=9:1); NMR (DMSO-$d_6$): δ 12.83 (s, 1H), 10.05 (s, 1H), 8.35–8.32 (m, 1H), 7.93–7.85 (m, 3H), 7.76–7.67 (m, 2H), 7.46 (t, J=8.1 Hz, 1H), 7.23 (d, J=7.8 Hz, 1H), 4.07 (brs, 1H), 3.05–2.97 (m, 2H), 2.33 (t, J=9.8 Hz, 2H), 1.61–1.42 (m, 4H), 1.35 (s, 9H), 1.05 (d, J=6.9 Hz, 6H).

EXAMPLE 23(3)

4-(3-(7-t-Butoxycarbonylaminoheptanoylamino)
phenyl)-2H-phthalazin-1-one

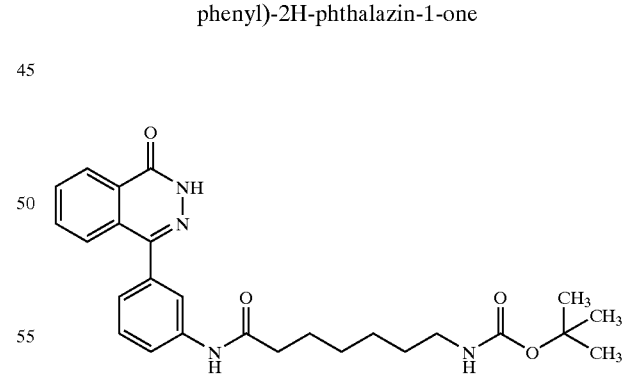

TLC: Rf 0.32 (Ethyl acetate:Hexane=2:1); NMR (CDCl$_3$): δ 10.84–10.72 (br, 1H), 8.54–8.46 (m, 1H), 8.15–8.01 (br, 1H), 7.87–7.76 (m, 5H), 7.46 (t, J=7.8 Hz, 1H), 7.30 (d, J=7.8 Hz, 1H), 4.69–4.54 (br, 1H), 3.15–3.06 (m, 2H), 2.37 (t, J=7.4 Hz, 2H), 1.80–1.66 (m, 2H), 1.541.33 (m, 15H).

EXAMPLE 23(4)

4-(3-(2-(2-t-Butoxycarbonylaminoethyloxy) acetylamino)phenyl)-2H-phthalazin-1-one

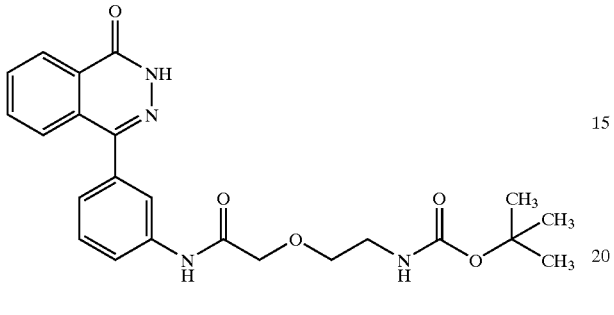

TLC: Rf 0.48 (Chloroform:Methanol=9:1); NMR (DMSO-d$_6$): δ 12.85 (s, 1H), 9.77 (s, 1H), 8.34 (m, 1H), 7.96–7.84 (m, 3H), 7.82 (m, 1H), 7.71 (m, 1H), 7.50 (t, J=7.8 Hz, 1H), 7.30 (d, J=7.8 Hz, 1H), 6.97 (m, 1H), 4.06 (s, 2H), 3.50 (t, J=6.0 Hz, 2H), 3.16 (m, 2H), 1.32 (s, 9H).

EXAMPLE 23(5)

4-(3-(5-(N-Butyl-N-t-butoxycarbonylamino) valerylamino)phenyl)-2H-phthalazin-1-one

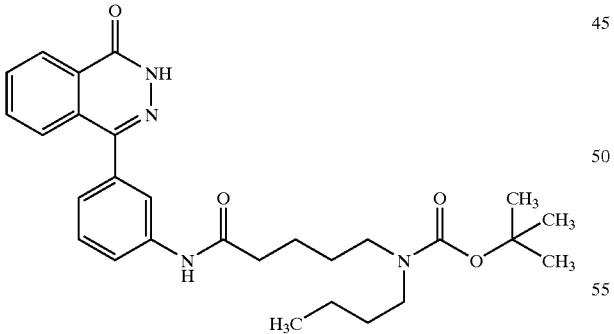

TLC: Rf 0.37 (Chloroform:Methanol:28% Ammonia water=19:1:0.1); NMR (CDCl$_3$): δ 10.73–10.52 (br, 1H), 8.55–8.47 (m, 1H), 8.38–8.24 (br, 1H), 7.82–7.73 (m, 5H), 7.46 (t, J=7.8 Hz, 1H), 7.29 (d, J=7.8 Hz, 1H), 3.25–3.11 (m, 4H), 2.43 (t, J=7.4 Hz, 2H), 1.80–1.18 (m, 17H), 0.90 (t, J=7.2 Hz, 3H).

EXAMPLE 23(6)

4-(3-(5-t-Butoxycarbonylaminovalerylamino)-4-dipropylaminophenyl)-2H-phthalazin-1-one

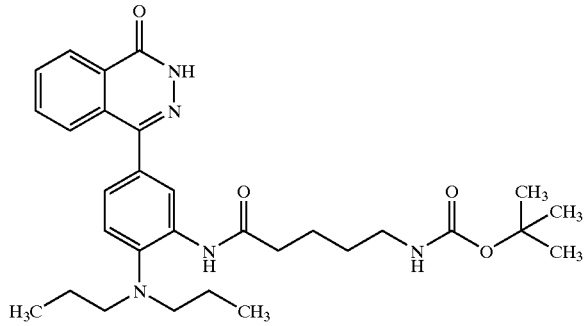

TLC: Rf 0.23 (Hexane:Ethyl acetate=1:1); NMR (CDCl$_3$): δ 10.23 (s, 1H), 8.91 (s, 1H), 8.70 (d, J=1.8 Hz, 1H), 8.53–8.48 (m, 1H), 7.93–7.75 (m, 3H), 7.32 (d, J=8.2 Hz, 1H), 7.29 (dd, J=8.2, 1.8 Hz, 1H), 4.75–4.45 (br, 1H), 3.20–3.11 (m, 2H), 2.89 (t, J=7.4 Hz, 4H), 2.43 (t, J=7.2 Hz, 2H), 1.84–1.36 (m, 17H), 0.91 (t, J=7.4 Hz, 6H).

EXAMPLE 23(7)

4-(3-(6-(N-Methyl-N-t-butoxycarbonylamino) hexanoylamino)phenyl)-2H-phthalazin-1-one

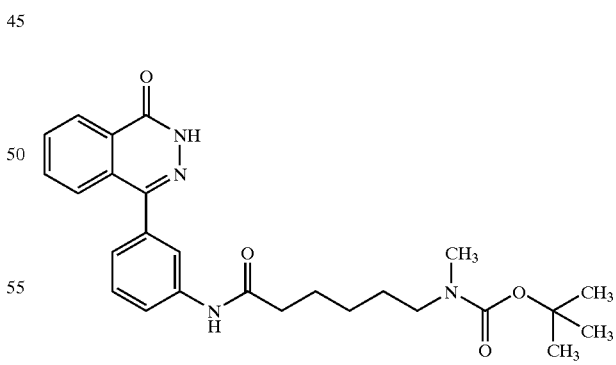

TLC: Rf 0.53 (Chloroform:Methanol=9:1); NMR (DMSO-d$_6$): δ 12.83 (s, 1H), 10.04 (s, 1H), 8.36–8.30 (m, 1H), 7.94–7.85 (m, 3H), 7.74–7.67 (m, 2H), 7.45 (t, J=7.8 Hz, 1H), 7.25–7.21 (m, 1H), 3.13 (t, J=7.2 Hz, 2H), 2.73 (s, 3H), 2.32 (t, J=7.2 Hz, 2H), 1.66–1.20 (m, 6H), 1.34 (s, 9H).

EXAMPLE 23(8)

4-(3-((3E)-5-t-Butoxycarbonylaminopentenoylamino)phenyl)-2H-phthalazin-1-one

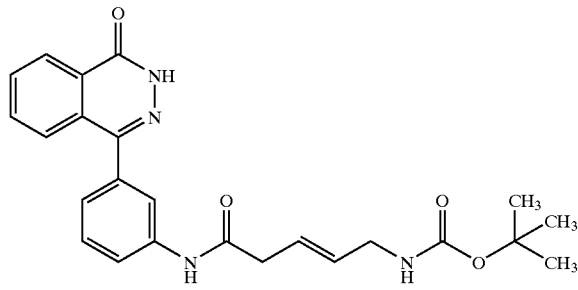

TLC: Rf 0.44 (Chloroform:Methanol=9:1); NMR (DMSO-$d_6$): δ 12.84 (s, 1H), 10.08 (s, 1H), 8.38–8.30 (m, 1H), 7.94–7.82 (m, 3H), 7.76–7.66 (m, 2H), 7.47 (t, J=7.8 Hz, 1H), 7.25 (d, J=7.8 Hz, 1H), 7.00–6.92 (m, 1H), 5.71–5.50 (m, 2H), 3.56–3.46 (m, 2H), 3.07 (d, J=6.2 Hz, 2H), 1.35 (s, 9H).

EXAMPLE 23(9)

4-(3-(5-(N-3-Methyl-2-butenyl-N-tbutoxycarbonylamino)valerylamino)phenyl)-2H-phthalazin-1-one

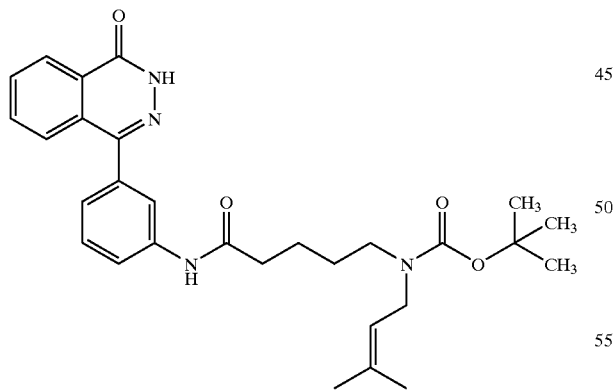

TLC: Rf 0.44 (Chloroform:Methanol=9:1); NMR (DMSO-$d_6$): δ 12.84 (s, 1H), 10.03 (s, 1H), 8.36–8.28 (m, 1H), 7.94–7.84 (m, 3H), 7.76–7.66 (m, 2H), 7.46 (t, J=7.8 Hz, 1H), 7.24 (d, J=7.2 Hz, 1H), 5.14–5.03 (m, 1H), 3.72 (d, J=6.4 Hz, 2H), 3.13–3.02 (m, 2H), 2.37–2.28 (m, 2H), 1.64 (s, 3H), 1.59 (s, 3H), 1.56–1.43 (m, 4H), 1.35 (s, 9H).

EXAMPLE 23(10)

4-(3-(5-(N-2-Butynyl-N-t-butoxycarbonylamino)valerylamino)phenyl)-2H-phthalazin-1-one

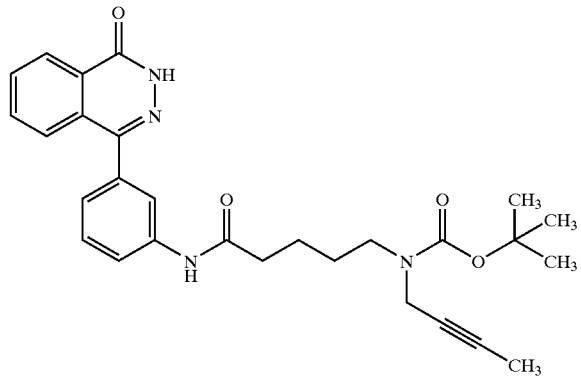

TLC: Rf 0.62 (Chloroform:Methanol=9:1); NMR (DMSO-$d_6$): δ 12.83 (s, 1H), 10.05 (s, 1H), 8.36–8.29 (m, 1H), 7.93–7.84 (m, 3H), 7.74–7.67 (m, 2H), 7.45 (t, J=7.8 Hz, 1H), 7.23 (d, J=7.8 Hz, 1H), 3.93 (brs, 2H), 3.24–3.16 (m, 2H), 2.36–2.30 (m, 2H), 1.74 (t, J=2.4 Hz, 3H), 1.58–1.49 (m, 4H), 1.36 (s, 9H).

EXAMPLE 23(11)

4-(3-(4-Amidinophenylcarbonylamino)phenyl)-2H-phthalazin-1-one Hydrochloride

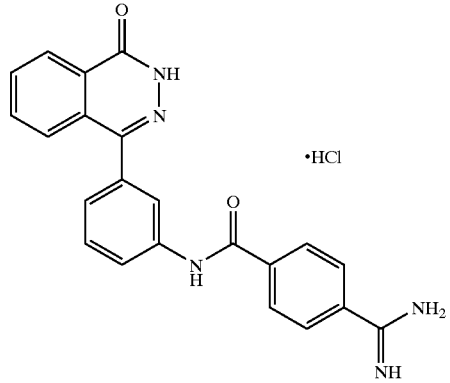

TLC: Rf 0.24 (Chloroform:Methanol:Acetic acid=8:2:1); NMR (DMSO-$d_6$): δ 12.88 (s, 1H), 10.71 (s, 1H), 9.51 (brs, 2H), 9.24 (brs, 2H), 8.37–8.34 (m, 1H), 8.19 (d, J=9.0 Hz, 1H), 8.13–7.87 (m, 7H), 7.79–7.76 (m, 1H), 7.56 (t, J=8.1 Hz, 1H), 7.36 (d, J=7.8 Hz, 1H).

EXAMPLE 23(12)

4-(3-(2-(2-Dimethylaminoethylthio)acetylamino)phenyl)-2H-phthalazin-1-one Hydrochloride

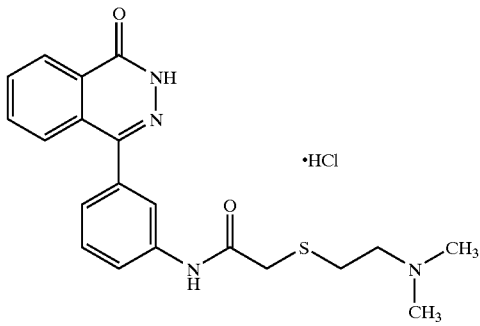

TLC: Rf 0.31 (Chloroform:Methanol:28% Ammonia water=9:1:0.1); NMR (DMSO-d$_6$): δ 12.85 (s, 1H), 10.72 (s, 1H), 10.23–10.00 (br, 1H), 8.35–8.31 (m, 1H), 7.91–7.84 (m, 3H), 7.78–7.68 (m, 2H), 7.48 (t, J=7.8 Hz, 1H), 7.27 (d, J=7.8 Hz, 1H), 3.48 (s, 2H), 3.39–3.29 (m, 2H), 3.02–2.94 (m, 2H), 2.75 (d, J=4.8 Hz, 6H).

EXAMPLE 23(13)

4-(3-(4-Carbamoylbutyrylamino)phenyl)-2H-phthalazin-1-one

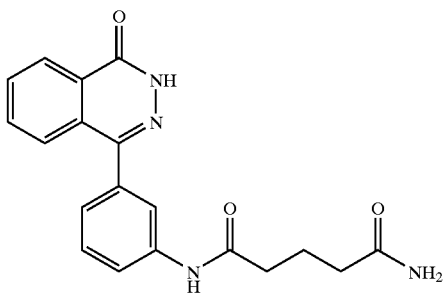

TLC: Rf 0.52 (Chloroform:Methanol=8:2); NMR (DMSO-d$_6$): δ 12.83 (s, 1H), 10.07 (s, 1H), 8.35–8.32 (m, 1H), 7.94–7.86 (m, 3H), 7.75–7.69 (m, 2H), 7.46 (t, J=7.5 Hz, 1H), 7.26–7.22 (m, 2H), 6.73 (s, 1H), 2.33 (t, J=7.8 Hz, 2H), 2.10 (t, J=7.5 Hz, 2H), 1.84–1.74 (m, 2H).

EXAMPLE 23(14)

4-(3-(4-(N-t-Butoxycarbonyl-N-methylamino)butyrylamino)phenyl)-2H-phthalazin-1-one

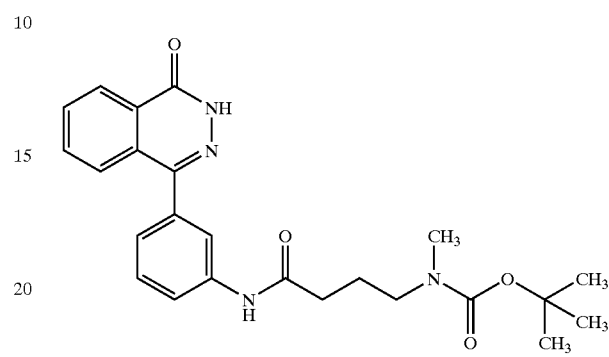

TLC: Rf 0.30 (Chloroform:Methanol=9:1); NMR (DMSO-d$_6$): δ 12.84 (s, 1H), 10.08 (s, 1H), 8.35–8.32 (m, 1H), 7.92–7.84 (m, 3H), 7.74–7.66 (m, 2H), 7.46 (t, J=7.8 Hz, 1H), 7.23 (d, J=7.8 Hz, 1H), 3.20 (t, J=6.6 Hz, 2H), 2.76 (s, 3H), 2.30 (t, J=7.5 Hz, 2H), 1.81–1.72 (m, 2H), 1.35 (s, 9H).

EXAMPLE 23(15)

4-(3-((2E)-5-t-Butoxycarbonylamino-2-pentenoylamino)phenyl)-2H-phthalazin-1-one

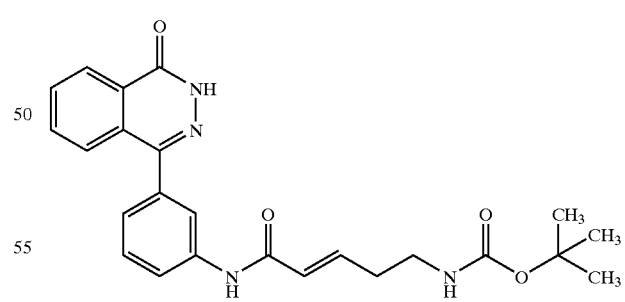

TLC: Rf 0.40 (Chloroform:Methanol=9:1); NMR (DMSO-d$_6$): δ 12.85 (s, 1H), 10.15 (s, 1H), 8.38–8.29 (m, 1H), 7.96–7.82 (m, 3H), 7.80–7.67 (m, 2H), 7.49 (t, J=7.8 Hz, 1H), 7.26 (d, J=7.8 Hz, 1H), 7.00–6.84 (m, 1H), 6.18–6.06 (m, 1H), 3.13–2.99 (m, 2H), 2.40–2.25 (m, 2H), 1.36 (s, 9H).

EXAMPLE 23(16)

4-(3-(3-(t-Butoxycarbonylamino)propionylamino)phenyl)-2H-phthalazin-1-one

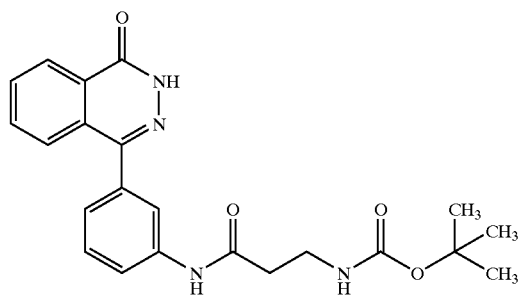

TLC: Rf 0.43 (Chloroform:Methanol=9:1); NMR (DMSO-d$_6$): δ 12.83 (s, 1H), 10.10 (s, 1H), 8.35–8.31 (m, 1H), 7.93–7.84 (m, 3H), 7.74–7.66 (m, 2H), 7.46 (t, J=7.8 Hz, 1H), 7.24 (d, J=7.8 Hz, 1H), 6.86 (t, J=5.1 Hz, 1H), 3.24–3.18 (m, 2H), 2.52–2.44 (m, 2H), 1.36 (s, 6H).

EXAMPLE 23(17)

4-(3-(trans-2-Benzyloxycarbonylaminomethyl-cyclopropylcarbonylamino)phenyl)-2H-phthalazin-1-one

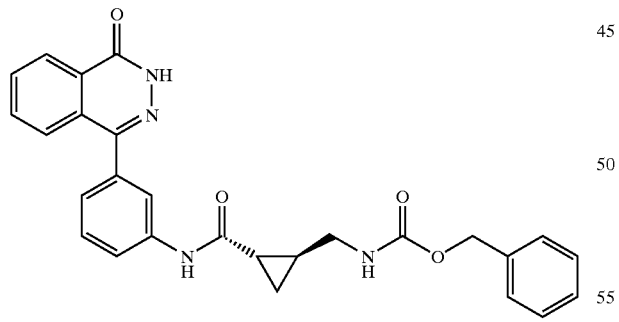

TLC: Rf 0.45 (Chloroform:Methanol=9:1); NMR (DMSO-d$_6$): δ 12.84 (s, 1H), 10.34 (s, 1H), 8.38–8.29 (m, 1H), 7.94–7.84 (m, 3H), 7.77–7.66 (m, 2H), 7.50–7.42 (m, 2H), 7.36–7.20 (m, 6H), 5.04 (s, 2H), 3.08–2.96 (m, 2H), 1.75–1.64 (m, 1H), 1.53–1.36 (m, 1H), 1.00–0.90 (m, 1H), 0.85–0.75 (m, 1H).

EXAMPLE 23(18)

4-(3-(5-(N-Benzyloxycarbonyl-N-tetrahydrofuran-3-ylamino)valerylamino)phenyl)-2H-phthalazin-1-one

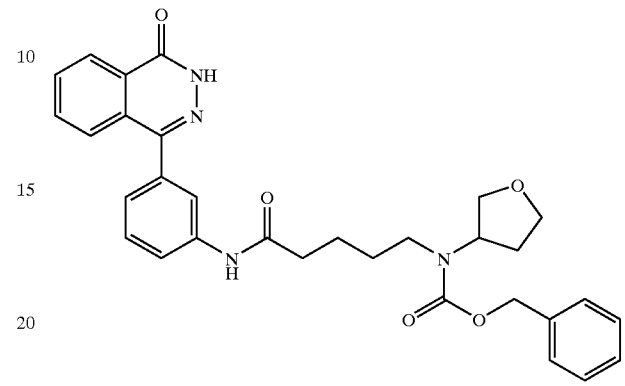

TLC: Rf 0.44 (Chloroform:Methanol=9:1); NMR (DMSO-d$_6$): δ 12.83 (s, 1H), 10.05 (s, 1H), 8.35–8.30 (m, 1H), 7.92–7.85 (m, 3H), 7.74.7.67 (m, 2H), 7.46 (t, J=7.8 Hz, 1H), 7.35–7.22 (m, 6H), 5.04 (s, 2H), 4.50–4.40 (m, 1H), 3.88–3.78 (m, 1H), 3.72–3.67 (m, 1H), 3.62–3.53 (m, 2H), 3.21–3.14 (m, 2H), 2.36–2.27 (m, 2H), 2.15–2.03 (m, 1H), 1.92–1.80 (m, 1H), 1.62–1.48 (m, 4H).

EXAMPLE 23(19)

4-(3-(2-(2-Morpholinoethylthio)acetylamino)phenyl)-2H-phthalazin-1-one Hydrochloride

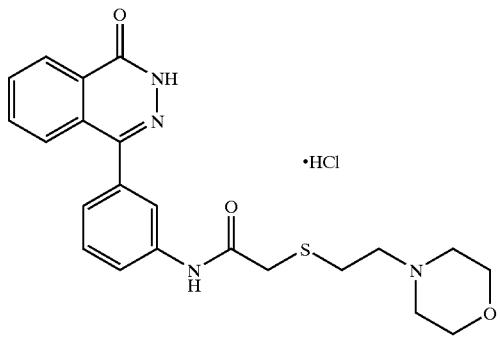

TLC: Rf 0.46 (Chloroform:Methanol=9:1); NMR (DMSO-d$_6$): δ 12.86 (s, 1H), 10.86–10.67 (br, 1H), 10.67 (s, 1H), 8.37.8.30 (m, 1H), 7.95–7.85 (m, 3H), 7.79–7.68 (m, 2H), 7.49 (t, J=7.8 Hz, 1H), 7.28 (d, J=7.8 Hz, 1H), 3.98–3.89 (m, 2H), 3.79–3.30 (m, 8H), 3.15–3.00 (m, 4H).

EXAMPLE 23(20)

4-(3-(2-(2-Morpholinoethyloxy)acetylamino)phenyl)-2H-phthalazin-1-one

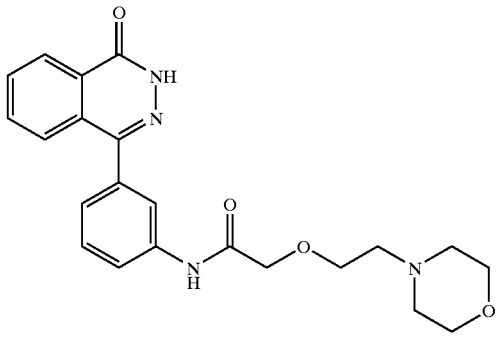

Salt-free:

TLC: Rf 0.16 (Chloroform:Methanol:Acetic acid=8:1:1); NMR (DMSO): δ 12.85 (s, 1H), 9.89 (s, 1H), 8.35–8.32 (m, 1H), 7.91–7.88 (m, 3H), 7.78–7.70 (m, 2H), 7.49 (t, J=7.8 Hz, 1H), 7.30–7.27 (m, 1H), 4.08 (s, 2H), 3.65 (t, J=5.7 Hz, 2H), 3.56–3.50 (m, 4H), 2.55–2.50 (m, overlapped DMSO, 2H), 2.46–2.38 (m, 4H).

Hydrochloride:

TLC: Rf 0.53 (Chloroform:Methanol=8:2); NMR (DMSO-d$_6$, DMSO=2.49 ppm): δ 12.85 (s, 1H), 10.84 (brs, 1H), 10.25 (s, 1H), 8.35–8.32 (m, 1H), 7.99 (s, 1H), 7.91–7.85 (m, 3H), 7.74–7.71 (m, 1H), 7.49 (t, J=7.8 Hz, 1H), 7.29 (d, J=7.8 Hz, 1H), 4.20 (s, 2H), 3.96–3.85 (m, 6H), 3.52–3.39 (m, 4H), 3.11 (m, 2H).

½ Sulfate:

TLC: Rf 0.23 (Chloroform:Methanol:Acetic acid=8:1:1); NMR (DMSO): δ 12.86 (s, 1H), 10.02 (s, 1H), 9.68 (brs, 1H), 8.36–8.32 (m, 1H), 7.92–7.88 (m, 3H), 7.76–7.69 (m, 2H), 7.51 (t, J=9.0 Hz, 1H), 7.31 (d, J=9.0 Hz, 1H), 4.18 (s, 2H), 3.88–3.68 (m, 6H), 3.40–2.90 (m, 6H).

Methanesulfonate:

TLC: Rf 0.38 (Chloroform:Methanol=9:1); NMR (DMSO): δ 12.86 (s, 1H), 10.08 (s, 1H), 9.78 (brs, 1H), 8.37–8.31 (m, 1H), 7.93–787 (m, 3H), 7.77–7.68 (m, 2H), 7.51 (t, J=7.8 Hz, 1H), 7.30 (d, J=7.8 Hz, 11H), 4.21 (s, 2H), 4.02–3.93 (m, 2H), 3.91–3.85 (m, 2H), 3.76–3.65 (m, 2H), 3.58–3.50 (m, 2H), 3.46–3.36 (m, 2H, overlapped with H$_2$O), 3.21–3.06 (m, 2H), 2.32 (s, 3H).

EXAMPLE 23(21)

4-(3-(2-(2-Morpholinoethylthio)-2-methylpropionylamino)phenyl)-2H-phthalazin-1-one Hydrochloride

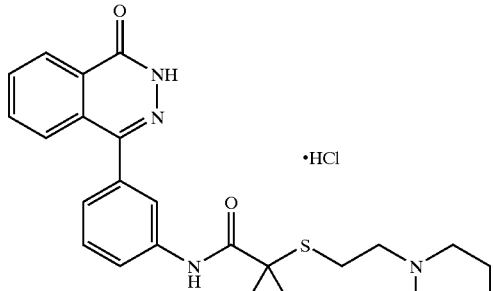

TLC: Rf 0.46 (Chloroform:Methanol=9:1); NMR (DMSO-d$_6$): δ 12.86 (s, 1H), 10.95–10.80 (br, 1H), 9.76 (s, 1H), 8.36–8.31 (m, 1H), 7.96–7.81 (m, 4H), 7.76–7.71 (m, 1H), 7.49 (t, J=7.8 Hz, 1H), 7.30 (d, J=7.8 Hz, 1H), 3.95–3.83 (m, 2H), 3.75–3.62 (m, 2H), 3.47–3.32 (m, 2H), 3.25–3.15 (m, 2H), 3.08–2.92 (m, 4H), 1.60 (s, 6H).

EXAMPLE 24~EXAMPLE 24(1)

The following compounds of the present invention were obtained by the same procedure as a series of reactions of example 7, furthermore, by converting to corresponding salts by conventional method, using the compound prepared in example 23(17) or example 23(18) instead of the compound prepared in example 4(2).

EXAMPLE 24

4-(3-(trans-2-Aminomethylcyclopropylcarbonylamino)phenyl)-2H-phthalazin-1-one Hydrochloride

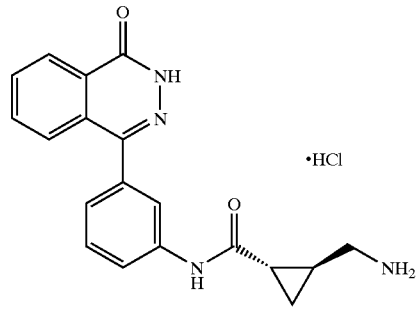

TLC: Rf 0.48 (Ethyl acetate:Acetic acid:Water=3:1:1); NMR (DMSO-d$_6$): δ 12.84 (s, 1H), 10.59 (s, 1H), 8.35–8.30 (m, 1H), 8.05 (brs, 3H), 7.94–7.85 (m, 3H), 7.76–7.68 (m, 2H), 7.47 (t, J=8.1 Hz, 1H), 7.24 (d, J=7.5 Hz, 1H), 2.88–2.74 (m, 2H), 1.95–1.89 (m, 1H), 1.58–1.44 (m, 1H), 1.101.04 (m, 1H), 0.97–0.91 (m, 1H).

EXAMPLE 24(1)

4-(3-(5-(Tetrahydrofuran-3-ylamino)valerylamino)phenyl)-2H-phthalazin-1-one Hydrochloride

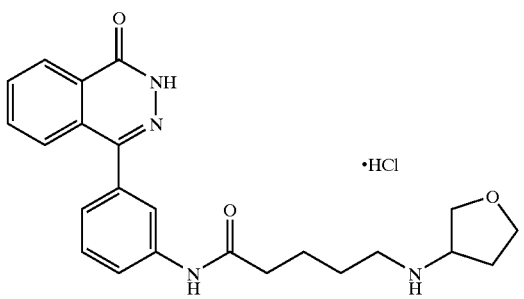

TLC: Rf 0.36 (Chloroform:Methanol:Acetic acid=9:1:1); NMR (DMSO-d$_6$): δ 12.85 (s, 1H), 10.26 (s, 1H), 8.95 (brs, 2H), 8.37–8.31 (m, 1H), 7.94–7.85 (m, 3H), 7.76–7.68 (m, 2H), 7.46 (t, J=7.8 Hz, 1H), 7.24 (d, J=7.5 Hz, 1H), 3.92–3.72 (m, 4H), 3.67–3.59 (m, 1H), 2.97–2.85 (m, 2H), 2.42–2.36 (m, 2H), 2.24–2.12 (m, 1H), 2.04–1.92 (m, 1H), 1.74–1.56 (m, 4H).

EXAMPLE 25

4-(3-(5-(2-Methoxyethylamino)valerylamino)phenyl)-2H-phthalazin-1-one Hydrochloride

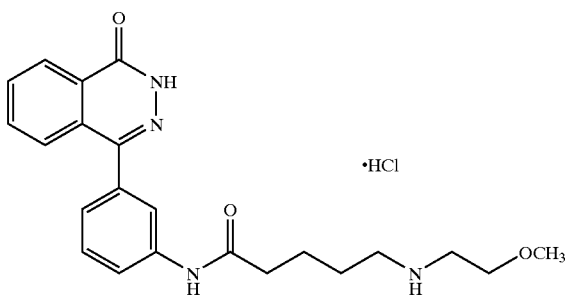

A mixture of the compound prepared in example 20 (100 mg) and 2-methoxyethylamine (0.50 ml) was stirred for 2 hours at 60° C. The reaction mixture was concentrated and the residue was dissolved into methanol. 1N Aqueous solution of sodium hydroxide (0.25 ml) was added to the solution and the mixture was stirred for 1 hour at room temperature. 2N Hydrochloric acid (0.25 ml) was added to the solution and the mixture was stirred for 1 hour at room temperature. The reaction mixture was concentrated and the residue was recrystallized from a mixture (methanol-methylene chloride-ethyl acetate) to give the compound (46.8 mg) of the present invention having the following physical data.

TLC: Rf 0.30 (Chloroform:Methanol:Acetic acid= 8:2:0.5); NMR (DMSO-d$_6$): δ 12.85 (s, 1H), 10.21 (s, 1H), 8.61 (brs, 2H), 8.35–8.32 (m, 1H), 7.91–7.89 (m, 3H), 7.73–7.70 (m, 2H), 7.46 (t, J=7.8 Hz, 1H), 7.24 (d, J=7.8 Hz, 1H), 3.56 (t, J=5.1 Hz, 2H), 3.28 (s, 3H), 3.08 (m, 2H), 2.91 (m, 2H), 2.37 (m, 2H), 1.63 (m, 4H).

EXAMPLE 25(1)~EXAMPLE 25(2)

The following compounds of the present invention were obtained by the same procedure as a series of reactions of example 25, using a corresponding amine derivative instead of 2-methoxyethylamine.

EXAMPLE 25(1)

4-(3-(5-(N-2-Methoxyethyl-N-methylamino)valerylamino)phenyl)-2H-phthalazin-1-one Hydrochloride

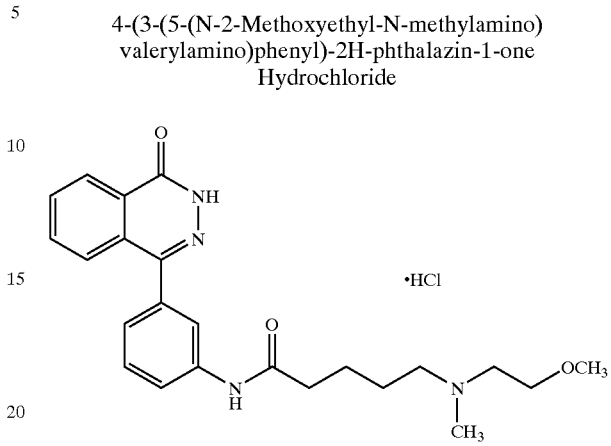

TLC: Rf 0.23 (Chloroform:Methanol=4:1); NMR (DMSO-d): δ 12.86 (s, 1H), 10.27 (s, 1H), 9.88 (brs, 1H), 8.36–8.32 (m, 1H), 7.90 (m, 3H), 7.73 (m, 2H), 7.47 (t, J=7.2 Hz, 1H), 7.24 (d, J=7.2 Hz, 1H), 3.66 (t, J=5.0 Hz, 2H), 3.28 (s, 3H), 3.27–3.00 (m, 4H), 2.73 (d, J=4.4 Hz, 3H), 2.40 (m, 2H), 1.64 (m, 4H).

EXAMPLE 25(2)

4-(3-(5-(N-2-Hydroxyethyl-N-methylamino)valerylamino)phenyl)-2H-phthalazin-1-one Hydrochloride

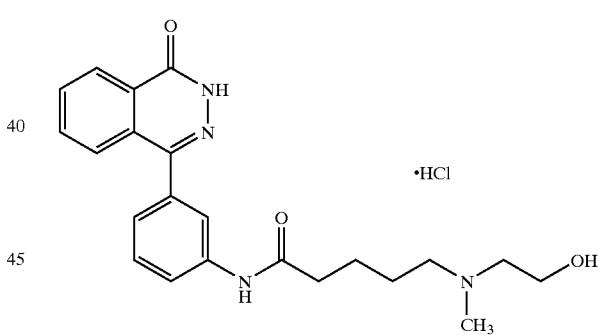

TLC: Rf 0.10 (Chloroform:Methanol:Acetic acid= 8:2:0.5); NMR (DMSO-d$_6$): δ 12.84 (s, 1H), 10.22 (s, 1H), 9.54 (brs, 1H), 8.35–8.32 (m, 1H), 7.91–7.89 (m, 3H), 7.73–7.71 (m, 2H), 7.46 (t, J=7.8 Hz, 1H), 7.24 (d, J=7.8 Hz, 1H), 3.72 (t, J=5.0 Hz, 2H), 3.18–3.05 (m, 4H), 2.74 (d, J=4.5 Hz, 3H), 2.42–2.37 (m, 2H), 1.67–1.61 (m, 4H).

REFERENCE EXAMPLE 5

5-Bromovaleryl Chloride

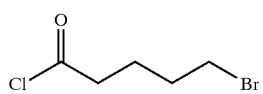

To a solution of 5-bromovaleric acid (1.81 g) in methylene chloride (20 ml) was added dimethylformamide (2 drops). To the mixture was added oxalyl chloride (0.9 ml) under cooling with ice. The mixture was stirred for 1 hour at room temperature. The reaction mixture was concentrated to give the title compound (2.37 g) having the following physical data.

NMR (CDCl$_3$): δ 3.41 (t, J=6.0 Hz, 2H), 2.95 (t, J=6.8 Hz, 2H), 2.01–1.79 (m, 4H).

REFERENCE EXAMPLE 6

Benzyl 5-bromovalerate

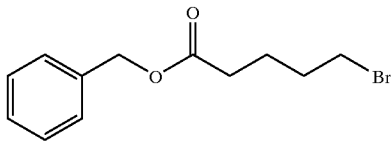

To a solution of benzyl alcohol (0.93 ml) in methylene chloride (20 ml) was added triethylamine (1.4 ml) and the compound prepared in reference example 5 (2.26 g) under cooling with ice, successively, and the mixture was stirred overnight at room temperature. To the reaction mixture was added 1N hydrochloric acid and the mixture was extracted with methylene chloride. The organic layer was washed with a saturated aqueous solution of sodium bicarbonate and a saturated aqueous solution of sodium chloride, successively, dried over anhydrous magnesium sulfate and concentrated to give the title compound (2.55 g) having the following physical data.

TLC: Rf 0.26 (Hexane:Ethyl acetate=9:1); NMR (CDCl$_3$): δ 7.39–7.31 (m, 5H), 5.12 (s, 2H), 3.40 (t, J=6.4 Hz, 2H), 2.40 (t, J=7.0 Hz, 2H), 1.98–1.72 (m, 4H).

REFERENCE EXAMPLE 7

Benzyl 5-(1,3-Dioxoisoindolin-2-yl)valerate

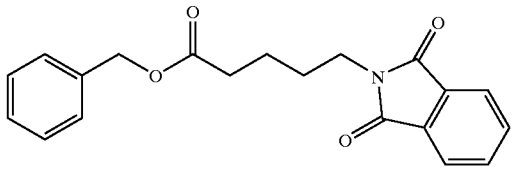

To a solution of the compound prepared in reference example 6 (2.54 g) in dimethylformamide (20 ml) was added potassium phthalimide (1.79 g) and the mixture was stirred for 2 hours at 80° C. The reaction mixture was cooled to room temperature, poured into ice and extracted with ethyl acetate. The organic layer was washed with a saturated aqueous solution of sodium chloride, dried over anhydrous magnesium sulfate and concentrated. The residue was purified by column chromatography on silica gel (hexane:ethyl acetate=3:1) to give the title compound (442 mg) having the following physical data.

TLC: Rf 0.32 (Hexane:Ethyl acetate=3:1); NMR (CDCl$_3$): δ 7.90–7.78 (m, 2H), 7.70–7.66 (m, 2H), 7.37–7.29 (m, 5H), 5.11 (s, 2H), 3.73–3.67 (m, 2H), 2.45–2.37 (m, 2H), 1.75–1.68 (m, 4H).

REFERENCE EXAMPLE 8

5-(1,3-Dioxoisoindolin-2-yl)valeric Acid

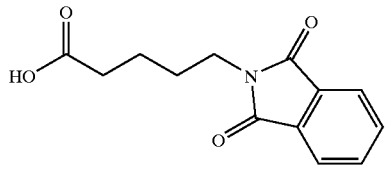

To a solution of the compound prepared in reference example 7 (2.89 g) in ethanol (80 ml) was added 5% palladium carbon (853 mg) under an atmosphere of argon and then the mixture was stirred overnight under an atmosphere of hydrogen. The reaction mixture was filtered and the filtrate was concentrated to give the compound (1.88 g) of the present invention having the following physical data.

TLC: Rf 0.56 (Chloroform:Methanol=9:1); NMR (CDCl$_3$): δ 7.90–7.79 (m, 2H), 7.77–7.67 (m, 2H), 3.72 (t, J=6.6 Hz, 2H), 2.41 (t, J=7.0 Hz, 2H), 1.84–1.60 (m, 4H).

REFERENCE EXAMPLE 9

5-(1,3-Dioxoisoindolin-2-yl)valeryl Chloride

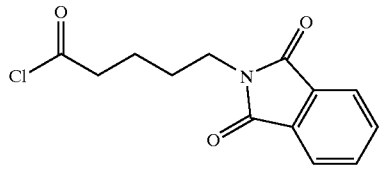

To a solution of the compound prepared in reference example 8 (397 mg) in methylene chloride (1.6 ml) was added dimethylformamide (1 drop). To the mixture was added oxalyl chloride (0.9 ml) under cooling with ice. The mixture was stirred for 30 minutes at room temperature. The reaction mixture was concentrated to give the title compound (2.37 g).

NMR (CDCl$_3$): δ 7.90–7.81 (m, 2H), 7.79–7.68 (m, 2H), 3.75–3.68 (m, 2H), 3.00–2.93 (m, 2H), 1.81–1.67 (m, 4H).

EXAMPLE 26

4-(3-(5-(1,3-Dioxoisoindolin-2-yl)valerylamino)-4-chlorophenyl)-2H-phthalazin-1-one

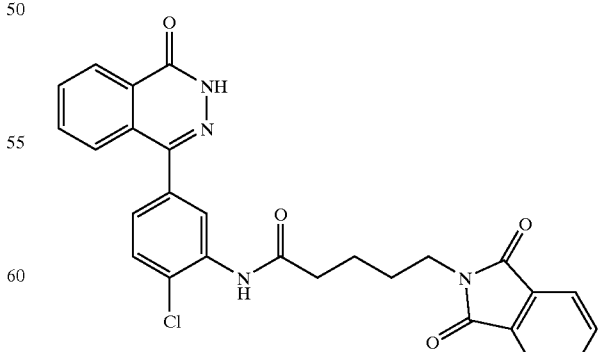

To a mixture of 4-(3-amino-4-chlorophenyl)-2H-phthalazin-1-one (386 mg) and dimethylaminopyridine (17 mg) in pyridine (6 ml) was added a solution of the compound prepared in reference example 9 (414 mg) in methylene chloride (2 ml) under cooling with ice. The reaction mixture was stirred overnight at room temperature. The precipitate was collected by filtration and washed with tetrahydrofuran. The solid was recrystallized from tetrahydrofuran to give the compound (471 mg) of the present invention having the following physical data.

TLC: Rf 0.23 (Ethyl acetate:Hexane=1:1); NMR (DMSO-$d_6$): δ 12.87 (s, 1H), 9.62 (s, 1H), 8.34–8.30 (m, 1H), 7.91–7.79 (m, 7H), 7.73–7.60 (m, 2H), 7.37 (dd, J=8.2, 2.0 Hz, 1H), 3.58 (t, J=6.4 Hz, 2H), 2.42 (t, J=6.0 Hz, 2H), 1.63–1.59 (m, 4H).

EXAMPLE 27

4-(3-(5-t-Butoxycarbonylaminovalerylamino)-4-chlorophenyl)-2H-phthalazin-1-one

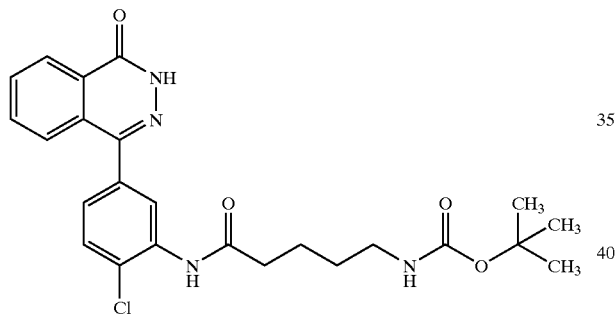

To a solution of the compound prepared in example 26 (219 mg) in ethanol (9 ml) was added hydrazine monohydrate (0.22 ml) and the mixture was refluxed for 2 hours. The reaction mixture was cooled to room temperature, concentrated. To a suspension of the residue in methanol (2 ml) was added di-t-butoxycarbonyl dicarbonate (0.6 ml) and the mixture was stirred overnight. The reaction mixture was concentrated and the residue was purified by column chromatography on silica gel (hexane:ethyl acetate=1:1→2:1) to give the compound (163 mg) of the present invention having the following physical data.

TLC: Rf 0.26 (Ethyl acetate:Hexane=2:1); NMR (CDCl): δ 10.52 (s, 1H), 8.63 (d, J=2.2 Hz, 1H), 8.54–8.49 (m, 1H), 7.85–7.79 (m, 4H), 7.53 (d, J=8.2 Hz, 1H), 7.32–7.27 (m, 1H), 4.70–4.58 (br, 1H), 3.22–3.13 (m, 2H), 2.50 (t, J=7.4 Hz, 2H), 1.86–1.72 (m, 2H), 1.66–1.52 (m, 2H), 1.43 (s, 9H).

EXAMPLE 27(1)

4-(3-(N-(5-t-Butoxycarbonylaminovaleryl)-N-methylamino)phenyl)-2H-phthalazin-1-one

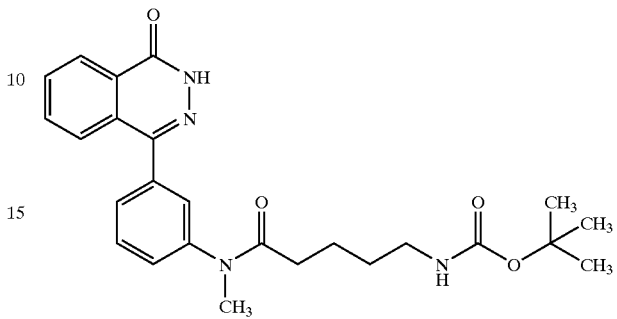

The compound having the following physical data was obtained by the same procedure as a series of reactions of example 26 example 27, using 4-(3-methylaminophenyl)-2H-phthalazin-1-one instead of 4-(3-amino-4-chlorophenyl)-2H-phthalazin-1-one.

TLC: Rf 0.57 (Chloroform:Methanol=9:1); NMR (DMSO-$d_6$): δ 12.87 (s, 1H), 8.36–8.29 (m, 1H), 7.94–7.84 (m, 2H), 7.70–7.44 (m, 5H), 6.76–6.66 (m, 1H), 3.22 (s, 3H), 2.85–2.77 (m, 2H), 2.21–1.99 (m, 2H), 1.50–1.20 (m, 13H).

REFERENCE EXAMPLE 10

1,3-bis(t-Butoxycarbonyl)guanidine

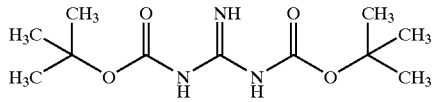

To a solution of guanidine hydrochloride (2.44 g) in dioxane (50 ml) as added 5N aqueous solution of sodium hydroxide and di-t-butoxycarbonyl dicarbonate (13 ml) and the mixture was stirred at room temperature. The reaction mixture was concentrated. The residue was neutralized by adding 1N hydrochloric acid and diluted with ethyl acetate. The organic layer was washed with a saturated aqueous solution of sodium bicarbonate, water and a saturated aqueous solution of sodium chloride, successively, dried over anhydrous magnesium sulfate. The mixture was concentrated and the residue was purified by column chromatography on silica gel to give the compound (3.87 g) having the following physical data.

TLC: Rf 0.32 (Chloroform Methanol=97:3); NMR (DMSO-$d_6$): δ 10.15 (brs, 1H), 8.53 (brs, 2H), 1.40 (s, 18H).

REFERENCE EXAMPLE 11

2-Trifluoroacetyl-1,3-bis(t-butoxycarbonyl)guanidine

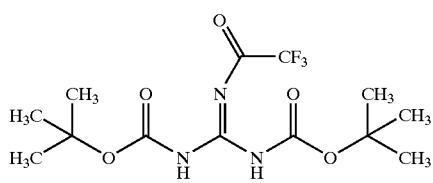

To a solution of the compound prepared in reference example 10 (1.10 g) in methylene chloride (40 ml) was added triethylamine (0.65 ml) and trifluoroacetic anhydride (0.75 ml) at −78° C. and the mixture was stirred at room temperature. The reaction mixture was diluted with methylene chloride, washed with 1N hydrochloric acid, a saturated aqueous solution of sodium bicarbonate, water and a saturated aqueous solution of sodium chloride, successively, dried over anhydrous magnesium sulfate. The mixture was concentrated and the residue was purified by column chromatography on silica gel to give the compound (1.38 g) having the following physical data.

TLC: Rf 0.81 (Chloroform:Methanol=97:3); NMR (DMSO-$d_6$): δ 11.05 (brs, 2H), 1.45 (s, 18H).

EXAMPLE 28

4-(3-(5-(2,3-Bis(t-butoxycarbonyl)guanidino)valerylamino)phenyl)-2H-phthalazin-1-one

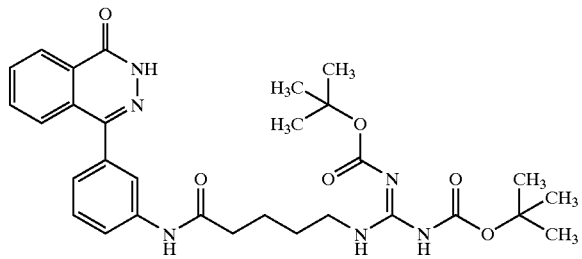

To a solution of the compound prepared in example 5 (122 mg) in dimethylformamide (4 ml) was added triethylamine (0.10 ml) and the compound prepared in reference example 11 (128 mg) and the mixture was stirred at room temperature. The reaction mixture was concentrated and then the residue was diluted with ethyl acetate. The minute was washed with 1N hydrochloric acid, a saturated aqueous solution of sodium bicarbonate, water and a saturated aqueous solution of sodium chloride, successively, dried over anhydrous magnesium sulfate. The mixture was concentrated and the residue was purified by column chromatography on silica gel to give the compound (141 mg) of the present invention having the following physical data. NMR (DMSO-$d_6$): δ 12.84 (s, 1H), 11.48 (s, 1H), 10.07 (s, 1H), 8.36–8.24 (m, 2H), 7.93–7.84 (m, 3H), 7.75–7.67 (m, 2H), 7.46 (t, J=7.8 Hz, 1H), 7.24 (d, J=7.8 Hz, 1H), 3.36–3.24 (m, 2H), 2.35 (t, J=5.2 Hz, 2H), 1.62–1.51 (m, 4H), 1.45 (s, 9H), 1.36 (s, 9H).

EXAMPLE 29~EXAMPLE 29(15)

The compounds of the present invention were obtained by the same procedure as a series of reactions of example 5, if necessary, converting to a corresponding salts by conventional method, using the compounds prepared in example 23, example 23(1)~example 23(10), example 23 (14) ~example 23(15), example 27~example 27(1) or example 28 instead of the compound prepared in example 4.

EXAMPLE 29

4-(3-(5-Ethylaminovalerylamino)phenyl)-2H-phthalazin-1-one

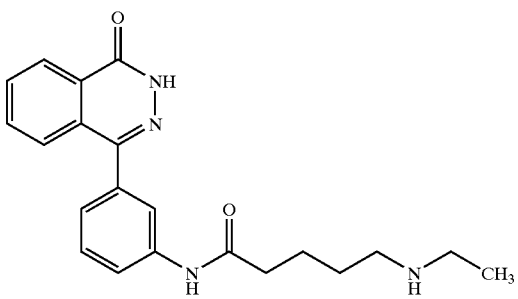

Hydrochloride:

TLC: Rf 0.34 (Chloroform:Methanol:Acetic acid=8:2:1); NMR (DMSO-$d_6$): δ 12.85 (s, 1H), 10.26 (s, 1H), 8.63 (brs, 2H), 8.36–8.31 (m, 1H), 7.94–7.85 (m, 3H), 7.74–7.69 (m, 2H), 7.46 (t, J=7.8 Hz, 1H), 7.24 (d, J=7.2 Hz, 1H), 2.96–2.82 (m, 4H), 2.41–2.36 (m, 2H), 1.68–1.59 (m, 4H), 1.17 (t, J=7.8 Hz, 3H).

Methanesulfonate:

TLC: Rf 0.56 (Chloroform:Methanol:Acetic acid= 8:2:0.5); NMR (DMSO-$d_6$): δ 12.85 (s, 1H), 10. 11 (s, 1H), 8.36–8.32 (m, 1H), 8.15 (brs, 2H), 7.91–7.88 (m, 3H), 7.73–7.69 (m, 2H), 7.47 (t, J=7.8 Hz, 1H), 7.25 (d, J=7.8 Hz, 1H), 2.96–2.89 (m, 4H), 2.38 (t, J=6.4 Hz, 2H), 2.28 (s, 3H), 1.63–1.61 (m, 4H), 1.15 (t, J=7.4 Hz, 3H).

EXAMPLE 29(1)

4-(3-(5-Propylaminovalerylamino)phenyl)-2H-phthalazin-1-one Hydrochloride

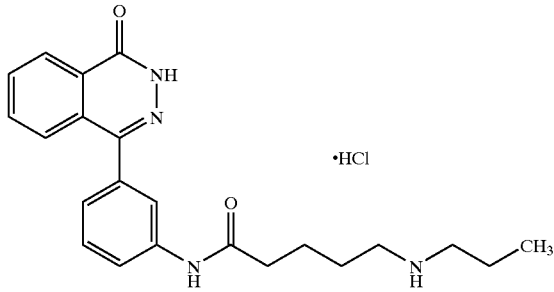

TLC: Rf 0.51 (Chloroform:Methanol:Acetic acid=8:2:1); NMR (DMSO-$d_6$): δ 12.85 (s, 1H), 10.25 (s, 1H), 8.61 (brs, 2H), 8.36–8.31 (m, 1H), 7.94–7.85 (m, 3H), 7.74–7.70 (m, 2H), 7.46 (t, J=7.8 Hz, 1H), 7.24 (d, J=7.5 Hz, 1H), 2.94–2.76 (m, 4H), 2.42–2.34 (m, 2H), 1.68–1.53 (m, 6H), 0.88 (t, J=7.2 Hz, 3H).

EXAMPLE 29(2)

4-(3-(5-Isopropylaminovalerylamino)phenyl)-2H-phthalazin-1-one Hydrochloride

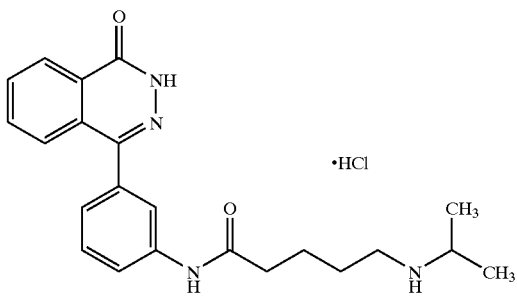

TLC: Rf 0.44 (Methanol:Chloroform:Acetic acid=2:8:1); NMR (DMSO-$d_6$): δ 12.85 (s, 1H), 10.24 (s, 1H), 8.54 (brs, 2H), 8.35–8.32 (m, 1H), 7.94–7.85 (m, 3H), 7.74–7.69 (m, 2H), 7.46 (t, J=7.8 Hz, 1H), 7.24 (d, J=7.5 Hz, 1H), 3.30–3.16 (m, 1H), 2.94–2.83 (m, 2H), 2.39 (t, J=6.3 Hz, 2H), 1.68–1.62 (m, 4H), 1.21 (d, J=6.6 Hz, 6H).

EXAMPLE 29(3)

4-(3-(7-Aminoheptanoylamino)phenyl)-2H-phthalazin-1-one Hydrochloride

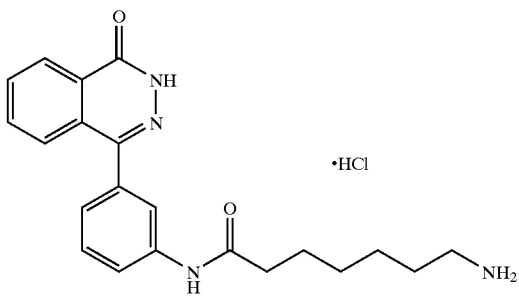

TLC: Rf 0.22 (Chloroform:Methanol:28% Ammonia water=4:1:0.1); NMR (DMSO-$d_6$): δ 12.84 (s, 1H), 10.21 (s, 1H), 8.35–8.30 (m, 1H), 7.94–7.68 (m, 8H), 7.44 (t, J=7.8 Hz, 1H), 7.22 (d, J=7.8 Hz, 1H), 2.81–2.65 (m, 2H), 2.33 (t, J=7.2 Hz, 2H), 1.61–1.46 (m, 4H), 1.40–1.21 (br, 4H).

EXAMPLE 29(4)

4-(3-(2-(2-Aminoethyloxy)acetylamino)phenyl)-2H-phthalazin-1-one Hydrochloride

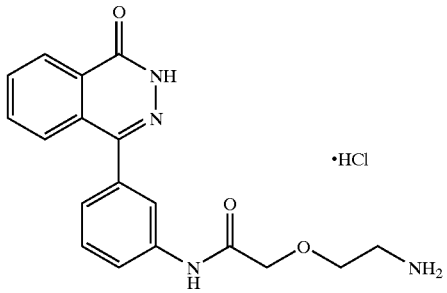

TLC: Rf 0.30 (Chloroform:Methanol:28% Ammonia water=4:1:0.1); NMR (DMSO-$d_6$): δ 12.86 (s, 1H), 10.03 (s, 1H), 8.34 (m, 1H), 8.08 (brs, 3H), 7.96–7.82 (m, 4H), 7.72 (m, 1H), 7.50 (t, J=7.8 Hz, 1H), 7.31 (d, J=7.8 Hz, 1H), 4.16 (s, 2H), 3.72 (t, J=5.0 Hz, 2H), 3.05 (m, 2H).

EXAMPLE 29(5)

4-(3-(5-Butylaminovalerylamino)phenyl)-2H-phthalazin-1-one Hydrochloride

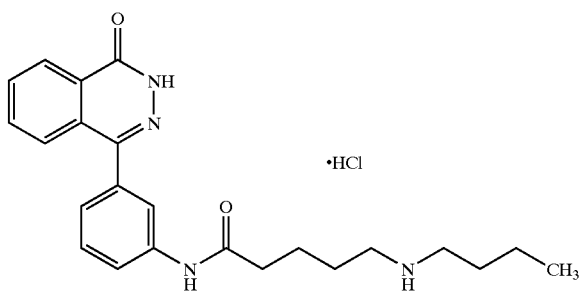

TLC: Rf 0.33 (Chloroform:Methanol:28% Ammonia water=4:1:0.1); NMR (DMSO-$d_6$): δ 12.84 (s, 1H), 10.30 (s, 1H), 8.84–8.62 (br, 2H), 8.35–8.30 (m, 1H), 7.94–7.83 (m, 3H), 7.75–7.68 (m, 2H), 7.45 (t, J=7.8 Hz, 1H), 7.23 (d, J=7.8 Hz, 1H), 2.96–2.73 (br, 4H), 2.43–2.31 (br, 2H), 1.64–1.48 (m, 6H), 1.38–1.20 (m, 2H), 0.85 (t, J=7.2 Hz, 3H).

EXAMPLE 29(6)

4-(3-(5-Aminovalerylamino)-4-dipropylaminophenyl)-2H-phthalazin-1-one Dihydrochloride

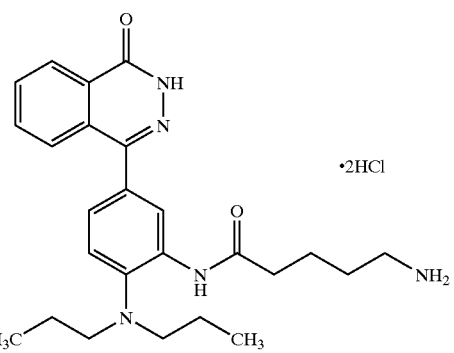

TLC: Rf 0.35 (Chloroform:Methanol:28% Ammonia water=4:1:0.1); NMR (CD$_3$OD): δ 8.48–8.42 (m, 1H), 7.98–7.78 (m, 6H), 3.69–3.61 (m, 4H), 3.02–2.95 (m, 2H), 2.70 (t, J=7.0 Hz, 2H), 1.90–1.36 (m, 8H), 0.97 (t, J=7.4 Hz, 6H).

EXAMPLE 29(7)

4-(3-(6-Methylaminohexanoylamino)phenyl)-2H-phthalazin-1-one Hydrochloride

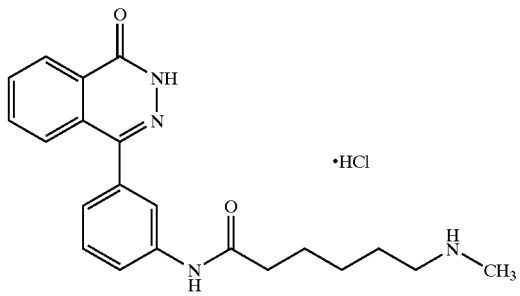

TLC: Rf 0.44 (Chloroform:Methanol:Acetic acid=8:2:0.5); NMR (DMSO-$d_6$): δ 12.84 (s, 1H), 10.20 (s, 1H), 8.76–8.60 (br, 2H), 8.36–8.30 (m, 1H), 7.94–7.85 (m, 3H), 7.75–7.69 (m, 2H), 7.46 (t, J=7.8 Hz, 1H), 7.23 (d, J=7.8 Hz, 1H), 2.89–2.78 (m, 2H), 2.51–2.48 (m, 3H), 2.35 (t, J=7.8 Hz, 2H), 1.67–1.53 (m, 4H), 1.40–1.28 (m, 2H).

EXAMPLE 29(8)

4-(3-((3E)-5-Amino-3-pentenoylamino)phenyl)-2H-phthalazin-1-one Hydrochloride

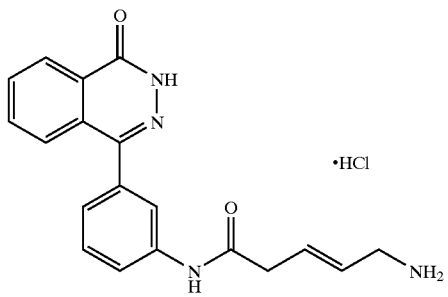

TLC: Rf 0.53 (Ethyl acetate:Acetic acid:Water=3:1:1); NMR (DMSO-$d_6$): δ 12.86 (s, 1H), 10.35 (s, 1H), 8.36–8.32 (m, 1H), 8.02 (brs, 3H), 7.94–7.84 (m, 3H), 7.77–7.67 (m, 2H), 7.48 (t, J=7.8 Hz, 1H), 7.26 (d, J=8.0 Hz, 1H), 6.06–5.90 (m, 1H), 5.74–5.60 (m, 1H), 3.52–3.36 (m, 2H), 3.19 (d, J=6.8 Hz, 2H).

EXAMPLE 29(9)

4-(3-(5-(3-Methyl-2-butenylamino)valerylamino)phenyl)-2H-phthalazin-1-one Hydrochloride

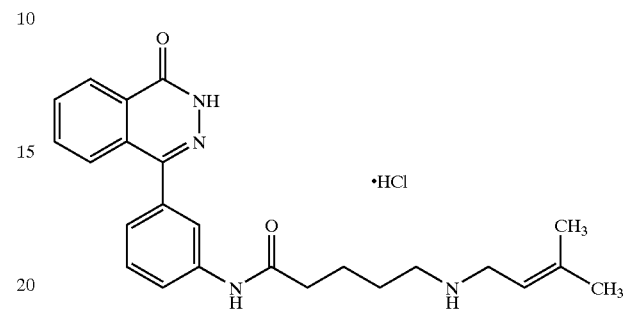

TLC: Rf 0.29 (Chloroform:Methanol:Acetic acid=9:1:1); NMR (DMSO-$d_6$): δ 12.85 (s, 1H), 10.25 (s, 1H), 8.68 (brs, 2H), 8.36–8.31 (m, 1H), 7.94–7.85 (m, 3H), 7.75–7.69 (m, 2H), 7.46 (t, J=7.8 Hz, 1H), 7.24 (d, J=7.5 Hz, 1H), 5.23 (t, J=7.5 Hz, 1H), 3.53–3.46 (m, 2H), 2.92–2.76 (m, 2H), 2.40–2.34 (m, 2H), 1.72 (s, 3H), 1.67–1.60 (m, 7H).

EXAMPLE 29(10)

4-(3-(5-(2-Butynylamino)valerylamino)phenyl)-2H-phthalazin-1-one Hydrochloride

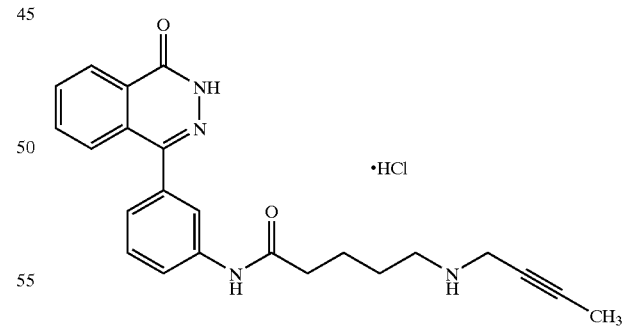

TLC: Rf 0.58 (Chloroform:Methanol:Acetic acid=8:2:1); NMR (DMSO-$d_6$): δ 12.85 (s, 1H), 10.22 (s, 1H), 9.08 (brs, 2H), 8.36–8.30 (m, 1H), 7.94–7.85 (m, 3H), 7.76–7.69 (m, 2H), 7.46 (t, J=7.8 Hz, 1H), 7.24 (d, J=7.8 Hz, 1H), 3.81 (brs, 2H), 2.90–2.86 (m, 2H), 2.41–2.32 (m, 2H), 1.85 (t, J=2.4 Hz, 3H), 1.88–1.77 (m, 4H).

EXAMPLE 29(11)

4-(3-(4-Methylaminobutyrylamino)phenyl)-2H-phthalazin-1-one Hydrochloride

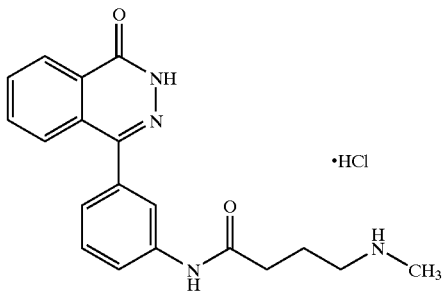

TLC: Rf 0.30 (Chloroform:Methanol:Acetic acid=8:2:1); NMR (DMSO-$d_6$): δ 12.85 (s, 1H), 10.32 (s, 1H), 8.73 (brs, 2H), 8.37–8.30 (m, 1H), 7.94–7.85 (m, 3H), 7.74–7.68 (m, 2H), 7.47 (t, J=7.81 Hz, 1H), 7.26–7.20 (m, 1H), 3.00–2.87 (m, 2H), 2.55–2.41 (m, 5H), 1.95–1.85 (m, 2H).

EXAMPLE 29(12)

4-(3-((2E)-5-Amino-2-pentenoylamino)phenyl)-2H-phthalazin-1-one Hydrochloride

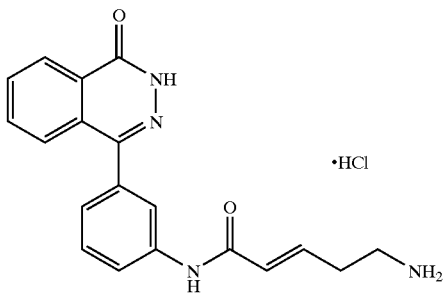

TLC: Rf 0.21 (Chloroform:Methanol:Acetic acid=8:2:1); NMR (DMSO-$d_6$): δ 12.85 (s, 1H), 10.38 (s, 1H), 8.35–8.31 (m, 1H), 7.95–7.69 (m, 8H), 7.49 (t, J=7.8 Hz, 1H), 7.27 (d, J=7.8 Hz, 1H), 6.77 (dt, J=15.3, 6.9 Hz, 1H), 6.24 (d, J=15.3 Hz, 1H), 3.01–2.90 (m, 2H), 2.55–2.46 (m, 2H).

EXAMPLE 29(13)

4-(3-(5-Aminovalerylamino)-4-chlorophenyl)-2H-phthalazin-1-one Hydrochloride

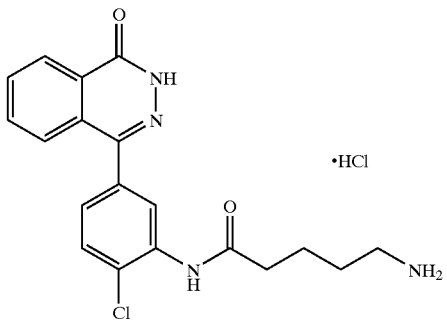

TLC: Rf 0.15 (Chloroform:Methanol:28% Ammonia water=4:1:0.1); NMR (DMSO-$d_6$): δ 12.90 (s, 1H), 9.73 (s, 1H), 8.35–8.31 (m, 1H), 7.93–7.63 (m, 8H), 7.40 (dd, J=8.2, 2.0 Hz, 1H), 2.82–2.73 (m, 2H), 2.44 (t, J=6.8 Hz, 2H), 1.68–1.53 (m, 4H).

EXAMPLE 29(14)

4-(3-(N-5-Aminovaleryl-N-methylamino)phenyl)-2H-phthalazin-1-one Hydrochloride

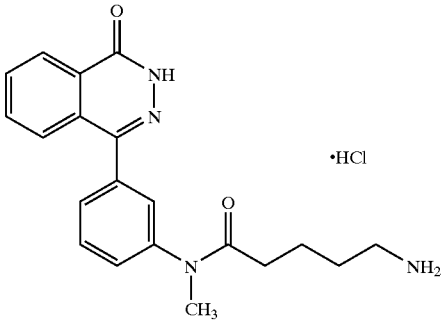

TLC: Rf 0.32 (Chloroform:Methanol:Acetic acid=8:2:1); NMR (DMSO-$d_6$): δ 12.90 (s, 1H), 8.36–8.33 (m, 1H), 7.96–7.87 (m, 2H), 7.84–7.48 (m, 8H), 3.23 (s, 3H), 2.76–2.64 (m, 2H), 2.24–2.08 (m, 2H), 1.58–1.42 (m, 4H).

EXAMPLE 29(15)

4-(3-(5-Guanidinovalerylamino)phenyl)-2H-phthalazin-1-one Hydrochloride

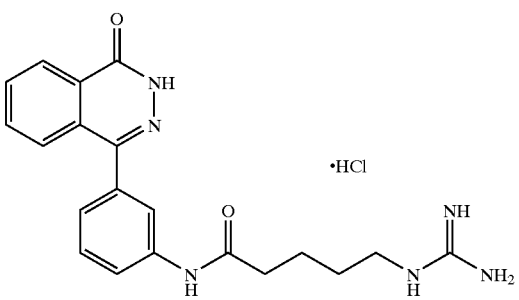

TLC: Rf 0.44 (Chloroform:Methanol:Acetic acid=8:2:1); NMR (DMSO-$d_6$): δ 12.84 (s, 1H), 10.21 (s, 1H), 8.35–8.32 (m, 1H), 7.93–7.86 (m, 3H), 7.74–7.62 (m, 3H), 7.48–6.70 (m, 6H), 3.16–3.09 (m, 2H), 2.37 (t, J=7.2 Hz, 2H), 1.68–1.44 (m, 4H).

EXAMPLE 30

4-(3-(3-(2-Morpholinoethyl)-2-thioureido)phenyl)-
2H-phthalazin-1-one Hydrochloride

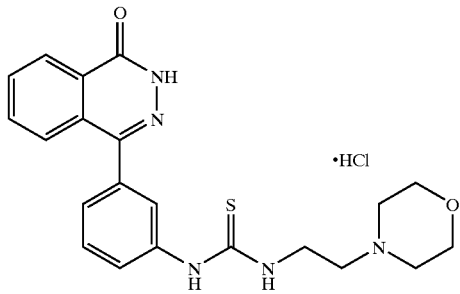

The compound of the present invention having the following physical data was obtained by the same procedure as a series of reactions of example 12, followed by converting to hydrochloride by conventional method, using 2-morpholinoethyl isothiocyanate instead of ethyl isothiocyanate.

TLC: Rf 0.30 (Chloroform:Methanol=10:1); NMR (DMSO-$d_6$): δ 12.86 (s, 1H), 10.55 (brs, 1H), 10.23 (s, 1H), 8.35–8.29 (m, 2H), 7.91–7.82 (m, 3H), 7.72 (s, 1H), 7.58–7.47 (m, 2H), 7.36 (d, J=7.5 Hz, 1H), 3.96–3.91 (m, 4H), 3.78–3.70 (m, 2H), 3.45–3.32 (m, 4H), 3.20–3.05 (m, 2H).

EXAMPLE 30(1)

4-(3-(3-(3-Morpholinopropyl)ureido)phenyl)-2H-
phthalazin-1-one Hydrochloride

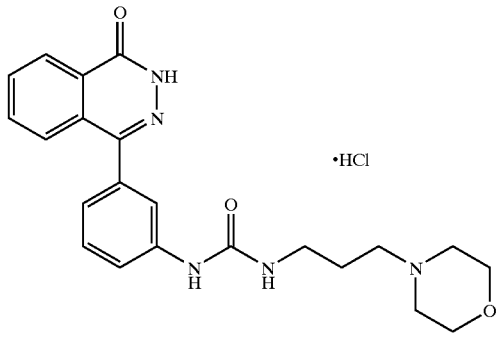

The compound of the present invention having the following physical data was obtained by the same procedure as a series of reactions of example 12, followed by converting to hydrochloride by conventional method, using 3-(2H-phthalazin-1-one-4-yl)phenyl isocyanate instead of ethyl isothiocyanate and using 3-morpholinopropylamine instead of 4-(3-aminophenyl)-2H-phthalazin-1-one.

TLC: Rf 0.35 (Chloroform:Methanol:Acetic acid= 8:2:0.5); NMR (DMSO-$d_6$): δ 12.81 (s, 1H), 10.46 (brs, 1H), 9.04 (s, 1H), 8.34–8.31 (m, 1H), 7.92–7.85 (m, 2H), 7.73–7.69 (m, 2H), 7.49 (d, J=7.8 Hz, 1H), 7.38 (t, J=7.8 Hz, 1H), 7.09 (d, J=7.8 Hz, 1H), 6.56 (brt, 1H), 3.95–3.91 (m, 2H), 3.76–3.69 (m, 2H), 3.41–3.02 (m, 8H), 1.88–1.83 (m, 2H).

EXAMPLE 30(2)

4-(3-(3-(3-Morpholinopropyl)-2-thioureido)phenyl)-
2H-phthalazin-1-one Hydrochloride

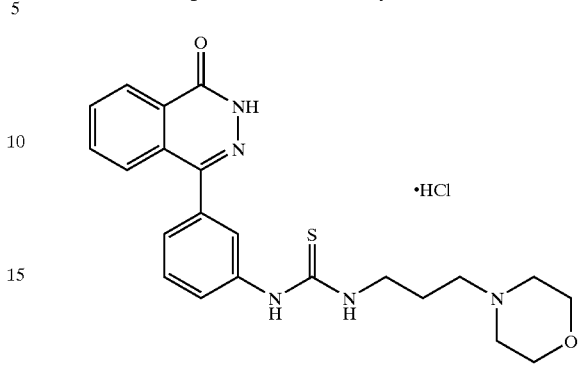

The compound of the present invention having the following physical data was obtained by the same procedure as a series of reactions of example 12, followed by converting to hydrochloride by conventional method, using 3-morpholinopropyl isothiocyanate instead of ethyl isothiocyanate.

TLC: Rf 0.43 (Chloroform:Methanol=10:1); NMR (DMSO): δ 12.85 (s, 1H), 10.43 (brs, 1H), 10.10 (brs, 1H), 8.35–8.26 (m, 2H), 7.93–7.83 (m, 3H), 7.73 (s, 1H), 7.57–7.46 (m, 2H), 7.33 (d, J=7.5 Hz, 1H), 3.98–3.90 (m, 2H), 3.72 (t, J=11.1 Hz, 2H), 3.62–3.52 (m, 2H), 3.46–3.32 (m, overlapped $H_2O$, 2H), 3.18–2.96 (m, 4H), 2.04–1.94 (m, 2H).

EXAMPLE 30(3)

4-(3-(2-Morpholinoethyloxycarbonylamino)phenyl)-
2H-phthalazin-1-one

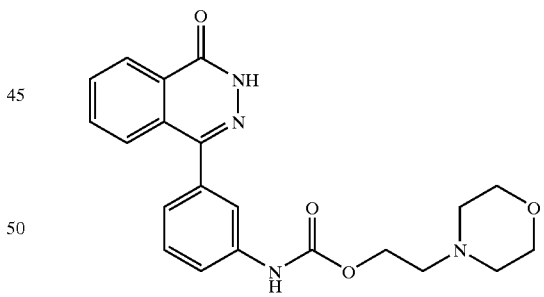

The compound of the present invention having the following physical data was obtained by the same procedure as a series of reactions of example 12, using 3-(2H-phthalazin-1-one-4-yl)phenyl isocyanate instead of ethyl isothiocyanate and using 2-morpholinoethanol instead of 4-(3-aminophenyl-2H-phthalazin-1-one.

TLC: Rf 0.79 (Chloroform:Methanol:Acetic acid= 8:2:0.5); NMR (DMSO-$d_6$, DMSO=2.49 ppm): δ 12.83 (s, 1H), 9.88 (s, 1H), 8.34–8.31 (m, 1H), 7.91–7.87 (m, 2H), 7.72–7.69 (m, 2H), 7.60 (d, J=7.8 Hz, 1H), 7.44 (t, J=7.8 Hz, 1H), 7.19 (d, J=7.8 Hz, 1H), 4.19 (t, J=5.7 Hz, 2H), 3.54 (t, J=4.5 Hz, 4H), 2.56 (t, J=5.7 Hz, 2H), 2.41 (t, J=4.5 Hz, 4H).

EXAMPLE 31

4-(3-(2-(2-(Piperidin-1-yl)ethyloxy)acetyl)aminophenyl)-2H-phthalazin-1-one Hydrochloride

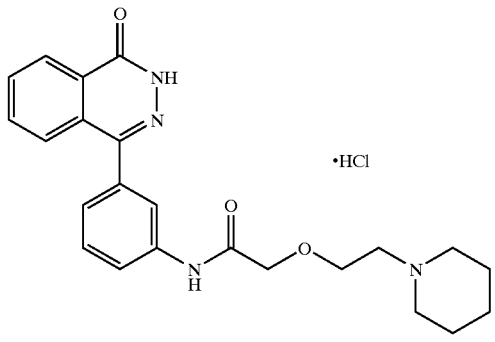

The compound of the present invention having the following physical data was obtained by the same procedure as a series of reactions of example 4, followed by converting to hydrochloride by conventional method, using 4(3-aminophenyl)-2H-phthalazin-1-one and 2-(2-(piperidin-1-yl)ethyloxy)acetic acid.

TLC: Rf 0.51 (Chloroform:Methanol:28% Ammonia water=9:1:0.2); NMR (DMSO-$d_6$): δ 12.85 (s, 1H), 10.39–10.22 (br, 1H), 10.32 (s, 1H), 8.36–8.30 (m, 1H), 8.01 (s, 1H), 7.94–7.86 (m, 3H), 7.76–7.70 (m, 1H), 7.49 (t, J=7.8 Hz, 1H), 7.29 (d, J=7.8 Hz, 1H), 4.18 (s, 2H), 3.86 (t, J=4.8 Hz, 2H), 3.52–3.40 (m, 2H, overlapped $H_2O$), 3.32–3.24 (m, 2H), 2.98–2.82 (m, 2H), 1.92–1.62 (m, 5H), 1.46–1.28 (m, 1H).

EXAMPLE 32~EXAMPLE 32(2)

The compounds of the present invention having the following physical data were obtained by the same procedure as a series of reactions of example 21, using the compound prepared in example 20(1) or corresponding halide compound and 4-methoxypiperidine.

EXAMPLE 32

4-(3-(5-(4-Methoxypiperidin-1-yl)valerylamino-4-methylphenyl)-2H-phthalazin-1-one Hydrochloride

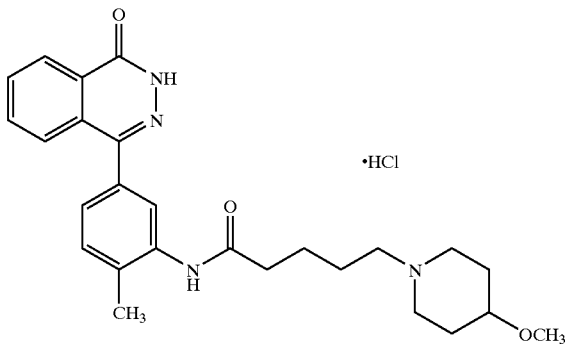

TLC: Rf 0.44 (Chloroform:Methanol:Acetic acid=8:1:1); NMR (DMSO): δ 12.82 (s, 1H), 9.80 (brs, 1H), 9.48 (s, 1H), 8.35–8.31 (m, 1H), 7.91–7.85 (m, 2H), 7.76–7.73 (m, 1H), 7.66 (s, 1H), 7.39–7.27 (m, 2H), 3.56–3.20 (m, 6H), 3.10–2.84 (m, 4H), 2.46–2.38 (m, 2H), 2.30 (s, 3H), 2.16–2.04 (m, 2H), 1.96–1.84 (m, 2H), 1.80–1.50 (m, 4H).

EXAMPLE 32(1)

4-(3-(5-(4-Methoxypiperidin-1-yl)valerylamino-4-chlorophenyl)-2H-phthalazin-1-one Hydrochloride

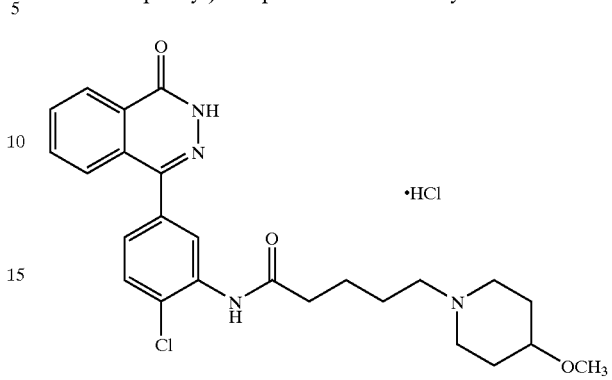

TLC: Rf 0.66 (Chloroform:Methanol:Acetic acid=9:1:1); NMR (DMSO): δ 12.90 (s, 1H), 10.01 (brs, 1H), 9.73 (s, 1H), 8.35–8.32 (m, 1H), 7.95–7.85 (m, 3H), 7.76–7.71 (m, 1H), 7.66 (d, J=7.8 Hz, 1H), 7.41 (dd, J=8.1, 1.8 Hz, 1H), 3.56–3.20 (m, 6H, overlapped with $H_2O$), 3.08–2.81 (m, 4H), 2.52–2.41 (m, 2H, overlapped with DMSO), 2.15–2.04 (m, 1H), 1.99–1.82 (m, 2H), 1.79–1.52 (m, 5H).

EXAMPLE 32(2)

4-(3-(5-(4-Methoxypiperidin-1-yl)valerylamino-4-fluorophenyl)-2H-phthalazin-1-one Hydrochloride

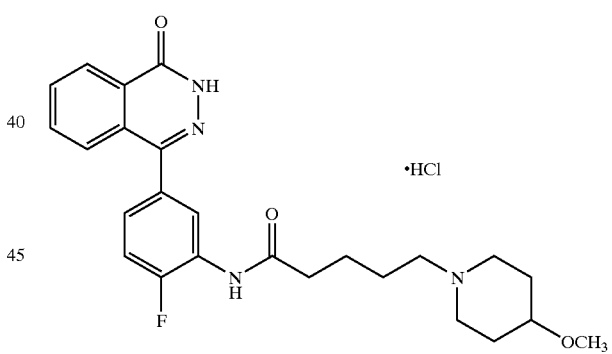

TLC: Rf 0.60 (Chloroform:Methanol:Acetic acid=9:1:1); NMR (DMSO): δ 12.86 (s, 1H), 10.02 (brs, 1H), 9.95 (s, 1H), 8.37–8.28 (m, 1H), 8.14 (dd, J=7.8, 1.8 Hz, 1H), 7.95–7.85 (m, 2H), 7.74–7.68 (m, 1H), 7.46–7.33 (m, 2H), 3.60–3.21 (m, 6H, overlapped with $H_2O$), 3.08–2.81 (m, 4H), 2.54–2.41 (m, 2H, overlapped with DMSO), 2.14–2.04 (m, 1H), 1.96–1.84 (m, 2H), 1.78–1.52 (m, 5H).

FORMULATION EXAMPLE

FORMULATION EXAMPLE 1

The following components were admixed in conventional method and punched out to obtain 100 tablets each containing 50 mg of active ingredient.

| | |
|---|---|
| 4-(3-(5-Aminovalerylamino)phenyl)-2H-phthalazin-1-one | 5.0 g |
| Carboxymethyl Cellulose calcium (disintegrating agent) | 0.2 g |
| Magnesium stearate (lubricating agent) | 0.1 g |
| Microcrystalline cellulose | 4.7 g |

FORMULATION EXAMPLE 2

The following components were admixed in conventional method. The solution was sterilized in conventional manner, placed 2 ml portions into 5 ml ampoules and freeze-dried to obtain 100 ampoules each containing 20 mg of the active ingredient.

| | |
|---|---|
| 4-(3-(5-Aminovalerylamino)phenyl)-2H-phthalazin-1-one | 2.0 g |
| mannitol | 20 g |
| distilled water | 500 ml |

What is claimed is:

1. A method for preventing and/or treating diseases induced by poly(ADP-ribose)polymerase, which comprises administering to a subject in need thereof an effective amount of a compound of formula (I)

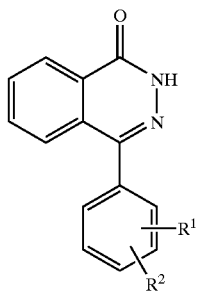
(I)

wherein $R^1$ is
  (i) C1–4 alkyl substituted by hydroxy or amino, or
  (ii)—$A^1$—$A^2$—$A^3$,
in which $A^1$ is
  (i)—$NR^3C(O)$—,
  (ii)—$NR^4C(S)$—,
  (iii)—$NR^5SO_2$—,
  (iv)—$CH_2$—$NR^6$—,
  (v)—$CH_2$—O—,
  (vi)—OC(O)—,
  (vii)—$CH_2$—$NR^7C(O)$—,
  (viii)—$NR^8C(O)NR^9$—,
  (ix)—$NR^{10}C(O)O$—,
  (x)—$NR^{11}C(S)NR^{12}$,
  (xi)—$N(R^{13})$—, or

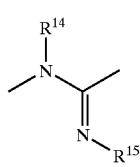
(xii)

with the proviso that the linkage of the right side of each group represented by $A^1$ binds to $A^2$, wherein $R^3, R^4, R^5, R^6, R^7, R^8, R^9, R^{10}, R^{11}, R^{12}, R^{13}, R^{14}$ and $R^{15}$ each, independently, is a hydrogen atom, C1–4 alkyl, phenyl or C1–4 alkyl substituted by phenyl,
$A^2$ is
  (i) C1–8 alkylene,
  (ii) C2–8 alkenylene,
  (iii) $Cyc^1$,
  (iv)—(C1–4 alkylene)—O—(C1–4 alkylene)—,
  (v)—(C1–4 alkylene)—S—(C1–4 alkylene)—,
  (vi)—(C1–4 alkylene)—$NR^{16}$—(C1–4 alkylene)—,
  (vii)—($Cyc^1$)—(C1–8 alkylene)—,
  (viii)—(C1–8 alkylene)—($Cyc^1$)—, or
  (ix)—(C1–4 alkylene)—($Cyc^1$)—(C1–4 alkylene),
$R^{16}$ is a hydrogen atom, C1–8 alkyl, C1–8 alkoxycarbonyl, phenyl or C1–8 alkyl substituted by phenyl,
$Cyc^1$ is
  (i) a 3–10 membered mono-cyclic or bi-cyclic carbocyclic ring, or
  (ii) a 3–10 membered mono-cyclic or bi-cyclic hetero ring having 1–4 nitrogen atoms, 1–2 oxygen atoms and/or one sulfur atom,
$A^3$ is
  (i) a hydrogen atom,
  (ii)—$NR^{17}R^{18}$,
  (iii) $Cyc^2$,
  (iv)—$OR^{19}$,
  (v)—$COOR^{20}$,
  (vi)—$CONR^{21}R^{22}$,
  (vii) C≡N,
  (viii) a halogen atom,

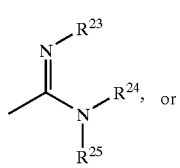
(ix)

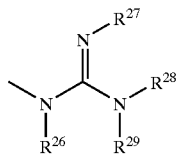
(x)

$R^{17}, R^{21}$ and $R^{22}$ each, independently, is
  (i) a hydrogen atom,
  (ii) C1–8 alkyl,
  (iii) C2–8 alkenyl,
  (iv) C2–8 alkynyl,
  (v) $Cyc^3$,
  (vi) C1–8 alkoxy,
  (vii) C2–8 alkenyloxy,
  (viii) C2–8 alkynyloxy, or
  (ix) C1–8 alkyl substituted by $Cyc^3$, C1–8 alkoxy, C1–8 alkylthio, C≡N, hydroxy or 1–3 of halogen atom,
$R^{18}$ is
  (i) a hydrogen atom,
  (ii) C1–8 alkyl,
  (iii) C2–8 alkenyl,
  (iv) C2–8 alkynyl,
  (v) C1–8 alkoxycarbonyl,
  (vi) C2–8 acyl,
  (vii) C3–8 cycloalkyl, (viii) C1–8 alkoxycarbonyl substituted by Cyc³ or 1–3 of halogen atom, or
(ix) C1–8 alkyl substituted by C1–8 alkoxy, R¹⁹ and R²⁰ each, independently, is a hydrogen atom or C1–8 alkyl, R²³, R²⁴, R²⁵, R²⁶, R²⁷, R²⁸ and R²⁹ each, independently, is a hydrogen atom, C1–4 alkyl, C1–8 alkoxycarbonyl, phenyl, or C1–4 alkyl substituted by phenyl, Cyc² is a 3–10 membered mono-cyclic or bi-cyclic hetero ring having 1–4 nitrogen atoms, 1–2 oxygen atoms and/or one sulfur atom, Cyc³ is
  (i) a 3–10 membered mono-cyclic or bi-cyclic carbocyclic ring, or
  (ii) a 3–10 membered mono-cyclic or bi-cyclic hetero ring having 1–4 nitrogen atoms, 1–2 oxygen atoms and/or one sulfur atom, the above-mentioned Cyc¹, Cyc² and Cyc³ each, independently, may be optionally substituted by 1–3 of substituents selected from the following (i)–(vii):
  (i) C1–8 alkyl,
  (ii) C2–8 alkenyl,
  (iii) C2–8 alkynyl,
  (iv) C1–8 alkoxy,
  (v) C1–8 alkoxycarbonyl,
  (vi) oxo, and
  (vii) C1–8 alkyl substituted by C1–8 alkoxy;

R² is a hydrogen atom, a halogen atom, nitro, hydroxy, —NR³⁰R³¹, C1–8 alkyl, C1–8 alkoxy, or C1–8 alkyl or C1–8 alkoxy substituted by 1–3 of halogen atoms, R³⁰ and R³¹ each, independently, is a hydrogen atom, C1–4 alkyl, C1–8 alkoxycarbonyl, phenyl, C1–4 alkyl substituted by phenyl, with the proviso that, R¹ is not dimethylamino, or a non-toxic salt thereof and a carrier.

2. A 2H-phthalazin-1-one derivative of the formula (Ia)

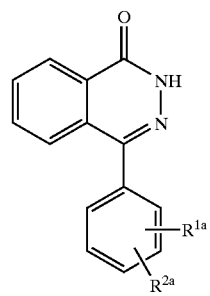

(Ia)

wherein R¹ᵃ is
  (i) C1–4 alkyl substituted by hydroxy or amino, or
  (ii) A¹ᵃ—A²ᵃ—A³ᵃ,
in which A¹ᵃ is
  (i) —NR³ᵃC(O)—,
  (ii) NR⁴ᵃC(S)—,
  (iii) —NR⁵ᵃSO₂—,
  (iv) —CH₂—NR⁶ᵃ—,
  (v) —CH₂—O—,
  (vi) —OC(O)—,
  (vii) —CH₂—NR⁷ᵃC(O)—,
  (viii) NR⁸ᵃC(O)NR⁹ᵃ—,
  (ix) —NR¹⁰ᵃC(O)O—,
  (x) —NR¹¹ᵃC(S)NR¹²ᵃ—,
  (xi) —NR(¹³ᵃ)—, or

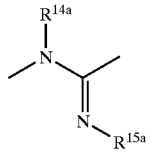

(xii)

with the proviso that the linkage of the right side of each group represented by A¹ᵃ binds to A²ᵃ, wherein R³ᵃ, R⁴ᵃ, R⁵ᵃ, R⁶ᵃ, R⁷ᵃ, R⁸ᵃ, R⁹ᵃ, R¹⁰ᵃ, R¹¹ᵃ, R¹²ᵃ, R¹³ᵃ, R¹⁴ᵃ and R¹⁵ᵃ each, independently, is a hydrogen atom, C1–4 alkyl, phenyl or C1–4 alkyl substituted by phenyl, A²ᵃ is
  (i) C1–8 alkylene,
  (ii) C2–8 alkenylene,
  (iii) Cyc¹ᵃ,
  (iv) —(C1–4 alkylene)—O—(C1–4 alkylene)—,
  (v) —(C1–4 alkylene)—S—(C1–4 alkylene)—,
  (vi) —(C1–4 alkylene)—NR¹⁶ᵃ(C1–4 alkylene)—,
  (vii) —(Cyc¹ᵃ)—(C1–8 alkylene)—,
  (viii) —(C1–8 alkylene)—(Cyc¹ᵃ)—, or
  (ix) —(C1–4 alkylene)—(Cyc¹ᵃ)—(C1–4 alkylene), R¹⁶ᵃ is a hydrogen atom, C1–8 alkyl, C1–8 alkoxycarbonyl, phenyl or C1–8 alkyl substituted by phenyl, Cyc¹ᵃ is
  (i) a 3–10 membered mono-cyclic or bi-cyclic carbocyclic ring, or
  (ii) a 3–10 membered mono-cyclic or bi-cyclic hetero ring having 1–4 nitrogen atoms, 1–2 oxygen atoms and/or one sulfur atom, A³ᵃ is
  (i) a hydrogen atom,
  (ii) —N¹⁷ᵃR¹⁸ᵃ,
  (iii) Cyc²ᵃ,
  (iv) OR¹⁹ᵃ,
  (v) —COOR²⁰ᵃ,
  (vi) —CONR²¹ᵃR²²ᵃ,
  (vii) C≡N,
  (viii) a halogen atom,

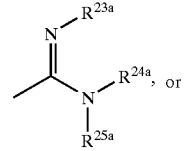

(ix)

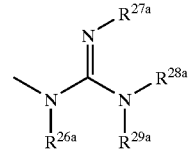

(x)

R¹⁷ᵃ, R²¹ᵃ and R²²ᵃ each, independently, is
  (i) a hydrogen atom,
  (ii) C1–8 alkyl,
  (iii) C2–8 alkenyl,
  (iv) C2–8 alkynyl,
  (v) Cyc³ᵃ, (vi) C1–8 alkoxy,
(vii) C2–8 alkenyloxy,
(viii) C2–8 alkynyloxy, or
(ix) C1–8 alkyl substituted by Cyc$^{3a}$, C1–8 alkoxy, C1–8 alkylthio, C≡N, hydroxy or 1–3 of halogen atom, R$^{18a}$ is
(i) a hydrogen atom,
(ii) C1–8 alkyl,
(iii) C2–8 alkenyl,
(iv) C2–8 alkynyl,
(v) C1–8 alkoxycarbonyl,
(vi) C2–8 acyl,
(vii) C3–8 cycloalkyl,
(viii) C1–8 alkoxycarbonyl substituted by Cyc$^{3a}$ or 1–3 of halogen atom, or
(ix) C1–8 alkyl substituted by C1–8 alkoxy, R$^{19a}$ and R$^{20}$ each, independently, is a hydrogen atom or C1–8 alkyl, R$^{23a}$, R$^{24a}$, R$^{25a}$, R$^{26a}$, R$^{27a}$, R$^{28a}$ and R$^{29a}$ each independently, is a hydrogen atom, C1–4 alkyl, C1–8 alkoxycarbonyl, phenyl, or C1–4 alkyl substituted by phenyl, Cyc$^{2a}$ is a 3–10 membered mono-cyclic or bi-cyclic hetero ring having 1–4 nitrogen atoms, 1–2 oxygen atoms and/or one sulfur atom, Cyc$^{3a}$ is
(i) a 3–10 membered mono-cyclic or bi-cyclic carbocyclic ring, or
(ii) a 3–10 membered mono-cyclic or bi-cyclic hetero ring having 1–4 nitrogen atoms, 1–2 oxygen atoms and/or one sulfur atom, the above-mentioned Cyc$^{1a}$, Cyc$^{2a}$ and Cyc$^{3a}$ each, independently, may be optionally substituted by 1–3 of substituents selected from the following (i)–(vii):
(i) C1–8 alkyl,
(ii) C2–8 alkenyl,
(iii) C2–8 alkynyl,
(iv) C1–8 alkoxy,
(v) C1–8 alkoxycarbonyl,
(vi) oxo, and
(vii) C1–8 alkyl substituted by C1–8 alkoxy;

R$^{2a}$ is a hydrogen atom, a halogen atom, nitro, hydroxy, —NR$^{30a}$R$^{31a}$, C1–8 alkyl, C1–8 alkoxy, or C1–8 alkyl or C1–8 alkoxy substituted by 1–3 of halogen atoms, R$^{30a}$ and R$^{31a}$ each, independently, is a hydrogen atom, C1–4 alkyl, C1–8 alkoxycarbonyl, phenyl, C1–4 alkyl substituted by phenyl, with the proviso that, R$^{1a}$ is not dimethylamino and the compound is not 4-(2-acetyloxyphenyl)-2H-phthalazin-1-one, or a non-toxic salt thereof.

3. A compound according to claim 2,
in which
R$^{16a}$ is a hydrogen atom, C1–4 alkyl, C1–8 alkoxycarbonyl, phenyl, or C1–4 alkyl substituted by phenyl, Cyc$^{1a}$ is
(i) a 3–10 membered mono-cyclic or bi-cyclic carbocyclic ring, or
(ii) a 3–10 membered mono-cyclic or bi-cyclic hetero ring having 1–4 nitrogen atoms, one oxygen atoms and/or one sulfur atom, and Cyc$^{1a}$ may be substituted by C1–8 alkoxycarbonyl, A$^{3a}$ is
(i) a hydrogen atom,
(ii) —N$^{17a}$R$^{18a}$,
(iii) Cyc$^{2a}$,
(iv) —OR$^{19a}$,
(v) —COOR$^{20a}$,
(vi) —CONR$^{21a}$R$^{22a}$,

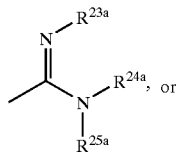
(ix)

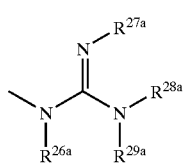
(x)

R$^{17a}$, R$^{21a}$ and R$^{22a}$ each, independently, is a hydrogen atom, C1–4 alkyl, phenyl, or C1–4 alkyl substituted by phenyl, R$^{18a}$ is a hydrogen atom, C1–4 alkyl, C1–8 alkoxycarbonyl, C2–5 acyl, or C1–4 alkoxycarbonyl substituted by phenyl, R$^{19a}$ and R$^{20a}$ each, independently, is a hydrogen atom or C1–4 alkyl, Cyc$^{2a}$ is a 3–10 membered mono-cyclic or bi-cyclic hetero ring having 1–4 nitrogen atoms, one oxygen atoms and/or one sulfur atom, substituted by C1–8 alkoxycarbonyl, R$^{2a}$ is a hydrogen atom, a halogen atom, nitro, or NR$^{30a}$R$^{31a}$.

4. A compound according to claim 2, wherein
R$^{1a}$ is —A$^{1a}$—A$^{2a}$—A$^{3a}$,
A$^{1a}$ and A$^{2a}$ is the same meaning as claim 2 defined,
A$^{3a}$ is (ii)—NR$^{17a}$R$^{16a}$, (iii) Cyc$^{2a}$, (vii)—C≡N, or (viii) a halogen atom, with the proviso that, when A$^{3a}$ is NR$^{17a}$R$^{18a}$, then R$^{17a}$ represents the groups except a hydrogen atom, C1–4 alkyl, phenyl, or C1–4 alkyl substituted by phenyl, Cyc$^{2a}$ is a 3–10 membered mono-cyclic or bi-cyclic hetero ring containing 1–4 nitrogen atoms, 1–2 oxygen atoms and/or one sulfur atom, substituted by 1–3 of substituent selected from C1–8 alkyl, C2–8 alkenyl, C2–8 alkynyl, C1–8 alkoxy, oxo, or C1–8 alkyl substituted by C1–8 alkoxy (with the proviso that when the substituent is selected from C1–8 alkyl, C1–8 alkoxy, or C1–8 alkyl substituted by C1–8 alkoxy, then the number of the substituent is 2 or 3).

5. A compound according to claim 2,
wherein
R$^{2a}$ is hydroxy, C1–8 alkyl, C1–8 alkoxy, or
C1–8 alkyl or C1–8 alkoxy substituted by 1–3 of halogen.

6. A compound according to claim 2,
wherein R$^{1a}$ is —A$^{1a}$—A$^{2a}$—A$^{3a}$ and
A$^{1a}$ is —NR$^{3a}$C(O)—.

7. A compound according to claim 2, which is
(1) 4-(3-(Hydroxymethyl)phenyl)-2H-phthalazin-1-one,
(2) 4-(3-(Aminomethyl)phenyl)-2H-phthalazin-1-one,
(3) 4-(3-(Dimethylaminomethyl)phenyl)-2H-phthalazin-1-one, (4) 4-(3-(5-(t-Butoxycarbonylamino)valerylamino)phenyl)-2H-phthalazin-1-one,
(5) 4-(3-(2-(t-Butoxycarbonylamino)acetylamino)phenyl)-2H-phthalazin-1-one,
(6) 4-(3-(4-(Benzyloxycarbonylamino)butyrylamino)phenyl)-2H-phthalazin-1-one,
(7) 4-(3-(6-(t-Butoxycarbonylamino)hexanoylamino)phenyl)-2H-phthalazin-1-one,
(8) 4-(3-(3-(Benzyloxycarbonylamino)propionylamino)phenyl)-2H-phthalazin-1-one,
(9) 4-(3-(2-(t-Butoxycarbonylamino)acetylaminomethyl)phenyl)-2H-phthalazin-1-one,
(10) 4-(3-(3-(t-Butoxycarbonylamino)propionylaminomethyl)phenyl)-2H-phthalazin-1-one,
(11) 4-(3-(1-t-Butoxycarbonylpiperidin-4-ylcarbonylamino)phenyl)-2H-phthalazin-1-one,
(12) 4-(3-(4-(t-Butoxycarbonylamino)butyrylaminomethyl)phenyl)-2H-phthalazin-1-one,
(13) 4-(3-(5-(t-Butoxycarbonylamino)valerylaminomethyl)phenyl)-2H-phthalazin-1-one,
(14) 4-(2-(5-(t-Butoxycarbonylamino)valerylamino)phenyl)-2H-phthalazin-1-one,
(15) 4-(3-(3-(Indol-3-yl)propionylamino)phenyl)-2H-phthalazin-1-one,
(16) 4-(3-(5-(Morpholin-4-yl)valerylamino)phenyl)-2H-phthalazin-1-one,
(17) 4-(3-(2-(Pyridin-4-yl)acetylamino)phenyl)-2H-phthalazin-1-one,
(18) 4-(3-(5-(Pyrrolidin-1-yl)valerylamino)phenyl)-2H-phthalazin-1-one,
(19) 4-(3-(5-(Dimethylamino)valerylamino)phenyl)-2H-phthalazin-1-one,
(20) 4-(3-(3-(Pyridin-3-yl)propionylamino)phenyl)-2H-phthalazin-1-one,
(21) 4-(3-(5-(N-Methyl-N-t-butoxycarbonylamino)valerylamino)phenyl)-2H-phthalazin-1-one,
(22) 4-(3-(2-(2-(t-Butoxycarbonylamino)ethylthio)acetylamino)phenyl)-2H-phthalazin-1-one,
(23) 4-(3-(2-(N-(2-(t-Butoxycarbonylamino)ethyl-N-t-butoxycarbonylamino)acetylamino)phenyl)-2H-phthalazin-1-one,
(24) 4-(3-(5-(t-Butoxycarbonylamino)valeryloxy)phenyl)-2H-phthalazin-1-one,
(25) 4-(3-(2-(3-(t-Butoxycarbonylamino)phenyl)acetylamino)phenyl)-2H-phthalazin-1-one,
(26) 4-(3-(3-(t-Butoxycarbonylaminomethyl)benzoylamino)phenyl)-2H-phthalazin-1-one,
(27) 4-(3-(trans-4-(t-Butoxycarbonylaminomethyl)cyclohexylcarbonylamino)phenyl)-2H-phthalazin-1-one,
(28) 4-(3-(4-(t-Butoxycarbonylamino)cyclohexylcarbonylamino)phenyl)-2H-phthalazin-1-one,
(29) 4-(3-(4-(t-Butoxycarbonylaminomethyl)benzoylamino)phenyl)-2H-phthalazin-1-one,
(30) 4-(3-(2-(4-(t-Butoxycarbonylamino)phenyl)acetylamino)phenyl)-2H-phthalazin-1-one,
(31) 4-(3-((E)-3-(1-(t-Butoxycarbonyl)imidazol-4-yl)propenoylamino)phenyl)-2H-phthalazin-1-one,
(32) 4-(3-(5-Aminovalerylamino)phenyl)-2H-phthalazin-1-one,
(33) 4-(3-(2-Aminoacetylamino)phenyl)-2H-phthalazin-1-one,
(34) 4-(3-(6-Aminohexanoylamino)phenyl)-2H-phthalazin-1-one,
(35) 4-(3-(2-Aminoacetylaminomethyl)phenyl)-2H-phthalazin-1-one,
(36) 4-(3-(3-Aminopropionylaminomethyl)phenyl)-2H-phthalazin-1-one,
(37) 4-(3-(Piperidin-4-ylcarbonylamino)phenyl)-2H-phthalazin-1-one,
(38) 4-(3-(4-Aminobutyrylaminomethyl)phenyl)-2H-phthalazin-1-one,
(39) 4-(3-(5-Aminovalerylaminomethyl)phenyl)-2H-phthalazin-1-one,
(40) 4-(2-(5-Aminovalerylamino)phenyl)-2H-phthalazin-1-one,
(41) 4-(3-(5-(Methylamino)valerylamino)phenyl)-2H-phthalazin-1-one,
(42) 4-(3-(2-(2-Aminoethylthio)acetylamino)phenyl)-2H-phthalazin-1-one,
(43) 4-(3-(2-(2-Aminoethylamino)acetylamino)phenyl)-2H-phthalazin-1-one,
(44) 4-(3-(5-Aminovaleryloxy)phenyl)-2H-phthalazin-1-one,
(45) 4-(3-(2-(3-Aminophenyl)acetylamino)phenyl)-2H-phthalazin-1-one,
(46) 4-(3-(3-(Aminomethyl)benzoylamino)phenyl)-2H-phthalazin-1-one,
(47) 4-(3-(trans-4-(Aminomethyl)cyclohexylcarbonylamino)phenyl)-2H-phthalazin-1-one,
(48) 4-(3-(4-Aminocyclohexylcarbonylamino)phenyl)-2H-phthalazin-1-one,
(49) 4-(3-(4-(Aminomethyl)benzoylamino)phenyl)-2H-phthalazin-1-one,
(50) 4-(3-(2-(4-Aminophenyl)acetylamino)phenyl)-2H-phthalazin-1-one,
(51) 4-(3-((E)-3-(Imidazol-4-yl)propenoylamino)phenyl)-2H-phthalazin-1-one,
(52) 4-(3-(Acetylamino)phenyl)-2H-phthalazin-1-one,
(53) 4-(3-(Hexanoylamino)phenyl)-2H-phthalazin-1-one,
(54) 4-(3-(Benzoylamino)phenyl)-2H-phthalazin-1-one,
(55) 4-(3-(Butyrylamino)phenyl)-2H-phthalazin-1-one,
(56) 4-(3-(Valerylamino)phenyl)-2H-phthalazin-1-one,
(57) 4-(3-(Mesylamino)phenyl)-2H-phthalazin-1-one,
(58) 4-(3-(Butylsulfonylamino)phenyl)-2H-phthalazin-1-one,
(59) 4-(2-(Acetylamino)phenyl)-2H-phthalazin-1-one,
(60) 4-(4-Chloro-3-(acetylamino)phenyl)-2H-phthalazin-1-one,
(61) 4-(3-(4-(Methoxycarbonyl)butyrylamino)phenyl)-2H-phthalazin-1-one,
(62) 4-(3-(Acetoxy)phenyl)-2H-phthalazin-1-one,
(63) 4-(3-(4-Aminobutyrylamino)phenyl)-2H-phthalazin-1-one,
(64) 4-(3-(3-Aminopropionylamino)phenyl)-2H-phthalazin-1-one,
(65) 4-(3-(4-Carboxybutyrylamino)phenyl)-2H-phthalazin-1-one,
(66) 4-(3-(5-Hydroxyvalerylamino)phenyl)-2H-phthalazin-1-one,
(67) 4-(3-(4-(t-Butoxycarbonylamino)butylaminomethyl)phenyl)-2H-phthalazin-1-one,

(68) 4-(3-(4-Aminobutylaminomethyl)phenyl)-2H-phthalazin-1-one,
(69) 4-(3-(3-Ethyl-2-thioureido)phenyl)-2H-phthalazin-1-one,
(70) 4-(3-(3-Ethylureido)phenyl)-2H-phthalazin-1-one,
(71) 4-(3-(Ethoxycarbonylamino)phenyl)-2H-phthalazin-1-one,
(72) 4-(3-(5-(t-Butoxycarbonylamino)pentylamino)phenyl)-2H-phthalazin-1-one,
(73) 4-(3-(5-Aminopentylamino)phenyl)-2H-phthalazin-1-one,
(74) 4-(3-(Propylthiocarbonylamino)phenyl)-2H-phthalazin-1-one,
(75) 4-(3-(5-(Acetylamino)valerylamino)phenyl)-2H-phthalazin-1-one,
(76) 4-(3-(3-(3-t-Butoxycarbonylaminopropyl)-2-thioureido)phenyl)-2H-phthalazin-1-one,
(77) 4-(3-(3-(3-Aminopropyl)-2-thioureido)phenyl)-2H-phthalazin-1-one,
(78) 4-(3-(6-Dimethylaminohexanoylamino)phenyl)-2H-phthalazin-1-one,
(79) 4-(3-(5-(Thiazolidin-3-yl)valerylamino)phenyl)-2H-phthalazin-1-one,
(80) 4-(3-(5-(Furan-2-ylmethylamino)valerylamino)phenyl)-2H-phthalazin-1-one,
(81) 4-(3-(5-(N-Methyl-N-propylamino)valerylamino)phenyl)-2H-phthalazin-1-one,
(82) 4-(3-(5-(2-Dimethylaminoethylamino)valerylamino)phenyl)-2H-phthalazin-1-one,
(83) 4-(3-(5-Diethylaminovalerylamino)phenyl)-2H-phthalazin-1-one,
(84) 4-(3-(5-(Azetidine-1-yl)valerylamino)phenyl)-2H-phthalazin-1-one,
(85) 4-(3-(5-Benzylaminovalerylamino)phenyl)-2H-phthalazin-1-one,
(86) 4-(3-(5-(N-(Furan-2-yl)methyl-N-methylamino)valerylamino)phenyl)-2H-phthalazin-1-one,
(87) 4-(3-(5-(N-t-Butyl-N-methylamino)valerylamino)phenyl)-2H-phthalazin-1-one,
(88) 4-(3-(5-(N-Isobutyl-N-methylamino)valerylamino)phenyl)-2H-phthalazin-1-one,
(89) 4-(3-(4-Morpholinobutyrylamino)phenyl)-2H-phthalazin-1-one,
(90) 4-(3-(5-(N-Ethyl-N-methylamino)valerylamino)phenyl)-2H-phthalazin-1-one,
(91) 4-(3-(5-(Thiophen-2-ylmethylamino)valerylamino)phenyl)-2H-phthalazin-1-one,
(92) 4-(3-(5-(N-Methyl-N-isopropylamino)valerylamino)phenyl)-2H-phthalazin-1-one,
(93) 4-(3-(5-(Tetrahydrofuran-2-ylmethylamino)valerylamino)phenyl)-2H-phthalazin-1-one,
(94) 4-(3-(5-t-Butylaminovalerylamino)phenyl)-2H-phthalazin-1-one,
(95) 4-(3-(5-sec-Butylaminovalerylamino)phenyl)-2H-phthalazin-1-one,
(96) 4-(3-(5-Ethylaminovalerylamino)-4-chlorophenyl)-2H-phthalazin-1-one,
(97) 4-(3-(5-Butylaminovalerylamino)-4-chlorophenyl)-2H-phthalazin-1-one,
(98) 4-(3-(5-Morpholinovalerylamino)-4-chlorophenyl)-2H-phthalazin-1-one,
(99) 4-(3-(5-Thiomorpholinovalerylamino)phenyl)-2H-phthalazin-1-one,
(100) 4-(3-(5-(4-Methylpiperazin-1-yl)valerylamino)phenyl)-2H-phthalazin-1-one,
(101) 4-(3-(5-Dimethylaminovalerylamino)4-fluorophenyl)-2H-phthalazin-1-one,
(102) 4-(3-(5-(N-Methyl-N-propylamino)valerylamino)-4-chlorophenyl)-2H-phthalazin-1-one,
(103) 4-(3-(5-Isobutylaminovalerylamino)phenyl)-2H-phthalazin-1-one,
(104) 4-(3-(5-(Piperidin-1-yl)valerylamino)phenyl)-2H-phthalazin-1-one,
(105) 4-(3-(5-(Perhydroazepin-1-yl)valerylamino)phenyl)-2H-phthalazin-1-one,
(106) 4-(3-(5-(N-Ethyl-N-2-methoxyethylamino)valerylamino)phenyl)-2H-phthalazin-1-one,
(107) 4-(3-(5-Morpholinovalerylamino)-4-fluorophenyl)-2H-phthalazin-1-one,
(108) 4-(3-(5-(1,2,5,6-Tetrahydropyridin-1-yl)valerylamino)phenyl)-2H-phthalazin-1-one,
(109) 4-(3-(5-(Pyrrolidin-1-yl)valerylamino)-4-chlorophenyl)-2H-phthalazin-1-one,
(110) 4-(3-(5-((2S)-2-Methoxymethylpyrrolidin-1-yl)valerylamino)phenyl)-2H-phthalazin-1-one,
(111) 4-(3-(5-(1,2,3-Triazol-1-yl)valerylamino)phenyl)-2H-phthalazin-1-one,
(112) 4-(3-(5-(N-2-Methoxyethyl-N-methylamino)valerylamino)-4-chlorophenyl)-2H-phthalazin-1-one,
(113) 4-(3-(5-(Imidazol-1-yl)valerylamino)phenyl)-2H-phthalazin-1-one,
(114) 4-(3-(5-(3-Methoxypyrrolidin-1-yl)valerylamino)phenyl)-2H-phthalazin-1-one,
(115) 4-(3-(5-(3-Methoxypiperidin-1-yl)valerylamino)phenyl)-2H-phthalazin-1-one,
(116) 4-(3-(5-((2R)2-Methoxymethylpyrrolidin-1-yl)valerylamino)phenyl)-2H-phthalazin-1-one,
(117) 4-(3-(5-(4-Methoxypiperidin-1-yl)valerylamino)phenyl)-2H-phthalazin-1-one,
(118) 4-(3-(5-Isobutylaminovalerylamino)-4-chlorophenyl)-2H-phthalazin-1-one,
(119) 4-(3-(5-(Pyrrolidin-1-yl)valerylamino)-4-fluorophenyl)-2H-phthalazin-1-one,
(120) 4-(3-(6-Morpholinohexanoylamino)phenyl)-2H-phthalazin-1-one,
(121) 4-(3-(5-(Perhydroazepin-1-yl)valerylamino)-4-chlorophenyl)-2H-phthalazin-1-one,
(122) 4-(3-(5-(2-Hydroxyethylamino)valerylamino)phenyl)-2H-phthalazin-1-one,
(123) 4-(3-(5-(3-Methoxypiperidin-1-yl)valerylamino)-4-chlorophenyl)-2H-phthalazin-1-one,
(124) 4-(3-(5-((3R)-3-Methoxypiperidin-1-yl)valerylamino)phenyl)-2H-phthalazin-1-one,
(125) 4-(3-(5-((3S)-3-Methoxypiperidin-1-yl)valerylamino)phenyl)-2H-phthalazin-1-one,
(126) 4-(3-(5-(3-Methoxypiperidin-1-yl)valerylamino)-4-fluorophenyl)-2H-phthalazin-1-one,
(127) 4-(3-(5-(3-Methoxymethylpiperidin-1-yl)valerylamino)phenyl)-2H-phthalazin-1-one,
(128) 4-(3-(4-Dimethylaminobutyrylamino)-4-chlorophenyl)-2H-phthalazin-1-one,
(129) 4-(3-(4-Dimethylaminobutyrylamino)phenyl)-2H-phthalazin-1-one, (130) 4-(4-Dimethylamino-3-(5-dimethylaminovalerylamino)phenyl)-2H-phthalazin-1-one, (131) 4-(3-(5-Dimethylaminovalerylamino)-4-chlorophenyl)-2H-phthalazin-1-one, (132) 4-(3-(3-Morpholinopropylsulfonylamino)phenyl)-2H-phthalazin-1-one, (133) 4-(3-(4-Morpholinobutylsulfonylamino)phenyl)-2H-phthalazin-1-one, (134) 4-(3-(5-Morpholino-2,2-dimethylvalerylamino)phenyl)-2H-phthalazin-1-one, (135) 4-(3-(4-Dimethylaminobutylsulfonylamino)phenyl)-2H-phthalazin-1-one, (136) 4-(3-(4-Morpholinobutylsulfonylamino)-4-fluorophenyl)-2H-phthalazin-1-one, (137) 4-(3-(4-(3-Methoxypiperidin-1-yl)butylsulfonylamino)phenyl)-2H-phthalazin-1-one, (138) 4-(3-(5-(N-t-Butoxycarbonyl-N-ethylamino)valerylamino)phenyl)-2H-phthalazin-1-one, (139) 4-(3-(5-(N-t-Butoxycarbonyl-N-propylamino)valerylamino)phenyl)-2H-phthalazin-1-one, (140) 4-(3-(5-(N-Isopropyl-N-t-butoxycarbonylamino)valerylamino)phenyl)-2H-phthalazin-1-one, (141) 4-(3-(7-t-Butoxycarbonylaminoheptanoylamino)phenyl)-2H-phthalazin-1-one, (142) 4-(3-(2-(2-t-Butoxycarbonylaminoethyloxy)acetylamino)phenyl)-2H-phthalazin-1-one, (143) 4-(3-(5-(N-Butyl-N-t-butoxycarbonylamino)valerylamino)phenyl)-2H-phthalazin-1-one, (144) 4-(3-(5-t-Butoxycarbonylaminovalerylamino)-4-dipropylaminophenyl)-2H-phthalazin-1-one, (145) 4-(3-(6-(N-Methyl-N-t-butoxycarbonylamino)hexanoylamino)phenyl)-2H-phthalazin-1-one, (146) 4-(3-((3E)-5-t-Butoxycarbonylaminopentenoylamino)phenyl)-2H-phthalazin-1-one, (147) 4-(3-(4-Amidinophenylcarbonylamino)phenyl)-2H-phthalazin-1-one, (148) 4-(3-(2-(2-Dimethylaminoethylthio)acetylamino)phenyl)-2H-phthalazin-1-one, (149) 4-(3-(4-Carbamoylbutyrylamino)phenyl)-2H-phthalazin-1-one, (150) 4-(3-(4-(N-t-Butoxycarbonyl-N-methylamino)butyrylamino)phenyl)-2H-phthalazin-1-one, (151) 4-(3-((2E)-5-t-Butoxycarbonylamino-2-pentenoylamino)phenyl)-2H-phthalazin-1-one, (152) 4-(3-(3-(t-Butoxycarbonylamino)propionylamino)phenyl)-2H-phthalazin-1-one, (153) 4-(3-(trans-2-Benzyloxycarbonylaminomethylcyclo propylcarbonylamino)phenyl)-2H-phthalazin-1-one, (154) 4-(3-(2-(2-Morpholinoethylthio)acetylamino)phenyl)-2H-phthalazin-1-one, (155) 4-(3-(2-(2-Morpholinoethyloxy)acetylamino)phenyl)-2H-phthalazin-1-one, (156) 4-(3-(2-(2-Morpholinoethylthio)-2-methylpropionylamino)phenyl)-2H-phthalazin-1-one, (157) 4-(3-(trans-2-Aminomethylcyclopropylcarbonylamino)phenyl)-2H-phthalazin-1-one, (158) 4-(3-(5-(2-Methoxyethylamino)valerylamino)phenyl)-2H-phthalazin-1-one, (159) 4-(3-(5-(N-2-Methoxyethyl-N-methylamino)valerylamino)phenyl)-2H-phthalazin-1-one, (160) 4-(3-(5-(N-2-Hydroxyethyl-N-methylamino)valerylamino)phenyl)-2H-phthalazin-1-one, (161) 4-(3-(5-t-Butoxycarbonylaminovalerylamino)-4-chlorophenyl)-2H-phthalazin-1-one, (162) 4-(3-(N-(5-t-Butoxycarbonylaminovaleryl)-N-methylamino)phenyl)-2H-phthalazin-1-one, (163) 4-(3-(5-(2,3-Bis(t-butoxycarbonyl)guanidino)valerylamino)phenyl)-2H-phthalazin-1-one, (164) 4-(3-(5-Ethylaminovalerylamino)phenyl)-2H-phthalazin-1-one, (165) 4-(3-(5-Propylaminovalerylamino)phenyl)-2H-phthalazin-1-one, (166) 4-(3-(5-Isopropylaminovalerylamino)phenyl)-2H-phthalazin-1-one, (167) 4-(3-(7-Aminoheptanoylamino)phenyl)-2H-phthalazin-1-one, (168) 4-(3-(2-(2-Aminoethyloxy)acetylamino)phenyl)-2H-phthalazin-1-one, (169) 4-(3-(5-Butylaminovalerylamino)phenyl)-2H-phthalazin-1-one, (170) 4-(3-(5-Aminovalerylamino)-4-dipropylaminophenyl)-2H-phthalazin-1-one, (171) 4-(3-(6-Methylaminohexanoylamino)phenyl)-2H-phthalazin-1-one, (172) 4-(3-((3E)-5-Amino-3-pentenoylamino)phenyl)-2H-phthalazin-1-one, (173) 4-(3-(4-Methylaminobutyrylamino)phenyl)-2H-phthalazin-1-one, (174) 4-(3-((2E)-5-Amino-2-pentenoylamino)phenyl)-2H-phthalazin-1-one, (175) 4-(3-(5-Aminovalerylamino)-4-chlorophenyl)-2H-phthalazin-1-one, (176) 4-(3-(N-5-Aminovaleryl-N-methylamino)phenyl)-2H-phthalazin-1-one, (177) 4-(3-(5-Guanidinovalerylamino)phenyl)-2H-phthalazin-1-one, (178) 4-(3-(3-(2-Morpholinoethyl)-2-thioureido)phenyl)-2H-phthalazin-1-one, (179) 4-(3-(3-(3-Morpholinopropyl)ureido)phenyl)-2H-phthalazin-1-one, (180) 4-(3-(3-(3-Morpholinopropyl)-2-thioureido)phenyl)-2H-phthalazin-1-one, (181) 4-(3-(2-Morpholinoethyloxycarbonylamino)phenyl)-2H-phthalazin-1-one, (182) 4-(3-(2-(2-(Piperidin-1-yl)ethyloxy)acetyl)aminophenyl)-2H-phthalazin-1-one, (183) 4-(3-(5-(4-Methoxypiperidin-1-yl)valerylamino-4-chlorophenyl)-2H-phthalazin-1-one, or (184) 4-(3-(5-(4-Methoxypiperidin-1-yl)valerylamino-4-fluorophenyl)-2H-phthalazin-1-one, or a non-toxic salt thereof.

8. A compound according to claim 2, which is (1) 4-(3-(5-Bromovalerylamino)phenyl)-2H-phthalazin-1-one, (2) 4-(3-(5-Bromovalerylamino)-4-chlorophenyl)-2H-phthalazin-1-one, (3) 4-(3-(5-Cyclohexylaminovalerylamino)-4-chlorophenyl)-2H-phthalazin-1-one, (4) 4-(3-(5-Cyclopentylaminovalerylamino)phenyl)-2H-phthalazin-1-one, (5) 4-(3-(5-Cyclohexylaminovalerylamino)phenyl)-2H-phthalazin-1-one, (6) 4-(3-(5-(N-Methyl-N-2-propynylamino)valerylaminomethyl)-2H-phthalazin-1-one, (7) 4-(3-(5-(2,2,2-Trifluoroethylaminovalerylamino)phenyl)-2H-phthalazin-1-one, (8) 4-(3-(5-Cyclopropylaminovalerylamino)phenyl)-2H-phthalazin-1-one, (9) 4-(3-(5-(Cyclohexylmethylamino)valerylamino)phenyl)-2H-phthalazin-1-one,

(10) 4-(3-(5-(N,N-Bis(2-methoxyethyl)amino)valerylamino)phenyl)-2H-phthalazin-1-one,

(11) 4-(3-(5—Neopentylaminovalerylamino)phenyl)-2H-phthalazin-1-one,

(12) 4-(3-(5-(2-Propynylamino)valerylamino)phenyl)-2H-phthalazin-1-one,

(13) 4-(3-(5-Cyclopropylmethylaminovalerylamino)phenyl)-2H-phthalazin-1-one,

(14) 4-(3-(5-Cyclopentylmethylaminovalerylamino)phenyl)-2H-phthalazin-1-one,

(15) 4-(3-(5-Cyclobutylaminovalerylamino)phenyl)-2H-phthalazin-1-one,

(16) 4-(3-(5-(2-Fluoroethylamino)valerylamino)phenyl)-2H-phthalazin-1-one,

(17) 4-(3-(5-(2-Methyl-2-propenylamino)valerylamino)phenyl)-2H-phthalazin-1-one,

(18) 4-(3-(5-(2-(1-Cyclohexen-1-yl)ethylamino)valerylamino)phenyl)-2H-phthalazin-1-one,

(19) 4-(3-(5-(1,2-Dimethylpropylamino)valerylamino)phenyl)-2H-phthalazin-1-one,

(20) 4-(3-(5-Cyclopropylaminovalerylamino)-4-chlorophenyl)-2H-phthalazin-1-one,

(21) 4-(3-(5-(2-Fluoroethylamino)valerylamino)-4-chlorophenyl)-2H-phthalazin-1-one,

(22) 4-(3-(5-(2-Methyl-2-propenylamino)valerylamino)-4-chlorophenyl)-2H-phthalazin-1-one,

(23) 4-(3-(5-(2-Propenylamino)valerylamino)phenyl)-2H-phthalazin-1-one,

(24) 4-(3-(5-(2-Propynylamino)valerylamino)-4-chlorophenyl)-2H-phthalazin-1-one,

(25) 4-(3-(5-(2-Propenyloxyamino)valerylamino)phenyl)-2H-phthalazin-1-one,

(26) 4-(3-(5-Cycloheptylaminovalerylamino)phenyl)-2H-phthalazin-1-one,

(27) 4-(3-(5-(2-Cyanoethylamino)valerylamino)phenyl)-2H-phthalazin-1-one,

(28) 4-(3-(5-Cyclobutylaminovalerylamino)-4-chlorophenyl)-2H-phthalazin-1-one,

(29) 4-(3-(5-(2,6-Dimethylmorpholin-4-yl)valerylamino)phenyl)-2H-phthalazin-1-one,

(30) 4-(3-(5-(2-Ethyl-4-methylimidazol-1-yl)valerylamino)phenyl)-2H-phthalazin-1-one,

(31) 4-(3-(5-Cyclopentylaminovalerylamino)-4-chlorophenyl)-2H-phthalazin-1-one,

(32) 4-(3-(5-(2-Methylthioethylamino)valerylamino)phenyl)-2H-phthalazin-1-one,

(33) 4-(3(5-(N-Methyl-N-2-propynylamino)valerylamino)-4-chlorophenyl)-2H-phthalazin-1-one,

(34) 4-(3-(5-(1-Methoxymethylcyclopentylamino)valerylamino)phenyl)-2H-phthalazin-1-one,

(35) 4-(3-(5-(Tetrahydropyran-4-ylamino)valerylamino)phenyl)-2H-phthalazin-1-one,

(36) 4-(3-(5-(2-Methoxycyclohexylamino)valerylamino)phenyl)-2H-phthalazin-1-one,

(37) 4-(3-(5-((1S, 2S)-2-Methoxycyclopentylamino)valerylamino)phenyl)-2H-phthalazin-1-one,

(38) 4-(3-(5-(2-Propenylamino)valerylamino)-4-chlorophenyl)-2H-phthalazin-1-one,

(39) 4-(3(5-(2-Fluoroethylamino)valerylamino)-4-fluorophenyl)-2H-phthalazin-1-one,

(40) 4-(3-(5-(Tetrahydropyran-4-ylamino)valerylamino)-4-chlorophenyl)-2H-phthalazin-1-one,

(41) 4-(3-(5-(3-Methylbutylamino)valerylamino)phenyl)-2H-phthalazin-1-one,

(42) 4-(3-(5-(N-Methyl-N-tetrahydropyran-4-yl)aminovalerylamino)phenyl)-2H-phthalazin-1-one,

(43) 4-(3-(5-(Piperidin-4-one-1-yl)valerylamino)phenyl)-2H-phthalazin-1-one,

(44) 4-(3-(5-((3R)-Tetrahydrofuran-3-ylamino)valerylamino)phenyl)-2H-phthalazin-1-one,

(45) 4-(3-(5-((3S)-Tetrahydrofuran-3-ylamino)valerylamino)phenyl)-2H-phthalazin-1-one,

(46) 4-(3-(4-Cyanobutyrylamino)-4-dimethylaminophenyl)-2H-phthalazin-1-one,

(47) 4-(3-(4-Cyanobutyrylamino)phenyl)-2H-phthalazin-1-one,

(48) 4-(3-(5-(N-3-Methyl-2-butenyl-N-t-butoxycarbonylamino)valerylamino)phenyl)-2H-phthalazin-1-one,

(49) 4-(3-(5-(N-2-Butynyl-N-t-butoxycarbonylamino)valerylamino)phenyl)-2H-phthalazin-1-one,

(50) 4-(3-(5-(N-Benzyloxycarbonyl-N-tetrahydrofuran-3-ylamino)valerylamino)phenyl)-2H-phthalazin-1-one,

(51) 4-(3-(5-(Tetrahydrofuran-3-ylamino)valerylamino)phenyl)-2H-phthalazin-1-one,

(52) 4-(3-(5-(1,3-Dioxoisoindolin-2-yl)valerylamino)-4-chlorophenyl)-2H-phthalazin-1-one,

(53) 4-(3-(5-(3-Methyl-2-butenylamino)valerylamino)phenyl)-2H-phthalazin-1-one, or

(54) 4-(3-(5-(2-Butynylamino)valerylamino)phenyl)-2H-phthalazin-1-one, or a non-toxic salt thereof.

9. A compound according to claim 2, which is (1) 4-(3-(5-Dimethylaminovalerylamino)-4-methoxyphenyl)-2H-phthalazin-1-one, (2) 4-(3-(5-Dimethylaminovalerylamino)-4-hydroxyphenyl)-2H-phthalazin-1-one, (3) 4-(3-(5-Dimethylaminovalerylamino)-4-methylphenyl)-2H-phthalazin-1-one, (4) 4-(3-(5-Morpholinovalerylamino)-4-methylphenyl)-2H-phthalazin-1-one, (5) 4-(3-(5-(3-Methoxypiperidin-1-yl)valerylamino)-4-methylphenyl)-2H-phthalazin-1-one, (6) 4-(3-(4-Morpholinobutylsulfonylamino)-4-methoxyphenyl)-2H-phthalazin-1-one, (7) 4-(3-(4-Morpholinobutylsulfonylamino)-4-methylphenyl)-2H-phthalazin-1-one, or (8) 4-(3-(5-(4-Methoxypiperidin-1-yl)valerylamino-4-methylphenyl)-2H-phthalazin-1-one, or a non-toxic salt thereof.

* * * * *